United States Patent
Caldwell et al.

[11] Patent Number: 5,877,191
[45] Date of Patent: Mar. 2, 1999

[54] PHENYL SPIROETHERCYCLOALKYL TACHYKININ RECEPTOR ANTAGONISTS

[75] Inventors: Charles G. Caldwell, Scotch Plains, N.J.; Yuan-Ching Chiang, East Lyme, Conn.; Conrad Dorn, Plainfield, N.J.; Paul Finke, Milltown, N.J.; Jeffrey Hale, Westfield, N.J.; Malcolm Maccoss, Freehold, N.J.; Sander Mills, Scotch Plains, N.J.; Albert Robichaud, Landenberg, Pa.

[73] Assignee: Merck & Co., Inc., Rahway, N.J.

[21] Appl. No.: 955,898

[22] Filed: Oct. 22, 1997

Related U.S. Application Data

[60] Provisional application No. 60/029,258, Oct. 25, 1996.
[51] Int. Cl.[6] .................. A61K 31/36; C07D 285/04; C07D 307/94; C07D 311/96
[52] U.S. Cl. .................. 514/337; 514/381; 514/465; 548/127; 548/128; 548/134; 548/136; 548/250; 548/253; 548/255; 548/262.2; 548/950; 549/345
[58] Field of Search ................... 548/253, 127, 548/128, 134, 136, 250, 255, 262.2, 950; 549/345; 514/337, 381, 465

[56] References Cited

U.S. PATENT DOCUMENTS 5,387,595 2/1995 Mills et al. .
5,688,806 11/1997 Desai et al. .

FOREIGN PATENT DOCUMENTS

WO 94/20500 9/1994 WIPO .
WO 96/20197 7/1996 WIPO .
WO 97/14671 4/1997 WIPO .
WO 97/19084 5/1997 WIPO .
WO 97/30055 8/1997 WIPO .
WO 97/30056 8/1997 WIPO .
WO 97/49710 12/1997 WIPO .

Primary Examiner—Johann Richter
Assistant Examiner—Taofiq A. Solola
Attorney, Agent, or Firm—J. Eric Thies; David L. Rose

[57] ABSTRACT

The present invention is directed to certain novel compounds represented by structural formula I:

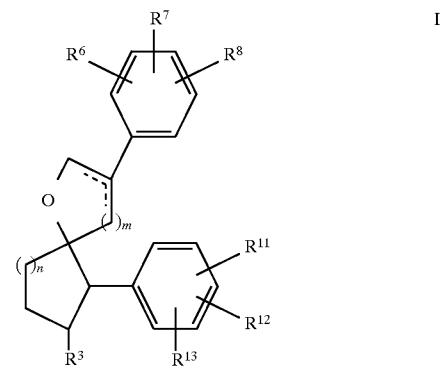

or a pharmaceutically acceptable salt thereof, wherein $R^3$, $R^6$, $R^7$, $R^8$, $R^{11}$, $R^{12}$, $R^{13}$, m, n and the dashed lines are defined herein. The invention is also concerned with pharmaceutical formulations comprising these novel compounds as active ingredients and the use of the novel compounds and their formulations in the treatment of certain disorders. The compounds of this invention are tachykinin receptor antagonists and are useful in the treatment of inflammatory diseases, pain or migraine, asthma and emesis.

16 Claims, No Drawings

PHENYL SPIROETHERCYCLOALKYL TACHYKININ RECEPTOR ANTAGONISTS

CROSS REFERENCE TO RELATED APPLICATION

This application claims priority under 35 U.S.C. §119(e) from U.S. Ser. No. 60/029,258, filed Oct. 25, 1996.

BACKGROUND OF THE INVENTION

Analgesia has historically been achieved in the central nervous system by opiates and analogs which are addictive, and peripherally by cyclooxygenase inhibitors that have gastric side effects. Substance P antagonists may induce analgesia both centrally and peripherally. In addition, substance P antagonists are inhibitory of neurogenic inflammation.

The neuropeptide receptors for substance P (neurokinin-1; NK-1) are widely distributed throughout the mammalian nervous system (especially brain and spinal ganglia), the circulatory system and peripheral tissues (especially the duodenum and jejunum) and are involved in regulating a number of diverse biological processes. This includes sensory perception of olfaction, vision, audition and pain, movement control, gastric motility, vasodilation, salivation, and micturition (B. Pernow, *Pharmacol. Rev.*, 1983, 35, 85–141). The NK-1 and NK-2 receptor subtypes are implicated in synaptic transmission (Laneuville et al., *Life Sci.*, 42: 1295–1305 (1988)).

The receptor for substance P is a member of the superfamily of G protein-coupled receptors. This superfamily is an extremely diverse group of receptors in terms of activating ligands and biological functions. In addition to the tachykinin receptors, this receptor superfamily includes the opsins, the adrenergic receptors, the muscarinic receptors, the dopamine receptors, the serotonin receptors, a thyroid-stimulating hormone receptor, a luteinizing hormone-choriogonadotropic hormone receptor, the product of the oncogene ras, the yeast mating factor receptors, a Dictyostelium cAMP receptor, and receptors for other hormones and neurotransmitters (A. D. Hershey, et al., *J. Biol. Chem.*, 1991, 226, 4366–4373).

Substance P (also called "SP" herein) is a naturally occurring undecapeptide belonging to the tachykinin family of peptides, the latter being so-named because of their prompt contractile action on extravascular smooth muscle tissue. The tachykinins are distinguished by a conserved carboxyl-terminal sequence Phe-X-Gly-Leu-Met-$NH_2$. In addition to SP the known mammalian tachykinins include neurokinin A and neurokinin B. The current nomenclature designates the receptors for SP, neurokinin A, and neurokinin B as NK-1, NK-2, and NK-3, respectively. More specifically, substance P is a neuropeptide that is produced in mammals and possesses a characteristic amino acid sequence (Chang et al, *Nature New Biol.* 232, 86 (1971); D. F. Veber et al, U.S. Pat. No. 4,680,283).

Substance P is a pharmacologically-active neuropeptide that is produced in mammals and acts as a vasodilator, a depressant, stimulates salivation and produces increased capillary permeability. It is also capable of producing both analgesia and hyperalgesia in animals, depending on dose and pain responsiveness of the animal (see R. C. A. Frederickson et al, *Science*, 199, 1359 (1978); P. Oehme et al., *Science*, 208, 305 (1980)) and plays a role in sensory transmission and pain perception (T. M. Jessell, *Advan. Biochem. Psychopharmacol.* 28, 189 (1981)). For example, substance P is believed to be involved in the neurotransmission of pain sensations [Otsuka et al, "Role of Substance P as a Sensory Transmitter in Spinal Cord and Sympathetic Ganglia" in 1982 Substance P in the Nervous System, Ciba Foundation Symposium 91, 13–34 (published by Pitman) and Otsuka and Yanagisawa, "Does Substance P Act as a Pain Transmitter?" TIPS, 8 506–510 (December 1987)], specifically in the transmission of pain in migraine (see B. E. B. Sandberg et al., *Journal of Medicinal Chemistry*, 25, 1009 (1982); M. A. Moskowitz, *Trends Pharmacol. Sci.*, 13, 307–311 (1992)), and in arthritis (Levine, et al. *Science*, 226 547–549 (1984); M. Lotz, et al., *Science*, 235, 893–895 (1987)). Tachykinins have also been implicated in gastrointestinal (GI) disorders and diseases of the GI tract, such as inflammatory bowel disease [*Neuroscience*, 25 (3), 817–37 (1988) and D. Regoli in "Trends in Cluster Headache" Ed. F. Sicuteri et al., Elsevier Scientific Publishers, Amsterdam, pp. 85–95 (1987)], and emesis [*Trends Pharmacol. Sci.*,9, 334–341 (1988), *Eur. J. Pharmacol.*, 249, R3–R4 (1993), *Brit. J. Pharmacol.*, 115, 84–94 (1995)].

It is also hypothesized that there is a neurogenic mechanism for arthritis in which substance P may play a role [Kidd et al., "A Neurogenic Mechanism for Symmetric Arthritis" in *The Lancet*, 11 November 1989 and Gronblad et al., "Neuropeptides in Synovium of Patients with Rheumatoid Arthritis and Osteoarthritis" in *J. Rheumatol.* 15(12) 1807–10 (1988)]. Therefore, substance P is believed to be involved in the inflammatory response in diseases such as rheumatoid arthritis and osteoarthritis [O'Byrne et al.,*Arhritis and Rheumatism*, 33 1023–8 (1990)].

Evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Chrohn's disease, ocular injury and ocular inflammatory diseases, proliferative vitreoretinopathy, irritable bowel syndrome and disorders of bladder function including cystitis and bladder detruser hyperreflexia is reviewed in "Tachykinin Receptors and Tachykinin Receptor Antagonists," C. A. Maggi, R. Patacchini, P. Rovero and A. Giachetti,*J. Auton. Pharmacol,* 13, 23–93 (1993); see also R. M. Snider, et al., *Chem. Ind.*, 11, 792–794 (1991). Neurokinin-1 receptor antagonists alone or in combination with bradykinin receptor antagonists may also be useful in the prevention and treatment of inflammatory conditions in the lower urinary tract, especially cystitis [Giuliani, et al., *J. Urology*, 150, 1014–1017 (1993)]. Other disease areas where tachykinin antagonists are believed to be useful are allergic conditions [Hamelet et al., *Can. J. Pharmacol. Physiol.*, 66, 1361–7 (1988)], immunoregulation [Lotz, et al., *Science*, 241 1218–21 (1988), Kimball, et al, *J. Immunol.*, 141 (10) 3564–9 (1988); A. Perianin, et al., *Biochem. Biophys. Res Commun.* 161, 520 (1989)], post-operative pain and nausea [C. Bountra, et al., *Eur. J. Pharmacol.*, 249, R3–R4 (1993), F. D. Tattersall, et al., *Neuropharmacology*, 33, 259–260 (1994)], vasodilation, bronchospasm, reflex or neuronal control of the viscera [Mantyh et al., *PNAS*, 85, 3235–9 (1988)] and, possibly by arresting or slowing β-amyloid-mediated neurodegenerative changes [Yankner et al., *Science*, 250, 279–82 (1990)] in senile dementia of the Alzheimer type, Alzheimer's disease and Downs Syndrome. Substance P may also play a role in demyelinating diseases such as multiple sclerosis and amyotrophic lateral sclerosis [J. Luber-Narod, et. al., poster C.I.N.P. XVIIIth Congress, 28th Jun.–2nd Jul., 1992], and in disorders of bladder function such as bladder detrusor hyperreflexia [*Lancet*, 16th May 1992, 1239]. Antagonists selective for the neurokinin-1 (NK-1) and/or the neurokinin-2 (NK-2) receptor may be useful in the treatment of asthmatic disease (Frossard et al., *Life Sci.*, 49, 1941–1953 (1991); Advenier, et al., *Biochem. Biophys. Res. Comm.*, 184(3), 1418–1424 (1992); P. Barnes, et al., *Trends Pharmacol. Sci.*, 11, 185–189 (1993)). Tachykinin antagonists may also be useful in the treatment of small cell carcinomas, in particular small cell lung cancer (SCLC) [Langdon et al., *Cancer Research*, 52, 4554–7 (1992)].

It has furthermore been suggested that tachykinin receptor antagonists have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophillic fascioliasis, reflex sympathetic dystrophy such as shoulder/hand syndrome, addiction disorders such as alcoholism, stress related somatic disorders, neuropathy, neuralgia, disorder related to immune enhancement or suppression such as systemic lupus erythmatosus (EPO Publication No. 0,436,334), ophthalmic diseases such as conjunctivitis, vernal conjunctivitis, and the like, and cutaneous diseases such as contact dermatitis, atopic dermatitis, urticaria, and other eczematoid dermatitis (EPO Publication No. 0,394,989).

Substance P antagonists may be useful in mediating neurogenic mucus secretion in mammalian airways and hence provide treatment and symptomatic relief in diseases characterized by mucus secretion, in particular, cystic fibrosis [S. Ramnarine, et al., abstract presented at 1993 ALA/ATS Int'l Conference, 16–19 May, 1993, published in *Am. Rev. of Respiratory Dis., May* 1993].

In the recent past, some attempts have been made to provide peptide-like substances that are antagonists for the receptors of substance P and other tachykinin peptides in order to more effectively treat the various disorders and diseases mentioned above. For example Lowe, *Drugs of the Future*, 17 (12) 1115–1121 (1992) and EPO Publication Nos. 0,347,802, 0,401,177 and 0,412,452 disclose various peptides as neurokinin A antagonists. Also, PCT Patent Publication WO 93/14113 discloses certain peptides as tachykinin antagonists. In addition, EPO Publication No. 0,336,230 discloses heptapeptides which are substance P antagonists useful in the treatment of asthma. U.S. Pat. No. 4,680,283 also discloses peptidal analogs of substance P. Certain inhibitors of tachykinins have been described in U.S. Pat. No. 4,501,733. by replacing residues in substance P sequence by Trp residues. A further class of tachykinin receptor antagonists, comprising a monomeric or dimeric hexa- or heptapeptide unit in linear or cyclic form, is described in GB-A-2216529. The peptide-like nature of such substances make them too labile from a metabolic point of view to serve as practical therapeutic agents in the treatment of disease. The non-peptidic antagonists of the present invention, on the other hand, do not possess this drawback, as they are expected to be more stable from a metabolic point of view than the previously-discussed agents.

It is known that in the central nervous system baclofen [β-(aminoethyl)-4-chlorobenzenepropanoic acid] effectively blocks the excitatory activity of substance P. WIPO patent applications (PCT Publication Nos. WO 90/05525, WO 90/05729, WO 91/18899, WO 92/12151 and WO 92/12152) and publications (*Science*, 251, 435–437 (1991); *Science*, 251, 437–439 (1991); *J. Med. Chem.* 35, 2591–2600 (1992)) disclose 2-arylmethyl-3-substituted amino-quinuclidine derivatives which are disclosed as being useful as substance P antagonists for treating gastrointestinal disorders, central nervous system disorders, inflammatory diseases and pain or migraine. A European patent application (EPO Publication No. 0,360,390) discloses various spirolactam-substituted amino acids and peptides which are antagonists or agonists of substance P. A WIPO patent application (PCT Publication No. WO 92/06079) discloses fused-ring analogs of nitrogen-containing nonaromatic heterocycles as useful for the treatment of diseases mediated by an excess of substance P. A WIPO patent application (PCT Publication No. WO 92/15585 discloses 1-azabicyclo[3.2.2]nonan-3-amine derivatives as substance P antagonists. A WIPO patent application (PCT Publication No. WO 93/10073) discloses ethylenediamine derivatives as substance P antagonists. PCT Publication No. WO 93/01169 discloses certain aromatic compounds as tachykinin receptor antagonists. A publication (*Life Sci.*, 50, PL101–PL106 (1992)) discloses a 4-phenyl piperidine derivative as an antagonist of the neurokinin A (NK2) receptor.

Howson et al. (*Biorg. & Med. Chem. Lett.*, 2 (6), 559–564 (1992)) disclose certain 3-amino and 3-oxy quinuclidine compounds and their binding to substance P receptors. EPO Publication 0,499,313 discloses certain 3-oxy and 3-thio azabicyclic compounds as tachykinin antagonists. U.S. Pat. No. 3,506,673 discloses certain 3-hydroxy quinuclidine compounds as central nervous system stimulants. EPO Publication 0,436,334 discloses certain 3-aminopiperidine compounds as substance P antagonists. U.S. Pat. No. 5,064,838 discloses certain 1,4-disubstituted piperidinyl compounds as analgesics. PCT Publication No. WO 92/12128 discloses certain piperidine and pyrrolidine compounds as analgesics. Peyronel, et al.(*Biorg & Med. Chem. Lett.*, 2 (1), 37–40 (1992)) disclose a fused ring pyrrolidine compound as a substance P antagonist. EPO Publication No. 0,360,390 discloses certain spirolactam derivatives as substance P antagonists. U.S. Pat. No. 4,804,661 discloses certain piperazine compounds as analgesics. U.S. Pat. No. 4,943,578 discloses certain piperazine compounds useful in the treatment of pain. PCT Publication No. WO 92/01679 discloses certain 1,4-disubstituted piperazines useful in the treatment of mental disorders in which a dopaminergic deficit is implicated. PCT Publication No. WO 94/00440, EPO Publication No. 0,577,394 and PCT Publication No. WO 95/16679 disclose certain morpholine and thiomorpholine compounds as substance P antagonists. U.S. Pat. No. 5,387,595 and *Bioorg. & Med. Chem. Lett.*, 1345 (1995) disclose certain alicyclic compounds as tachykinin receptor antagonist. PCT Publications WO 95/06645 and WO 95/08549 discloses certain 3-amino-piperidines as tachykinin antagonists. PCT Publication No. WO 96/20197 disclose certain spiroketal morpholine compounds as substance P antagonists.

SUMMARY OF THE INVENTION

The present invention is directed to compounds of the structural formula I:

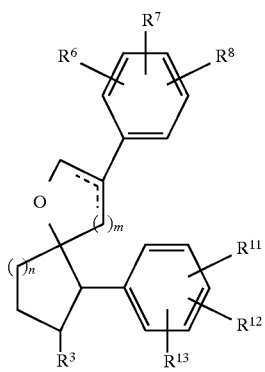

or a pharmaceutically acceptable salt thereof, wherein $R^3$, $R^6$, $R^7$, $R^8$, $R^{11}$, $R^{12}$, $R^{13}$, m, n and the dashed lines are hereinafter defined. The invention is also concerned with pharmaceutical formulations comprising these novel compounds as active ingredients and the use of the novel compounds and their formulations in the treatment of certain disorders. The compounds of this invention are tachykinin receptor antagonists and are useful in the treatment of inflammatory diseases, pain or migraine, asthma and emesis.

DETAILED DESCRIPTION OF THE INVENTION

The present invention is directed to the novel compound of the structural formula I:

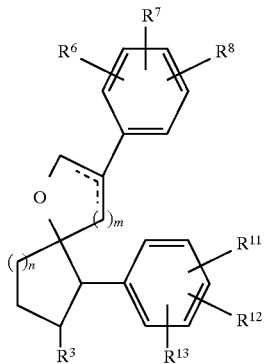

or a pharmaceutically acceptable salt thereof, wherein:
$R^3$ is selected from the group consisting of:
(1) hydrogen,
(2) $C_{1-8}$ alkyl,
(3) —$R^4$, and
(4) $C_{1-6}$ alkyl substituted with —$R^4$;
$R^4$ is selected from the group consisting of:
(1) hydroxy,
(2) $C_{1-6}$ alkoxy,
(3) phenyl-$C_{1-3}$ alkoxy,
(4) phenyl,
(5) —CN,
(6) halo, wherein halo is fluoro, chloro, bromo or iodo,
(7) —$NR^9R^{10}$, wherein $R^9$ and $R^{10}$ are independently selected from:
  (a) hydrogen,
  (b) $C_{1-6}$ alkyl,
  (c) $C_{2-6}$ alkenyl,
  (d) $C_{2-6}$ alkoxy,
  (e) phenyl,
  (f) ($C_{1-6}$ alkyl)-phenyl,
  (g) ($C_{1-6}$ alkyl)-hydroxy,
  (h) ($C_{1-6}$ alkyl)-halo,
  (i) ($C_{1-6}$ alkyl)-poly-halo,
  (j) ($C_{1-6}$ alkyl)-$CONR^{11}R^{12}$, wherein $R^{11}$ and $R^{12}$ are independently selected from hydrogen and $C_{1-4}$ alkyl, and
  (k) ($C_{1-6}$ alkyl)-($C_{1-4}$ alkoxy),
  or $R^9$ and $R^{10}$ may be joined together to form a 3–8 membered heterocyclic ring which may contain another heterogroup selected from: —O—, —NH—, —N($C_{1-6}$ alkyl)—, and —S—;
(8) —$NR^9$—$COR^{10}$,
(9) —$NR^9$—$CO_2R^{10}$,
(10) —CO—$NR^9R^{10}$,
(11) —$COR^9$,
(12) —$CO_2R^9$,
(13) heterocycle, wherein the heterocycle is selected from the group consisting of:
  (A) benzimidazolyl,
  (B) benzofuranyl,
  (C) benzothiophenyl,
  (D) benzoxazolyl,
  (E) furanyl,
  (F) imidazolyl,
  (G) indolyl,
  (H) isooxazolyl,
  (I) isothiazolyl,
  (J) oxadiazolyl,
  (K) oxazolyl,
  (L) pyrazinyl,
  (M) pyrazolyl,
  (N) pyridyl,
  (O) pyrimidyl,
  (P) pyrrolyl,
  (Q) quinolyl,
  (R) tetrazolyl,
  (S) thiadiazolyl,
  (T) thiazolyl,
  (U) thienyl,
  (V) triazolyl,
  (W) azetidinyl,
  (X) 1,4-dioxanyl,
  (Y) hexahydroazepinyl,
  (Z) piperazinyl,
  (AA) piperidinyl,
  (AB) pyrrolidinyl,
  (AC) morpholinyl,
  (AC) thiomorpholinyl,
  (AD) dihydrobenzimidazolyl,
  (AE) dihydrobenzofuranyl,
  (AF) dihydrobenzothiophenyl,
  (AG) dihydrobenzoxazolyl,
  (AH) dihydrofuranyl,
  (AI) dihydroimidazolyl,
  (AJ) dihydroindolyl,
  (AK) dihydroisooxazolyl,
  (AL) dihydroisothiazolyl,
  (AM) dihydrooxadiazolyl,
  (AN) dihydrooxazolyl,
  (AO) dihydropyrazinyl,
  (AP) dihydropyrazolyl,
  (AQ) dihydropyridinyl,
  (AR) dihydropyrimidinyl,
  (AS) dihydropyrrolyl,
  (AT) dihydroquinolinyl, (AU) dihydrotetrazolyl,
(AV) dihydrothiadiazolyl,
(AW) dihydrothiazolyl,
(AX) dihydrothienyl,
(AY) dihydrotriazolyl,
(AZ) dihydroazetidinyl,
(BA) tetrahydrofuranyl, and
(BB) tetrahydrothienyl,
and wherein the heterocycle is unsubstituted or substituted with one or more substituent(s) selected from:
(i) $C_{1-6}$ alkyl, unsubstituted or substituted with halo, $-CF_3$, $-OCH_3$, or phenyl,
(ii) $C_{1-6}$ alkoxy,
(iii) oxo,
(iv) hydroxy,
(v) thioxo,
(vi) $-SR^9$,
(vii) halo,
(viii) cyano,
(ix) phenyl,
(x) trifluoromethyl,
(xi) $-(CH_2)_p-NR^9R^{10}$, wherein p is 0, 1, 2, 3 or 4,
(xii) $-NR^9COR^{10}$,
(xiii) $-CONR^9R^{10}$,
(xiv) $-CO_2R^9$, and
(xv) $-(CH_2)_p-OR^9$,
(14) $-CO$-heterocycle, wherein heterocycle is as defined above,
(15) $-NR^9$-heterocycle, wherein heterocycle is as defined above,
(16) $-NR^9-C_{1-4}$ alkyl-heterocycle, wherein heterocycle is as defined above;
$R^6$, $R^7$ and $R^8$ are independently selected from the group consisting of:
(1) hydrogen,
(2) $C_{1-6}$alkoxy,
(3) halo,
(4) $C_{1-6}$ alkyl, unsubstituted or substituted with one or more of the substituents selected from:
(a) hydroxy,
(b) oxo,
(c) $C_{1-6}$ alkoxy,
(d) phenyl-$C_{1-3}$ alkoxy,
(e) phenyl,
(f) $-CN$,
(g) halo,
(h) $-NR^9R^{10}$,
(i) $-NR^9-COR^{10}$,
(j) $-NR^9-CO_2R^{10}$,
(k) $-CO-NR^9R^{10}$,
(l) $-COR^9$,
(m) $-CO_2R^9$,
(n) heterocycle, wherein heterocycle is as defined above,
(5) hydroxy,
(6) $-CN$,
(7) $-CF_3$,
(8) $-OCF_3$,
(9) $-OCF_2H$,
(10) $-OCFH_2$,
(11) $-NO_2$,
(12) $-SR^{14}$, wherein $R^{14}$ is hydrogen or $C_{1-6}$alkyl,
(13) $-SOR^{14}$,
(14) $-SO_2R^{14}$,
(15) $-NR^9-COR^{10}$,
(16) $-CO-NR^9-COR^{10}$,
(17) $-NR^9R^{10}$,
(18) $-NR^9-CO_2R^{10}$,
(19) $-COR^9$,
(20) $-CO_2R^9$,
(21) heterocycle, wherein heterocycle is as defined above,
(22) $-(C_{1-6}alkyl)$-heterocycle, wherein heterocycle is as defined above, and
(23) $-N(heterocycle)-SO_2R^{14}$, wherein heterocycle is as defined above;
$R^{11}$, $R^{12}$ and $R^{13}$ are independently selected from:
(1) hydrogen,
(2) $C_{1-6}$ alkyl, unsubstituted or substituted with one or more of the substituents selected from:
(a) hydroxy,
(b) oxo,
(c) $C_{1-6}$ alkoxy,
(d) phenyl-$C_{1-3}$ alkoxy,
(e) phenyl,
(f) $-CN$,
(g) halo,
(h) $-NR^9R^{10}$,
(i) $-NR^9-COR^{10}$,
(j) $-NR^9-CO_2R^{10}$,
(k) $-CO-NR^9R^{10}$,
(l) $-COR^9$, and
(m) $-CO_2R^9$,
(3) halo,
(4) $-CN$,
(5) $-CF_3$,
(6) $-NO_2$,
(7) hydroxy,
(8) $C_{1-6}$alkoxy,
(9) $-COR^9$, and
(10) $-CO_2R^9$;
m is an integer selected from 1 or 2;
n is an integer selected from 0, 1 or 2;
each of the two dashed lines denotes the presence of a either a single or a double bond between the indicated carbon atoms, with the proviso that at least one of the dashed lines indicates the presence of a single bond.

Asymmetric centers may be present in the compounds of the instant invention depending upon the nature of the various substituents on the molecule. Each such asymmetric center will independently produce two optical isomers and it is intended that all of the possible optical isomers and diastereomers in mixture and as pure or partially purified compounds are included within the ambit of this invention.

In addition compounds with carbon-carbon double bonds may occur in Z- and E-forms with all isomeric forms of the compounds being included in the present invention.

When any variable (e.g., alkyl, aryl, Q, W, X, Y, Z, $R^4$, $R^6$, $R^7$, $R^8$, $R^9$, $R^{10}$, $R^{11}$, $R^{12}$, $R^{13}$, $R^{14}$, $R^{15}$, etc.) occurs more than one time in any variable or in Formula I, its definition on each occurrence is independent of its definition at every other occurrence.

As used herein, the term "alkyl" includes those alkyl groups of a designated number of carbon atoms of either a straight, branched, or cyclic configuration. Examples of "alkyl" include methyl, ethyl, propyl, isopropyl, butyl, iso- sec- and tert-butyl, pentyl, hexyl, heptyl, 3-ethylbutyl, cyclopropyl, cyclobutyl, cyclopentyl, cyclohexyl, cycloheptyl, norbornyl, and the like. "Alkoxy" represents an alkyl group of indicated number of carbon atoms attached through an oxygen bridge, such as methoxy, ethoxy, propoxy, butoxy and pentoxy. "Alkenyl" is intended to include hydrocarbon chains of a specified number of carbon atoms of either a straight- or branched-configuration and at least one unsaturation, which may occur at any point along the chain, such as ethenyl, propenyl, butenyl, pentenyl, dimethylpentyl, and the like, and includes E and Z forms, where applicable. "Halogen" or "halo", as used herein, means fluoro, chloro, bromo and iodo.

The term "aryl" means phenyl or naphthyl either unsubstituted or substituted with one or more substituents selected from the group consisting of halo, $C_{1-4}$-alkyl, $C_{1-4}$-alkoxy, —$NO_2$, —$CF_3$, $C_{1-4}$-alkylthio, OH, —$N(R^9R^{10})$, —$CO_2R^9$, $C_{1-4}$-perfluoroalkyl, $C_{3-6}$-perfluorocycloalkyl, and tetrazol-5-yl.

The term "heteroaryl" means an unsubstituted, monosubstituted or disubstituted five or six membered aromatic heterocycle comprising from 1 to 3 heteroatoms selected from the group consisting of O, N and S and wherein the substituents are members selected from the group consisting of —OH, —SH, —$C_{1-4}$-alkyl, —$C_{1-4}$-alkoxy, —$CF_3$, halo, —$NO_2$, —$CO_2R^9$, —$N(R^9R^{10})$ and a fused benzo group.

As will be understood by those skilled in the art, pharmaceutically acceptable salts include, but are not limited to salts with inorganic acids such as hydrochloride, sulfate, phosphate, diphosphate, hydrobromide, and nitrate or salts with an organic acid such as malate, maleate, fumarate, tartrate, succinate, citrate, acetate, lactate, methanesulfonate, p-toluenesulfonate, 2-hydroxyethylsulfonate, pamoate, salicylate and stearate. Similarly, pharmaceutically acceptable cations include, but are not limited to sodium, potassium, calcium, aluminum, lithium and ammonium.

A preferred embodiment of the present invention includes those compounds of structural formula I, or a pharmaceutically acceptable salt thereof, wherein:

$R^3$ is selected from the group consisting of:
(1) —$R^4$, and
(2) $C_{1-6}$ alkyl substituted with —$R^4$;

$R^4$ is selected from the group consisting of:
(1) —$NR^9R^{10}$, wherein $R^9$ and $R^{10}$ are independently selected from:
  (a) hydrogen,
  (b) $C_{1-6}$ alkyl,
  (c) ($C_{1-6}$ alkyl)-hydroxy, and
  (d) ($C_{1-6}$ alkyl)-($C_{1-4}$ alkoxy),
(2) —CO—$NR^9R^{10}$,
(3) —$NR^9$—$COR^{10}$,
(4) heterocycle, wherein the heterocycle is selected from the group consisting of:
  (A) imidazolyl,
  (B) triazolyl,
  (C) tetrazolyl,
  (D) pyridyl,
  (E) piperazinyl,
  (F) piperidinyl,
  (G) pyrrolidinyl,
  (H) morpholinyl,
and wherein the heterocycle is unsubstituted or substituted with one or more substituent(s) selected from:
  (i) $C_{1-6}$ alkyl, unsubstituted or substituted with halo, —$CF_3$, —$OCH_3$, or phenyl,
  (ii) $C_{1-6}$ alkoxy,
  (iii) oxo, and
  (iv) hydroxy,
(5) —CO-heterocycle, wherein heterocycle is as defined above;

$R^6$, $R^7$ and $R^8$ are independently selected from the group consisting of:
(1) hydrogen,
(2) —$CF_3$,
(3) —$OCF_3$,
(4) —F,
(5) $C_{1-6}$alkyl,
(6) $C_{1-6}$alkoxy, and
(7) heterocycle, wherein the heterocycle is selected from the group consisting of:
  (A) imidazolyl,
  (B) triazolyl,
  (C) tetrazolyl,
  (D) pyridyl,
  (E) piperazinyl,
  (F) piperidinyl,
  (G) pyrrolidinyl, and
  (H) morpholinyl,
and wherein the heterocycle is unsubstituted or substituted with one or more substituent(s) selected from:
  (i) $C_{1-6}$ alkyl, unsubstituted or substituted with halo, —$CF_3$, —$OCH_3$, or phenyl,
  (ii) $C_{1-6}$ alkoxy,
  (iii) oxo, and
  (iv) hydroxy;

$R^{11}$, $R^{12}$ and $R^{13}$ are independently selected from:
(1) hydrogen, and
(2) fluoro;

m is an integer selected from 1 or 2;

n is an integer selected from 1 or 2;

the dashed line denotes the presence of a single or a double bond.

In the present invention it is preferred that $R^3$ is selected from the group consisting of:
(1) —$CH_2$—$N(C_{1-6}$ alkyl)($C_{1-6}$ alkyl),
(2) —$CH_2$—$NH(C_{1-6}$ alkyl),
(3) —$CH_2$—$N(C_{1-6}$ alkyl)($CH_2CH_2$—F),
(4) —$CH_2$-pyrrolidinyl,
(5) —$CH_2$-morpholinyl,
(6) —$N(C_{1-6}$ alkyl)($C_{1-6}$ alkyl), and
(7) —$NH(C_{1-6}$ alkyl).

In the present invention it is more preferred that $R^3$ is selected from the group consisting of:
(1) —$R^4$, and
(2) $C_{1-6}$ alkyl substituted with —$R^4$.

In the compounds of the present invention wherein $R^3$ is —$R^4$ or $C_{1-6}$ alkyl substituted with —$R^4$, it is preferred that $R^4$ is selected from the group consisting of:
(1) —$NR^9R^{10}$, wherein $R^9$ and $R^{10}$ are independently selected from:
  (a) hydrogen,
  (b) $C_{1-6}$ alkyl,
  (c) ($C_{1-6}$ alkyl)-hydroxy, and
  (d) ($C_{1-6}$ alkyl)-halo,
(2) —CO—$NR^9R^{10}$,
(3) —$NR^9$—$COR^{10}$,
(4) heterocycle, wherein the heterocycle is selected from the group consisting of:
  (A) imidazolyl,
  (B) triazolyl,
  (C) tetrazolyl,
  (D) pyridyl, (E) piperazinyl,
(F) piperidinyl,
(G) pyrrolidinyl,
(H) morpholinyl, and wherein the heterocycle is unsubstituted or substituted with one or more substituent(s) selected from:
  (i) $C_{1-6}$ alkyl, unsubstituted or substituted with halo, —$CF_3$, —$OCH_3$, or phenyl,
  (ii) $C_{1-6}$ alkoxy,
  (iii) oxo, and
  (iv) hydroxy,
(5) —CO-heterocycle, wherein heterocycle is as defined above.

In the present invention it is particularly preferred that $R^6$, $R^7$ and $R^8$ are independently selected from the group consisting of:
(1) hydrogen,
(2) —$CF_3$,
(3) —$OCF_3$,
(4) $C_{1-4}$alkoxy, and
(5) heterocycle, wherein the heterocycle is selected from the group consisting of:
  (A) tetrazolyl,
  (B) imidazolyl,
  (C) triazolyl,
  (D) pyridyl, and
  (E) isooxazolyl, and wherein the heterocycle is unsubstituted or substituted with one or more substituent(s) selected from:
  (i) $C_{1-4}$ alkyl,
  (ii) -cyclopropyl, and
  (iii) —$CF_3$.

In the present invention it is more preferred that $R^6$, $R^7$ and $R^8$ are independently selected from the group consisting of:
(1) 2-methoxy,
(2) 2-trifluoromethoxy,
(3) 5-trifluoromethoxy,
(4) 2-isopropyl,
(5) 2-chloro,
(6) 2-isopropoxy,
(7) 2-methylthio,
(8) 5-(5-trifluoromethyl-tetrazol-1-yl),
(9) 5-(3-trifluoromethyl-imidazol-1-yl),
(10) 5-(3-methyl-isoxazol-4-yl),
(11) 5-(1-methyl-4-trifluoromethyl-imidazol-5-yl), and
(12) 5-(N-trifluoroacetyl)(N-methyl)amino.

In the present invention a particularly preferred embodiment is directed to those compounds in which the phenyl ring bearing $R^6$, $R^7$ and $R^8$ is selected from:
  3,5-bis(trifluoromethyl)phenyl,
  2-methoxy-5-tetrazol-1-yl-phenyl,
  2-methoxy-5-(5-methyl-tetrazol-1-yl)-phenyl,
  2-methoxy-5-(5-ethyl-tetrazol-1-yl)-phenyl,
  2-methoxy-5-(5-propyl-tetrazol-1-yl)-phenyl,
  2-methoxy-5-(5-trifluoromethyl-tetrazol-1-yl)-phenyl,
  2-methoxy-5-(5-cyclopropyl-tetrazol-1-yl)-phenyl,
  2-methoxy-5-(5-methylsulfanyl-tetrazol-1-yl)-phenyl,
  2-trifluoromethoxy-phenyl,
  2-isopropyl-5-(5-trifluoromethyl-tetrazol-1-yl)-phenyl,
  2-methoxy-5-trifluoromethoxy-phenyl, and
  2-isopropyl-5-trifluoromethoxy-phenyl.

In the present invention it is particularly preferred that $R^{11}$, $R^{12}$ and $R^{13}$ are independently selected from:
(1) hydrogen, and
(2) fluoro.

In the present invention it is particularly preferred that m is 1 or 2 and n is 1.

In the present invention a particularly preferred embodiment is directed to those compounds in which the phenyl ring bearing $R^{11}$, $R^{12}$ and $R^{13}$ is unsubstituted phenyl or is para-fluorophenyl.

Preferred compounds within the present invention include:

methyl[3-(S),5-(R),6-(S),7-(S)]-6-(4-fluorophenyl)-3-(2-methoxy-5-((5-trifluoromethyl)tetrazol-1-yl)phenyl)-1-oxaspiro[4.4]nonane-7-carboxylate;

[3-(S),5-(R),6-(S),7-(S)]-7-(1-(pyrrolidinyl)methyl)-6-(4-fluorophenyl)-3-(2-methoxy-5-((5-trifluoromethyl)tetrazol-1-yl)phenyl)-1-oxaspiro[4.4]nonane;

(3S,5R,6S,7S)-6-(4-fluorophenyl)-7-(pyrrolidin-1-yl)methyl-3-(2-methyl-3-fluoro-5-(5-trifluoromethyltetrazol-1-yl)phenyl)-1-oxaspiro[4.4]nonane;

(5R,6S,7S)-6-(4-fluorophenyl)-3-[2-methoxy-5-(N-methyl-N-acetylamino)phenyl]-1-oxaspiro[4.4]non-3-ene-7-carboxylic acid methyl ester;

(5R,6S,7S)-6-(4-fluorophenyl)-3-[2-methoxy-5-(N-methyl-N-trifluoroacetylamino)phenyl]-1-oxaspiro[4.4]non-3-ene-7-carboxylic acid methyl ester;

(5R,6S,7S)-6-(4-fluorophenyl)-3-[2-methoxy-5-(N-ethyl-N-acetylamino)phenyl]-1-oxaspiro[4.4]non-3-ene-7-carboxylic acid methyl ester;

(3S,5R,6S,7S)-6-(4-fluorophenyl)-3-[2-methoxy-5-(N-methyl-N-acetylamino)phenyl]-1-oxaspiro[4.4]nonane-7-carboxylic acid methyl ester;

(3S,5R,6S,7S)-6-(4-fluorophenyl)-3-[2-methoxy-5-(N-methyl-N-trifluoroacetylamino)phenyl]-1-oxaspiro[4.4]nonane-7-carboxylic acid methyl ester;

(3S,5R,6S,7S)-6-(4-fluorophenyl)-3-[2-methoxy-5-(N,N-dimethylamino)phenyl]-1-oxaspiro[4.4]nonane-7-carboxylic acid methyl ester;

(3S,5R,6S,7S)-6-(4-fluorophenyl)-3-(5-cyano-2-isopropoxy-phenyl)-1-oxaspiro[4.4]nonane-7-carboxylic acid methyl ester;

(5R,6S,7S)-6-(4-fluorophenyl)-3-(2-methoxy-5-(2-(trifluoromethyl)imidazol-1-yl)phenyl)-1-oxaspiro[4.4]non-3-ene-7-carboxylic acid methyl ester;

(3S,5R,6S,7S)-6-(4-fluorophenyl)-3-(2-methoxy-5-(2-(trifluoromethyl)imidazol-1-yl)phenyl)-1-oxaspiro[4.4]nonane-7-carboxylic acid methyl ester;

(5R,6S,7S)-(6-(4-fluorophenyl)-3-(2-methoxy-5-(2-(trifluoromethyl)imidazol-1-yl)phenyl)-1-oxaspiro[4.4]non-3-ene-7-ylmethyl)methylamine;

(3S,5R,6S,7S)-(6-(4-fluorophenyl)-3-(2-methoxy-5-(2-(trifluoromethyl)imidazol-1-yl)phenyl)-(1-oxaspiro[4.4]nonane-7-ylmethyl)methylamine;

(5R,6S,7S)-6-(4-fluorophenyl)-3-(2-methoxy-5-(3-methylisoxazol-4-yl)phenyl)-1-oxaspiro[4.4]non-3-ene-7-carboxylic acid methyl ester;

(5R,6S,7S)-6-(4-fluorophenyl)-3-(2-methoxy-5-(2,5-dimethylpyrrol-1-yl)phenyl)-1-oxaspiro[4.4]non-3-ene-7-carboxylic acid methyl ester;

(5R,6S,7S)-6-(4-fluorophenyl)-3-(2-methoxy-5-(4-trifluoromethyl-1-methylimidazol-5-yl)phenyl)-1-oxaspiro[4.4]non-3-ene-7-carboxylic acid methyl ester;

(5R,6S,7S)-6-phenyl-3-(2-methoxy-5-(trifluoromethoxy)phenyl)-7-(hydroxymethyl)-1-oxaspiro[5.4]dec-3-ene;

(5R,6S,7S)-6-(4-fluorophenyl)-3-(2-methoxy-5-fluoro)phenyl-1-oxaspiro[5.4]non-3-ene-7-carboxylic acid methyl ester;

(5R,6S,7S)-6-(4-fluorophenyl)-3-(2-isopropoxy-5-fluoro) phenyl-1-oxaspiro[5.4]non-3-ene-7-carboxylic acid methyl ester;

(5R,6S,7S)-6-(4-fluorophenyl)-3-(2-isopropyl-5-(N-trifluoroacetyl-N-methyl)amino)phenyl-1-oxaspiro[5.4] non-3-ene-7-carboxylic acid methyl ester;

(5R,6S,7S)-6-(4-fluorophenyl)-3-(2-isopropyl-5-(5-(trifluoromethyl)tetrazol-1-yl)phenyl-1-oxaspiro[5.4] non-3-ene-7-carboxylic acid methyl ester;

(5R,6S,7S)-6-(4-fluorophenyl)-3-(2-isopropyl-5-(2-(trifluoromethyl)imidazol-1-yl)phenyl-1-oxaspiro[5.4] non-3-ene-7-carboxylic acid methyl ester;

(3S,5R,6S,7S)-6-(4-fluorophenyl)-3-(2-methoxy-5-(N-(dimethylaminosulfonyl)-N-methyl)amino)phenyl-1-oxaspiro[5.4]nonane-7-carboxylic acid methyl ester;

(5R,6S,7S)-6-(4-fluorophenyl)-3-(2-methoxy-5-(dimethylaminocarbonyl))-phenyl-1-oxaspiro[5.4]non-3-ene-7-carboxylic acid methyl ester;

(5R,6S,7S)-6-(4-fluorophenyl)-3-(2-trifluoromethoxy-5-(N-(methanesulfonyl)-N-methyl)amino)phenyl-1-oxaspiro [5.4]non-3-ene-7-carboxylic acid methyl ester;

(3S,5R,6S,7S)-6-(4-fluorophenyl)-3-(2-methoxy-5-fluoro) phenyl-1-oxaspiro[5.4]nonane-7-carboxylic acid methyl ester;

(3S,5R,6S,7S)-6-(4-fluorophenyl)-3-(2-isopropoxy-5-fluoro)phenyl-1-oxaspiro[5.4]nonane-7-carboxylic acid methyl ester;

(3S,5R,6S,7S)-6-(4-fluorophenyl)-3-(2-methoxy-5-(N-(methanesulfonyl)-N-methyl)amino)phenyl-1-oxaspiro [5.4]nonane-7-carboxylic acid methyl ester;

(3S,5R,6S,7S)-6-(4-fluorophenyl)-3-(2-isopropyl-5-(N-trifluoroacetyl-N-methyl)amino)phenyl-1-oxaspiro[5.4] nonane-7-carboxylic acid methyl ester;

(3S,5R,6S,7S)-6-(4-fluorophenyl)-3-(2-isopropyl-5-(5-(trifluoromethyl)-tetrazol-1-yl)phenyl-1-oxaspiro[5.4] nonane-7-carboxylic acid methyl ester;

(3S,5R,6S,7S)-6-(4-fluorophenyl)-3-(2-methoxy-5-(dimethylaminocarbonyl))phenyl-1-oxaspiro[5.4] nonane-7-carboxylic acid methyl ester;

(3S,5R,6S,7S)-6-(4-fluorophenyl)-3-(2-trifluoromethoxy-5-(N-(methanesulfonyl)-N-methyl)amino)phenyl-1-oxaspiro[5.4]nonane-7-carboxylic acid methyl ester;

(5R,6S,7S)-6-(4-fluorophenyl)-3-(2-isopropoxy-5-fluoro) phenyl-7-(hydroxymethyl)-1-oxaspiro[5.4]non-3-ene;

(5R,6S,7S)-6-(4-fluorophenyl)-3-(2-isopropyl-5-(2-(trifluoromethyl)imidazol-1-yl)phenyl-7-(hydroxymethyl)-1-oxaspiro[5.4]non-3-ene;

(5R,6S,7S)-6-(4-fluorophenyl)-3-(2-isopropyl-5-(5-(trifluoromethyl)tetrazol-1-yl)phenyl-7-(hydroxymethyl)-1-oxaspiro[5.4]non-3-ene;

(5R,6S,7S)-6-(4-fluorophenyl)-3-(2-isopropoxy-5-chloro) phenyl-7-(hydroxymethyl)-1-oxaspiro[5.4]non-3-ene;

(5R,6S,7S)-6-(4-fluorophenyl)-3-(2,5-dichloro)phenyl-7-(hydroxymethyl)-1-oxaspiro[5.4]non-3-ene;

(5R,6S,7S)-6-(4-fluorophenyl)-3-(2-fluoro-5-trifluoromethyl)phenyl-7-(hydroxymethyl)-1-oxaspiro [5.4]non-3-ene;

(5R,6S,7S)-6-(4-fluorophenyl)-3-(2-isopropoxy-5-isopropyl)phenyl-7-(hydroxymethyl)-1-oxaspiro[5.4] non-3-ene;

(5R,6S,7S)-6-(4-fluorophenyl)-3-(2-methyl-5-chloro) phenyl-7-(hydroxymethyl)-1-oxaspiro[5.4]non-3-ene;

(5R,6S,7S)-6-(4-fluorophenyl)-3-(2-isopropoxy-5-methyl) phenyl-7-(hydroxymethyl)-1-oxaspiro[5.4]non-3-ene;

(5R,6S,7S)-6-(4-fluorophenyl)-3-(2-chloro-5-methyl) phenyl-7-(hydroxymethyl)-1-oxaspiro[5.4]non-3-ene (5R,6S,7S)-6-(4-fluorophenyl)-3-(2-methoxy-5-methyl) phenyl-7-(hydroxymethyl)-1-oxaspiro[5.4]non-3-ene;

(5R,6S,7S)-6-(4-fluorophenyl)-3-(2-cyclopropylmethyl-5-fluoro)phenyl-7-(hydroxymethyl)-1-oxaspiro[5.4]non-3-ene;

(5R,6S,7S)-6-(4-fluorophenyl)-3-(2-isopropyl-5-methyl) phenyl-7-(hydroxymethyl)-1-oxaspiro[5.4]non-3-ene;

(5R,6S,7S)-6-(4-fluorophenyl)-3-(2-methoxy-5-isopropyl) phenyl-7-(hydroxymethyl)-1-oxaspiro[5.4]non-3-ene;

(5R,6S,7S)-6-(4-fluorophenyl)-3-(2-fluoro-5-methyl) phenyl-7-(hydroxymethyl)-1-oxaspiro[5.4]non-3-ene;

(5R,6S,7S)-6-(4-fluorophenyl)-3-(2-cyclobutyloxy-5-fluoro)phenyl-7-(hydroxymethyl)-1-oxaspiro[5.4]non-3-ene;

(5R,6S,7S)-6-(4-fluorophenyl)-3-(2-methoxy-5-((N,N-dimethylamino)carbonylmethyl)phenyl-7-(hydroxymethyl)-1-oxaspiro[5.4]non-3-ene;

(5R,6S,7S)-6-(4-fluorophenyl)-3-(2-trifluoromethoxy-5-(N-(methanesulfonyl)-N-methylamino)phenyl-7-(hydroxymethyl)-1-oxaspiro[5.4]non-3-ene;

(5R,6S,7S)-6-(4-fluorophenyl)-3-(2-trifluoromethoxy-5-(N-(3,5-dimethylisoxazol-4-ylcarbonyl)-N-methylamino) phenyl-7-(hydroxymethyl)-1-oxaspiro[5.4]non-3-ene;

(5R,6S,7S)-6-(4-fluorophenyl)-3-(2-trifluoromethoxy-5-(N-(5-methylisoxazol-3-ylcarbonyl)-N-methylamino) phenyl-7-(hydroxymethyl)-1-oxaspiro[5.4]non-3-ene;

(5R,6S,7S)-6-(4-fluorophenyl)-3-(2-isopropyl-5-(5-(trifluoromethyl)tetrazol-1-yl)phenyl-7-(N,N-dimethylaminomethyl)-1-oxaspiro[5.4]non-3-ene;

(5R,6S,7S)-6-(4-fluorophenyl)-3-(2-isopropyl-5-(5-(trifluoromethyl)tetrazol-1-yl)phenyl-7-(pyrrolidin-1-ylmethyl)-1-oxaspiro[5.4]non-3-ene;

(5R,6S,7S)-6-(4-fluorophenyl)-3-(2-isopropyl-5-(5-(trifluoromethyl)tetrazol-1-yl)phenyl-7-(morpholin-1-ylmethyl)-1-oxaspiro[5.4]non-3-ene;

(5R,6S,7S)-6-(4-fluorophenyl)-3-(2-isopropyl-5-(5-(trifluoromethyl)tetrazol-1-yl)phenyl-7-(N-(2-fluoroethyl)aminomethyl)-1-oxaspiro[5.4]non-3-ene;

(5R,6S,7S)-6-(4-fluorophenyl)-3-(2-isopropyl-5-(5-(trifluoromethyl)tetrazol-1-yl)phenyl-7-(N-cyclopropylaminomethyl)-1-oxaspiro[5.4]non-3-ene;

(5R,6S,7S)-6-(4-fluorophenyl)-3-(2-isopropyl-5-(2-(trifluoromethyl)imidazol-1-yl)phenyl-7-(methylaminomethyl)-1-oxaspiro[5.4]non-3-ene;

(5R,6S,7S)-6-(4-fluorophenyl)-3-(2-isopropyl-5-(2-(trifluoromethyl)imidazol-1-yl)phenyl-7-(N-(2,2,2-trifluoroethyl)aminomethyl)-1-oxaspiro[5.4]non-3-ene;

(5R,6S,7S)-6-(4-fluorophenyl)-3-(2-isopropyl-5-(2-(trifluoromethyl)imidazol-1-yl)phenyl-7-(morpholin-4-ylmethyl)-1-oxaspiro[5.4]non-3-ene;

(5R,6S,7S)-6-(4-fluorophenyl)-3-(2-isopropyl-5-(2-(trifluoromethyl)imidazol-1-yl)phenyl-7-(pyrrolidin-1-ylmethyl)-1-oxaspiro[5.4]non-3-ene;

(3S,5R,6S,7S)-6-(4-fluorophenyl)-3-(2-isopropyl-5-(5-(trifluoromethyl)-tetrazol-1-yl)phenyl-7-(hydroxymethyl)-1-oxaspiro[5.4]nonane;

(3S,5R,6S,7S)-6-(4-fluorophenyl)-3-(2-isopropoxy-5-fluoro)phenyl-7-(hydroxymethyl)-1-oxaspiro[5.4] nonane;

(3S,5R,6S,7S)-6-(4-fluorophenyl)-3-(2-isopropoxy)phenyl-7-(hydroxymethyl)-1-oxaspiro[5.4]nonane;

(3S,5R,6S,7S)-6-(4-fluorophenyl)-3-phenyl-7-(hydroxymethyl)-1-oxaspiro[5.4]nonane;

(3S,5R,6S,7S)-6-(4-fluorophenyl)-3-(2-fluoro-5-trifluoromethyl)phenyl-7-(hydroxymethyl)-1-oxaspiro [5.4]nonane;

(3S,5R,6S,7S)-6-(4-fluorophenyl)-3-(2-isoproxy-5-isopropyl)phenyl-7-(hydroxymethyl)-1-oxaspiro[5.4] nonane;

(3S,5R,6S,7S)-6-(4-fluorophenyl)-3-(2-methoxy-5-(N-(2,2,2-trifluoroethyl)-N-isopropyl)amino)phenyl-7-(hydroxymethyl)-1-oxaspiro[5.4]nonane;
(3S,5R,6S,7S)-6-(4-fluorophenyl)-3-(2-trifluoromethoxy-5-(N-(methanesulfonyl)-N-methyl)amino)phenyl-7-(hydroxymethyl)-1-oxaspiro[5.4]nonane;
(3S,5R,6S,7S)-6-(4-fluorophenyl)-3-(2-isopropoxy-5-methyl)phenyl-7-(hydroxymethyl)-1-oxaspiro[5.4]nonane;
(3S,5R,6S,7S)-6-(4-fluorophenyl)-3-(3-methyl)phenyl-7-(hydroxymethyl)-1-oxaspiro[5.4]nonane;
(3S,5R,6S,7S(-6-(4-fluorophenyl)-3-(2-methyl)phenyl-7-(hydroxymethyl)-1-oxaspiro[5.4]nonane;
(3S,5R,6S,7S)-6-(4-fluorophenyl)-3-(2-methoxy-5-methyl)phenyl-7-(hydroxymethyl)-1-oxaspiro[5.4]nonane;
(3S,5R,6S,7S)-6-(4-fluorophenyl)-3-(2-cyclopropylmethyl-5-fluoro)phenyl-7-(hydroxymethyl)-1-oxaspiro[5.4]nonane;
(3S,5R,6S,7S)-6-(4-fluorophenyl)-3-(2-isopropyl-5-methyl)phenyl-7-(hydroxymethyl)-1-oxaspiro[5.4]nonane;
(3S,5R,6S,7S)-6-(4-fluorophenyl)-3-(2-fluoro-5-methyl)phenyl-7-(hydroxymethyl)-1-oxaspiro[5.4]nonane;
(3S,5R,6S,7S)-6-(4-fluorophenyl)-3-(2-methoxy-5-isopropyl)phenyl-7-(hydroxymethyl)-1-oxaspiro[5.4]nonane;
(3S,5R,6S,7S)-6-(4-fluorophenyl)-3-(2-cyclobutyloxy-5-fluoro)phenyl-7-(hydroxymethyl)-1-oxaspiro[5.4]nonane;
(3S,5R,6S,7S)-6-(4-fluorophenyl)-3-(2-methoxy-5-((N,N-dimethylamino)carbonylmethyl)phenyl-7-(hydroxymethyl)-1-oxaspiro[5.4]nonane;
(3S,5R,6S,7S)-6-(4-fluorophenyl)-3-(2-isopropyl-5-(5-(trifluoromethyl)tetrazol-1-yl)phenyl-7-(aminomethyl)-1-oxaspiro[5.4]nonane;
(3S,5R,6S,7S)-6-(4-fluorophenyl)-3-(2-isopropoxy-5-fluoro)phenyl-7-(N,N-dimethylaminomethyl)-1-oxaspiro[5.4]nonane;
(3S,5R,6S,7S)-6-(4-fluorophenyl)-3-(2-isopropoxy-5-fluoro)phenyl-7-(pyrrolidin-1-ylmethyl)-1-oxaspiro[5.4]nonane;
(3S,5R,6S,7S)-6-(4-fluorophenyl)-3-(2-isopropoxy-5-fluoro)phenyl-7-(N-(2,2,2-trifluoroethyl)aminomethyl)-1-oxaspiro[5.4]nonane;
(3S,5R,6S,7S)-6-(4-fluorophenyl)-3-(2-isopropoxy-5-fluoro)phenyl-7-(N-(2,2,2-trifluoroethyl)-N-methylaminomethyl)-1-oxaspiro[5.4]nonane;
(3S,5R,6S,7S)-6-(4-fluorophenyl)-3-(2-isopropoxy-5-fluoro)phenyl-7-(N-(cyclopropyl)aminomethyl)-1-oxaspiro[5.4]nonane;
(3S,5R,6S,7S)-6-(4-fluorophenyl)-3-(2-isopropoxy-5-fluoro)phenyl-7-(N-(cyclopropyl)-N-methylaminomethyl)-1-oxaspiro[5.4]nonane;
(3S,5R,6S,7S)-6-(4-fluorophenyl)-3-(2-isopropoxy-5-fluoro)phenyl-7-(morpholin-4-ylmethyl)-1-oxaspiro[5.4]nonane;
(3S,5R,6S,7S)-6-(4-fluorophenyl)-3-(2-isopropoxy-5-fluoro)phenyl-7-(2-(fluoroethyl)aminomethyl)-1-oxaspiro[5.4]nonane;
(5R,6S,7S)-6-(4-fluorophenyl)-3-(5-cyano-2-isopropoxy-phenyl)-1-oxaspiro[4.4]non-3-ene-7-methanol;
(5R,6S,7S)-7-(Dimethylamino)-6-(4-fluorophenyl)-3-(5-cyano-2-isopropoxy-phenyl)-1-oxaspiro[4.4]non-3-ene;
(3S,5R,6S,7S)-6-(4-fluorophenyl)-3-(5-cyano-2-isopropoxy-phenyl)-7-(pyrrolidin-1-yl)methyl)-1-oxaspiro[4.4]nonane;
(3S,5R,6S,7S)-6-(4-fluorophenyl)-3-(2-methylthio-5-(5-(trifluoromethyl)tetrazol-1-yl)phenyl)-1-oxaspiro[4.4]non-3-ene-7-methanol;

(3S,5R,6S,7S)-6-(4-fluorophenyl)-3-(2-methylthio-5-(5-(trifluoromethyl)tetrazol-1-yl)phenyl)-1-oxaspiro[4.4]nonane-7-methanol;
(3S,5R,6S,7S)-7-(1-(pyrrolidinyl)methyl)-6-(4-fluorophenyl)-3-(2-methylthio-5-(5-(trifluoromethyl)tetrazol-1-yl)phenyl)-1-oxaspiro[4.4]nonane;
(3S,5R,6S,7S)-6-(4-fluorophenyl)-3-(2-methylthio-5-(5-(trifluoromethyl)imidazol-1-yl)phenyl)-1-oxaspiro[4.4]non-3-ene-7-methanol;
(3S,5R,6S,7S)-6-(4-fluorophenyl)-3-(2-methylthio-5-(5-(trifluoromethyl)imidazol-1-yl)phenyl)-1-oxaspiro[4.4]nonane-7-methanol;
(3S,5R,6S,7S)-7-(1-(morpholinyl)methyl)-6-(4-fluorophenyl)-3-(2-methylthio-5-(5-(trifluoromethyl)imidazol-1-yl)phenyl)-1-oxaspiro[4.4]nonane;
(3S,5R,6S,7S)-7-(morpholinyl)methyl)-6-(4-fluorophenyl)-3-(2-methylthio-5-(5-(trifluoromethyl)imidazol-1-yl)phenyl)-1-oxaspiro[4.4]nonane;
(3R,5R,6S,7S)-6-(4-fluorophenyl)-3-(2-methylthio-5-(5-(trifluoromethyl)tetrazol-1-yl)phenyl)-1-oxaspiro[4.4]nonane-7-carboxylic acid methyl ester;
(3S,5R,6S,7S)-6-(4-fluorophenyl)-3-(2-methylthio-5-(5-(trifluoromethyl)tetrazol-1-yl)phenyl)-1-oxaspiro[4.4]nonane-7-carboxylic acid methyl ester;
(3S,5R,6S,7S)-6-(4-fluorophenyl)-3-(2-methylthio-5-(5-(trifluoromethyl)tetrazol-1-yl)phenyl)-1-oxaspiro[4.4]non-3-ene-7-carboxylic acid methyl ester;
(3S,5R,6S,7S)-6-(4-fluorophenyl)-3-(2-methylthio-5-(5-(trifluoromethyl)tetrazol-1-yl)phenyl)-1-oxaspiro[4.4]non-3-ene-7-carboxylic acid methyl ester;
(3S,5R,6S,7S)-6-(4-fluorophenyl)-3-(2-methylthio-5-(5-(trifluoromethyl)tetrazol-1-yl)phenyl)-1-oxaspiro[4.4]non-4-ene-7-carboxylic acid methyl ester;
(3S,5R,6S,7S)-6-(4-fluorophenyl)-3-(2-methylthio-5-(5-(trifluoromethyl)imidazol-1-yl)phenyl)-1-oxaspiro[4.4]non-3-ene-7-carboxylic acid methyl ester
(3S,5R,6S,7S)-6-(4-fluorophenyl)-3-(2-isopropylthio-5-(5-(trifluoromethyl)imidazol-1-yl)phenyl)-1-oxaspiro[4.4]non-3-ene-7-carboxylic acid methyl ester;
(3S,5R,6S,7S)-6-(4-fluorophenyl)-3-(2-isopropylthio-5-(5-(trifluoromethyl)tetrazol-1-yl)phenyl)-1-oxaspiro[4.4]nonane-7-carboxylic acid methyl ester;
(3S,5R,6S,7S)-6-(4-fluorophenyl)-3-(2-methylthio-5-(5-(trifluoromethyl)imidazol-1-yl)phenyl)-1-oxaspiro[4.4]nonane-7-carboxylic acid methyl ester;
(3S,5R,6S,7S)-6-(4-fluorophenyl)-3-(2-isopropylthio-5-(5-(trifluoromethyl)imidazol-1-yl)phenyl)-1-oxaspiro[4.4]nonane-7-carboxylic acid methyl ester;
(3S,5R,6S,7S)-6-(4-fluorophenyl)-3-(2-isopropylthio-5-(5-(trifluoromethyl)imidazol-1-yl)phenyl)-1-oxaspiro[4.4]nonane-7-carboxylic acid methyl ester;
methyl[3-(S),5-(R),6-(S),7-(S)]-6-(4-fluorophenyl)-3-(2-methoxy-5-((5-trifluoromethyl)tetrazol-1-yl)phenyl)-1-oxaspiro[4.4]nonane-7-ylmethyl)methylamine;
(5R,6S,7S)-6-(4-fluorophenyl)-3-(2-methoxy-5-(2-(trifluoromethyl)triazol-1-yl)phenyl)-1-oxaspiro[4.4]non-3-ene-7-carboxylic acid methyl ester;
(5R,6S,7S)-6-(4-fluorophenyl)-3-(2-methoxy-5-(2-(trifluoromethyl)triazol-1-yl)phenyl)-1-oxaspiro[4.4]nonane-7-hydroxymethyl;
(5R,6S,7S)-6-(4-fluorophenyl)-3-(2-methoxy-5-(triazol-1-yl)phenyl)-1-oxaspiro[4.4]nonane-7-hydroxymethyl;
(5R,6S,7S)-6-(4-fluorophenyl)-3-(2-(N,N-dimethylamino)-5-(2-(trifluoromethyl)tetrazol-1-yl)phenyl)-1-oxaspiro[4.4]non-3-ene-7-carboxylic acid methyl ester;
(5R,6S,7S)-6-(4-fluorophenyl)-3-(2-isopropoxy-5-(2-(trifluoromethyl)tetrazol-1-yl)phenyl)-1-oxaspiro[4.4]non-3-ene-7-carboxylic acid methyl ester;

(5R,6S,7S)-6-(4-fluorophenyl)-3-(2-isopropoxy-5-(2-(trifluoromethyl)imidazol-1-yl)phenyl)-1-oxaspiro[4.4]non-3-ene-7-carboxylic acid methyl ester;

(5R,6S,7S)-6-(4-fluorophenyl)-3-(2-methoxy-5-(2-(methyl)triazol-1-yl)phenyl)-1-oxaspiro[4.4]non-3-ene-7-carboxylic acid methyl ester;

(5R,6S,7S)-6-(4-fluorophenyl)-3-(2-(N,N-dimethylamino)-5-(2-(trifluoromethyl)tetrazol-1-yl)phenyl)-1-oxaspiro[4.4]nonane-7-carboxylic acid methyl ester;

(5R,6S,7S)-6-(4-fluorophenyl)-3-(2-isopropoxy-5-(2-(trifluoromethyl)tetrazol-1-yl)phenyl)-1-oxaspiro[4.4]nonane-7-carboxylic acid methyl ester;

(5R,6S,7S)-6-(4-fluorophenyl)-3-(2-isopropoxy-5-(2-(trifluoromethyl)imidazol-1-yl)phenyl)-1-oxaspiro[4.4]nonane-7-carboxylic acid methyl ester;

(5R,6S,7S)-6-(4-fluorophenyl)-3-(2-methoxy-5-(2-(methyl)triazol-1-yl)phenyl)-1-oxaspiro[4.4]nonane-7-carboxylic acid methyl ester;

(5R,6S,7S)-6-(4-fluorophenyl)-3-(2-methoxycarbonyl-5-(triazol-1-yl)phenyl)-1-oxaspiro[4.4]non-3-ene-7-carboxylic acid methyl ester;

(5R,6S,7S)-6-(4-fluorophenyl)-3-(2-methoxycarbonyl-5-(2-(trifluoromethyl)tetrazol-1-yl)phenyl)-1-oxaspiro[4.4]non-3-ene-7-carboxylic acid methyl ester;

(5R,6S,7S)-6-(4-fluorophenyl)-3-(2-cyclopentoxy-5-(2-(trifluoromethyl)tetrazol-1-yl)phenyl)-1-oxaspiro[4.4]non-3-ene-7-carboxylic acid methyl ester;

(5R,6S,7S)-6-(4-fluorophenyl)-3-(2-cyclopentoxy-5-(2-(trifluoromethyl)imidazol-1-yl)phenyl)-1-oxaspiro[4.4]non-3-ene-7-carboxylic acid methyl ester;

(5R,6S,7S)-6-(4-fluorophenyl)-3-(2-methoxycarbonyl-5-(triazol-1-yl)phenyl)-1-oxaspiro[4.4]nonane-7-carboxylic acid methyl ester;

(5R,6S,7S)-6-(4-fluorophenyl)-3-(2-methoxycarbonyl-5-(2-(trifluoromethyl)tetrazol-1-yl)phenyl)-1-oxaspiro[4.4]nonane-7-carboxylic acid methyl ester;

(5R,6S,7S)-6-(4-fluorophenyl)-3-(2-cyclopentoxy-5-(2-(trifluoromethyl)tetrazol-1-yl)phenyl)-1-oxaspiro[4.4]nonane-7-carboxylic acid methyl ester;

(5R,6S,7S)-6-(4-fluorophenyl)-3-(2-cyclopentoxy-5-(2-(trifluoromethyl)imidazol-1-yl)phenyl)-1-oxaspiro[4.4]nonane-7-carboxylic acid methyl ester;

(5R,6S,7S)-6-(4-fluorophenyl)-3-(2-methoxy-5-(2-(trifluoromethyl)triazol-1-yl)phenyl)-1-oxaspiro[4.4]non-3-ene-7-hydroxymethyl;

(5R,6S,7S)-6-(4-fluorophenyl)-3-(2-methoxy-5-(2-(trifluoromethyl)triazol-1-yl)phenyl)-1-oxaspiro[4.4]nonane-7-ylmethyl)(1-fluoroethyl)amine;

(5R,6S,7S)-6-(4-fluorophenyl)-3-(2-isopropoxy-5-(2-(trifluoromethyl)tetrazol-1-yl)phenyl)-1-oxaspiro[4.4]non-3-ene-7-hydroxymethyl;

(5R,6S,7S)-6-(4-fluorophenyl)-3-(2-isopropoxy-5-(2-(trifluoromethyl)tetrazol-1-yl)phenyl)-1-oxaspiro[4.4]nonane-7- ylmethyl)(1-fluoroethyl)amine;

5R,6S,7S)-6-(4-fluorophenyl)-3-(2-methoxy-5-(2,5-(dimethyl)triazol-1-yl)phenyl)-1-oxaspiro[4.4]non-3-ene-7-carboxylic acid methyl ester;

(5R,6S,7S)-6-(4-fluorophenyl)-3-(2-phenoxy-5-(2-(trifluoromethyl)tetrazol-1-yl)phenyl)-1-oxaspiro[4.4]non-3-ene-7-carboxylic acid methyl ester;

(5R,6S,7S)-6-(4-fluorophenyl)-3-(2-methoxy-5-(2,5-(dimethyl)triazol-1-yl)phenyl)-1-oxaspiro[4.4]nonane-7-carboxylic acid methyl ester;

(5R,6S,7S) 6-(4-fluorophenyl)-3-(2-phenoxy-5-(2-(trifluoromethyl)tetrazol-1-yl)phenyl)-1-oxaspiro[4.4]nonane-7-carboxylic acid methyl ester;

(5R,6S,7S)-6-phenyl-3-(2-(trifluoromethoxy)-5-(2-trifluoromethyl)tetrazole) phenyl-7-(hydroxymethyl)-1-oxaspiro[5.4]dec-3-ene;

(3S,5R,6S,7S)-6-phenyl-3-(2-(trifluoromethoxy)-5-(2-trifluoromethyl)tetrazole)phenyl-7-(hydroxymethyl)-1-oxaspiro[5.4]decane;

(3R,5R,6S,7S)-6-phenyl-3-(2-(trifluoromethoxy)-5-(2-trifluoromethyl)tetrazole)phenyl-7-(hydroxymethyl)-1-oxaspiro[5.4]decane;

(3S,5R,6S,7S)-6-phenyl-3-(2-(trifluoromethoxy)-5-(2-trifluoromethyl)tetrazole)phenyl-7-(morpholin-4-ylmethyl)-1-oxaspiro[5.4]decane;

(3S,5R,6S,7S)-6-phenyl-3-(2-(trifluoromethoxy)-5-(2-trifluoromethyl)tetrazole)phenyl-7-(pyrrolidin-1-ylmethyl)-1-oxaspiro[5.4]decane;

(3S,5R,6S,7S)-6-phenyl-3-(2-(trifluoromethoxy)-5-(2-trifluoromethyl)tetrazole)phenyl-7-(methyl-(2-fluoro ethylamino))-1-oxaspiro[5.4]decane;

(3R,5R,6S,7S)-6-phenyl-3-(2-(trifluoromethoxy)-5-(2-trifluoromethyl)tetrazole)phenyl-7-(methyl-(2-fluoro ethylamino))-1-oxaspiro[5.4]-decane;

(3R,5R,6S,7S)-6-phenyl-3-(2-methoxy-5-(trifluoromethoxy))phenyl-7-(hydroxymethyl)-1-oxaspiro[5.4]decane;

(3S,5R,6S,7S)-6-phenyl-3-(2-methoxy-5-(trifluoromethoxy))phenyl-7-(hydroxymethyl)-1-oxaspiro[5.4]decane;

(3R,5R,6S 7S)-6-phenyl-3-(2-methoxy-5-(trifluoromethoxy))phenyl-7-(methyl-(2-fluoroethylamino))-1-oxaspiro[5.4]decane;

(5R,6S,7S)-6-phenyl-3-(2,2 Difluoro-5-trifluoroacetamide)benzodioxole-7-(hydroxymethyl)-1-oxaspiro[5.4]dec-3-ene;

(3R,5R,6S,7S)-6-phenyl-3-(2,2 Difluoro-5-trifluoroacetamide)benzodioxole-7-(hydroxymethyl)-1-oxaspiro[5.4]decane;

(3S,5R,6S,7S)-6-(4-fluorophenyl)-3-(2-methoxy-5-(4-(trifluoromethyl)-1-methylimidazol-5-yl)phenyl)-1-oxaspiro[4.4]nonane-7-carboxylic acid methyl ester;

(3S,5R,6S,7S)-(6-(4-fluorophenyl)-3-(2-methoxy-5-(4-(trifluoromethyl)-1-methylimidazol-5-yl)phenyl)-1-oxaspiro[4.4]non-7-yl)methanol;

N-(2-fluoroethyl)((3S,5R,6S,7S)-6-(4-fluorophenyl)-3-(2-methoxy-5-(4-(trifluoromethyl)-1-methylimidazol-5-yl)phenyl)-2-oxaspiro[4.4]non-7-ylmethyl)amine;

(5R,6S,7S)-6-(4-fluorophenyl)-3-(2-isopropoxy-5-(trifluoromethyl)phenyl)-1-oxaspiro[4.4]non-3-ene-7-carboxylic acid methyl ester;

(3S,5R,6S,7S)-6-(4-fluorophenyl)-3-(2-isopropoxy-5-(trifluoromethyl)phenyl)-1-oxaspiro[4.4]nonane-7-carboxylic acid methyl ester;

(3S,5R,6S,7S)-(6-(4-fluorophenyl)-3-(2-isopropoxy-5-(trifluoromethyl)phenyl)-1-oxaspiro[4.4]non-7-yl)methanol;

N-(2-fluoroethyl)((3S,5R,6S,7S)-6-(4-fluorophenyl)-3-(2-isopropoxy-5-(trifluoromethyl)phenyl)-2-oxaspiro[4.4]non-7-ylmethyl)amine;

(3R,5R,6S,7S)-(6-(4-fluorophenyl)-3-(2-methoxy-5-(trifluoromethyl)phenyl)-1-oxaspiro[4.4]non-7-yl)methanol;

(3S,5R,6S,7S)-(6-(4-fluorophenyl)-3-(2-methoxy-5-(2-trifluoromethylimidazol-1-yl)phenyl)-1-oxaspiro[4.4]non-7-yl)methanol;

N-(2-fluoroethyl)((3S,5R,6S,7S)-6-(4-fluorophenyl)-3-(2-methoxy-5-(2-(trifluoromethyl)imidazol-1-yl)phenyl)-1-oxaspiro[4.4]non-7-ylmethyl)amine;

N-Methyl((3S,5R,6R,7S)-6-(4-fluorophenyl)-3-(2-methoxy-5-(2-(trifluoromethyl)imidazol-1-yl)phenyl)-1-oxaspiro[4.4]non-7-yl)amine;

N,N-Dimethyl((3S,5R,6R,7S)-6-(4-fluorophenyl)-3-(2-methoxy-5-(2-(trifuoromethyl)imidazol-1-yl)phenyl)-1-oxaspiro[4.4]non-7-yl)amine;

(3S,5R,6R,7S)-6-(4-fluorophenyl)-3-(2-methoxy-5-(2-(trifluoromethyl)imidazol-1-yl)phenyl)-1-oxaspiro[4.4]non-7-ylamine;

(3R,5R,6S,7S)-6-(4-fluorophenyl)-3-(2-methoxy-5-(2-(trifluoromethyl)imidazol-1-yl)phenyl)-1-oxaspiro[4.4]nonane-7-carboxylic acid methyl ester;

(3R,5R,6S,7S)-(6-(4-fluorophenyl)-3-(2-methoxy-5-(2-trifluoromethylimidazol-1-yl)-phenyl)-1-oxaspiro[4.4]non-7-yl)methanol;

(5R,6S,7S)-6-(4-fluorophenyl)-3-(2-methoxy-5-(3-(trifluoromethyl)isoxazol-4-yl)phenyl)-1-oxaspiro[4.4]non-3-ene-7-carboxylic acid methyl ester;

(5R,6S,7S)-6-(4-fluorophenyl)-3-(2-methoxy-5-(3,5-dimethylisoxazol-4-yl)phenyl)-1-oxaspiro[4.4]non-3-ene-7-carboxylic acid methyl ester;

(5R,6S,7S)-6-(4-fluorophenyl)-3-(2-isopropoxy-5-(3,5-dimethylisoaxol-4-yl)phenyl)-1-oxaspiro[4.4]non-3-ene-7-carboxylic acid methyl ester;

(3S,5R,6S,7S)-6-(4-fluorophenyl)-3-(2-isopropoxy-5-(2-oxopropyl)phenyl)-1-oxaspiro[4.4]nonane-7-carboxylic acid methyl ester;

(5R,6S,7S)-6-(4-fluorophenyl)-3-(2-isopropoxy-5-(2-amino-4-methylthioazol-5-yl)phenyl)-1-oxaspiro[4.4]non-3-ene-7-carboxylic acid methyl ester;

(5R,6S,7S)-6-(4-fluorophenyl)-3-(2-isopropoxy-5-(4-methylthiazol-5-yl)phenyl)-1-oxaspiro[4.4]non-3-ene-7-carboxylic acid methyl ester;

(3R,5R,6S,7S)-6-(4-fluorophenyl)-3-(2-isopropoxy-5-(trifluoromethyl)phenyl)-1-oxaspiro[4.4]nonane-7-carboxylic acid methyl ester;

(5R,6S,7S)-6-(4-fluorophenyl)-3-(2-isopropyl-5-(trifluoromethyl)phenyl)-1-oxaspiro[4.4]non-3-ene-7-carboxylic acid methyl ester;

(3S,5R,6S,7S)-6-(4-fluorophenyl)-3-(2-isopropyl-5-(trifluoromethyl)phenyl)-1-oxaspiro[4.4]nonane-7-carboxylic acid methyl ester;

(3R,5R,6S,7S)-6-(4-fluorophenyl)-3-(2-isopropyl-5-(trifluoromethyl)phenyl)-1-oxaspiro[4.4]nonane-7-carboxylic acid methyl ester;

(5R,6S,7S)-6-(4-fluorophenyl)-3-(2-(trifluoromethoxy)-5-isopropylphenyl)-1-oxaspiro[4.4]non-3-ene-7-carboxylic acid methyl ester;

(3R,5R,6S,7S)-6-(4-fluorophenyl)-3-(2-trifluoromethoxy-5-isopropyl)phenyl)-1-oxaspiro[4.4]nonane-7-carboxylic acid methyl ester;

(3S,5R,6S,7S)-6-(4-fluorophenyl)-3-(2-trifluoromethoxy-5-isopropyl)phenyl)-1-oxaspiro[4.4]nonane-7-carboxylic acid methyl ester;

and pharmaceutically acceptable salts and individual diastereomers thereof.

There are several acceptable methods of naming the compounds discussed herein.

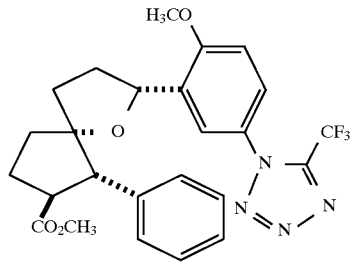

A

For example compound A shown above can be named either as:

Methyl[3-(S),5-(R),6-(S),7-(S)]-6-(4-fluorophenyl)-3-2-methoxy-5-((5-trifluoromethyl)tetrazol-1-yl)phenyl)-1-oxaspiro[4.4]nonane-7-carboxylate or (3S,5R,6S,7S)-6-(4-Fluorophenyl)-3-(2-methoxy-5-(5-(trifluoromethyl)tetrazol-1-yl)phenyl)-1-oxaspiro[4.4]nonane-7-carboxylic acid methyl ester.

Throughout the instant application, the following abbreviations are used with the following meanings:

Reagents:

| | |
|---|---|
| Cbz—Cl | benzyl chloroformate |
| BOP | benzotriazol-1-yloxy tris(dimethylamino)-phosphonium hexafluorophosphate |
| CDI | 1,1'-carbonyldimidazole |
| ACE—Cl | alpha-chloroethyl chloroformate |
| MCPBA | m-chloroperbenzoic acid |
| DBU | 1,8-diazabicyclo[5.4.0]undec-7-ene |
| DCC | N,N'-dicyclohexylcarbodiimide |
| DCU | N,N'-dicyclohexylurea |
| DIBAL | diisobutylaluminum hydride |
| iPr$_2$NEt or DIPEA | N,N-diisopropylethylamine |
| EDC | 1-(3-dimethylaminopropyl)-3-ethylcarbodiimide hydrochloride |
| DMAP | 4-dimethylaminopyridine |
| Me$_2$SO$_4$ | dimethyl sulfate |
| EDAC hydrochloride | 1-ethyl-3-(3-dimethylaminopropyl)carbo-diimide |
| HOBt | 1-hydroxybenzotriazole hydrate |
| NHS | N-hydroxysuccinimide |
| LAH | lithium aluminum hydride |
| LHMDS | lithium bis(trimethylsilyl)amide |
| NMM | N-methylmorpholine |
| KHMDS | potassium bis(trimethylsilyl)amide |
| NaOEt | sodium ethoxide |
| Et$_3$N | triethylamine |
| Ph$_3$P | triphenylphosphine |
| TFA | trifluoroacetic acid |
| DEAD | diethyl azodicarboxylate |

Solvents:

| | |
|---|---|
| AcOH | acetic acid |
| MeCN | acetonitrile |
| AmOH | n-amyl alcohol |
| DMSO | dimethylsulfoxide |
| DMF | N,N-dimethylformamide |
| EtOH | ethanol |
| EtOAc | ethyl acetate |
| MeOH | methanol |
| THF | tetrahydrofuran |

Others:

| | |
|---|---|
| Am | n-amyl |
| Ar | aryl |
| BOC | tert-butoxycarbonyl |
| Bn | benzyl |
| Bu | butyl |
| Cbz | carbobenzyloxy (benzyloxycarbonyl) |
| calc. | calculated |
| cat. | catalytic |
| EI-MS | electron ion-mass spectroscopy |
| Et | ethyl |
| eq. | equivalent(s) |
| FAB-MS | fast atom bombardment mass spectrometry |
| HPLC | high pressure liquid chromatography |
| iPr | isopropyl |
| MPLC | medium pressure liquid chromatography |
| Me | methyl |
| MHz | megahertz |
| MF | molecular formula |
| NMR | nuclear magnetic resonance |
| Ph | phenyl |
| PTC | phase transfer catalyst |
| prep. | prepared or preparative |
| Pr | propyl |
| rt | room temperature |
| TLC | thin layer chromatography |
| TMS | tetramethylsilane |

The preparation of compounds of Formula I of the present invention may be carried out in sequential or convergent synthetic routes. Syntheses detailing the preparation of the compounds of Formula I in a sequential manner are presented in the following reaction schemes. The skills required in carrying out the reaction and purification of the resulting reaction products are known to those in the art. Purification procedures includes crystallization, normal phase or reverse phase chromatography.

Several methods for preparing the compounds of this invention are illustrated in the following Schemes and Examples wherein R, R', R", $R^3$, $R^4$, $R^5$, $R^6$, $R^7$, $R^8$, $R^9$, $R^{10}$, $R^{11}$, $R^{12}$ and $R^{13}$ are as defined above (or as defined herein).

SCHEME 1

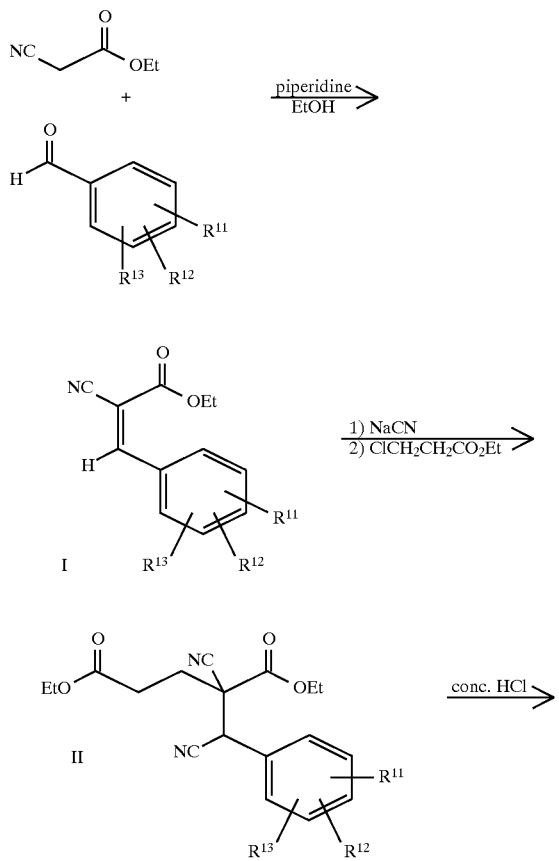

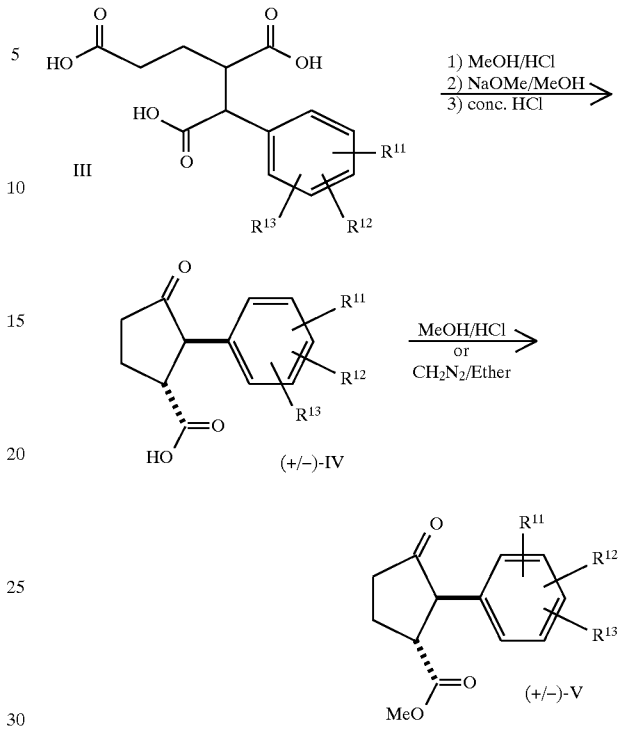

Intermediates for preparation of the compounds of the present invention in which the central ring is 5-membered may be synthesized by the general route outlined in Scheme 1. Thus, according to the procedure of Baker and Leeds (*J. Chem. Soc* 1948, 974), condensation of ethyl cyanoacetate and benzaldehyde (with or without substituents) in the presence of a base such as piperidine provides the unsaturated derivative I. Exposure of this olefin to sodium cyanide followed by ethyl 3-chloropropionate gives the dicyano derivative II, which after aqueous acidic hydrolysis yields triacid III. After esterification with acidic methanol, the triester can be cyclized by heating with sodium methoxide in dry methanol followed by treatment with aqueous HCl, to provide racemic cyclopentanone IV. The methyl ester V can be formed from ketone IV by treatment with acidic methanol or diazomethane in ether.

SCHEME 2

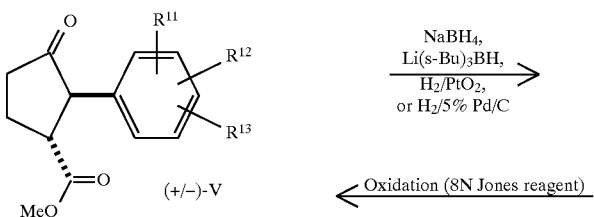

-continued
SCHEME 2

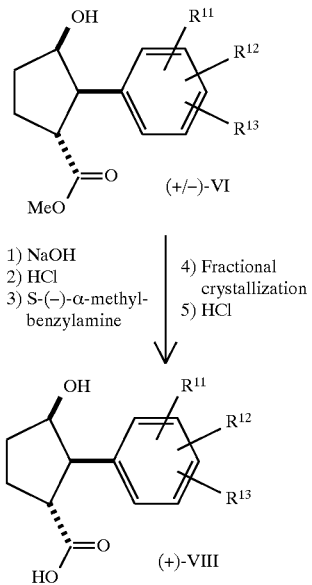

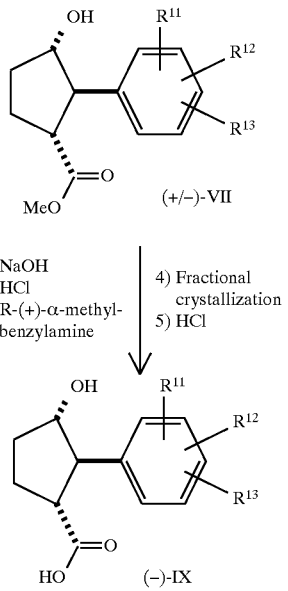

The reduction of ketone V may be accomplished with various reducing agents, for example, sodium borohydride, lithium tri(sec-butyl)-borohydride and the like, or with hydrogen in the presence of a suitable catalyst, such as platinum oxide or 5% palladium on carbon, which provide the corresponding cis- and trans- alcohols VI and VII, respectively (Scheme 2). The ratio of VI to VII thus obtained is dependent on the reducing agent employed. Alcohols VI and VII may be interconverted by oxidation to ketone V with chromium trioxide, pyridinium chlorochromate, DMSO/oxalyl chloride/triethylamine or similar agents followed by reduction with one of the reagents given above. Separation of the enantiomers of esters VI and VII may be carried out by hydrolysis to the corresponding acids VIII and IX followed by fractional crystallization of the salts formed with R-(−)-α- or S-(+)-α-methylbenzylamine or other suitable chiral, non-racemic bases.

SCHEME 3

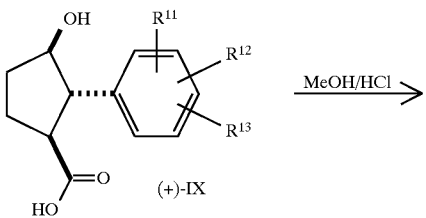

-continued
SCHEME 3

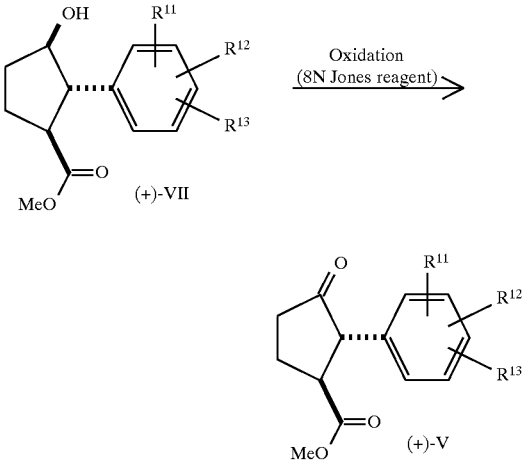

Conversion of the free acids to the keto-ester V is accomplished as shown in Scheme 3, by esterification with acidic methanol followed by oxidation with chromium trioxide, pyridinium chlorochromate, DMSO/oxalyl chloride/triethylamine or similar agents.

SCHEME 4

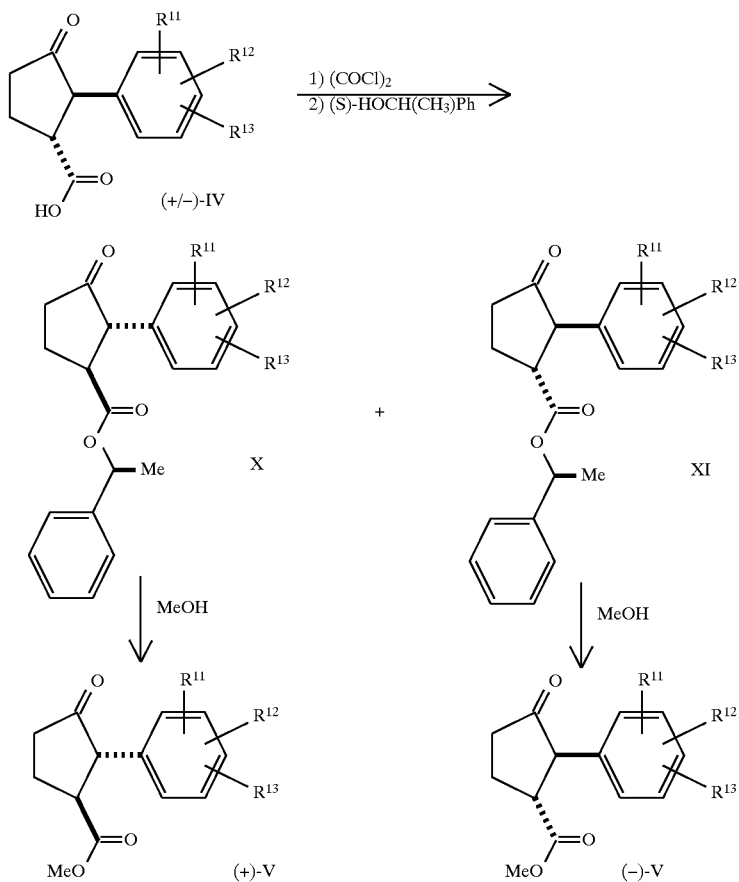

An alternative method of resolution is shown in Scheme 4. The racemic acid (±)-IV is activated with, for example, oxalyl chloride, DCC, EDAC/HOBt or similar condensing reagents, and then allowed to react with a chiral, non-racemic alcohol, such as (S)-alpha-methylbenzyl alcohol, to give the esters X and XI. After separating these diastereomers, they are individually transesterified with methanol to provide the separate enantiomers (+)-V and (−)-V.

SCHEME 5

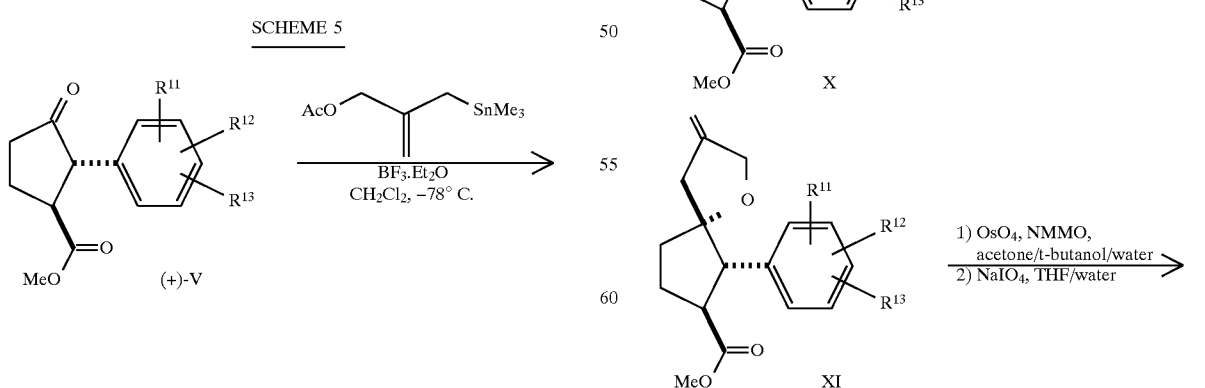

SCHEME 5
-continued

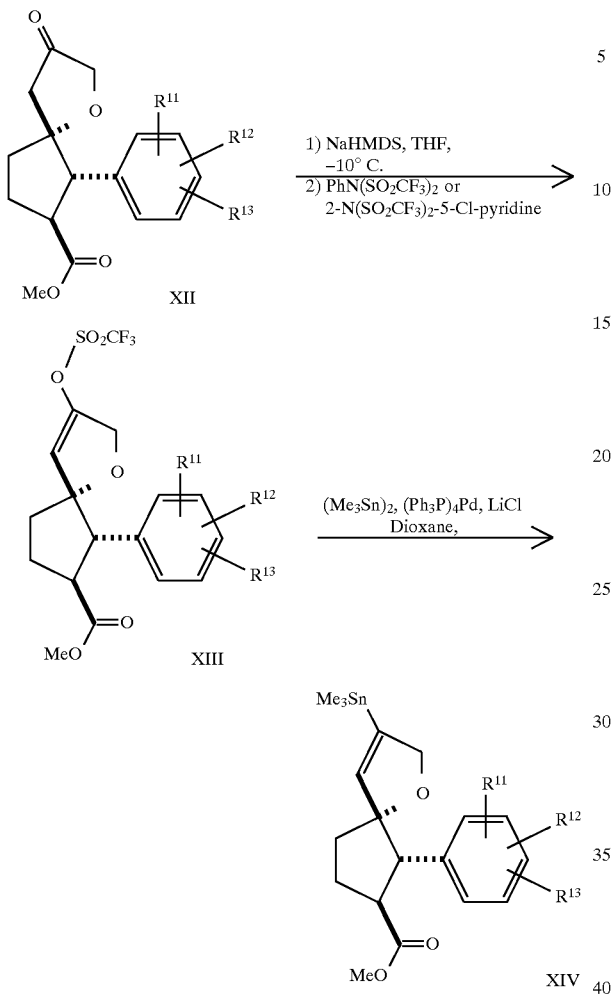

SCHEME 6

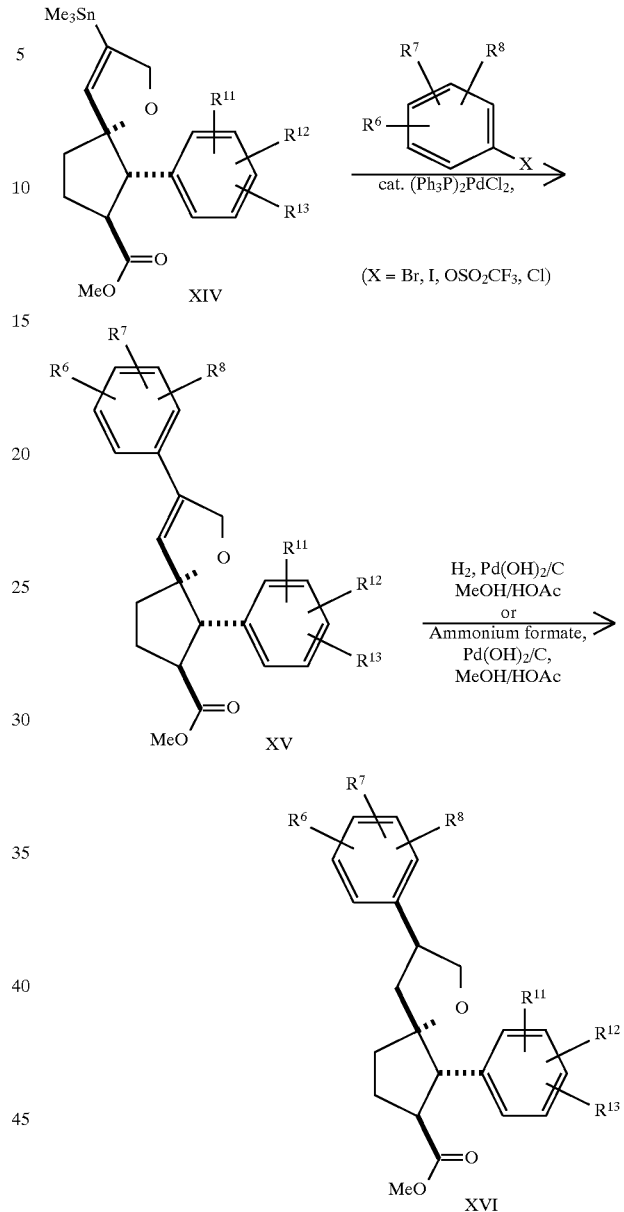

The 1-oxaspiro[4.4]non-3-ene ring system is prepared as shown in Scheme 5. The ketone V is treated with 2-(acetoxymethyl)-3-(trimethylstannyl)propene and boron trifluoride etherate at low temperature in methylene chloride to provide the desired diastereomer X and lesser amounts of the epimeric product. After separation of the diastereomers, alcohol X is cyclized by treatment with tetrakis (triphenylphosphine)palladium in the presence of LiHMDS and ZnCl$_2$, to provide the spirocycle XI. Oxidative cleavage of the exocyclic olefin with either osmium tetroxide followed by sodium periodate or with ozone at low temperature gave the ketone XII. Formation of the enolate of XII with a suitable strong base, such as lithium, sodium, or potassium hexamethyldisilazide, lithium diisopropylamide, lithium tetramethylpiperidide, or similar agents, followed by treatment with N-phenyl triflimide, 2-[N,N-trifluoromethylsulfonyl)-amino]-5-chloropyridine (or related agents designed to transfer a trifluoromethanesulfonyl group to an alkoxide or enolate oxygen), provided the enol triflate XIII. Formation of the corresponding vinylstannane was then carried out by exposure of triflate XIII to hexamethylditin in the presence of catalytic tetrakis (triphenylphosphine)palladium and lithium chloride, to give the desired unsaturated tin derivative XIV.

Formation of the 3-aryl derivative is carried out as described in Scheme 6. Treatment of stannane XIV with an appropriate aryl halide or aryl trifluoromethanesulfonate in the presence of catalytic bis(triphenylphosphine) palladium dichloride or related palladium catalysts provides the unsaturated 3-aryl spirocycle XV. Alternatively, XV may be prepared by coupling enol triflate and aryl boronic acids in the presence of one of the above described catalytic systems. Hydrogenation of the double bond under standard conditions, such as transfer hydrogenation by treatment with ammonium formate in the presence of palladium hydroxide on carbon at elevated temperature, or by exposure to hydrogen gas at or above atmospheric pressure in the presence of a precious metal catalyst (such as palladium on carbon, ruthenium on carbon, platinum on carbon, rhodium on carbon and the like) or Raney nickel catalyst, provided the saturated derivative XVI.

SCHEME 7

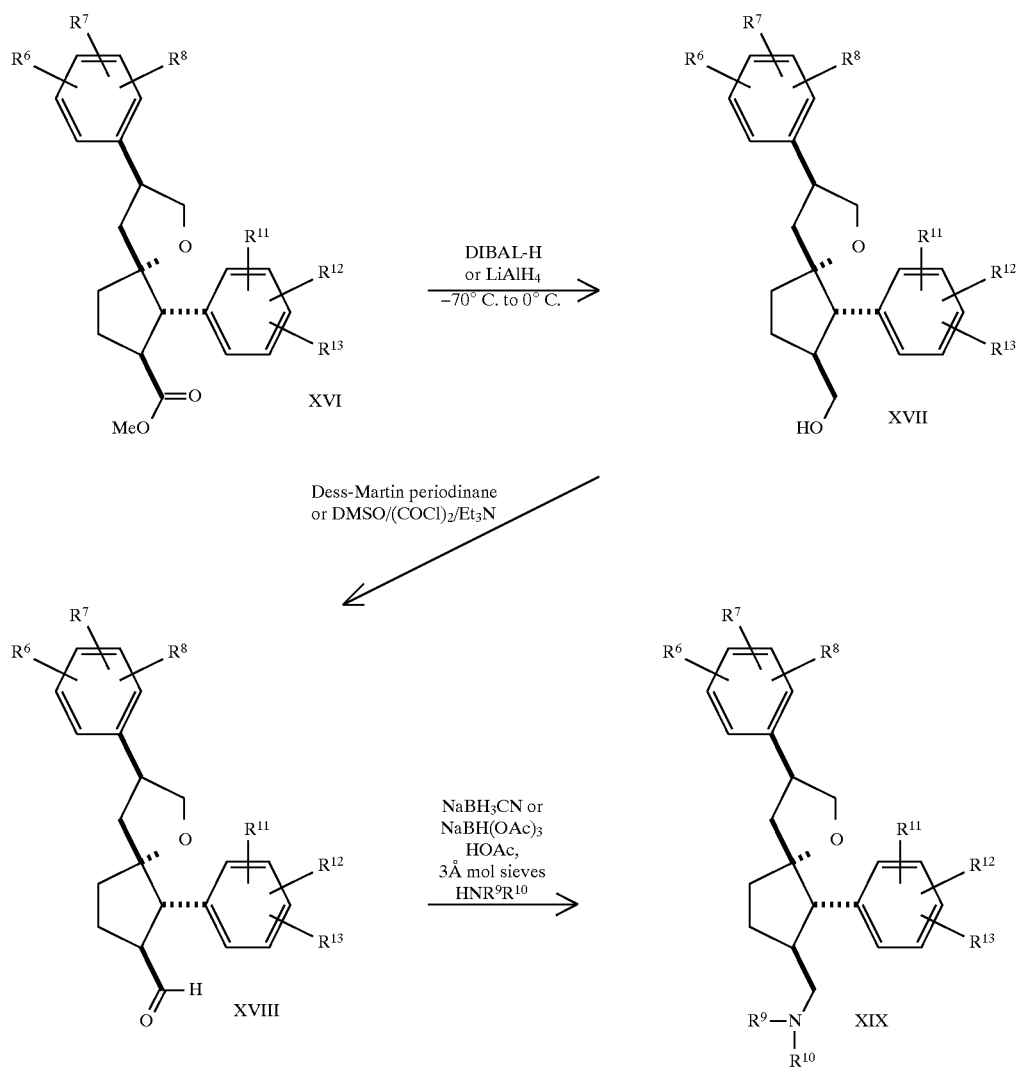

For the preparation of compounds bearing basic substituents on C7, two strategies may be used. In the first (depicted in Scheme 7), reduction of the ester, for example with diisobutyl aluminum hydride or with lithium aluminum hydride, provides primary alcohol XVII. Oxidation of this alcohol under mild conditions, for example employing the conditions described by Swern (dimethyl sulfoxide, oxalyl chloride and triethylamine at low temperature) or by using the Dess-Martin periodinane, provides aldehyde XVIII. Reductive amination under standard conditions, for example by treatment with ammonia, a primary or secondary amine, along with sodium cyanoborohydride or sodium tris(acetoxy) borohydride in the presence of acetic acid and molecular sieves, provides the amine XIX.

SCHEME 8

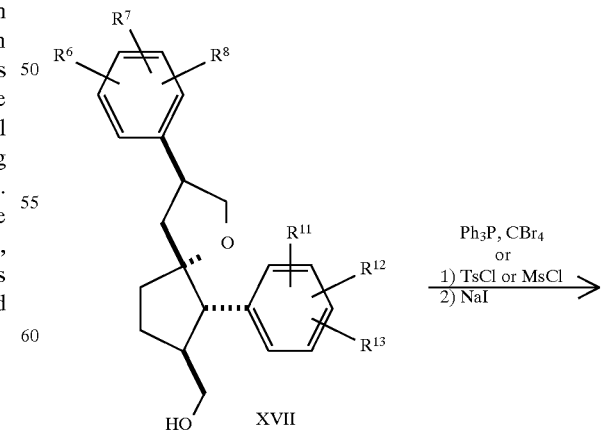

SCHEME 8 (continued)

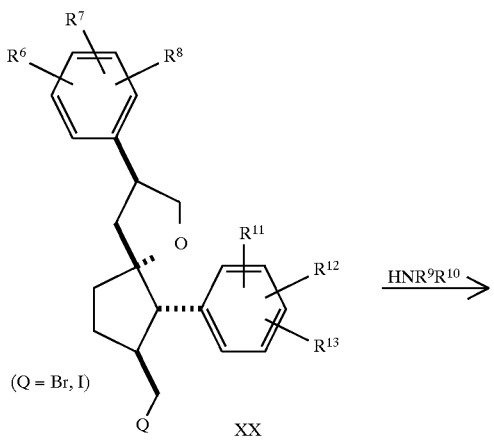

As shown in Scheme 8, the alcohol can also be converted into a leaving group, for example by treatment with triphenylphosphine/carbon tetrabromide or by formation of the corresponding tosylate or mesylate, followed by displacement with sodium iodide, to give either the bromide or iodide XX. Treatment with an appropriate amine provides compound XIX.

SCHEME 9

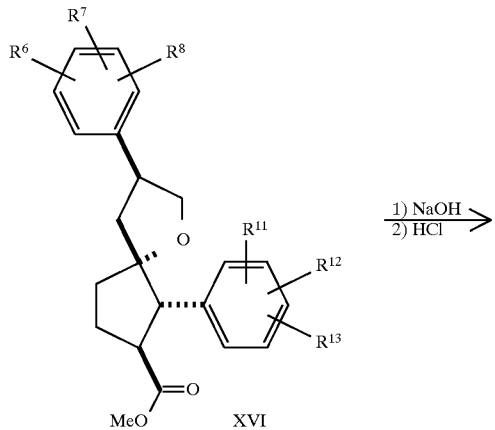

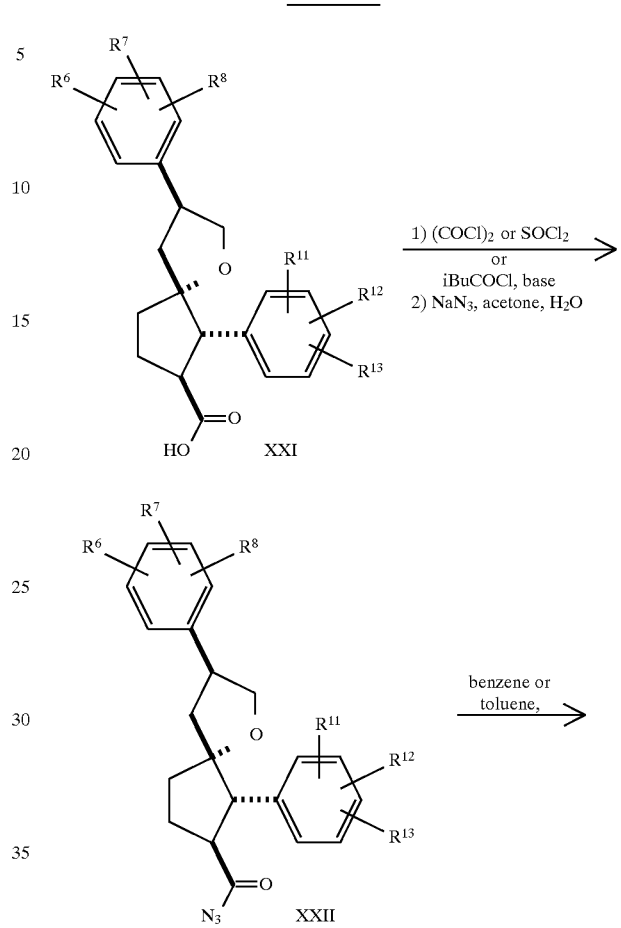

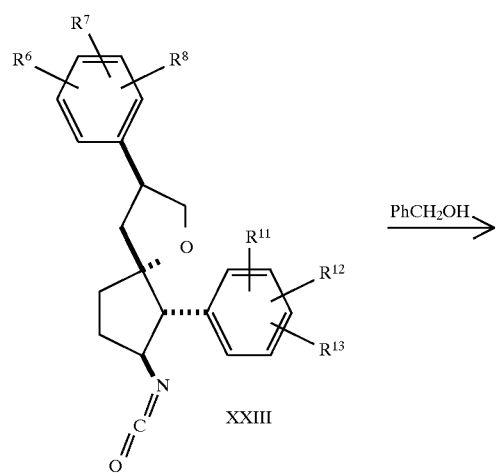

SCHEME 9 -continued

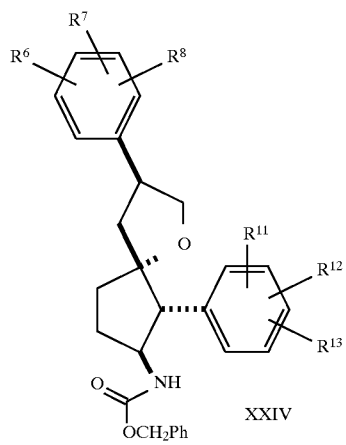

XXIV

The second strategy places the amine directly on the C7 carbon (see Scheme 9). Hydrolysis of ester XVI under standard conditions gives the corresponding acid XXI, which can be activated under a number of conditions, such as by treatment with oxalyl chloride or through mixed anhydride formation. The activated acyl derivative can then be treated with an azide salt, to provide acyl azide XXII. Thermolysis under anhydrous conditions provides the rearranged isocyanate XXIII, which can be treated with benzyl alcohol to give the CBZ protected amine XXIV. Alternatively, acid XXI may be treated with $Ph_2P(O)N_3$ (diphenyl phosphoryl azide) followed by thermolysis to directly provide isocyanate XXIII.

SCHEME 10

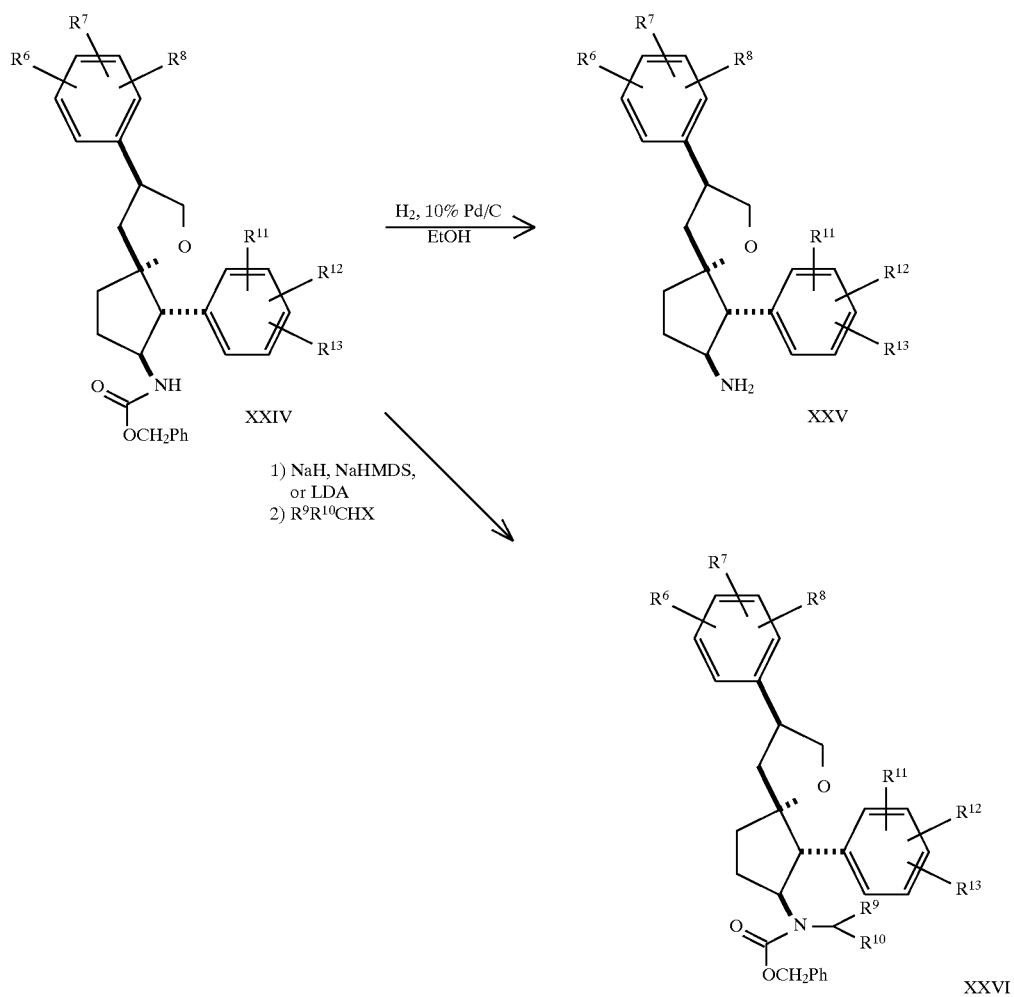

-continued
SCHEME 10

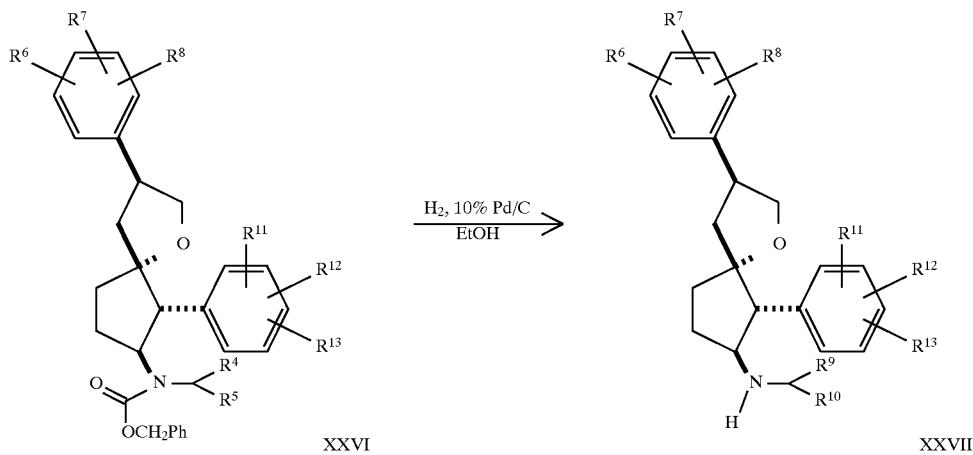

As shown in Scheme 10, this material may then be deprotected to provide the free amine XXV. Alternatively, it can be treated with a strong base (such as sodium hydride, LDA or NaHMDS) followed by a suitable alkyl or aralkyl halide, to give protected amine XXVI. Deprotection under standard conditions provides the free amine XXVII.

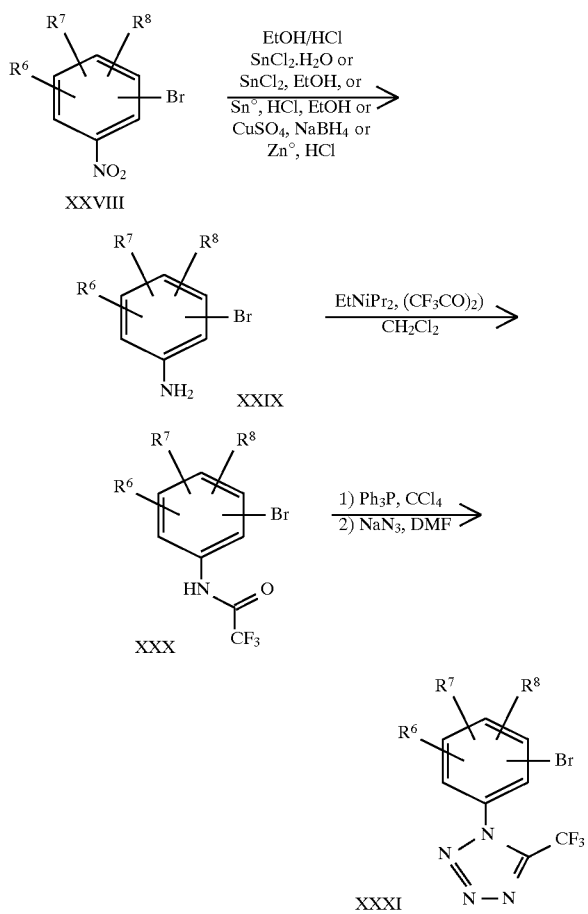

A number of routes are available for the preparation of the aryl halides that are coupled to the C3 position of the spirocyclic core. For example, if a 5-(5-trifluoromethyltetrazol-1-yl) group is desired on the aryl subunit, an appropriate nitro-containing precursor (XXVIII) can be reduced to the required aryl amine (XXIX) without affecting a bromo substituent. This can be carried out by treatment with stannous chloride in acidic ethanol, or by heating with stannous chloride in neutral ethanol, or by treatment with metallic tin in acidic ethanol, or by treatment with copper (II) sulfate and sodium borohydride, or by treatment with metallic zinc in acetic acid (Scheme 11). The aniline derivative can then be acylated with trifluoroacetic anhydride, and the resulting trifluoroacetamide can be converted to the imino chloride in situ with triphenylphosphine and carbon tetrachloride. Direct treatment of the imino chloride with sodium azide in DMF then provides the desired tetrazole derivative XXXI.

SCHEME 12

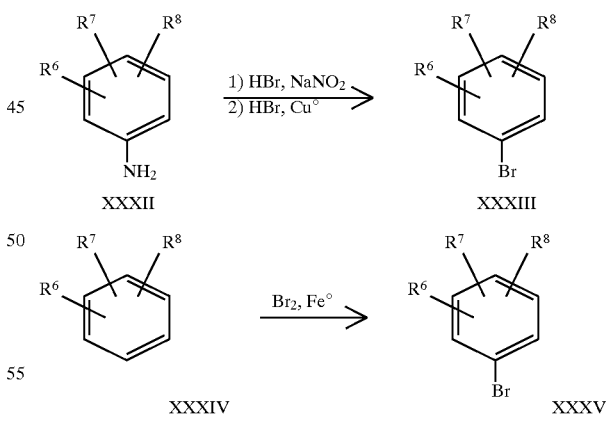

Preparation of aryl bromides from the corresponding aryl amines can be carried out by diazotization (for example with sodium nitrite in the presence of HBr) followed by treatment with HBr and copper metal (Scheme 12). Alternatively, aromatic systems can be brominated by a wide variety of conditions, for example by treatment with bromine and iron. This latter protocol sometimes results in the formation of isomers which can be separated by crystallization or chromatography.

SCHEME 13

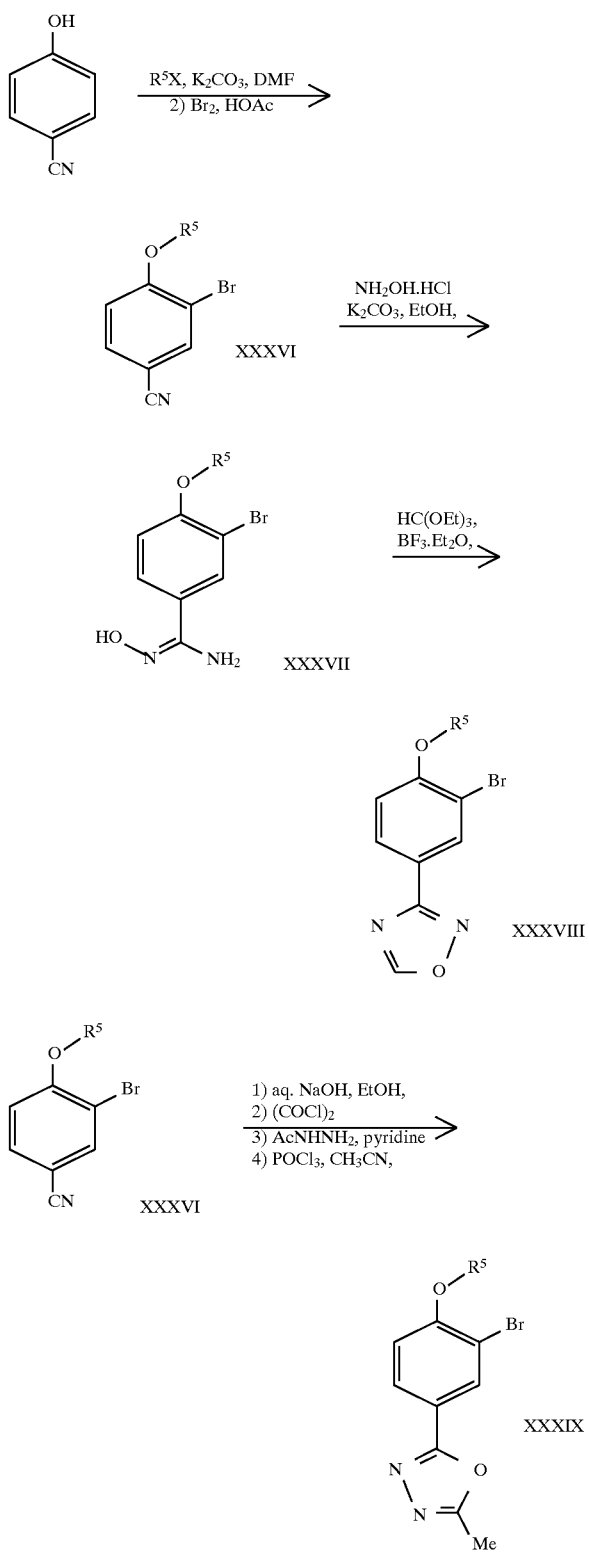

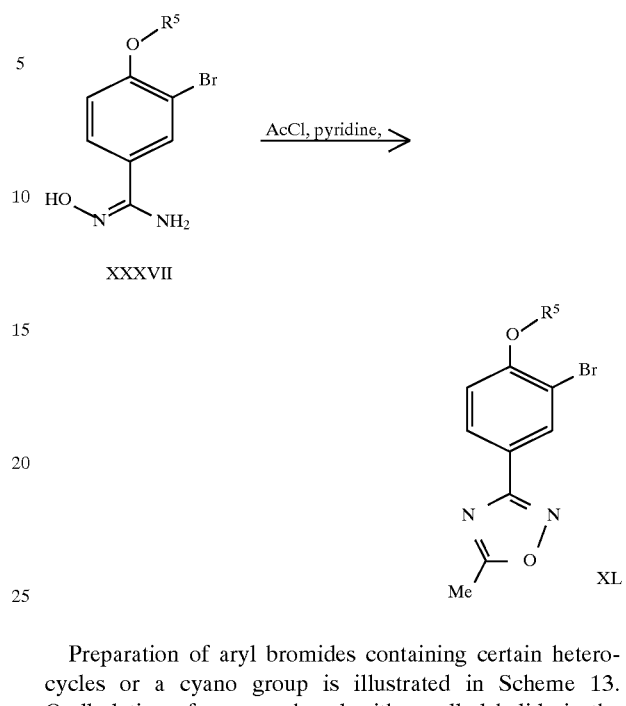

Preparation of aryl bromides containing certain heterocycles or a cyano group is illustrated in Scheme 13. O-alkylation of p-cyanophenol with an alkyl halide in the presence of potassium carbonate in DMF followed by standard bromination yields the nitrile XXXVI. If desired, this compound can be functionalized further by treatment with hydroxylamine HCl under basic conditions, followed by reaction with triethyl orthoformate in the presence of boron trifluoride etherate, to give the oxadiazole derivative XXXVIII. Alternatively, the cyano group in XXXVI can be hydrolysed under basic conditions, converted to the acid chloride, allowed to react with acetylhydrazine, and finally treated with phosphorus oxychloride to give the isomeric oxadiazole XXXIX. If desired, hydroxyamidine XXXVII can be treated with acetyl chloride in pyridine to directly provide the substituted oxadiazole XL.

SCHEME 14

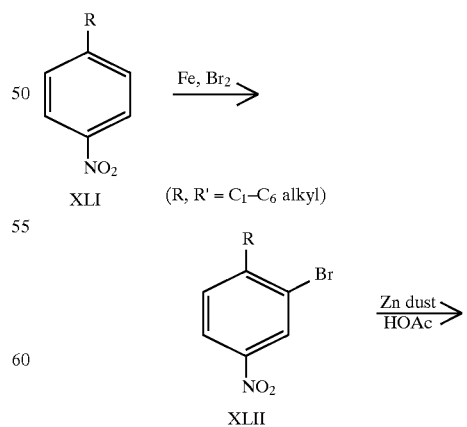

(R, R' = $C_1$–$C_6$ alkyl)

-continued
SCHEME 14

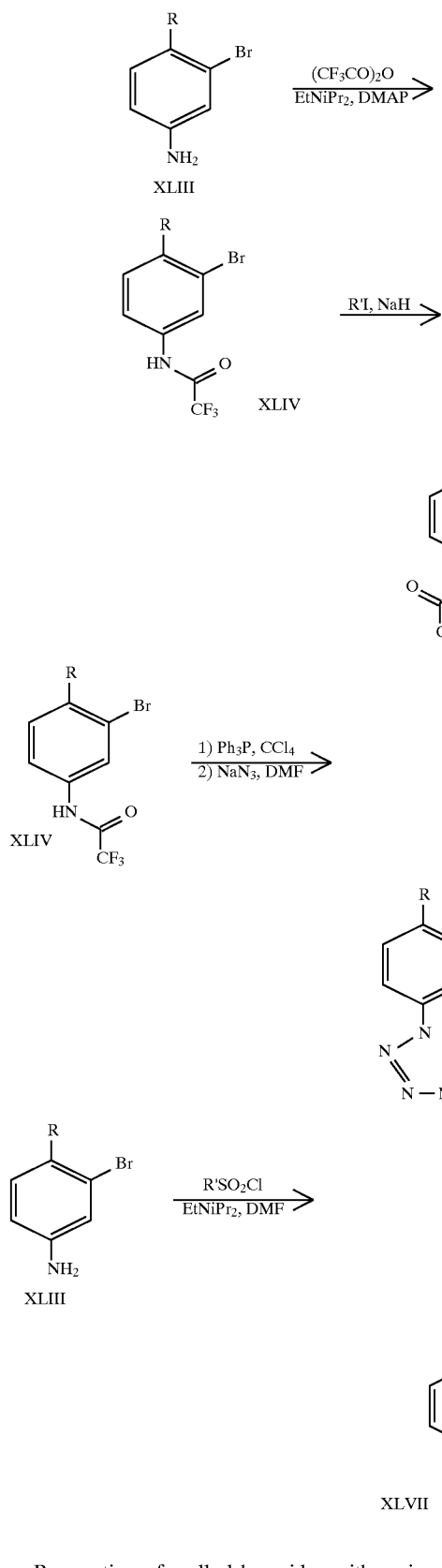

14. Bromination of the commercially available 4-alkyl nitrobenzene derivatives provides the 3-bromo intermediate XLII. Selective reduction of the nitro group with zinc dust and acetic acid provides the substituted aniline XLIII. In one variation, the amino nitrogen can be acylated, for example with trifluoroacetic anhydride, to provide amide XLIV. Alkylation of this compound under basic conditions by treatment with sodium hydride followed by an alkyl halide provides tertiary amide XLV. Alternatively, amide XLIV can be treated with carbon tetrachloride in the presence of triphenylphosphine to provide the imino chloride, which on exposure to sodium azide in DMF yields the tetrazole XLVI. In addition, aniline XLIII can also be sulfonylated by treatment with sulfonyl chlorides in the presence of a hindered base to provide the corresponding sulfonamide XLVII.

SCHEME 15

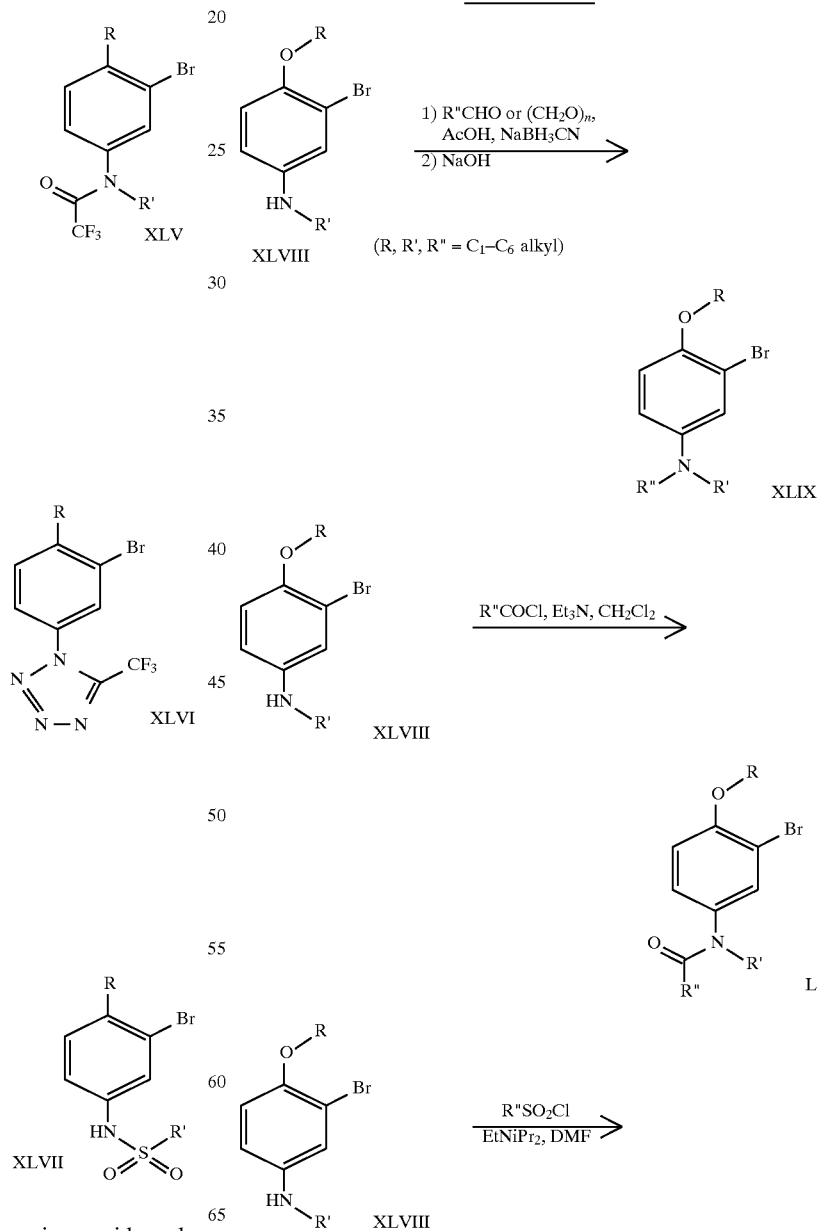

Preparation of aralkyl bromides with amine, amide, sulfonamide or heterocyclic side chains is illustrated in Scheme

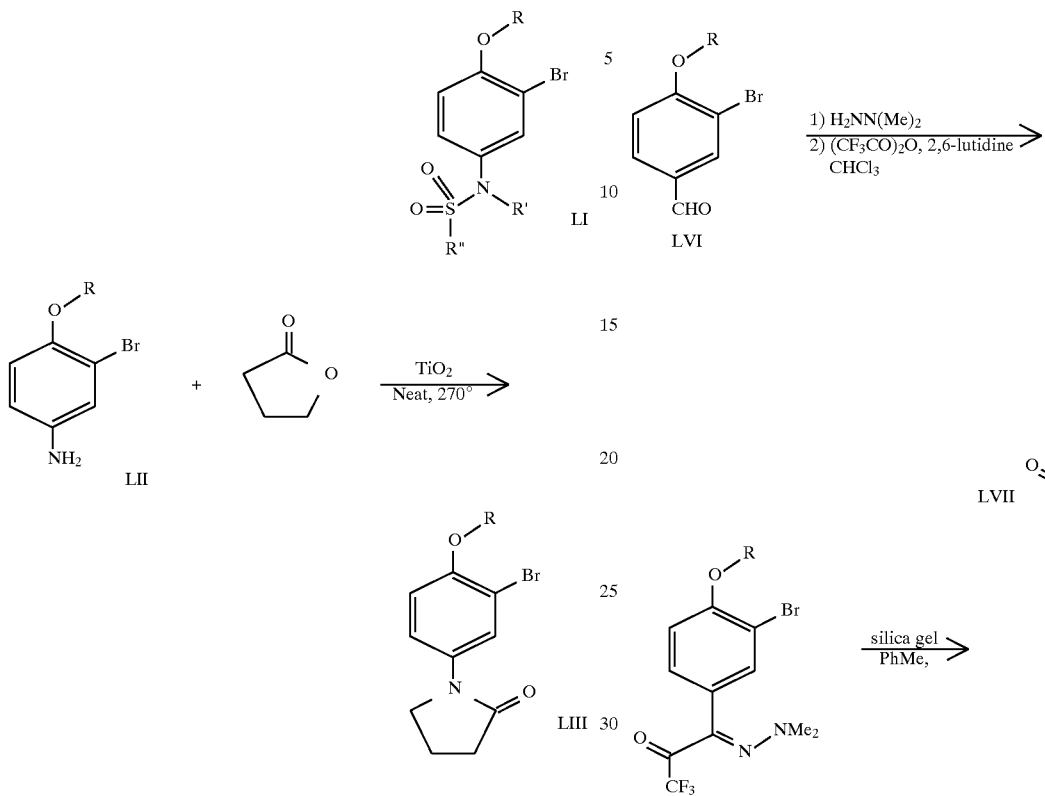

Preparation of alkoxyaryl bromides with amine, amide, sulfonamide or heterocyclic slide chains is illustrated in Scheme 15. Reductive alkylation of aniline XLVIII under standard conditions provides tertiary amine XLIX. Alternatively, acylation with a suitably activated acyl derivative, such as an acid chloride, provides the amide L. The amine XLVII can also be treated with a sulfonyl chloride to provide the sulfonamide LI. Preparation of the pyrrolidin-2-one derivative LIII can be carried out by treatment of amine LII with butyrolactone in the presence of a solid phase titanium dioxide catalyst at elevated temperature.

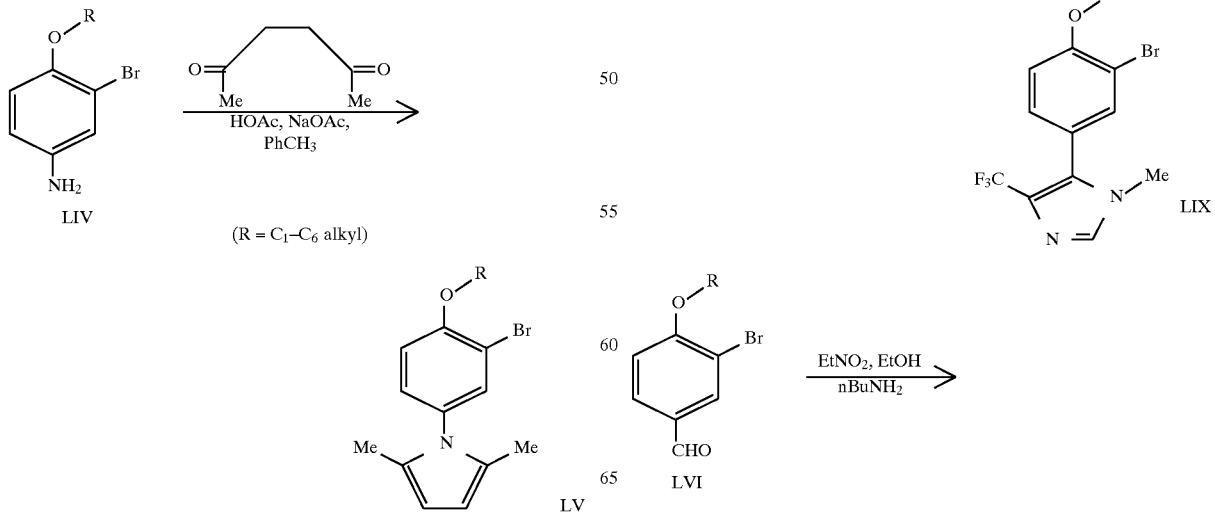

-continued
SCHEME 16

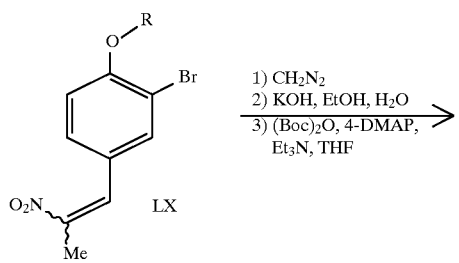

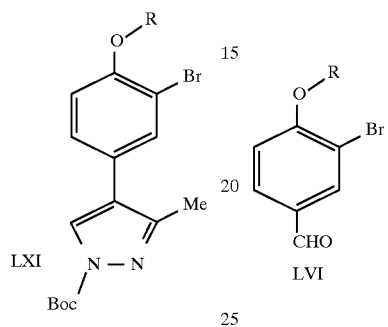

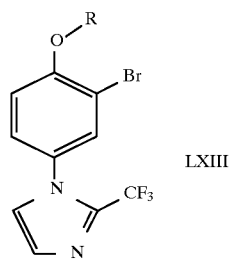

-continued
SCHEME 17

The syntheses of additional heterocyclic substituents are illustrated in Scheme 16. Treatment of aniline derivative LIV with 2,5-hexanedione in the presence of an acetate buffer system in toluene provides the pyrrole derivative LV. Alternatively, treatment of benzaldehyde LVI with N,N-dimethylhydrazine, followed by exposure to trifluoroacetic anhydride and a mild hindered base such as 2,6-lutidine provides the trifluoroacetyl derivative LVII. Treatment with silica gel in toluene at elevated temperature provides a mixture of the substituted imidazoles LVIII and LIX. Benzaldehyde LVI can also be converted into the substituted pyrazole LXI by exposure to nitroethane under basic conditions (to give LX), followed by sequential treatment with diazomethane, aqueous ethanolic potassium hydroxide, and then t-butyl carbonic anhydride. If desired, the t-butoxycarbonyl group can be removed by treatment with strong anhydrous acid or with strong aqueous base and heat.

SCHEME 17

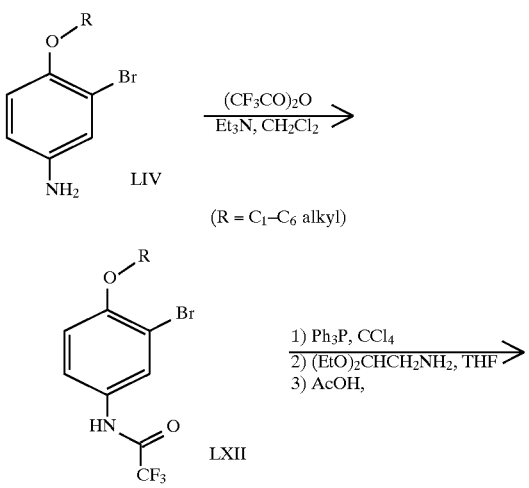

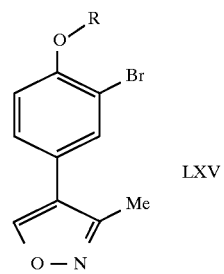

Preparations of aryl bromides containing a 2-trifluoromethyl-imidazol-1-yl substituent or an 3-methylisoxazol-4-yl substituent are illustrated in Scheme 17. Treatment of aniline derivative LIV with trifluoroacetic anhydride and triethylamine provides the trifluoroacetyl compound LXII. Conversion to the imino chloride in situ by exposure to triphenylphosphine and carbon tetrachloride, followed by addition of 2-aminoacetaldehyde diethyl acetal and then heating in acetic acid provides the target imidazole LXIII. To prepare the above mentioned isoxazole, benzaldehyde LVI is treated with triphenyl(methoxymethyl) phosphonium chloride in the presence of potassium t-butoxide, to give enol ether LXIV. Dipolar cycloaddition with the reagent generated by combining nitroethane, phenyl isocyanate, and triethylamine in toluene followed by treatment with aqueous ethanolic acid then provides isoxazole LXV.

SCHEME 18

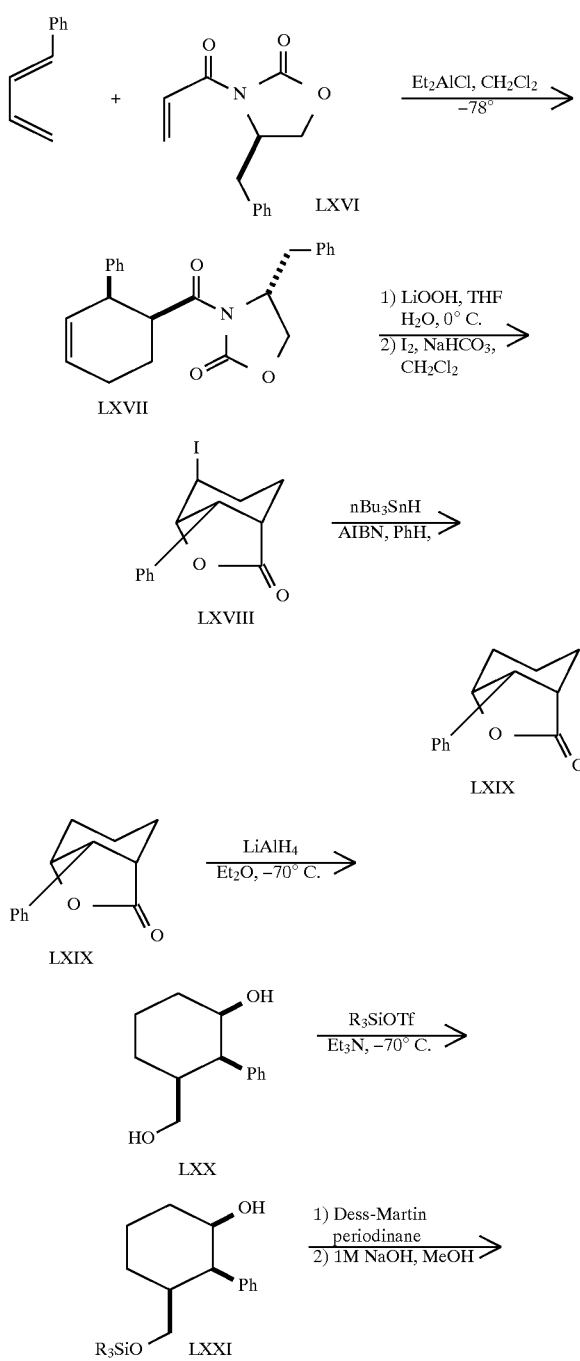

tive LXVII. Removal of the chiral auxilary with lithium hydroperoxide followed by iodolactonization with iodine and sodium bicarbonate in methylene chloride then provides the bicyclic lactone LXVIII. Selective removal of the iodo group is effected by treatment with tri(n-butyl)tin hydride in the presence of a radical initiator such as AIBN, in refluxing benzene, to give lactone LXIX, which can be reduced to diol LXX with a strong reducing agent such as lithium aluminum hydride. Selective silylation of the primary alcohol with a suitable agent such as t-butyl-dimethylsilyl chloride, t-butyl-dimethylsilyl triflate, triisopropylsilyl chloride, triisopropyl-silyl triflate, t-butyldiphenylsilyl chloride or t-butyldiphenylsilyl triflate provides siloxy alcohol LXXI. Oxidation of the hydroxyl group, for example with the Dess-Martin periodinane, chromium trioxide/pyridine, oxalyl chloride/dimethyl sulfoxide/triethylamine at low temperature (Swern conditions), or other suitable oxidants then provides the ketone LXXII.

SCHEME 19

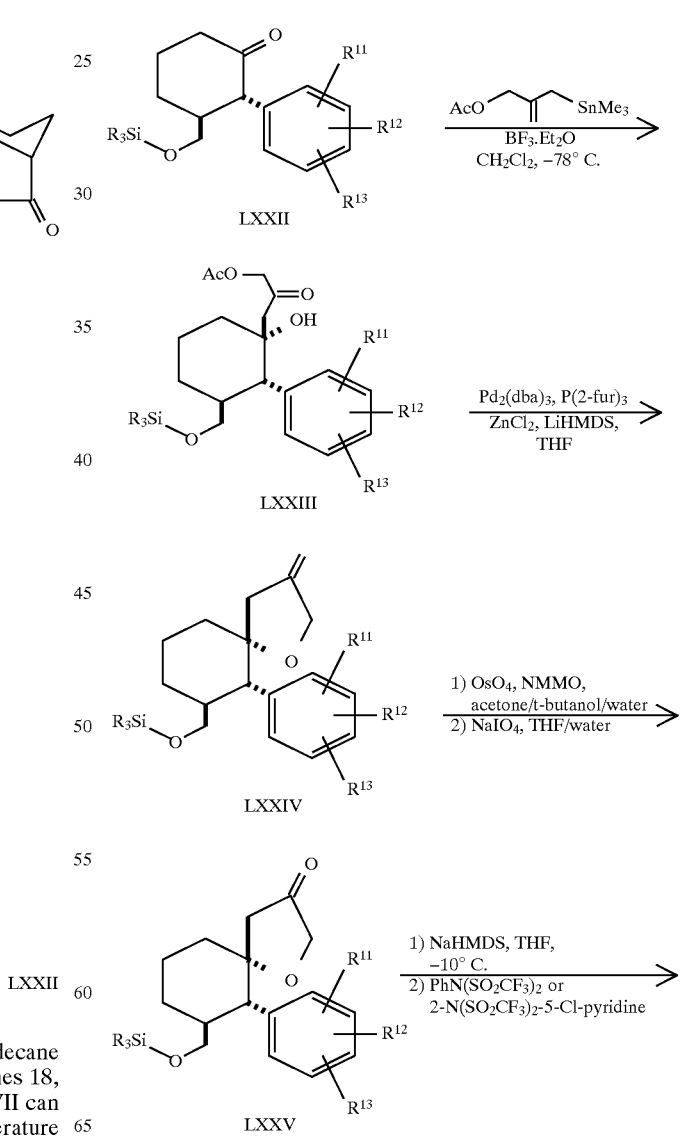

Preparation of compounds with a 1-oxaspiro[5.4]decane core structure can be carried out as outlined in Schemes 18, 19 and 20. Preparation of the chiral cyclohexene LXVII can be achieved by the Lewis acid catalyzed low temperature cycloaddition of 1-phenyl-butadiene with the chiral acrylate derivative LXVI to provide the chiral cyclohexene deriva- -continued
SCHEME 19

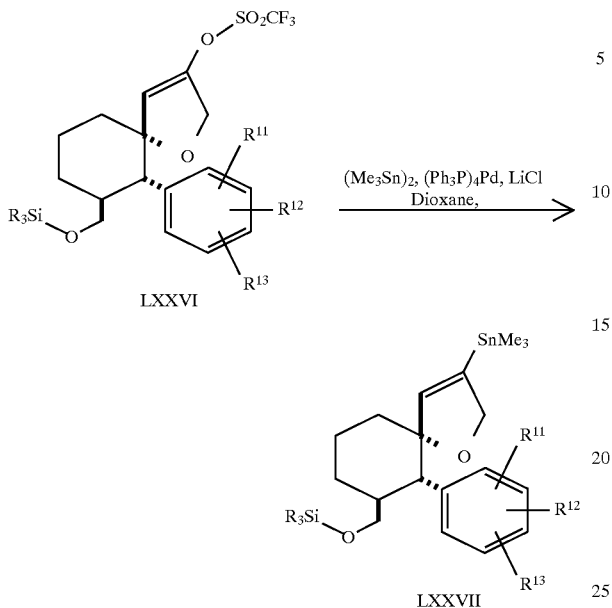

-continued
SCHEME 20

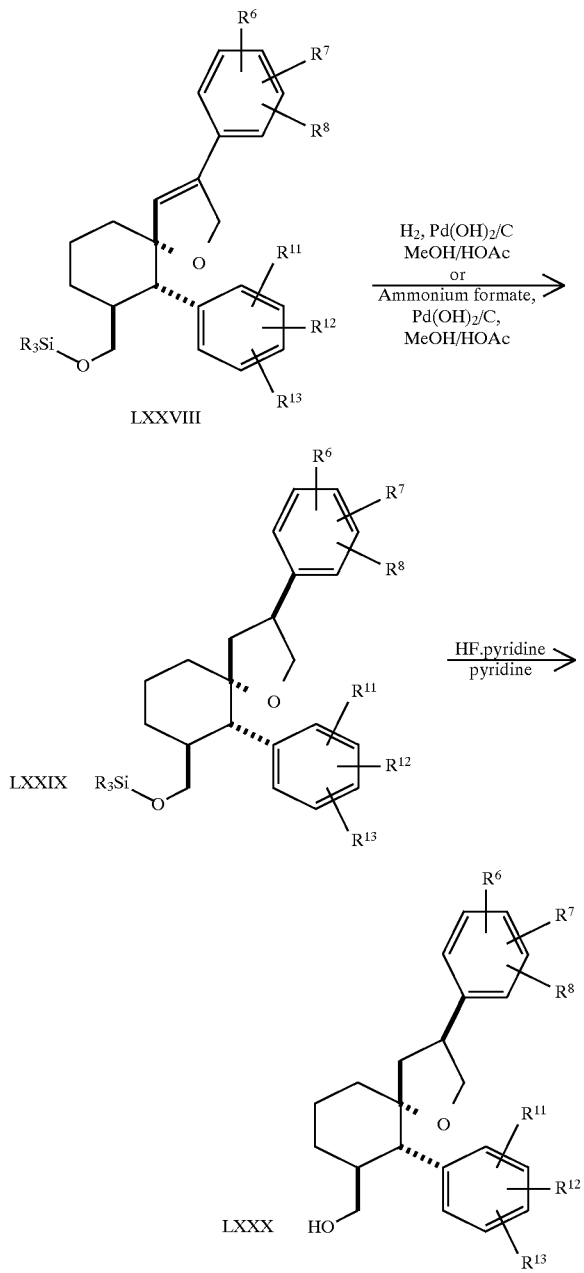

As shown in Scheme 19, cyclohexanone LXXII is treated with 2-(acetoxymethyl)-3-trimethylstannyl)propene and boron trifluoride etherate at low temperature in methylene chloride, to provide the desired diastereomer LXXIII. After separation of the diastereomers, alcohol LXXIII is cyclized by treatment with tetrakis(triphenylphosphine)palladium (formed in-situ) in the presence of n-butyllithium and DBU, to provide the spirocycle LXXIV. Oxidative cleavage of the exocyclic olefin with either osmium tetroxide followed by sodium periodate or with ozone at low temperature gave the ketone LXXV. Formation of the enolate of LXXV with a suitable strong base, such as lithium, sodium, or potassium hexamethyldisilazide, lithium diisopropylamide, lithium tetramethylpiperidide, or similar agents, followed by treatment with N-phenyl triflimide, 2-[N,N-triiluoromethylsulfonyl)amino]-5-chloropyridine (or related agents designed to transfer a trifluoromethanesulfonyl group to an alkoxide or enolate oxygen), provided the enol triflate LXXVI. Formation of the corresponding vinylstannane was then carried out by exposure of triflate LXXVI to hexamethylditin in the presence of catalytic tetrakis (triphenylphosphine)palladium and lithium chloride, to give the desired unsaturated tin derivative LXXVII.

SCHEME 20

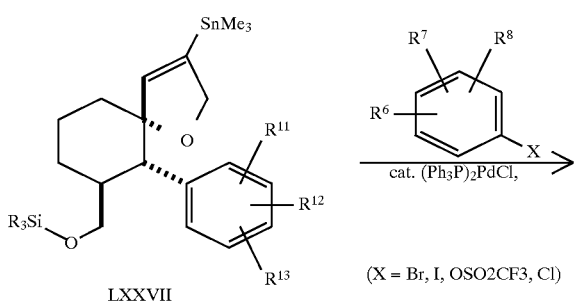

Formation of the 3-aryl derivative of spirocycle LXXVII is carried out as described in Scheme 20. Treatment of stannane LXXVII with an appropriate aryl halide or aryl trifluoromethanesulfonate in the presence of catalytic bis (triphenylphosphine) palladium dichloride or related palladium catalysts provides the unsaturated 3-aryl spirocycle LXXVIII. Hydrogenation of the double bond under standard conditions, such as transfer hydrogenation by treatment with ammonium formate in the presence of palladium hydroxide on carbon at elevated temperature, or by exposure to hydrogen gas at or above atmospheric pressure in the presence of a precious metal catalyst (such as palladium on carbon, ruthenium on carbon, platinum on carbon, rhodium on carbon and the like) or Raney nickel catalyst, provided the saturated derivative LXXIX. The silyl ether in LXXIX may be selectively cleaved, for example with tetrabutylammonium fluoride in THF, with HF.pyridine complex in pyridine, or by exposure to moderate to strong acid, to give alcohol LXXX.

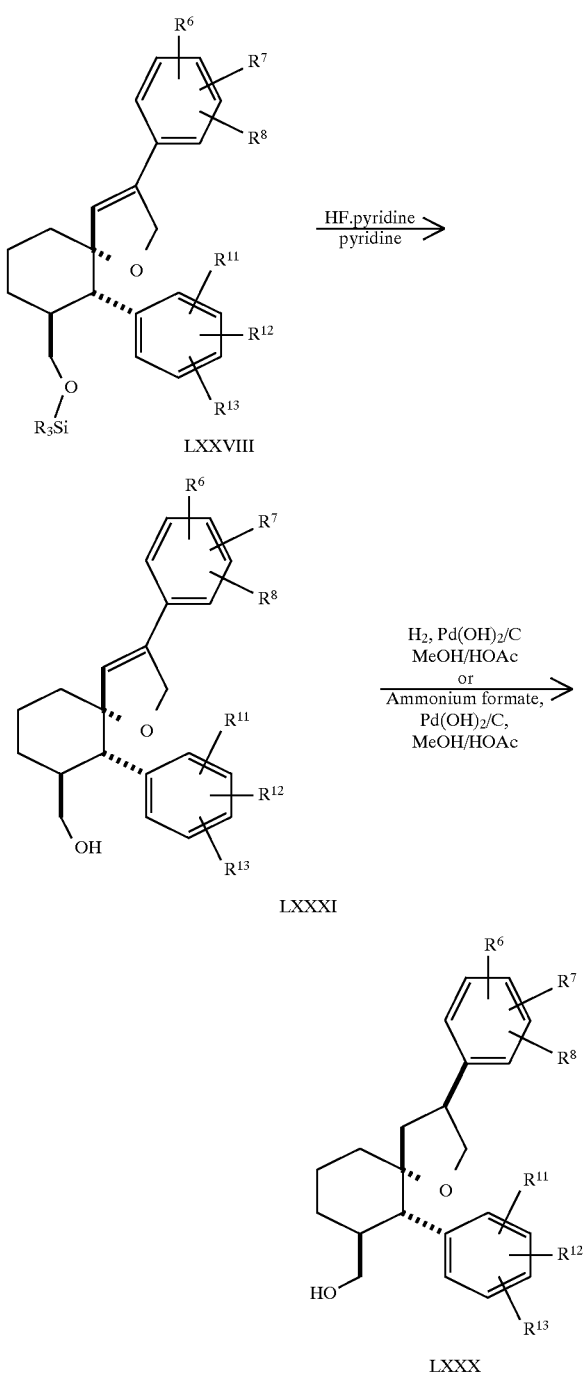

SCHEME 21

Alternatively, as shown in Scheme 21, the silyl ether in LXXVIII can be cleaved first, using the conditions noted above, to give alcohol LXXXI. Hydrogenation of LXXXI as described above then provides saturated alcohol LXXX.

It is noted that in some cases the order of carrying out the foregoing reaction schemes may be varied to facilitate the synthesis or to avoid unwanted reaction products.

TACHYKININ ANTAGONISM ASSAY

The compounds of this invention are useful for antagonizing tachykinins, in particular substance P and neurokinin A in the treatment of gastrointestinal disorders, central nervous system disorders, inflammatory diseases, pain or migraine and asthma in a mammal in need of such treatment. This activity can be demonstrated by the following assays.

A. Receptor Expression in COS

To express the cloned human neurokinin-1 receptor (NK1R) transiently in COS, the cDNA for the human NK1R was cloned into the expression vector pCDM9 which was derived from pCDM8 (INVITROGEN) by inserting the ampicillin resistance gene (nucleotide 1973 to 2964 from BLUESCRIPT SK+) into the Sac II site. Transfection of 20 ug of the plasmid DNA into 10 million COS cells was achieved by electroporation in 800 ul of transfection buffer (135 mM NaCl, 1.2 mM $CaCl_2$, 1.2 mM $MgCl_2$, 2.4 mM $K_2HPO_4$, 0.6 mM $KH_2PO_4$, 10 mM glucose, 10 mM HEPES pH 7.4) at 260 V and 950 uF using the IBI GENEZAPPER (IBI, New Haven, Conn.). The cells were incubated in 10% fetal calf serum, 2 mM glutamine, 100 U/ml penicillin-streptomycin, and 90% DMEM media (GIBCO, Grand Island, N.Y.) in 5% $CO_2$ at 37° C. for three days before the binding assay.

B. Stable Expression in CHO

To establish a stable cell line expressing the cloned human NK1R, the cDNA was subcloned into the vector pRcCMV (INVITROGEN). Transfection of 20 ug of the plasmid DNA into CHO cells was achieved by electroporation in 800 ul of transfection buffer supplemented with 0.625 mg/ml Herring sperm DNA at 300 V and 950 uF using the IBI GENEZAPPER (IBI). The transfected cells were incubated in CHO media[10% fetal calf serum, 100 U/ml penicillin-streptomycin, 2 mM glutamine, 1/500 hypoxanthine-thymidine (ATCC), 90% IMDM media (JRH BIOSCIENCES, Lenexa, Kans.), 0.7 mg/ml G418 (GIBCO)] in 5% $CO_2$ at 37° C. until colonies were visible. Each colony was separated and propagated. The cell clone with the highest number of human NK1R was selected for subsequent applications such as drug screening.

C. Assay Protocol using COS or CHO

The binding assay of human NK1R expressed in either COS or CHO cells is based on the use of $^{125}$I-substance P ($^{125}$I-SP, from DU PONT, Boston, Mass.) as a radioactively labeled ligand which competes with unlabeled substance P or any other ligand for binding to the human NK1R. Monolayer cell cultures of COS or CHO were dissociated by the non-enzymatic solution (SPECIALTY MEDIA, Lavallette, N.J.) and resuspended in appropriate volume of the binding buffer (50 mM Tris pH 7.5, 5 mM $MnCl_2$, 150 mM NaCl, 0.04 mg/ml bacitracin, 0.004 mg/ml leupeptin, 0.2 mg/ml BSA, 0.01 mM phosphoramidon) such that 200 ul of the cell suspension would give rise to about 10,000 cpm of specific $^{125}$I-SP binding (approximately 50,000 to 200,000 cells). In the binding assay, 200 ul of cells were added to a tube containing 20 ul of 1.5 to 2.5 nM of $^{125}$I-SP and 20 ul of unlabeled substance P or any other test compound. The tubes were incubated at 4° C. or at room temperature for 1 hour with gentle shaking. The bound radioactivity was separated from unbound radioactivity by GF/C filter (BRANDEL, Gaithersburg, Md.) which was pre-wetted with 0.1% polyethylenimine. The filter was washed with 3 ml of wash buffer (50 mM Tris pH 7.5, 5 mM $MnCl_2$, 150 mM NaCl) three times and its radioactivity was determined by gamma counter.

The activation of phospholipase C by NK1R may also be measured in CHO cells expressing the human NK1R by determining the accumulation of inositol monophosphate which is a degradation product of $IP_3$. CHO cells are seeded in 12-well plate at 250,000 cells per well. After incubating in CHO media for 4 days, cells are loaded with 0.025 uCi/ml of $^3$H-myoinositol by overnight incubation. The extracellular radioactivity is removed by washing with phosphate buffered saline. LiCl is added to the well at final concentration of 0.1 mM with or without the test compound, and incubation is continued at 37° C. for 15 min. Substance P is added to the well at final concentration of 0.3 nM to activate the human NK1R. After 30 min of incubation at 37° C., the media is removed and 0.1N HCl is added. Each well is sonicated at 4° C. and extracted with $CHCl_3$/methanol (1:1). The aqueous phase is applied to a 1 ml Dowex AG 1×8 ion exchange column. The column is washed with 0.1N formic acid followed by 0.025M ammonium formate-0.1N formic acid. The inositol monophosphate is eluted with 0.2M ammonium formate-0. 1N formic acid and quantitated by beta counter.

In particular, the intrinsic tachykinin receptor antagonist activities of the compounds of the present invention may be demonstrated by this assay. The compounds of the following examples have activity in the aforementioned assay in the range of 0.05 nM to 10 $\mu$M. The activity of the present compounds may also be demonstrated by the assay disclosed by Lei, et al., *British J. Pharmacol.,* 105, 261–262 (1992).

The compounds of the present invention are useful in the prevention and treatment of a wide variety of clinical conditions which are characterized by the presence of an excess of tachykinin, in particular substance P, activity. These conditions may include disorders of the central nervous system such as anxiety, depression, psychosis and schizophrenia; epilepsy; neurodegenerative disorders such as dementia, including senile dementia of the Alzheimer type, Alzheimer's disease and Down's syndrome; demyelinating diseases such as multiple sclerosis (MS) and amyotrophic lateral sclerosis (ALS; Lou Gehrig's disease) and other neuropathological disorders such as peripheral neuropathy, for example AIDS related neuropathy, diabetic neuropathy, chemotherapy-induced neuropathy, and postherpetic and other neuralgias; small cell carcinomas such as small cell lung cancer; respiratory diseases, particularly those associated with excess mucus secretion, such as chronic obstructive airways disease, bronchopneumonia, chronic bronchitis, acute bronchitis, diffuse panbronchilitis, emphysema, cystic fibrosis, asthma, and bronchospasm; airways disease modulated by neurogenic inflammation; laryngopharhngitis; bronchiectasis; conoisis; whooping cough; pulmonary tuberculosis; diseases associated with decreased glandular secretions, including lacrimation, such as Sjogren's syndrome, hyperlipoproteinemias IV and V, hemochromatosis, sarcoidosis, or amyloidosis; iritis; inflammatory diseases such as inflammatory bowel disease, inflammatory intestinal disease, psoriasis, fibrositis, ocular inflammation, osteoarthritis, rheumatoid arthritis, pruritis, and sunburn; hepatitis; allergies such as eczema and rhinitis; hypersensitivity disorders such as poison ivy; ophthalmic diseases such as conjunctivitis, vernal conjunctivitis, dry eye syndrome, and the like; ophthalmic conditions associated with cell proliferation such as proliferative vitreoretinopathy; cutaneous diseases such as contact dermatitis, atopic dermatitis, urticaria, and other eczematoid dermatitis; hemodialysis-associated itching; lichen planus; oedema, such as oedema caused by thermal injury; addiction disorders such as alcoholism; mental disease, particularly anxiety and depression; stress related somatic disorders; reflex sympathetic dystrophy such as shoulder/hand syndrome; dysthymic disorders; tenalgia attended to hyperlipidemia; post-operative neuroma, particularly of mastectomy; vulvar vestibulitis; amniogenesis; adverse immunological reactions such as rejection of transplanted tissues and disorders related to immune enhancement or suppression, such as systemic lupus erythmatosus; gastrointestinal (I) disorders, including inflammatory disorders, and diseases of the GI tract, such as gastritis, gastroduodenal ulcers, gastric carcinomas, gastric lymphomas, disorders associated with the neuronal control of viscera such as ulcerative colitis, Crohn's disease, irritable bowel syndrome, nausea, and emesis, including acute, delayed, post-operative, late-phase, and anticipatory emesis, such as emesis or nausea induced by for example chemotherapy, radiation, surgery, migraine, toxins, such as metabolic or microbial toxins, viral or bacterial infections, pregnancy, vestibular disorder, motion, mechanical stimulation, gastrointestinal obstruction, reduced gastrointestinal motility, visceral pain, psychological stress or disturbance, high altitude, weightlessness, opioid analgesics, intoxication, resulting for example from consumption of alcohol, and variations in intercranial pressure, in particular, for example, drug or radiation induced emesis or post-operative nausea and vomiting; disorders of bladder function such as cystitis, bladder detrusor hyperreflexia, and incontinence; fibrosing and collagen diseases such as scleroderma and eosinophilic fascioliasis; disorders of blood flow caused by vasodilation and vasospastic diseases such as angina, migraine and Reynaud's disease; sleep disorders and sleep disturbances including: sleep problems associated with insomnia, hypersomnia, sleep apnea, narcolepsy, nocturnal myoclonus, REM sleep interruptions, jet-lag, shift workers' sleep disturbances, dysomnias, night terror, insomnias associated with depression or with emotional/mood disorders, as well as sleep walking and enuresis, as well as sleep disorders which accompany aging, conditions associated with circadian rhythmicity, mental and physical disorders associated with travel across time zones and with rotating shift-work schedules, or syndromes such as fibromyalgia which are manifested by non-restorative sleep and muscle pain or sleep apnea which is associated with respiratory disturbances during sleep; altering circadian rhythms; enhancing and improving the quality of sleep; and pain or nociception, for example, chronic pain or that attributable to or associated with any of the foregoing conditions especially the transmission of pain in migraine, or such as headache, toothache, cancerous pain, back pain, post-operative pain, neuritic pain symptoms, fibromyalgia and superficial pain on congelation, burn, herpes zoster or diabetic neuropathy. Hence, these compounds may be readily adapted to therapeutic use for the treatment of physiological disorders associated with an excessive stimulation of tachykinin receptors, especially neurokinin-1, and as neurokinin-1 antagonists in the control and/or treatment of any of the aforesaid clinical conditions in mammals, including humans.

The compounds of the present invention are also of value in the treatment of a combination of the above conditions, in particular in the treatment of combined post-operative pain and post-operative nausea and vomiting.

The compounds of the present invention are particularly useful in the treatment of nausea or emesis, including acute, delayed, post-operative, late-phase, and anticipatory emesis, such as emesis or nausea induced by for example chemotherapy, radiation, surgery, migraine, toxins, such as metabolic or microbial toxins, viral or bacterial infections, pregnancy, vestibular disorder, motion, mechanical stimulation, gastrointestinal obstruction, reduced gastrointestinal motility, visceral pain, psychological stress or disturbance, high altitude, weightlessness, opioid analgesics, intoxication, resulting for example from consumption of alcohol, and variations in intercranial pressure. Most especially, the compounds are of use in the treatment of emesis induced by antineoplastic (cytotoxic) agents including those routinely used in cancer chemotherapy.

Examples of such chemotherapeutic agents include alkylating agents, for example, nitrogen mustards, ethyleneimine compounds, alkyl sulfonates and other compounds with an alkylating action such as nitrosoureas, cisplatin, and dacarbazine; antimetabolites, for example, folic acid, purine or pyrimidine antagonists; mitotic inhibitors, for example, vinca alkaloids and derivatives of podophyilotoxin; and cytotoxic antibiotics.

Particular examples of chemotherapeutic agents are described, for example, by D. J. Stewart in "Nausea and Vomiting: Recent Research and Clinical Advances", Eds. J. Kucharczyk, et al, CRC Press Inc., Boca Raton, Fla., U.S.A. (1991), pages 177–203, especially page 188. Commonly used chemotherapeutic agents include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin, and chlorambucil[R. J. Gralla, et al., *Cancer Treatment Reports*, 68(1), 163–172 (1984)].

The compounds of the present invention are also of use in the treatment of emesis induced by radiation including radiation therapy such as in the treatment of cancer, or radiation sickness, and in the treatment of post-operative nausea and vomiting.

The compounds of the present invention are also of use in the prevention or treatment of disorders of the central nervous system such as anxiety, psychosis and schizophrenia; neurodegenerative disorders such as senile dementia of the Alzheimer type, Alzheimer's disease and Down's syndrome; respiratory diseases, particularly those associated with excess mucus secretion, such as chronic obstructive airways disease, broncho-pneumonia, chronic bronchitis, cystic fibrosis and asthma, and bronchospasm; inflammatory diseases such as inflammatory bowel disease, osteoarthritis, rheumatoid arthritis and fibromyalgia; adverse immunological reactions such as rejection of transplanted tissues; gastrointestinal (GI) disorders and diseases of the GI tract such as disorders associated with the neuronal control of viscera such as ulcerative colitis, Crohn's disease and incontinence; disorders of blood flow caused by vasodilation; and pain or nociception, for example, that attributable to or associated with any of the foregoing conditions or the transmission of pain in migraine (both prophylaxis and acute treatment).

The compounds of the present invention are also particularly useful in the treatment of pain or nociception and/or inflammation and disorders associated therewith such as, for example: neuropathy, such as diabetic or peripheral neuropathy and chemotherapy-induced neuropathy; postherpetic and other neuralgias; inflammatory bowel disease; acute and chronic pain, such as post-operative pain, cancer-related pain, neuritic pain syndromes, and fibromyalgia; asthma; osteoarthritis; rheumatoid arthritis; psoriasis; and especially migraine, either alone or in combination or co-administration with other antiinflammatory or analgesic agents.

The compounds of the present invention are also particularly useful in the treatment of diseases characterized by neurogenic mucus secretion, especially cystic fibrosis.

In the treatment of the clinical conditions noted above, the compounds of this invention may be utilized in compositions such as tablets, capsules or elixirs for oral administration, suppositories for rectal administration, sterile solutions or suspensions for parenteral or intramuscular administration, and the like.

The pharmaceutical compositions of this invention may be used in the form of a pharmaceutical preparation, for example, in solid, semisolid or liquid form, which contains one or more of the compounds of the present invention, as an active ingredient, in admixture with an organic or inorganic carrier or excipient suitable for external, enteral or parenteral applications. The active ingredient may be compounded, for example, with the usual non- toxic, pharmaceutically acceptable carriers for tablets, pellets, capsules, suppositories, solutions, emulsions, suspensions, and any other form suitable for use. The carriers which can be used are water, glucose, lactose, gum acacia, gelatin, mannitol, starch paste, magnesium trisilicate, talc, corn starch, keratin, colloidal silica, potato starch, urea and other carriers suitable for use in manufacturing preparations, in solid, semisolid, or liquid form, and in addition auxiliary, stabilizing, thickening and coloring agents and perfumes may be used. The active object compound is included in the pharmaceutical composition in an amount sufficient to produce the desired effect upon the process or condition of the disease.

The present invention is further directed to a method for the manufacture of a medicament for antagonizing the effect of substance P or another tachykinin at its receptor site or for the blockade of neurokinin-1 receptors or other tachykin receptors in a mammal comprising combining a compound of the present invention with a pharmaceutical carrier or diluent.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solution, suitably flavoured syrups, aqueous or oil suspensions, and emulsions with acceptable oils such as cottonseed oil, sesame oil, coconut oil or peanut oil, or with a solubilizing or emulsifying agent suitable for intravenous use, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulized by use of inert gases. Nebulized solutions may be breathed directly from the nebulizing device or the nebulizing device may be attached to a face mask, tent or intermittent positive pressure breathing machine. Solution, suspension or powder compositions may be administered, preferably orally or nasally, from devices which deliver the formulation in an appropriate manner.

For the treatment of the clinical conditions and diseases noted above, the compounds of this invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

For the treatment of certain conditions it may be desirable to employ a compound of the present invention in conjunction with another pharmacologically active agent(s). A compound of the present invention and the other pharmacologically active agent(s) may be administered to a patient simultaneously, sequentially or in combination. For example, the present compound may employed directly in combination with the other active agent(s), or it may be administered prior, concurrent or subsequent to the administration of the other active agent(s). In general, the currently available dosage forms of the known therapeutic agents for use in such combinations will be suitable.

For example, a compound of the present invention may be presented together with another therapeutic agent as a combined preparation for simultaneous, separate, or sequential use for the relief of emesis. Such combined preparations may be, for example, in the form of a twin pack. A preferred combination comprises a compound of the present invention with a chemotherapeutic agent such as an alkylating agent, antimetabolite, mitotic inhibitor, or cytotoxic antibiotic, as described above.

Similarly, for the treatment or prevention of pain or inflammatory diseases, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, aspirin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levodesoxy-ephedrine; an antiitussive such as codeine, hydrocodone, caramiphen, carbetapentane, or dextramethorphan; a diuretic; and a sedating or non-sedating antihistamine.

Also, for the treatment of respiratory diseases, such as asthma, a compound of the present invention may be used in conjunction with a bronchodilator, such as a $\beta_2$-adrenergic receptor agonist or a tachykinin antagonist which acts at neurokinin-2 receptors. Suitable β2-adrenergic receptor agonist include: Bambuterol (U.S. Pat. No. 4,419,364 issued to Draco on Dec. 16, 1983); Bitolterol mesylate (U.S. Pat. No. 4,138,581 issued to Sterling Feb. 6, 1979); Brosaterol (U.S. Pat. No. 4,276,299 issued to Zambon Jun. 30, 1981 and U.S. Pat. No. 4,520,200 issued to Zambon May 28, 1985); Carbuterol (U.S. Pat. No. 3,763,232 issued to Smith Kline Oct. 21, 1973); Clenbuterol (U.S. Pat. No. 3,536,712 issued to Boehringer Ingelheim Oct. 27, 1970); Cimaterol (U.S. Pat. No. 4,407,819 issued to American Cyanamid Oct. 4, 1983); Docarpamine (U.S. Pat. No. 4,228,183 issued to Tanabe Oct. 14, 1980); Dopexamine (U.S. Pat. No. 4,645,768 issued to Fisons Feb. 24, 1987); Formoterol (U.S. Pat. No. 3,994,974 issued to Yamanouchi Nov. 30, 1976); Mabuterol (U.S. Pat. No. 4,119,710 issued to Boehringer Ingelheim Oct. 10, 1978); Pirbuterol hydrochloride (U.S. Pat. No. 3,700,681 issued to Pfizer Oct. 24, 1972); Procaterol hydrochloride (U.S. Pat. No. 4,026,897 issued to Otsuka May 31, 1977); Ritodrine hydrochloride (U.S. Pat. No. 3,410,944 issued to North American Philips Nov. 12, 1968); or Salmeterol (U.S. Pat. No. 4,992,474 issued to Glaxo Feb. 21, 1991 and U.S. Pat. No. 5,091,422 issued to Glaxo Feb. 25, 1992).

Also, for the treatment of conditions that require antagonism of both neurokinin-1 and neurokinin-2, including disorders associated with bronchoconstriction and/or plasma extravasation in airways, such as asthma, chronic bronchitis, airways disease, or cystic fibrosis; neuropathy, such as diabetic or peripheral neuropathy and chemotherapy-induced neuropathy; osteoarthritis; rheumatoid arthritis; and migraine, a compound of the present invention may be used in conjunction with a tachykinin antagonist which acts at neurokinin-2 receptors, or with tachykinin receptor antagonist which acts at both neurokinin-1 and neurokinin-2 receptors.

Likewise, a compound of the present invention may be employed with a leucotriene antagonist, such a leucotriene $D_4$ antagonist, exemplfied by those disclosed in Patent Pub. EP 0,480,717, published Apr. 15, 1992; Patent Pub. EP 0 604,114, published June 1994; U.S. Pat. No. 5,270,324, issued Dec. 14, 1993; and U.S. Pat. No. 4,859,692, issued Aug. 22, 1989. This combination is particularly useful in the treatment of respiratory diseases such as asthma, chronic bronchitis and cough.

A compound of the present invention further may be used in conjunction with a corticosteroid such as Dexamethasone, Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712.

Similarly, for the prevention or treatment of emesis a compound of the present invention may be used in conjunction with other anti-emetic agents, especially $5HT_3$ receptor antagonists, such as ondansetron, granisetron, tropisetron, decadron, and zatisetron, or $GABA_B$ receptor agonists, such as baclofen. Likewise, for the prevention or treatment of migraine a compound of the present invention may be used in conjunction with other anti-migraine agents, such as ergotamines or $5HT_1$ agonists, especially sumatriptan.

Likewise, for the treatment of behavioral hyperalgesia, a compound of the present invention may be used in conjunction with an antagonist of N-methyl D-aspartate (NMDA), such as dizocilpine. For the prevention or treatment of inflammatory conditions in the lower urinary tract, especially cystitis, a compound of the present invention may be used in conjunction with an antiinflammatory agent, such as a bradykinin receptor antagonist. The compound of the present invention and the other pharmacologically active agent may be administered to a patient simultaneously, sequentially or in combination.

The compounds of this invention may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician.

In the treatment of a condition associated with an excess of tachykinins, an appropriate dosage level will generally be about 0.001 to 50 mg per kg patient body weight per day which may be administered in single or multiple doses. Preferably, the dosage level will be about 0.01 to about 25 mg/kg per day; more preferably about 0.05 to about 10 mg/kg per day. For example, in the treatment of conditions involving the neurotransmission of pain sensations, a suitable dosage level is about 0.001 to 25 mg/kg per day, preferably about 0.05 to 10 mg/kg per day, and especially about 0.1 to 5 mg/kg per day. A compound may be administered on a regimen of multiple times per day, such as 1 to 4 times per day, preferably once or twice per day. In the treatment of emesis using an injectable formulation, a suitable dosage level is about 0.001 to 10 mg/kg per day, preferably about 0.005 to 5 mg/kg per day, and especially about 0.05 to 5 mg/kg per day. A compound may be administered on a regimen of multiple times per day, such as 1 to 4 times per day, preferably once or twice per day.

The following examples are provided for the purpose of further illustration only and are not intended to be limitations on the disclosed invention.

EXAMPLE 1

Methyl trans-(±)-2-phenylcyclopentan-3-one-1-carboxylate

Step A: γ-δ-Dicarboxy-δ-phenyl-n-valeric acid

A mixture of 47 g of benzaldehyde and 50 g of ethyl cyanoacetate in 200 mL of absolute ethanol was treated with 2 mL of piperidine and the reaction was gently warmed. After the initial exothermic reaction had subsided, the reaction was heated to 60° C. (internal temperature) and then allowed to cool to room temperature. After 1 h, 22 g of powdered sodium cyanide was added in portions over 25 min and a mild exotherm ensued. The reaction was heated to an internal temperature of 80° C. and then allowed to cool to 35° C. before slow addition of 60 g of ethyl β-chloropropionate over 10 min. After heating in an oil bath at 80° C. for 5 h, the reaction was cooled and filtered to remove the precipitated sodium chloride. The filtrate was concentrated and to the residue was added 250 mL of water and 500 mL of concentrated HCl. The mixture was heated at reflux for 48 h and, while still hot, was treated with charcoal and filtered through Celite to remove some insoluble tarry material. On cooling, 25.8 g of the title compound as a pale yellow solid was obtained after filtration and air drying. The filtrate was extracted with EtOAc, washed with brine, dried with sodium sulfate and evaporated to provide an additional 32.8 g of less pure product which could be used directly.

Step B: Trimethyl γ-δ-dicarboxy-δ-phenyl-n-valerate.

Into a solution of 21.2 g of the above triacid dissolved in 200 mL of methanol was bubbled 48.6 g of HCl gas. After heating at reflux overnight, the cooled reaction was concentrated and diluted with toluene. Most of the aqueous bottom phase was removed via pipette and the toluene was evaporated. The residue was taken up in 200 mL of methanol and resaturated with HCl gas (53.5 g). After heating for another 20 h, the reaction was concentrated and the residue was dissolved in ether and washed with water, saturated NaHCO$_3$, and brine, then dried with sodium sulfate, and evaporated to provide 25.7 g of an oil which crystallized in the freezer. Trituration with 5% EtOAc in hexanes and filtration gave 18.4 g of the title triester as a white solid.

Step C: trans-(±)-2-Phenylcyclopentan-3-one-1-carboxylic acid

To 50 mL of anhydrous methanol was added a solution of 26 mL of 25% by wt sodium methoxide in methanol followed by 18.4 g of the above triester dissolved in 25 mL of methanol. After heating at reflux for 5.5 h, the solvent was evaporated and the residue was dissolved in 150 mL of concentrated HCl and 75 mL of water and heated at reflux overnight. The reaction, while still hot, was treated with charcoal and filtered through Celite. After cooling, 7.65 g of title compound was obtained as a white solid after filtration and air drying. An additional 4.76 g of triacid was recovered by extraction of the filtrate with EtOAc.

Step D: Methyl trans-(±)-2-phenylcyclopentan-3-one-1-carboxylate

A solution of 4.17 g of above acid in 200 mL of methanol was saturated with HCl gas and stirred overnight. After cooling, the reaction was concentrated to a wet solid. This was taken up in EtOAc and washed with water, saturated NaHCO$_3$ solution, and brine, then dried with sodium sulfate and evaporated to furnish 4.4 g of the title product as a white solid. NMR (CDCl$_3$): δ 2.0–2.15 (m, 1H), 2.3–2.5 (m, 2H), 2.62 (br dd, 1H), 3.25 (dt, 1H), 3.65 (s, 3H), 3.70 (br d, 1H), 7.12 (m, 2H), 7.24 (m, 1H), 7.32 (m, 2H).

EXAMPLE 2

Methyl 3-(SR)-(hydroxy)-2-(SR)-phenylcyclopentane-1-(SR)carboxylate (Racemic 2, 3-cis isomer) and methyl 3-(SR)-hydroxy)2-(RS)-phenylcyclopentane-1-(RS)-carboxylate (Racemic 2, 3-trans isomer)

Method A

To a solution of 4.43 g of methyl trans-(±)-2-phenylcyclopentan-3-one-1-carboxylate from Example 1, Step D in 65 mL of absolute methanol cooled in an ice/ethanol bath was added 807 mg of NaBH$_4$ in portions. After 1 h, the reaction was quenched with aqueous NH$_4$Cl. The solvent was evaporated and the residual oil was partitioned between EtOAc and water. The organic layer was washed with brine, dried with sodium sulfate and purified by Prep LC eluting first with 20% EtOAc in hexanes to provide 1.18 g of the higher R$_f$ 2,3-cis isomer. NMR (CDCl$_3$): δ 1.8–2.0 (m, 2H), 2.05–2.2 (m,1H), 2.3–2.4 (m,1H), 3.3–3.45 (m, 2H), 3.59 (s, 3H), 4.30 (m, 1H), 7.2–7.35 (m, 5H). Further elution with 40% EtOAc in hexanes provided 3.90 g of the lower R$_f$ 2,3-trans isomer. NMR (CDCl$_3$): δ 1.82 (m, 1H), 2.10 (m, 3H), 2.95 (q, 1H), 3.22 (dd, 1H), 3.60 (s, 3H), 4.20 (q, 1H), 7.22 (m, 3H), 7.31 (m, 2H).

Method B

To a solution of 100 mg of methyl trans-(±)-2-phenylcyclopentan-3-one-1-carboxylate from Example 1, Step D in 5 mL of dry THF under $N_2$ and cooled in a dry ice/acetone bath was added dropwise 0.55 mL of 1M L-Selectride in THF. After 1 h, the reaction was quenched with dilute HCl. The mixture was extracted twice with ether and the organic layers were washed with brine, combined, dried with sodium sulfate and evaporated. The residue was purified by flash chromatography eluting with 20% EtOAc in hexanes to give only the higher $R_f$ 2,3-cis product isomer. The NMR was same as the higher $R_f$ isomer in Method A.

EXAMPLE 3

Methyl trans-(±)-2-(4-fluorophenyl)cyclopentan-3-one-1-carboxylate

Using essentially the same procedures as described in Example 1 but starting with 4-fluorobenzaldehyde, the title compound was prepared. NMR ($CD_3OD$): δ 2.0–2.2 (m, 1H), 2.3–2.5 (m, 2H), 2.56–2.76 (m, 1H), 3.1–3.3 (m, 1H), 3.68 (s, 3H), 3.72 (br d, 1H), 6.98–7.16 (m, 4H).

EXAMPLE 4

Methyl 3-(SR)-(hydroxy)-2-(SR)-(4-fluorophenyl)cyclopentane-1-(SR)-carboxylate (Racemic 2,3-cis isomer) and methyl 3-(SR)-(hydroxy)-2-(RS)-(4-fluorophenyl)cyclopentane-1-(RS)-carboxylate (Racemic 2.3-transisomer)

Using essentially the same procedures as described in Example 2 but starting with the 4-fluorophenyl derivative, the title compounds were prepared. Higher $R_f$ isomer. NMR ($CDCl_3$): δ 1.86–2.0 (m, 2H), 2.1–2.2 (m, 1H), 2.29–2.36 (m, 1H), 3.28–3.4 (m, 2H), 3.6 (s, 3H), 4.28 (m, 1H), 7.0 (m, 2H), 7.24 (m, 2H). Lower $R_f$ isomer. NMR ($CDCl_3$): δ 1.80–1.86 (m, 1H), 2.06–2.17 (m, 3H), 2.87 (q, 1H), 3.19 (dd, 1H), 3.6 (s, 3H), 4.14 (q, 1H), 6.99 (m, 2H) 7.18 (m, 2H).

EXAMPLE 5

Methyl 2-(S)-(4-fluorophenyl)cyclopentan-3-one-1-(S)-carboxylate

Step A: (R)-α-Methylbenzylammonium 3-(S)-(hydroxy)-2-(R)-(4-fluorophenyl)cyclopentane-1-(R)-carboxylate To a solution of 3.0 gm of the lower $R_f$ trans alcohol of Example 4 in 20 mL of methanol was added 13 mL of 5N NaOH. The reaction was stirred at room temperature for 20 h and then concentrated in vacuo. The residue was taken up in water, acidified with 2N HCl, and extracted with three portions of EtOAc. The organic layers were washed with a portion of brine, combined, dried over sodium sulfate and evaporated to afford the crude acid as a white solid. To a warm solution of 2.3 gm of the above crude acid in 35 mL of isopropanol was added 930 mg (0.75 eq) of (R)-(±)-α-methylbenzyl amine. The solution was seeded and aged at room temperature for 4 hr, the solid was filtered, washed with isopropanol and then ether, and air dried to give 1.8 gm white solid. Recrystallization from another 30 mL of isopropanol afforded 1.1 gm of the title compound as a white solid. $[\alpha]_D$ (EtOH)=−11.3 (c=0.37).

Step B: (S)-(−)-α-Methylbenzylammonium 3-(R)-(hydroxy)-2-(S)-(4-fluorophenyl)cyclopentane-1-(S)-carboxylate The mother liquors from Step A were combined and concentrated. The residue was taken up in water and acidified with 2N HCl and was extracted with 3 portions of EtOAc. The organic layers were washed with a portion of brine, combined, dried sodium sulfate and evaporated. The residue was dissolved in 25 mL of isopropanol and 0.75 gm (0.95 eq) of (S)-(−)-α-methylbenzyl amine was added. The solution was seeded and left at room temperature overnight after which the solid was filtered, washed with isopropanol and then ether, and air dried to give 1.56 gm white solid. Recrystallization from another 30 mL of isopropanol afforded 1.3 gm of the title compound as a white solid.$[\alpha]_D$ (EtOH)=+12.5 (c=0.44).

Step C: 3-(S)-(Hydroxy)-2-(R)-(4-fluorophenyl)cyclopentane-1-(R)-carboxylic acid The salt from Step A was dissolved in water and acidified with 2N HCl and was extracted with 3 portions of EtOAc. The organic layers were washed with a portion of brine, combined, dried over sodium sulfate and evaporated to give a white solid. $[\alpha]_D$ (EtOH)=−19.9 (c=0.675).

Step D: 3-(R)-(Hydroxy)-2-(S)-(4-fluorophenyl)cyclopentane-1-(S)-carboxylic acid The salt from Step B was dissolved in water and acidified with 2N HCl and was extracted with 3 portions of EtOAc. The organic layers were washed with a portion of brine, combined, dried over sodium sulfate and evaporated to give a white solid. $[\alpha]D$ (EtOH)=+21.6 (c=2.55).

Step E: Methyl 3-(S)-(hydroxy)-2-(R)-(4-fluorophenyl)cyclopentane-1-(R)-carboxylate Method A The salt from Step A was converted to the free acid as in Step C and dissolved in ether and a solution of diazomethane was added portionwise until the yellow color persisted. The excess diazomethane was quenched with acetic acid and the volatiles were removed in vacuo. The residue was purified by flash chromatography eluting with 20 to 40% EtOAc in hexanes to obtain 800 mg of title compound as an oil. $[\alpha]_D$ (EtOH)=−30 (c=0.390).

Method B (R)-salt (8.7 gm) obtained as in Step A was converted to the free acid as in Step C to give 5.7 gm of crude acid.$[\alpha]_D$ (EtOH)=−19.9 (c=0.675). This was taken up in 200 mL of methanol and saturated with HCl gas. The solution was stirred at room temperature for 16 h and then concentrated in vacuo. The residue was dissolved in water and extracted twice with ether. The organic layers were washed with a portion of brine, combined, dried over sodium sulfate and evaporated to give 6.0 gm of oil.$[\alpha]_D$ (EtOH)=−30.5 (c=0.98).

Step F: Methyl 3-(R)-(hydroxy)-2-(S)-(4-fluorophenyl)cyclopentane-1-(S)-carboxylate Using essentially the same procedures as in Step E, the acid from the (S)-salt (7.50 gm) afforded 4.92 gm of the title compound as an oil.$[\alpha]_D$ (EtOH)=+37 (c=1.05).

Step G: Methyl 2-(S)-(4-fluorophenyl)cyclopentan-3-one-1-(S)-carboxylate

Method A

To a solution of 3.35 g of non-racemic alcohol obtained in Step F was added dropwise 5:8 mL of 8N Jones reagent over 1 min. After stirring at room temperature for 30 min, the reaction was concentrated in vacuo. The residue was diluted with water and extracted twice with ether. The organic layers were washed with a portion of brine, combined, dried over sodium sulfate and evaporated to give 0.55 gm of oil. Flash chromatography with 20 to 40% EtOAc in hexanes afforded 2.63 gm of title compound as a white solid. $[\alpha]_D$ (EtOH)=+25 (c=0.62).

Method B

A solution of 20.25 mL of oxalyl chloride in 200 mL of methylene chloride was cooled to <−70° C. in a dry ice/ acetone bath. A solution of 32 mL of DMSO in 50 mL of methylene chloride was added dropwise while maintaining the temperature at <−60° C. After a further 15 min of stirring, a solution of 21.75 g of non-racemic alcohol obtained as in Step F in 100 mL of methylene chloride was added dropwise while maintaining the temperature at <−60° C. After a further 60 min of stirring, a solution of 127 mL of DIPEA in 100 mL of methylene chloride was added dropwise while maintaining the temperature at <−60° C. The ice bath was then removed and the reaction was allowed to warm to 0° C. over 1 h. The reaction was then slowly added (some gas evolution) to a mixture of 500 mL of ice water and 250 mL of 2N HCl. The layers were separated and the aqueous layer was extracted with a second portion of methylene chloride. The organic layers were each washed with brine, dried over sodium sulfate, combined and evaporated. The residue was purified by flash chromatography using a gradient of 20 to 30% ethyl acetate/hexanes as eluent. Evaporation of the product fractions afforded 21.7 g of title product as a white solid.[α]$_D$ (EtOH)=+27 (c=0.84).

EXAMPLE 6

Methyl[3-(SR),5-(RS),6-(SR),7-(SR)]-6-(4-fluorophenyl)-3-(2-methoxy-5-((5-trifluoromethyl)tetrazol-1-yl)phenyl)-1-oxaspiro[4.4]nonane-7-carboxylate Step A: Methyl[1-(RS),2-(SR),3-(SR)]-2-(4-fluorophenyl)-1-(2-(acetoxymethyl)-prop-2-enyl)-1-(hydroxy)cyclopentane-3-carboxylate and methyl[1-(SR),2-(SR),3-(SR)]-2-(4-fluorophenyl)-1-(2-(acetoxymethylene)-prop-2-enyl)-1-hydroxy)cyclopentane-3-carboxylate A solution of 1.85 g (7.8 mmol) of methyl 2-(RS)-(4-fluorophenyl)cyclopentanone-3-(RS)-carboxylate (from Example 3) and 3.15 g (10.8 mmol) of 3-acetoxy-2[(trimethylstannyl)methyl]-1-propene in 8 mL of $CH_2Cl_2$ at −78° C. was treated with 1.60 mL (13.0 mmol) of boron trifluoride etherate. The reaction was warmed to −10° C. and was stirred for 20 h. The reaction was quenched with 40 mL of sat'd $NH_4Cl$; the resulting mixture was partitioned between 250 mL of ether and 150 mL of $H_2O$ and the layers were separated. The organic layer was washed with 200 mL sat'd KF, 200 mL sat'd NaCl, dried over $MgSO_4$ and concentrated in vacuo. Flash chromatography on 150 g of silica gel using 5:1 v/v hexanes/ether afforded 1.61 g (59%) of methyl [1-(RS),2-(SR),3-(SR)]-2-(4-fluorophenyl)-1-(2-(acetoxymethyl)-prop-2-enyl)-1-(hydroxy)cyclopentane-3-carboxylate as an oil. The eluant was changed to 1:1 v/v hexanes/ether to afford 0.95 g (33%) of methyl [1-(SR),2-(SR),3-(SR)]-2-(4-fluorophenyl)-1-(2-(acetoxymethyl)-prop-2-enyl)-1-(hydroxy)cyclopentane-3-carboxylate as an oil. For methyl[1-(RS),2-(SR),3-(SR)]-2-(4-fluorophenyl)-1-(2-(acetoxymethyl)-prop-2-enyl)-1-(hydroxy)cyclopentane-3-carboxylate: $^1$H NMR (500 MHz, CDCl$_3$): δ 1.86 (s, 1H), 1.89–2.02 (m, 2H), 2.01 (s, 3H), 2.07 (d, J=14.0, 1H), 2.23 (d, J=14.0), 2.28–2.32 (m, 2H), 3.12 (d, J=11.5, 1H), 3.38 (dt, J=6.5, 11.5, 1H), 3.56 (s, 3H), 4.51 (q, J=13.5, 2H), 4.98 (s, 1H), 5.13 (s, 1H), 7.02 (app t, J=9.0), 7.26–7.29 (m, 2H). HPLC: Chiralpak AD® 4.6×250 mm column, 80:20 v/v hexanes/iPrOH, 0.5 mL/min, 220 nm. Retention times: 1-(R),2-(S),3-(S) enantiomer, 11.9 min; 1-(S),2-(R),3-(R) enantiomer, 19.3 min. For methyl[1-(SR),2-(SR),3-(SR)]-2-(4-fluorophenyl)-1-(2-(acetoxymethyl)-prop-2-enyl)-1-(hydroxy)cyclopentane-3-carboxylate: $^1$H NMR (500 MHz, CDCl$_3$): δ 1.75 (d, J=14.5, 1H), 1.84 (d, J=14.5, 1H), 1.83–2.00 (m, 2H), 2.03 (s, 3H), 2.13–2.23 (m, 2H), 2.79 (s, 1H), 3.15 (app q, J=9.0, 1H), 3.49 (d, J=8.0, 1H), 3.65 (s, 3H), 4.53 (s, 2H), 4.89 (s, 1H), 5. 11 (s, 1H), 7.01 (app t, J=8.0, 2H), 7.16–7.19 (m, 2H).

Step B: Methyl[5-(RS),6-(SR),7-(SR)]-6-(4-fluorophenyl)-3-(methylene)-1-oxaspiro[4.4]nonane-7-carboxylate A solution of 1.40 g (4.0 mmol) of methyl[1-(RS),2-(SR),3-(SR)]-2-(4-fluorophenyl)-1-(2-(acetoxymethyl)-prop-2-enyl)-1-(hydroxy)cyclopentane-3-carboxylate (from Example 6, Step A) in 25 mL of THF at −10° C. was treated with 4.0 mL of 1.0M lithium bis(trimethylsilyl)amide solution in THF. The resulting solution was stirred cold for 5 min, then treated with 8.0 mL of 0.5 mL $ZnCl_2$ solution in THF. The cooling bath was removed and the reaction mixture was stirred at rt for 35 min. Tetrakis(triphenylphosphine)palladium(0) (230 mg, 0.2 mmol) was added and the resulting mixture was heated at reflux for 20 h. The reaction was cooled, quenched with 50 mL of sat'd $NH_4Cl$, partitioned between 200 mL of ether and 50 mL of $H_2O$ and the layers were separated. The organic layer was washed with 50 mL of sat'd $NaHCO_3$, 50 mL of sat'd NaCl, dried over $MgSO_4$ and concentrated in vacuo. Flash chromatography on 50 g of silica gel using 15:1 v/v hexanes/ether as the eluant afforded 1.03 g (88%) of the title compound as an oil. $^1$H NMR (500 MHz, CDCl$_3$): δ 1.84–1.95 (m, 2H), 2.04–2.09 (m, 1H), 2.22–2.31 (m, 1H), 2.47 (s, 2H), 3.17 (d, J=11.5, 1H), 3.31–3.36 (m, 1H), 3.56 (s, 3H), 3.93 (d, J=13.0, 1H), 4.19 (d, J =13.0, 1H), 4.67–4.69 (m, 1H), 4.78–4.80 (m, 1H), 6.95 (app t, J=8.5, 2H), 7.26–7.30 (m, 2H). Mass Spectrum (NH$_3$—CI): m/z 308 (M+NH$_4^+$, 100%).

Step C: Methyl[5-(RS),6-(SR),7-(SR)]-6-(4-fluorophenyl)-3-(oxo)-1-oxaspiro[4.4]nonane-7-carboxylate A solution of 1.10 g (3.8 mmol) of methyl[5-(RS), 6-(SR), 7-(SR)]-6-(4-fluorophenyl)-3-(methylene)-1-oxaspiro-[4.4]nonane-7-carboxylate (from Example 6, Step B) in 15 mL of 2:1 v/v acetone/$H_2O$ was treated with 5.0 mL of 2.5% $OsO_4$ solution in t-butanol and stirred at rt for 5 min. The resulting dark brown solution was treated with 700 mg (6.0 mmol) of 4-methylmorpholine N-oxide and stirred at rt for 2 h. The reaction was quenched with 2.0 g of sodium bisulfite; the quenched mixture was partitioned between 200 mL of $CH_2Cl_2$ and 100 mL of $H_2O$ and the layers were separated. The organic layer was dried over $MgSO_4$. The aqueous layer was extracted with 200 mL of $CH_2Cl_2$; the extract was dried and combined with the original organic layer. The combined organic layers were concentrated in vacuo.

The crude diol was dissolved in 40 mL of 4:1 v/v THF/$H_2O$; the resulting solution was treated with 1.50 g (7.0 mmol) of sodium periodate and stirred for 20 h at rt. The reaction mixture was partitioned between 250 mL of ether and 100 mL of $H_2O$ and the layers were separated. The organic layer was dried over $MgSO_4$. The aqueous layer was extracted with 250 mL of ether; the extract was dried and combined with the original organic layer. The combined organics were concentrated in vacuo. Flash chromatography on 40 g of silica gel using 3:1 v/v hexanes/ether afforded 1.02 g (92%) of the title compound as an oil. $^1$H NMR (500 MHz, CDCl$_3$): δ 1.98–2.02 (m, 2H), 2.20–2.25 (m, 1H), 2.35–2.39 (m, 1H), 2.46 (s, 2H), 3.26 (d, J=11.0), 3.42–3.50 (m, 1H), 3.54 (d, J=17.5, 1H), 3.58 (s, 3H), 3.85 (d, J=17.5, 1H), 6.99 (app t, J=9.0), 7.26–7.32 (m, 2H). Mass Spectrum (NH$_3$—CI): δ 310 (M+NH$_4^+$, 100%).

Step D: Methyl[5-(RS),6-(SR),7-(SR)]-6-(4-fluorophenyl)-3-(trifluoromethylsulfonyl-oxy)-1-oxaspiro[4.4]non-3-ene-7-carboxylate A solution of 773 mg (2.6 mmol) of methyl[5-(RS), 6-(SR),7-(SR)]-6-(4-fluorophenyl)-3-(oxo)-1-oxaspiro[4.4] nonane-7-carboxylate (from Example 6, Step C) in 25 mL of THF at −78° C. was treated with 5.80 mL of sodium bis(trimethylsilyl)amide solution in THF and stirred cold for 30 min. The resulting solution was treated with 1.40 g (3.6 mmol) of 5-chloro-2-N-bis(trifluoromethylsulfonyl)pyridine in one portion as a solid. The reaction was warmed to −10° C. and stirred for 45 min. The reaction was quenched with 25 mL of 2.0N HCl and partitioned between 150 mL of ether and 50 mL of H$_2$O and the layers were separated. The organic layer was washed with 50 mL of sat'd NaHCO$_3$, 50 mL of sat'd NaCl, dried over MgSO$_4$ and concentrated in vacuo. Flash chromatography on 50 g of silica gel using 10:1 v/v hexanes /ether as the eluant afforded 857 mg (77%) of the title compound as a foam. $^1$H NMR (500 MHz, CDCl$_3$): δ 1.93–2.00 (m, 1H), 2.07–2.21 (m, 2H), 2.30–2.37 (m, 1H), 3.25 (d, J=11.5, 1H), 3.37–3.43 (m, 1H), 3.56 (s, 3H), 3.77 (dd, J=12.5, 2.0, 1H), 4.35 (dd, J=12.5, 2.0, 1H), 5.66 (t, J=2.0, 1H), 6.96 (app t, J=9.0, 2H), 7.23–7.26 (m, 2H). Mass Spectrum (NH$_3$—CI) m/z 442 (M+NH$_4^+$, 100%).

Step E: Methyl[5-(RS),6-(SR),7-(SR)]-6-(4-fluorophenyl)-3-(trimethylstannyl)-1-oxaspiro[4.4]non-3-ene-7-carboxylate A mixture of 855 mg (2.0 mmol) of methyl[5-(RS),6-(SR),7-(SR)]-6-(4-fluorophenyl)-3-(trifluoromethylsulfonyloxy)-1-oxaspiro[4,4]non-3-ene-7-carboxylate (from Example 6, Step D), 1.50 g (4.6 mmol) of hexamethylditin, 2.75 mg (6.5 mmol) of LiCl and 45 mg (0.04 mmol) of tetrakis(triphenylphosphine)palladium(0) in 10 mL of dioxane was heated at 100° C. for 1 h. The reaction mixture was cooled, partitioned between 100 mL of ether and 50 mL of 50% sat'd NaHCO$_3$ and the layers were separated. The organic layer was washed with 50 mL of sat'd NaCl, dried over MgSO$_4$ and concentrated in vacuo. Flash chromatography on 50 g of silica gel using 15:1 v/v hexanes/ether as the eluant afforded 717 mg (81%) of the title compound as an oil. $^1$H NMR (500 MHz, CDCl$_3$): δ 0.06 (t, J=27.5, 9H), 1.91–2.00 (m, 2H), 2.14–2.21 (m, 1H), 2.27–2.35 (m, 1H), 3.14 (d, J=11.5, 1H), 3.40–3.45 (m, 1H), 3.57 (s, 3H), 3.62 (dd, J=12.5, 2.0, 1H), 4.43 (dd, J=12.5, 2.0, 1H), 5.62–5.70 (m, 1H), 6.89 (app t, J=8.5, 2H), 7.18–7.21 (m, 2H).

Step F: Methyl[5-(RS),6-(SR),7-(SR)]-6-(4-fluorophenyl)-3-(2-methoxy-5-((5-trifluoromethyl)tetrazol-1-yl)phenyl)-1-oxaspiro[4.4]non-3-ene-7-carboxylate a) 2-Bromo-4-aminoanisole A mixture of 670 mg (2.9 mmol) of 2-bromo-4-nitroanisole and 1.20 g (21.1. mmol) of iron powder in 10 mL of 1:1 v/v HOAc/H$_2$O was heated at 80° C. for 1.5 h. The mixture was cooled and filtered onto a pad of Celite. The flask and filtered solids were rinsed with 100 mL of EtOAc and 100 mL of H$_2$O. The filtrate was transferred to a separatory funnel and the layers were separated. The organic layer was washed with 50 mL of sat'd NaHCO$_3$, 50 mL sat'd NaCl, dried over MgSO$_4$ and concentrated in vacuo. Flash chromatography on 25 g of silica gel using 3:2 v/v hexanes/ether as the eluant afforded 504 mg (86%) of the title compound as an oil. $^1$H NMR (500 MHz, CDCl3): δ 3.54 (br s, 2H), 3.81 (s, 3H), 6.60 (dd, J=8.5, 2.5, 1H), 6.74 (d, J=8.5, 1H), 6.93 (d, J=2.5, 1H).

b) 2-Bromo-4-(trifluoroacetamido)anisole

A solution of 500 mg (2.5 mmol) of 2-bromo-4-aminoanisole and 1.31 mL (7.5 mmol) of DIEA in 10 mL of CH$_2$Cl$_2$ at 0° C. was treated with 0.71 mL (5.0 mmol) of trifluoroacetic anhydride. The cooling bath was removed and the resulting mixture was stirred at rt for 20 h. The reaction mixture was partitioned between 100 mL of ether and 50 mL of H$_2$O and the layers were separated. The organic layer was washed with 50 mL of 2.0N HCl, 50 mL of sat'd NaHCO$_3$, 50 mL of sat'd NaCl, dried over MgSO$_4$ and concentrated in vacuo. Flash chromatography on 30 g of silica gel using 4:1 v/v hexanes/ether as the eluant afforded 709 mg (95%) of the product as an oil. $^1$H NMR (400 MHz, CDCl$_3$): δ 3.91 (s, 3H), 6.91 (d, J=8.8), 7.51 (dd, J=8.8, 2.4, 1H), 7.78 (d, J=2.4, 1H).

c) 2-Bromo-4-(5-(trifluoromethyl)tetrazol-1-yl)anisole

A mixture of 705 mg (2.4 mmol) of 2-bromo-4-(trifluoroacetamido)anisole and 625 mg (2.4 mmol) of triphenylphosphine in 25 mL of CCl4 was heated at reflux. After 4 h, a second 625 mg portion of triphenylphosphine was added and heating was continued for 16 h. The reaction mixture was cooled and concentrated in vacuo. The residue was dissolved in 15 mL of DMF, treated with 650 mg (10.0 mmol) of NaN$_3$ and stirred at rt. After 1.5 h, the reaction mixture was concentrated in vacuo and the residue was partitioned between 200 mL of ether and 100 mL of H$_2$O. The layers were separated; the organic layer was washed with 2×100 mL of H$_2$O, dried over MgSO$_4$ and concentrated in vacuo. Flash chromatography on 40 g of silica gel using 4:1 v/v hexanes/ether as the eluant afforded 700 mg compound as an oil. $^1$H NMR (500 MHz, CDCl$_3$): δ 4.01 (s, 3H), 7.07 (d, J=8.5, 1H), 7.43 (dd, J=8.5, 2.5), 7.71 (d, J=2.5, 1H).

d) Methyl[5-(RS),6-(SR),7-(SR)]-6-(4-fluorophenyl)-3-(2-methoxy-5-((5-trifluoromethyl)tetrazol-1-yl)phenyl)-1-oxaspiro[4.4]non-3-ene-7-carboxylate A mixture of 107 mg (0.24 mmol) of methyl[5-(RS),6-(SR),7-(SR)]-6-(4-fluorophenyl)-3-(trimethylstannyl)-1-oxaspiro[4,4]non-3-ene-7-carboxylate (from Example 6, Step E), 115 mg (0.36 mmol) of 2-bromo-4-(5-(trifluoromethyl)tetrazol-1-yl)anisole, 30 mg (0.71 mmol) of LiCl and 6 mg (0.0052 mmol) of tetrakis(triphenylphosphine)palladium(0) in 3 mL of dioxane was heated at 100° C. under nitrogen for 1.5 h. Alternatively, (Ph$_3$P)$_2$PdCl$_2$ in toluene can be used in place of (Ph$_3$P)$_4$Pd and LiCl in dioxane. The reaction mixture was cooled and partitioned between 40 mL of ether and 20 mL of H2O and the layers were separated. The organic layer was washed with 20 mL of sat'd KF, 20 mL of sat'd NaCl, dried over MgSO$_4$ and concentrated in vacuo. Flash chromatography on 12 g of silica gel using 10:1 v/v hexanes/EtOAc as the eluant afforded 81 mg (65%) of the title compound as an oil. $^1$H NMR (500 MHz, CDCl$_3$): δ 1.88–2.03 (m, 1H), 2.07–2.13 (m, 1H), 2.23–2.30 (m, 1H), 2.33–2.39 (m, 1H), 3.32 (d, 1H), 3.40–3.48 (m, 1H), 3.59 (s, 3H), 3.94 (s, 3H), 4.07 (dd, J=12.0, 2.0), 4.71 (dd, J=12.0, 2.0), 6.39 (t, J=2.0, 1H), 6.85–6.91 (m, 2H), 6.96 (d, J=2.0, 1H), 7.02 (d, J=8.5, 1H), 7.25–7.28 (m, 2H), 7.32 (dd, J=8.5, 2.0, 1H).

Step G: Methyl[3-(SR),5-(RS),6-(SR),7-(SR)]-6-(4-fluorophenyl)-3-2-methoxy-5-((5-trifluoromethyl)tetrazol-1-yl)phenyl)-1-oxaspiro[4.4]nonane-7-carboxylate A mixture of 110 mg (0.21 mmol) of methyl[5-(RS),6-(SR),7-(SR)]-6-(4-fluorophenyl)-3-(2-methoxy-5-((5-trifluoromethyl)tetrazol-1-yl)phenyl)-1-oxaspiro[4.4]non-3-ene-7-carboxylate (from Example 1, Step F) and 25 mg of 20% Pd(OH)$_2$/C in 10 mL of 20:1 v/v MeOH/HOAc was hydrogenated at 45 psi for 1.5 h. The catalyst was filtered onto a pad of Celite, the reaction flask and filter cake were rinsed with 100 mL of EtOAc and the filtrate was concentrated in vacuo. The residue was partitioned between 50 mL of ether and 25 mL of sat'd NaHCO$_3$ and the layers were separated. The organic layer was washed with 25 mL of sat'd NaCl, dried over MgSO$_4$ and concentrated in vacuo. Flash chromatography on 6 g of silica gel using 20:7:2 v/v/v hexanes/CH$_2$Cl$_2$/ether as the eluant afforded 36 mg (33%) of the title compound as an oil. $^1$H NMR (500 MHz, CDCl$_3$): δ 1.88–2.00 (m, 3H), 2.18–2.25 (m, 2H), 2.29–2.35 (m, 1H), 3.12 (t, J=8.5, 1H), 3.21 (d, J=11.0, 1H), 3.30–3.36 (m, 1H), 3.56 (s, 3H), 3.73–3.80 (m, 1H), 3.82 (s, 3H), 4.10 (t, J=11.0, 1H), 6.71 (d, J=2.5, 1H), 6.87–6.92 (m, 2H), 7.23 (dd, J=8.5, 2.5, 1H), 7.29–7.32 (m, 2H). Mass Spectrum (NH$_3$—CI): m/z 538 (M+NH$_4^+$, 65%), 521 (M+H, 70%).

EXAMPLE 7

Methyl[3-(SR),5-(RS),6-(SR),7-(SR)]-6-(4-fluorophenyl)-3-(2-methoxy-5-(trifluoromethoxy)phenyl)-1-oxaspiro[4.4]nonane-7-carboxylate The title compound was prepared using procedures identical to those described in Example 6, except that 2-bromo-4-(trifluoromethoxy)anisole was substituted for 2-bromo-4-(5-(trifluoromethyl)tetrazol-1-yl)anisole in Step F. $^1$H NMR (500 MHz, CDCl$_3$): δ 1.89–1.98 (m, 3H), 2.16–2.21 (m, 2H), 2.29–2.33 (m, 1H), 3.03 (t, J=9.0, 1H), 3.21 (d, J=11.0, 1H), 3.32–3.38 (m, 1H), 3.57 (s, 3H), 3.64–3.71 (m, 1H), 3.70 (s, 3H), 4.03 (t, J=9.0, 1H), 6.49 (d, J=2.5, 1H), 6.71 (d, J=9.0, 1H), 6.96 (dd, J=9.0, 2.5, 1H), 7.00 (t, J=8.5, 2H), 7.33–7.36 (m, 2H). Mass Spectrum (NH$_3$—CI): m/z 486 (M+NH$_4^+$, 75%), 469 (M+H, 100%).

2-Bromo-4-(trifluoromethoxy)anisole a) 2-Bromo-4-(trifluoromethoxy)phenol

A solution of 1.78 g (10.0 mmol) of 4-trifluoromethoxyphenol in 5 mL of CH$_2$Cl$_2$ at 0° C. was treated with a solution of 2.20 g (14.0 mmol) of bromine in 5 mL of CH$_2$Cl$_2$. The cooling bath was removed and the resulting mixture was stirred at rt for 20 h. The reaction quenched with 5% aqueous Na$_2$S$_2$O$_3$ and the resulting mixture was partitioned between 150 mL of ether and 150 mL of H$_2$O. The layers were separated; the organic layer was dried over MgSO$_4$ and concentrated in vacuo. Flash chromatography on 125 g of silica gel using 9:1 v/v hexanes/CH$_2$Cl$_2$ as the eluant afforded 1.45 g (56%) of the title compound as an oil. $^1$H NMR (500 MHz, CDCl$_3$): δ 5.50 (s, 1H), 7.02 (d, J=9.0, 1H), 7.12 (dd, J=9.0, 2.0, 1H), 7.37 (d, J=2.0, 1H).

b) 2-Bromo-4-(trifluoromethoxy)anisole

A mixture of 608 mg (2.4 mmol) of 2-bromo-4-trifluoromethoxyphenol, 0.35 mL (5.6 mmol) of iodomethane and 775 mg (5.6 mmol) of K$_2$CO$_3$ in 2 mL of DMF was stirred at rt for 2.5 h. The reaction mixture was partitioned between 100 mL of hexanes and 100 mL of H$_2$O and the layers were separated. The organic layer was washed with 2×100 mL of H$_2$O, dried over MgSO$_4$ and concentrated in vacuo. Flash chromatography on 25 g of silica gel using hexanes as the eluant afforded 579 mg (89%) of the title compound as an oil. $^1$H NMR (400 MHz, CDCl$_3$): δ 3.91 (s, 3H), 6.88 (d, J=9.2, 1H), 7.15–7.18 (m, 1H), 7.45 (app d, J=3.2, 1H).

EXAMPLE 8

Methyl[3-(SR),5-(RS),6-(SR),7-(SR)]-6-(4-fluorophenyl)-3-(2-cyclopropylmethoxy-5-(trifluoromethoxy)phenyl)-1-oxaspiro[4.4]nonane-7-carboxylate The title compound was prepared using procedures identical to those described in Example 6, except that 1-cyclopropylmethoxy-2-bromo-4-(trifluoromethoxy)benzene was substituted for 2-bromo-4-(5-(trifluoromethyl)tetrazol-1-yl)anisole in Step F. $^1$H NMR (500 MHz, CDCl$_3$): δ 0.28–0.31 (m, 2H), 0.59–0.63 (m, 2H), 1.16–1.26 (m, 1H), 1.88–2.00 (m, 4H), 2.18–2.30 (m, 2H), 2.31–2.36 (m, 1H), 3.01 (t, J=9.5, 1H), 3.22 (d, J=11.5, 1H), 3.32–3.38 (m, 1H), 3.57 (s, 3H), 3.68–3.77 (m, 3H), 4.13 (t, J=7.5, 1H), 6.49 (d, J=2.0, 1H), 6.68 (d, J=8.5, 1H), 6.92 (dd, J=8.5, 2.5, 1H), 6.99 (t, J=8.5, 2H), 7.33–7.36 (m, 2H).

1-Cyclopropylmethoxy-2-bromo-4-(trifluoromethoxy)benzene

The title compound was prepared using procedures identical to those described in Example 7, except that bromomethylcyclopropane was substituted for iodomethane. $^1$H NMR (200 MHz, CDCl$_3$): δ 0.36–0.44 (m, 2H), 0.62–0.71 (m, 2H), 1.24–1.35 (m, 1H), 3.89 (d, J=6.8, 2H), 6.85 (d, J=6.8, 1H), 7.09–7.15 (m, 1H), 7.45 (app d, J=2.8, 1H).

EXAMPLE 9

Methyl[3-(S),5-(R),6-(S),7-(S)]-6-(4-fluorophenyl)-3-(2-methoxy-5-((5-trifluoromethyl)tetrazol-1-yl)phenyl)-1-oxaspiro[4.4] nonane-7-carboxylate The title compound was prepared using procedures identical to those described in Example 6, except that methyl 2-(S)-(4 -fluorophenyl)cyclopentanone-3-(S)-carboxylate (from Example 5) was substituted for methyl 2-(RS)-(4-fluorophenyl)cyclopentanone-3-(RS)-carboxylate in Step A.

EXAMPLE 10

[3-(S),5-(R),6-(S),7-(S)]-7-(1-(Pyrrolidinyl)methyl)-6-(4-fluorophenyl)-3-(2-methoxy-5-((5-trifluoromethyl)tetrazol-1-yl)phenyl)-1-oxaspiro[4.4]nonane Step A:[3-(S),5-(R),6-(S),7-(S)]-6-(4-Fluorophenyl)-3-(2-methoxy-5-((5-trifluoromethyl)tetrazol-1-yl)phenyl)-1-oxaspiro[4.4]nonane-7-methanol A solution of 159 mg (0.31 mmol) of methyl[3-(S),5-(R),6-(S),7-(S)]-6-(4-fluorophenyl)-3-(2-methoxy-5-((5-trifluoromethyl)tetrazol-1-yl)phenyl)-1-oxaspiro[4.4]nonane-7-carboxylate (from Example 9) in 5 mL of CH$_2$Cl$_2$ at 0° C. was treated with 0.61 mL of 1.5M DIBALH solution in toluene. After 10 min, the reaction was quenched with 6.0 mL of sat'd potassium sodium tartrate and the resulting mixture was diluted with 25 mL of ether and stirred for 1.5 h. The layers were separated, the organic layer was washed with 20 mL of sat'd NaCl, dried over MgSO$_4$ and concentrated in vacuo. Flash chromatography on 20 g of silica gel using 95:5 v/v CH$_2$Cl$_2$/EtOAc as the eluant afforded 64 mg (43%) of the title compound as an oil. $^1$H-NMR (500 MHz, CDCl$_3$): δ 1.58–1.66 (m, 1H), 1.84–1.97 (m, 2H), 2.13–2.22 (m, 3H), 2.69–2.71 (m, 2H), 3.10 (t, 1H), 3.48–3.51 (m, 1H), 3.61–4.15 (m, 6H), 3.84 (s, 3H), 6.69–7.38 (m, 7H).

Step B:[3-(S),5-(R),6-(S),7-(S)]-7-(1-(Pyrrolidinyl)methylene)-6-(4-fluorophenyl)-3-(2-methoxy-5-((5-trifluoromethyl)tetrazol-1-yl)phenyl)-1 -oxaspiro[4.4]nonane A solution of 62 mg (0.13 mmol) of[3-(S),5-(R),6-(S),7-(S)]-6-(4-fluorophenyl)-3-(2-methoxy-5-((5-trifluoromethyl)tetrazol-1-yl)phenyl)-1-oxaspiro[4.4]nonane-7-methanol (from Example 10, Step A) in 5 mL of CH$_2$Cl$_2$ was treated with 64 mg (0.15 mmol) of Dess-Martin reagent. After 40 min, the reaction was quenched with 1.0 mL of 1.0N KOH. The resulting mixture was partitioned between 25 mL of ether and 15 mL of H$_2$O. The layers were separated and the organic layer was washed with 15 mL of H$_2$O, 15 mL of sat'd NaCl, dried over MgSO$_4$ and concentrated in vacuo.

The crude aldehyde, 45 mg (0.63 mmol) of pyrrolidine, 100 mg of 4 A molecular sieves, 250 μl of acetic acid and 24 mg (0.38 mmol) of Na(CN)BH$_3$ were dissolved in 6.0 mL of methanol. After 1 h, the reaction was filtered on a pad of Celite; the flask and filtered solids were rinsed well with EtOAc (250 mL). The filtrate was transferred to a separatory funnel, washed with 75 mL of sat'd NaHCO$_3$, 75 mL of sat'd NaCl, dried over MgSO$_4$, and concentrated in vacuo. Flash chromatography on 23 g of silica gel using 98:2 v/v CH$_2$Cl$_2$/ CH$_3$OH+0.5% NH$_4$OH as the eluant afforded 31 mg (45%) of the title compound as an oil. $^1$H-NMR (500 MHz, CDCl$_3$): δ 1.52–1.61 (m, 1H), 1.66–1.78 (m, 4H), 1.83–1.96 (m, 2H), 2.15–2.27 (m, 4H), 2.33–2.47 (m, 5H), 2.47 (d, J=10.8, 1H), 2.56–2.68 (m, 1H), 3.04 (t, J=8.4, 1H), 3.70–3.78 (m, 1H), 3.83 (s, 3H), 4.08 (t, J=8.4, 1H), 6.71 (d, J=2.4, 1H), 6.86–6.92 (m, 3H), 7.21–7.29 (m, 3H). Mass Spectrum (NH$_3$—CI): m/z 546 (M+H, 100%).

EXAMPLE 11

Methyl[3-(S),5-(R),6-(S),7-(S)]-6-(4-fluorophenyl)-3-(2-methoxy-5-((5-trifluoromethyl)tetrazol-1-yl) phenyl)-1-oxaspiro[4.4]nonane-7-carboxylate Step A: Methyl[5-(S),6-(S),7-(S)]-6-(4-fluorophenyl)-3-(methylene)-1-oxaspiro[4.4]nonane-7-carboxylate A solution of 1.5 g (4.3 mmol) of methyl[1-(S),2-(S),3-(S)]-2-(4-fluorophenyl)-1-(2-(acetoxymethylene)-prop-2-enyl)-1-(hydroxy)cyclopentane-3-carboxylate (from Example 6, Step A) in 25 mL of THF was cooled to −78° C. and treated with 4.3 mL of 1.0M lithium bis(trimethylsilyl) amide solution in THF and the resulting mixture was stirred cold for 5 min. The resulting solution was treated with 8.6 mL of 0.5M zinc chloride solution in THF, the cooling bath was removed and the resulting mixture was warmed to rt. Tetrakis(triphenyl-phosphine)palladium(0) (250 mg, 0.22 mmol) was added, the reaction flask was fitted with a reflux condenser and the reaction was heated at reflux for 18 h. The reaction was and quenched with 50 mL of sat'd NH$_4$Cl. The mixture was partitioned between 200 mL of ether and 50 mL of H$_2$O and the layers were separated. The organic layer was washed with 50 mL of sat'd NaHCO$_3$, 50 mL of sat'd NaCl, dried over MgSO$_4$ and concentrated in vacuo. Flash chromatography on 40 g of silica gel using 9:1 v/v, then 3:1 v/v hexanes/ether as the eluant afforded 540 mg (44%) of the title compound and 316 mg (23%) of[1-(S),4-(R),7-(S)]-1-(2-(acetoxymethyl)prop-2-enyl)-3-oxo-7-(4-fluorophenyl)-2-oxabicyclo[2.2.1]heptane, both as oils.

For methyl[5-(S),6-(S),7-(S)]-6-(4-fluorophenyl)-3-(methylene)-1-oxaspiro[4.4]nonane-7-carboxylate: $^1$H-NMR (500 MHz, CDCl$_3$): δ 1.84–1.95 (m, 2H), 2.05–2.09 (m, 1H), 2.22–2.31 (m, 1H), 3.17 (d, J=11.0, 1H), 3.31–3.36 (m, 1H), 3.56 (s, 3H), 3.93 (d, J=12.5, 1H), 4.19 (d, J=12.5, 1H), 4.68 (app t, J=2.0, 1H), 4.79 (app t, J=2.0, 1H), 6.95 (t, J=8.5, 2H), 7.26–7.30 (m, 2H).

For[1-(S),4-(R),7-(S)]-1-(2-(acetoxymethyl)prop-2-enyl) -3-oxo-7-(4-fluorophenyl)-2-oxabicyclo[2.2.1]heptane: $^1$H-NMR (500 MHz, CDCl$_3$): δ 1.82–2.03 (m, 3H), 2.03 (s, 3H), 2.11–2.17 (m, 1H), 2.76 and 2.85 (AB q, J=15.0, 2H), 3.07 (d, J=4.0, 1H), 3.45 (s, 1H), 4.61 and 4.64 (AB q, J=21.5, 2H), 5.07 (s, 1H), 5.21 (s, 1H). Mass Spectrum (NH$_3$—CI): m/z 336 (M+NH$_4^+$, 100%).

Step B: Methyl[3-(S),5-(R),6-(S),7-(S)]-6-(4-fluorophenyl) -3-(2-methoxy-5-((5-trifluoromethyl)tetrazol-1-yl)phenyl)-1-oxaspiro[4.4]nonane-7-carboxylate The title compound was prepared from methyl[5-(S),6-(S),7-(S)]-6-(4-fluorophenyl)-3-(methylene)-1-oxaspiro [4.4]nonane-7 -carboxylate (from Example 11, Step A) using procedures analogous to those described in Example 6, Steps C–G. $^1$H-NMR (500 MHz, CDCl$_3$): δ 1.57–1.64 (m, 1H), 1.85–1.93 (m, 1H), 2.09–2.15 (m, 2H), 3.07–3.12 (m, 1H), 3.48 (t, J=8.5, 1H), 3.63 (s, 3H), 3.68 (d, J=11.0, 1H), 3.78–3.85 (m, 1H), 3.84 (s, 3H), 4.15 (t, J=8.5, 1H), 6.83 (d, J=2.0, 1H), 6.91–6.95 (m, 3H), 7.18–7.21 (m, 2H), 7.26 (dd, J=8.5, 2.0). Mass Spectrum (NH$_3$—CI): m/z 538 (M+NH$_4^+$, 100%), 521 (M+H, 40%).

EXAMPLE 12

(5R,6S,7S)-6-(4-Fluorophenyl)-3-(2,5-bis-(trifluoromethyl)phenyl)-1-oxaspiro[4.4]non-3-ene-7-carboxylic acid methyl ester Step A: 2,5-Bis-trifluoromethylbromobenzene A suspension of the HBr salt of 2,5-bis-trifluoromethylaniline (1.0 gm, 4.4 mmol) was prepared by addition of 48% HBr (3 gm, 17.5 mmol) and 5 mL of water. This was cooled in an ice bath while a solution of sodium nitrite (335 mg, 4.8 mmol) in 1 mL of water was added dropwise. The reaction was stirred a farther 0.5 hr at which time copper powder (1 gm) and another 3 gm portion of 48% HBr were added. The reaction was heated to reflux and after 10 min the distillate was collected until no organic material was evident with the water. The distillate was extracted twice with ether and the ether layers were washed with brine, dried over sodium sulfate, combined and evaporated. The residue was purified by flash chromatography (5% ethyl acetate/hexanes) to afford the title compound as an oil. NMR (CDCl$_3$): δ 7.68 (d, 1H, J=8 Hz), 7.81 (d, 1H, J=8 Hz), 7.96 (s, 1H).

Step B: (5R,6S,7S)-6-(4-Fluorophenyl)-3-(2,5-bis-(trifluoromethyl)-phenyl)-1-oxaspiro[4.4]non-3-ene-7-carboxylic acid methyl ester The title compound was prepared by the procedure given in Example 6, Step F (d), employing 2,5-bis-trifluoromethylbromobenzene in place of 2-bromo-4-(5-(trifluoromethyl)tetrazol-1-yl)anisole. MS (NH$_3$/CI): m/e= 489 (M+1).

EXAMPLE 13

(3S,5R,6S,7S)-6-(4-Fluorophenyl)-3-(2,5-bis-(trifluoromethyl)phenyl)-1-oxaspiro[4.4]nonane-7-carboxylic acid methyl ester The title compound was prepared by the procedure given in Example 6, Step G, employing (5R,6S,7S)-6-(4-fluorophenyl)-3-(2,5-bis-(trifluoromethyl)phenyl)-1-oxaspiro[4.4]non-3-ene-7-carboxylic acid methyl ester in place of methyl[5-(RS),6-(SR),7-(SR)]-6-(4-fluorophenyl)-3-(2-methoxy-5-((5-trifluoromethyl)tetrazol-1-yl)phenyl)-1-oxaspiro[4.4]non-3-ene-7-carboxylate, except that acetic acid was not used as a cosolvent and the reaction time was extended to between 2 and 16 hr. MS (NH$_3$/CI): m/e=491 (M+1).

EXAMPLE 14

(5R,6S,7S)-6-(4-Fluorophenyl)-3-(2-methyl-3-fluoro-5-(5-trifluoromethyltetrazo-1-yl)phenyl)-1-oxaspiro[4.4]non-3-ene-7-carboxylic acid methyl ester Step A: 3-Bromo-5-fluoro-4-methylnitrobenzene To 3-fluoro-4-methylnitrobenzene (4.0 gm, 25.8 mmol) was added bromine (5.2 gm, 32 mmol) and iron powder (100 mg). The mixture was heated under a condenser at 100° C. for 40 hr and then poured into ice water containing enough sodium sulfite to quench the excess bromine. The aqueous layer was extracted twice with ether and the ether layers were washed with brine, dried over sodium sulfate, combined and evaporated. The residue was purified by FC (10–20% ethyl acetate/hexanes) to afford 1.4 gm of the title compound as a white solid (the major and highest $R_f$ isomer). NMR (CDCl$_3$): δ 2.41 (d, 3H, J=3 Hz), 7.85 (dd, 1H, J=2.1 and 9 Hz), 8.24 (dd, 1H, J=1.8 and 2.1 Hz).

Step B: 3-Bromo-5-fluoro-4-methylaniline

To 3-bromo-5-fluoro-4-methylnitrobenzene (1.4 gm, 6.0 mmol) in ethanol (100%, 25 mL) was added (c) HCl (7.0 mL) and stannous chloride dihydrate (4.1 gm, 18 mmol). The solution was stirred at room temperature for 16 hr and then concentrated in vacuo. The residue was diluted with water, made basic with 2N NaOH and extracted twice with ether. The ether layers were each washed with brine, dried over sodium sulfate, combined and evaporated to give 1.3 gm of crude title compound as an oil. NMR (CDCl$_3$): δ 2.17 (d, 3H, J=3 Hz), 6.31 (dd, 1H, J=2.2 and 11 Hz), 6.67 (dd, 1H, J=1.8 and 2.2 Hz).

Step C: 3-Bromo-5-fluoro-4-methyltrifluoroacetanilide

A solution of 3-bromo-5-fluoro-4-methylaniline (650 mg, 3.0 mmol) in methylene chloride (20 mL) was cooled in an ice bath. Trifluoroacetic anhydride (1.25 gm, 6 mmol) was added and then diisopropylethylamine (1.0 gm, 7.5 mmol) was added dropwise over 1 min and the ice bath was removed. After 1 hr, the reaction was quenched into water containing 2N HCl (5 mL) and extracted twice with methylene chloride. The organic layers were each washed with brine, dried over sodium sulfate, combined and evaporated. The residue was purified by FC (15% ethyl acetate/hexanes) to give 650 mg of title compound as a white solid. NMR (CDCl$_3$): δ 2.29 (d, 3H, J=2.3 Hz), 7.41 (dd, 1H, J=2.1 and 10.5 Hz), 6.67 (br t, 1H, J=2 Hz), 7.79 (br s, 1H).

Step D: 3-Fluoro-2-methyl-5-(5-(trifluoromethyl)tetrazo-1-yl)bromobenzene

To a solution of 3-bromo-5-fluoro-4-methyltrifluoroacetanilide (650 mg, 2.2 mmol) in carbon tetrachloride (10 mL) was added triphenylphosphine (835 mg, 3.3 mmol). The reaction was heated at 90° C. for 16 hr at which time NMR of an aliquot indicated complete reaction of the starting material. The volatiles were removed in vacuo to give the crude imino chloride. The above residue was taken up in DMF and sodium azide (290 mg, 4.4 mmol) was added. The reaction was stirred at room temperature for 2 hr at which time TLC indicated a mixture of starting amide and product. The reaction was quenched with water and extracted twice with ether. The ethers layers were each washed with brine, dried over sodium sulfate, combined and evaporated. The residue was purified by prep TLC (20% ethyl acetate/hexanes) to give 450 mg of title compound as a white solid. NMR (CDCl$_3$): δ 2.44 (d, 3H, J=2.4 Hz), 7.20 (dd, 1H, J=2.0 and 8.5 Hz), 6.67 (br t, 1H, J=2 Hz).

Step E: (5R,6S,7S)-6-(4-Fluorophenyl)-3-(2-methyl-3-fluoro-5-(5-(trifluoromethyl)tetrazo-1-yl)phenyl)-1-oxaspiro[4.4]non-3-ene-7-carboxylic acid methyl ester The title compound was prepared by the procedure given in Example 6, Step F (d), employing 3-Fluoro-2-methyl-5-(5-trifluoromethyltetrazo-1-yl)bromobenzene in place of 2-bromo-4-(5-(trifluoromethyl)tetrazol-1-yl)anisole. MS (NH$_3$/CI): m/e=521 (M+1).

EXAMPLE 15

(3S,5R,6S,7S)-6-(4-Fluorophenyl)-3-(2-methyl-3-fluoro-5-(5-(trifluoromethyl)tetrazol-1-yl)phenyl)-1-oxaspiro[4.4]nonane-7-carboxylic acid methyl ester The title compound was prepared by the procedure given in Example 6, Step G, employing ((5R,6S,7S)-6-(4-Fluorophenyl)-3-(2-methyl-3-fluoro-5-(5-trifluoromethyltetrazo-1-yl)phenyl)-1-oxaspiro[4.4]non-3-ene-7-carboxylic acid methyl ester in place of methyl[5-(RS),6-(SR),7-(SR)]-6-(4-fluorophenyl)-3-(2-methoxy-5-((5-trifluoromethyl)tetrazol-1-yl)phenyl)-1-oxaspiro[4.4]non-3-ene-7-carboxylate, except that acetic acid was not used as a cosolvent and the reaction time was extended to between 2 and 16 hr. MS (NH$_3$/CI): m/e=523 (M+1).

EXAMPLE 16

(5R,6S,7S)-6-(4-Fluorophenyl)-3-(2-methyl-5-(5-trifluoromethyltetrazo-1-yl)phenyl)-1-oxaspiro[4.4]non-3-ene-7-carboxylic acid methyl ester Step A: 2-Methyl-5-(5-trifluoromethyltetrazo-1-yl)bromobenzene The title compound was prepared starting with 2-bromo-4-nitrotoluene using essentially the same procedures as in Example 14, Steps B–D. NMR (CDCl$_3$): δ 2.51 (s, 3H), 7.33 (dd, 1H, J=2 and 8 Hz), 7.46 (d, 1H, J=8 Hz), 7.69 (d, 1H, J=2 Hz).

Step B: (5R,6S,7S)-6-(4-Fluorophenyl)-3-(2-methyl-5-(5-trifluoromethyltetrazo-1-yl)phenyl)-1-oxaspiro[4.4]non-3-ene-7-carboxylic acid methyl ester The title compound was prepared by the procedure given in Example 6, Step F (d), employing 2-methyl-5-(5-trifluoromethyltetrazo-1-yl)bromobenzene in place of 2-bromo-4-(5-(trifluoromethyl)tetrazol-1-yl)anisole. MS (NH$_3$/CI): m/e=503 (M+1).

EXAMPLE 17

(3S,5R,6S,7S)-6-(4-Fluorophenyl)-3-(2-methyl-5-(5-trifluoromethyltetrazo-1-yl)phenyl)-1-oxaspiro[4.4]nonane-7-carboxylic acid methyl ester The title compound was prepared by the procedure given in Example 6, Step G, employing (5R,6S,7S)-6-(4-fluorophenyl)-3-(2-methyl-5-(5-trifluoromethyltetrazo-1-yl)phenyl)-1-oxaspiro[4.4]non-3-ene-7-carboxylic acid methyl ester in place of methyl[5-(RS),6-(SR),7-(SR)]-6-(4-fluorophenyl)-3-(2-methoxy-5-((5-trifluoromethyl)tetrazol-1-yl)phenyl)-1-oxaspiro[4.4]non-3-ene-7-carboxylate, except that acetic acid was not used as a cosolvent and the reaction time was extended to between 2 and 16 hr. MS (NH$_3$/CI): m/e=505 (M+1).

The compounds of Examples 18–21 were prepared according to the procedure given in Example 6, Step F (d), employing the appropriate commercially available aryl bromide in place of 2-bromo-4-(5-(trifluoromethyl)tetrazol-1-yl)anisole.

EXAMPLE 18

(5R,6S,7S)-6-(4-Fluorophenyl)-3-(2,4-bis-(trifluoromethyl)phenyl)-1-oxaspiro[4.4]non-3-ene-7-carboxylic acid methyl ester MS (NH$_3$/CI): m/e=489 (M+1).

EXAMPLE 19

(5R,6S,7S)-6-(4-Fluorophenyl)-3-(3,5-bis-(trifluoromethyl)phenyl)-1-oxaspiro[4.4]non-3-ene-7-carboxylic acid methyl ester MS (NH$_3$/CI): m/e=489 (M+1).

EXAMPLE 20

(5R,6S,7S)-6-(4-Fluorophenyl)-3-(2-chloro-5-(trifluoromethyl)phenyl)-1-oxaspiro[4.4]non-3-ene-7-carboxylic acid methyl ester MS (NH$_3$/CI): m/e =455 (M+1).

EXAMPLE 21

(5R,6S,7S)-6-(4-Fluorophenyl)-3-(2-fluoro-5-(trifluoromethyl)phenyl)-1-oxaspiro[4.4]non-3-ene-7-carboxylic acid methyl ester MS (NH$_3$/CI): m/e=439 (M+1).

The compounds of Examples 22–24 were prepared according to the procedure given in Example 6, Step G, except without acetic acid and for 2–16 hr, and substituting the appropriate oxaspiro[4.4]non-3-ene from Examples 18,19 and 21, respectively.

EXAMPLE 22

(3S,5R,6S,7S)-6-(4-Fluorophenyl)-3-(2,4-bis-(trifluoromethyl)phenyl)-1-oxaspiro[4.4]nonane-7-carboxylic acid methyl ester MS (NH$_3$/CI): m/e=491 (M+1).

EXAMPLE 23

(3S,5R,6S,7S)-6-(4-Fluorophenyl)-3-(3,5-bis-(trifluoromethyl)phenyl)-1-oxaspiro[4.4]nonane-7-carboxylic acid methyl ester MS (NH$_3$/CI): m/e=491 (M+1).

EXAMPLE 24

(3S,5R,6S,7S)-6-(4-Fluorophenyl)-3-(2-fluoro-5-trifluoromethylphenyl)-1-oxaspiro[4.4]nonane-7-carboxylic acid methyl ester MS (NH$_3$/CI): m/e=441 (M+1).

EXAMPLE 25

(3S,5R,6S,7S)-6-(4-Fluorophenyl)-7-hydroxymethyl-3-(2-methyl-3-fluoro-5-(5-trifluoromethyltetrazo-1-yl)phenyl)-1-oxaspiro[4.4]nonane A solution of 80 mg (0.15 mmol) of (3S,5R,6S,7S)-6-(4-fluorophenyl)-3-(2-methyl-3-fluoro-5-(5-trifluoromethyltetrazo-1-yl)phenyl)-1-oxaspiro[4.4]nonane-7-carboxylic acid methyl ester (from example 15) in THF (3 mL) was cooled to −70° C. under nitrogen. A 1M solution of diisopropylaluminum hydride (DIBAL) in THF (800 uL, 0.8 mmol) was added and the reaction was stirred for 0.5 hr. TLC of an aliquot indicated that starting material was still present, thus another 300 uL of DIBAL was added. After a further 0.5 hr, the reaction was quenched into water containing 2N HCl (1 mL) and was extracted twice with ether. The ether layers were washed with brine, dried over sodium sulfate, combined and evaporated. The residue was purified by FC (40–50% ethyl acetate/hexanes) to afford 67 mg of the title compound. NMR (CDCl$_3$): δ 1.4–1.6 (m, 1H), 1.6–1.7 (m, 1H), 1.7–1.9 (m, 2H), 2.05–2.2 (m, 2H), 2.24 (d, 3H, J=2.2 Hz), 2.27 (dd, 1H, J=8 and 13 Hz), 2.65 (m, 2H), 3.17 (t, 1H, J=8 Hz), 3.44 (dd, 1 H, 5.5 and 11 Hz), 3.5–3.7 (m, 2H), 4.04 (t, 1H, J=8 Hz), 6.41 (br s, 1H), 6.80 (t, 2H, J=8.5 Hz), 6.96 (dd, 1H, J=2 and 9 Hz), 7.24 (dd, 2H, J=6.5 and 8.5 Hz). MS (NH$_3$/CI): m/e=495 (M+1).

EXAMPLE 26

(3S,5R,6S,7S)-6(4-Fluorophenyl)-3-(2-methyl-3-fluoro-5-(5-trifluoromethyltetrazo-1-yl)phenyl)-1-oxaspiro[4.4]nonane-7-carboxaldehyde A solution of oxalyl chloride (30 uL, 0.33 mmol) in methylene chloride (1 mL) was cooled to −70° C. and DMSO (51 mg, 0.65 mmol) was added. After 15 min, 65 mg (0.13 mmol) of (3S,5R,6S,7S)-6-(4-fluorophenyl)-7-hydroxymethyl-3-(2-methyl-3-fluoro-5-(5-trifluoromethyltetrazo-1-yl)phenyl)-1-oxaspiro[4.4]nonane (from example 25) in methylene chloride (0.5 mL) was added and the reaction was stirred for 1 hr. At this time, diisopropylethylamine (225 uL, 1.3 mmol) was added and the reaction was allowed to warm to 0° C. over 1 hr. The reaction was diluted with water and extracted 3× with methylene chloride. The organic layers were each washed with a portion of brine, dried over sodium sulfate, combined and evaporated. The residue was purified by FC (20–30% ethyl acetate/hexanes) to give 54 mg of title compound. NMR (CDCl$_3$): δ 1.7–1.8 (m, 1H), 1.83 (dd, 1H, J=9.5 and 13 Hz), 1.95–2.1 (m, 1H), 2.15–2.25 (m, 1H), 2.24 (d, 3H, J=2.3 Hz), 2.27 (dd, 1H, J=9.5 and 13 Hz), 3.15 (d, 1H, J=10 Hz), 3.20 (dd, 1H, J=7.5 and 8 Hz), 3.35–3.45 (m, 1H), 3.63 (p, 1H, J=9 Hz), 4.05 (dd, 1H, J=7.5 and 8 Hz), 6.40 (br s, 1H), 6.82 (t, 2 H, J=8.5 Hz), 6.97 (dd, 1H, J=2 and 9 Hz), 7.27 (dd, 2H, J=5.3 and 8.5 Hz), 9.63 (d, 1H, J=2 Hz).

EXAMPLE 27

(3S,5R,6S,7S)-6-(4-Fluorophenyl)-7-(pyrrolidin-1-yl)methyl-3-(2-methyl-3-fluoro-5-(5-trifluoromethyltetrazo-1-yl)phenyl)-1-oxaspiro[4.4]nonane A solution of 25 mg (0.051 mmol) of (3S,5R,6S,7S)-6-(4-fluorophenyl)-3-(2-methyl-3-fluoro-5-(5-trifluoromethyltetrazo-1-yl)phenyl)-1-oxaspiro[4.4]nonane-7-carboxaldehyde (from example 26), 9 mg (0.15 mmol) of acetic acid, 36 mg (0.51 mmol) of pyrrolidine and 1 gm of 3A molecular sieves was stirred for 0.5 hr and then 31 mg (0.15 mmol) of sodium triacetoxyborohydride was added. The reaction was stirred at room temperature for 16 hr and then quenched with water and extracted 3× with ethyl acetate. The organic layers were each washed with a portion of brine, dried over sodium sulfate, combined and evaporated. The residue was purified by Prep TLC (5% methanol/ methylene chloride) to give 25 mg of title compound. NMR (CDCl$_3$): δ 1.6–1.7 (m, 1H), 1.7–1.95 (m, 7H), 2.05–2.2 (m, 2H), 2.24 (d, 3H, J=2.2 Hz), 2.2–2.4 (m, 2H), 2.46 (d, 1H, J=11 Hz), 2.4–2.65 (m, 5H), 3.13 (t, 1H, J=8 Hz), 3.60 (p, 1H, J=8 Hz), 4.02 (t, 1H, J=8 Hz), 6.40 (br s, 1H), 6.80 (t, 2H, J=8.5 Hz), 6.96 (dd, 1 H,J=2and 9Hz), 7.20 (dd,2H, J=6.5and 8.5 Hz). MS (NH$_3$/CI): m/e=548 (M+1).

Examples 28 through 45 were prepared by alkylation, acylation or sulfonylation of commercially available aniline derivatives by the standard procedures discussed above. If the nitro derivative was commercially available, it was reduced employing the selective conditions previously discussed to provide the aniline derivative, which was then carried on as noted above. The aryl bromides were coupled to the 1-oxaspiro[4.4]non-3-ene framework via the conditions given in Example 6, step F (d).

EXAMPLE 28

(5R,6S,7S)-6-(4-Fluorophenyl)-3-[2-t-butyl-5-((2-trifluoromethyl)tetrazol-1-yl)phenyl]-1-oxaspiro[4.4] non-3-ene-7-carboxylic acid methyl ester MS: CI, m/z=545.2 (m$^+$+1), 562.2 (m$^+$+18). $^1$H NMR (400 MHz, CDCl$_3$) δ 7.44 (dd, 1H), 7.18 (d, 1H), 7.10–7.13 (m, 2H), 7.02 (d, 1H), 7.0 (t, 2H), 4.99 (s, 1H), 4.46 (d, 1H), 3.88 (dd, 1H), 3.53 (s, 3H), 3.30–3.33 (m, 1H), 3.06 (d, 1H), 2.24–2.27 (m, 1H), 1.86–1.93 (m, 3H), 1.30 (s, 9H).

EXAMPLE 29

(5R,6S,7S)-6-(4-Fluorophenyl)-3-[2-methoxy-5-(N-methyl-N-acetylamino)phenyl]-1-oxaspiro[4.4]non-3-ene-7-carboxylic acid methyl ester MS: CI, m/z=454.3 (m$^+$+1), 471.4 (m$^+$+18). $^1$H NMR (400 MHz, CDCl$_3$) δ 4.68 (d, 1H), 4.05 (d, 1H), 3.83 (s, 3H), 3.56 (s, 3H), 3.15 (s, 3H), 1.78 (s, 3H).

EXAMPLE 30

(5R,6S,7S)-6-(4-Fluorophenyl)-3-[2-methoxy-5-(N-methyl-N-trifluoroacetylamino)phenyl]-1-oxaspiro[4.4]non-3-ene-7-carboxylic acid methyl ester MS: CI, m/z=508.1 (m$^+$+1), 525.2 (m$^+$+18). $^1$H NMR (400 MHz, CDCl$_3$) δ 4.68 (d, 1H), 4.01 (d, 1H), 3.84 (s, 3H), 3.56 (s, 3H), 3.38–3.47 (m, 2H), 3.25–3.30 (s+m, 4H), 2.20–2.38 (m, 2H), 1.88–2.12 (m, 2H).

EXAMPLE 31

(5R,6S,7S)-6-(4-Fluorophenyl)-3-[2-methoxy-5-(N-ethyl-N-acetylamino)phenyl]-1-oxaspiro[4.4]non-3-ene-7-carboxylic acid methyl ester MS: CI, m/z=468.2 (m$^+$+1). $^1$H NMR (400 MHz, CDCl$_3$) δ 4.69 (dd, 1H), 4.03 (dd, 1H), 3.83 (s, 3H), 3.56–3.64 (s+m, 5H), 3.39–3.46 (m, 1H), 3.29 (d, 1H), 1.73 (s, 3H), 1.03 (t, 3H).

EXAMPLE 32

(5R,6S,7S)-6-(4-Fluorophenyl)-3-[2-methoxy-5-(N-methyl-N-(5-methylisoxazole-3-carbonyl)amino)phenyl]-1-oxaspiro[4.4]non-3-ene-7-carboxylic acid methyl ester $^1$H NMR (400 MHz, CDCl$_3$) δ 7.21–7.25 (m, 2H), 7.97–7.00 (dd, 1H), 6.84–6.88 (m, 2H), 6.76 (d, 1H), 6.58 (d, 1H), 6.26 (s, 1H), 5.87 (s, 1H), 4.60–4.64 (dd, 1H), 3.94–3.97 (dd, 1H), 3.80 (s, 3H), 3.56 (s, 3H), 3.33–3.43 (s+m, 4H), 3.27 (d, 1H), 2.26–2.33 (s+m, 4H), 2.15–2.24 (m, 1H), 1.94–2.08 (m, 2H).

EXAMPLE 33

(5R,6S,7S)-6-(4-Fluorophenyl)-3-[2-methoxy-5-(2-oxo-pyrrolidin-1-yl)phenyl]-1-oxaspiro[4.4]non-3-ene-7-carboxylic acid methyl ester MS: CI, m/z=466.2. (m$^+$+1), $^1$H NMR (400 MHz, CDCl$_3$) δ 7.34–7.37 (dd, 1H), 7.23–7.26 (m, 1H), 7.08 (d, 1H), 6.81–6.88 (m, 3H), 6.27 (t, 1H), 4.69–4.73 (dd, 1H), 4.04–4.08 (dd, 1H), 3.72–3.77 (s+m, 5H), 3.56 (s, 3H), 3.42–3.45 (m, 1H), 3.28 (d, 1H), 2.54 (t, 2H), 2.21–2.33 (m, 2H), 2.06–2.16 (m, 3H), 1.91–2.00 (m, 1H).

EXAMPLE 34

(5R,6S,7S)-6-(4-Fluorophenyl)-3-[2-methoxy-5-(N-methyl-N-trimethylacetylamino)phenyl]-1-oxaspiro[4.4]non-3-ene-7-carboxylic acid methyl ester MS: CI, m/z=496.2 (m$^+$+1). $^1$H NMR (400 MHz, CDCl$_3$) δ 4.65 (d, 1H), 3.96 (d, 1H), 3.84 (s, 3H), 3.56 (s, 3H), 3.10 (s, 3H), 0.96 (s, 9H).

EXAMPLE 35

(5R,6S,7S)-6-(4-Fluorophenyl)-3-[2-methoxy-5-(N-methyl-N-isobutyrylamino)phenyl]-1-oxaspiro[4.4]non-3-ene-7-carboxylic acid methyl ester MS: CI, m/z=482.2 (m$^+$+1). $^1$H NMR (400 MHz, CDCl$_3$) δ 7.23–7.27 (m, 2H), 6.98 (d, 1H), 6.83–6.88 (m, 3H), 6.63 (d, 1H), 6.29 (s, 1H), 4.69 (dd, 1H), 4.01 (dd, 1H), 3.83 (s, 3H), 3.56 (s, 3H), 3.39–3.43 (m, 1H), 3.27–3.30 (dd, 1H), 3.13 (s, 3H), 2.20–2.30 (m, 2H), 1.92–2.10 (m, 2H), 0.95 (t, 6H).

EXAMPLE 36

(5R,6S,7S)-6-(4-Fluorophenyl)-3-[2-methoxy-5-(N-isopropyl-N-acetylamino)phenyl]-1-oxaspiro[4.4]non-3-ene-7-carboxylic acid methyl ester MS: CI, m/z=482.2 (m$^+$+1). $^1$H NMR (400 MHz, CDCl$_3$) δ 4.87–4.95 (m, 1H), 4.69 (d, 1H), 3.94–4.02 (m, 1H), 3.83 (s, 3H), 3.56 (s, 3H), 3.42–3.47 (m, 1H), 3.27–3.30 (d, 1H), 1.67 (s, 3H), 0.91–0.95 (m, 6H).

EXAMPLE 37

(5R,6S,7S)-6-(4-Fluorophenyl)-3-[2-methoxy-5-(N-isopropyl-N-trifluoroacetylamino)phenyl]-1-oxaspiro[4.4]non-3-ene-7-carboxylic acid methyl ester MS: CI, m/z=536.2 (m$^+$+1), 553.2 (m$^+$+18). $^1$H NMR (400 MHz, CDCl$_3$) δ 4.78–4.84 (m, 1H), 4.65 (t, 1H), 3.92 (dd, 1H), 3.84 (s, 3H), 3.57 (s, 3H), 3.44–3.48 (m, 2H), 3.28 (d, 1H), 2.22–2.35 (m, 2H), 2.05–2.10 (m, 1H), 1.93–2.02 (m, 1H), 0.94–1.03 (m, 6H).

EXAMPLE 38

(5R,6S,7S)-6-(4-Fluorophenyl)-3-[2-methoxy-5-(N-methyl-N-methylsulfonylamino)phenyl]-1-oxaspiro[4.4]non-3-ene-7-carboxylic acid methyl ester MS: CI, m/z=490.2 (m$^+$+1), 507.3 (m$^+$+18). $^1$H NMR (400 MHz, CDCl$_3$) δ 7.24–7.27 (m, 2H), 7.16 (d, 1H), 6.81–6.89 (m, 4H), 6.26 (s, 1H), 4.70 (d, 1H), 4.05 (d, 1H), 3.79 (s, 3H), 3.56 (s, 3H), 3.39–3.45 (m, 1H), 3.21–3.28 (s+d, 4H), 2.78,2.83 (2s, 3H), 2.19–2.35 (m, 2H), 1.92–2.08 (m, 2H).

EXAMPLE 39

(5R,6S,7S)-6-(4-Fluorophenyl)-3-[2-methoxy-5-(N-methyl-N-dimethylsulfamoylamino)phenyl]-1-oxaspiro[4.4]non-3-ene-7-carboxylic acid methyl ester MS: CI, m/z=519.4 (m$^+$+1), 536.4 (m$^+$+18). $^1$H NMR (400 MHz, CDCl$_3$) δ 7.22–7.27 (m, 3H), 6.79–6.88 (m, 4H), 6.28 (s, 1H), 4.68 (d, 1H), 4.02 (d, 1H), 3.80 (s, 3H), 3.56 (s, 3H), 3.40–3.48 (m, 1H), 3.28 (d, 1H), 3.13 (s, 3H), 2.70 (s, 6H). 2.20–2.38 (m, 2H), 1.92–2.10 (m, 2H).

EXAMPLE 40

(5R,6S,7S)-6-(4-Fluorophenyl)-3-[2-methoxy-5-(N-methyl-N-(4-methyl-1,2,3-thiadiazole-5-carbonyl)amino)phenyl]-1-oxaspiro[4.4]non-3-ene-7-carboxylic acid methyl ester MS: CI, m/z=538.4.(m$^+$+1), $^1$H NMR (400 MHz, CDCl$_3$) δ 6.29 (t, 1H), 4.55–4.59 (dd, 1H), 3.92–3.96 (dd, 1H), 3.83 (s, 3H), 3.56 (s, 3H), 3.39–3.46 (m, 1H), 3.36 (s, 3H), 3.27 (d, 1H), 2.79 (s, 3H), 2.20–2.34 (m, 2H), 1.96–2.10 (m, 2H).

EXAMPLE 41

(5R,6S,7S)-6-(4-Fluorophenyl)-3-[2-methoxy-5-(N-methyl-N-(3,5-dimethylisoxazole-4-sulfonyl)amino)phenyl]-1-oxaspiro[4.4]non-3-ene-7-carboxylic acid methyl ester MS: ESI, m/z=571.4 (m$^+$+1), 588.5 (m$^+$+18). $^1$H NMR (400 MHz, CDCl$_3$) δ 6.25 (t, 1H), 4.62–4.64(dd, 1H), 3.94–3.98 (dd, 1H), 3.80 (s, 1H), 3.56 (s, 3H), 3.40–3.45 (m, 1H), 3.25, 3.28 (d, 1H), 3.13 (s, 3H), 2.19–2.36 (s+m, 5H), 1.93–2.10 (s+m, 5H).

EXAMPLE 42

(5R,6S,7S)-6-(4-Fluorophenyl)-3-[2-methoxy-5-(N-methyl-N-(5-nitrothiazol-2-yl)amino)phenyl]-1-oxaspiro[4.4]non-3-ene-7-carboxylic acid methyl ester MS: ESI, m/z=540.4 (m$^+$+1), $^1$H NMR (400 MHz, CDCl$_3$) δ 8.13 (s, 1H), 7.24–7.27 (m, 2H), 7.16, 7.17 (d, 1H), 6.86–6.94 (m, 3H), 6.80(d, 1H), 6.33 (s, 1H), 4.68 (d, 1H), 4.03 (d, 1H), 3.86 (s, 3H), 3.56 (s, 3H), 3.48 (s, 3H), 3.39–3.47 (m, 1H), 3.28, 3.31 (d, 1H), 2.20–2.38 (m, 2H), 2.02–2.10 (m, 1H), 1.92–2.00 (m, 1H).

EXAMPLE 43

(5R,6S,7S)-6-(4-Fluorophenyl)-3-[2-methoxy-5-(N,N-dimethylamino)phenyl]-1-oxaspiro[4.4]non-3-ene-7-carboxylic acid methyl ester MS: CI, m/z=426.2 (m$^+$+1), $^1$H NMR (400 MHz, CDCl$_3$) δ 7.23–7.27 (m, 2H), 6.84–6.88 (m, 2H), 6.77 (d, 1H), 6.61–6.64 (dd, 1H), 6.31 (d, 1H), 6.22 (t, 1H), 4.70–4.74 (dd, 1H), 4.05–4.08 (dd, 1H), 3.69 (s, 3H), 3.56 (s, 3H), 3.40–3.48 (m, 1H), 3.28 (d, 1H), 2.79 (s, 6H), 2.20–2.36 (m, 2H), 2.04–2.10 (m, 1H), 1.90–2.00 (m, 1H).

EXAMPLE 44

(5R,6S,7S)-6-(4-Fluorophenyl)-3-[2-methoxy-5-(N-methyl-N-isopropylamino)phenyl]-1-oxaspiro[4.4]non-3-ene-7-carboxylic acid methyl ester MS: CI, m/z=454.2 (m$^+$+1), $^1$H NMR (400 MHz, CDCl$_3$) δ 6.36 (d, 1H), 6,21 (s, 1H), 4.70 (dd, 1H), 4.06 (dd, 1H), 3.71–3.80 (m, 1H), 3.70 (s, 3H), 3.56 (s, 3H), 3.40–3.48 (m, 1H), 3.27 (d, 1H), 2.59 (s, 3H), 1.06 (s, 3H), 1.07 (s, 3H).

EXAMPLE 45

(5R,6S,7S)-6-(4-Fluorophenyl)-3-[2-methoxy-5-(N-methyl-N-(1-methylimidazole-4-sulfonyl)amino)phenyl]-1-oxaspiro[4.4]non-3-ene-7-carboxylic acid methyl ester MS: CI, m/z=556.2 (m$^+$+1), $^1$H NMR (400 MHz, CDCl$_3$) δ 4.62 (d, 1H), 3.96 (d, 1H), 3.78 (s, 3H), 3.65 (s, 3H), 3.56 (s, 3H), 3.25–3.28 (s+m, 4H), 2.18–2.35 (m, 2H), 1.92–2.07 (m, 2H).

The title compounds of Examples 46 through 60 were prepared by hydrogenation of the appropriate 1-oxaspiro[4.4]non-3-ene derivatives (described previously herein) essentially according to the procedure of Example 6, step G.

EXAMPLE 46

(3S,5R,6S,7S)-6-(4-Fluorophenyl)-3-[2-t-butyl-5-((2-trifluoromethyl)tetrazol-1-yl)phenyl]-1-oxaspiro[4.4]nonane-7-carboxylic acid methyl ester MS: CI, m/z=547.2 (m$^+$+1), 564.2 (m$^+$+18). $^1$H NMR (400 MHz, CDCl$_3$) δ 7.35–7.39 (m, 2H), 7.28–7.31 (dd, 1H), 7.02–7.07 (m, 3H), 6.74 (d, 1H), 3.81 (t, 1H), 3.55 (s, 3H), 3.27–3.33 (m, 1H), 3.17 (d, 1H), 3.09 (t, 1H), 2.52 (quintet, 1H), 2.21–2.27 (m, 1H), 2.07–2.16 (m, 1H), 1.81–1.98 (m, 3H), 1.75–1.78 (m, 1H), 1.16 (s, 9H).

EXAMPLE 47

(3S,5R,6S,7S)-6-(4-Fluorophenyl)-3-[2-t-butyl-5-(N-methyl-N-acetylamino)phenyl]-1-oxaspiro[4.4]nonane-7-carboxylic acid methyl ester MS: CI, m/z=482.2 (m$^+$+1). $^1$H NMR (400 MHz, CDCl$_3$) δ 7.38–7.42 (m, 2H), 7.14 (dd, 1H), 7.04 (t, 2H), 6.92 (d, 1H), 6.56 (s, 1H), 3.90–3.93 (m, 1H), 3.56 (s, 3H), 3.33–3.40 (m, 2H), 3.20 (d, 1H), 3,13, 3.05–3.09 (s+m, 4H), 2.27–2.35 (m, 1H), 2.13–2.19 (m, 2H), 1.85–1.93 (m, 3H), 1.72, 1.65 (s,s,3H), 1.12 (s, 9H).

EXAMPLE 48

(3S,5R,6S,7S)-6-(4-Fluorophenyl)-3-[2-t-butyl-5-(N-methyl-N-trifluoroacetylamino)phenyl]-1-oxaspiro[4.4]nonane-7-carboxylic acid methyl ester MS: CI, m/z=536.2 (m$^+$+1), 553.2 (m$^+$+18). $^1$H NMR (400 MHz, CDCl$_3$) δ 3.91 (q, 1H), 3.56 (s, 3H), 3.23–3.37 (m, 2H), 3.18–3.21(2S+d, 4H), 2.28–2.31 (m, 1H), 2.13–2.22 (m, 2H), 1.83–1.96 (m, 3H), 1.11 (s, 9H).

EXAMPLE 49

(3S,5R,6S,7S)-6-(4-Fluorophenyl)-3-[2-methoxy-5-(N-methyl-N-acetylamino)phenyl]-1-oxaspiro[4.4]nonane-7-carboxylic acid methyl ester MS: CI, m/z=456.2 (m$^+$+1). $^1$H NMR (400 MHz, CDCl$_3$) δ 4.04 (t, 1H), 3.82 (d, 1H), 3.69 (s, 3H), 3.55 (s, 3H), 3.10 (s, 3H), 1.71 (s, 3H).

EXAMPLE 50

(3S,5R,6S,7S)-6-(4-Fluorophenyl)-3-[2-methoxy-5-(N-methyl-N-trifluoroacetylamino)phenyl]-1-oxaspiro[4.4]nonane-7-carboxylic acid methyl ester MS: CI, m/z=510.1 (m$^+$+1), 527.2 (m$^+$+18). $^1$H NMR (400 MHz, CDCl$_3$) δ 4.01 (t, 1H), 3.62–3.71 (s+m, 4H), 3.55 (s, 3H), 3.28–3.35, 3.17–3.21 (m+S, 5H), 2.96 (t, 1H).

EXAMPLE 51

(3S,5R,6S,7S)-6-(4-Fluorophenyl)-3-[2-methoxy-5-(N-ethyl-N-acetylamino)phenyl]-1-oxaspiro[4.4]nonane-7-carboxylic acid methyl ester MS: CI, m/z=470.2 (m$^+$+1). $^1$H NMR (400 MHz, CDCl$_3$) δ 4.03 (t, 1H), 3.55–3.70 (2s+m, 8H), 3.28–3.38 (m, 1H), 3.17, 3.20 (d, 1H), 1.94 (t, 1H), 1.67 (s, 3H), 0.98 (t, 3H).

EXAMPLE 52

(3S,5R,6S,7S)-6-(4-Fluorophenyl)-3-[2-methoxy-5-(N-methyl-N-(5-methylisoxazole-3-carbonyl)amino)phenyl]-1-oxaspiro[4.4]nonane-7-carboxylic acid methyl ester MS: CI, m/z=523.5.(m$^+$+1), 540.4 (m$^+$+18). $^1$H NMR (400 MHz, CDCl$_3$) δ 3.96 (t, 1H), 3.72 (s, 3H), 3.54 (s, 3H), 3.29 (s, 3H), 3.17 (d, 1H), 2.84 (t, 1H), 2.25 (s, 3H).

EXAMPLE 53

(3S,5R,6S,7S)-6-(4-Fluorophenyl)-3-[2-methoxy-5-(2-oxo-pyrrolidin-1-yl)phenyl]-1-oxaspiro[4.4]nonane-7-carboxylic acid methyl ester MS: CI, m/z=468.2.(m$^+$+1). $^1$H NMR (400 MHz, CDCl$_3$) δ 7.33–7.43 (m, 2H), 7.24–7.26 (m, 1H), 6.95–7.00 (m, 2H), 6.72–6.75 (m, 1H), 6.66–6.68 (m, 1H), 4.00–4.03 (m, 1H), 3.60–3.70 (s+m, 4H), 3.53–3.59 (s+m, 5H), 3.28–3.38 (m, 1H), 3.16–3.22 (m, 1H), 1H), 3.06–3.12 (m, 1H), 2.52–2.58 (m, 2H), 2.25–2.35 (m, 1H), 2.06–2.20 (m, 4H), 1.88–1.98 (m, 3H).

EXAMPLE 54

(3S,5R,6S,7S)-6-(4-Fluorophenyl)-3-[2-methoxy-5-(N-methyl-N-(trimethylacetyl)amino)phenyl]-1-oxaspiro[4.4]nonane-7-carboxylic acid methyl ester MS: CI, m/z=498.2 (m$^+$+1). $^1$H NMR (400 MHz, CDCl$_3$) δ 7.31–7.34 (m, 2H), 6.91–6.97 (m, 3H), 6.69–6.72 (d, 1H), 6.49–6.50 (d, 1H), 4.04–4.06 (t 1H), 3.62–3.71 (s+m, 4H), 3.55 (s, 3H), 3.28–3.33 (m, 1H), 3.16–3.19 (d, 1H), 3.06 (s, 3H), 2.89 (t, 1H), 2.25–2.33 (m, 1H), 2.10–2.19 (m, 2H), 1.87–1.96 (m, 3H), 0.89 (s, 9H).

EXAMPLE 55

(3S,5R,6S,7S)-6-(4-Fluorophenyl)-3-[2-methoxy-5-(N-methyl-N-isobutyrylamino)phenyl]-1-oxaspiro[4.4]nonane-7-carboxylic acid methyl ester MS: CI, m/z=484.2 (m$^+$+1). $^1$H NMR (400 MHz, CDCl$_3$) δ 4.05 (t, 1H), 3.62–3.71 (s+m, 4H), 3.55 (s, 3H), 3.27–3.35 (m, 1H), 3.19 (d, 1H), 3.09 (s, 3H), 2.93 (t, 1H), 0.88–0.93 (m, 6H).

EXAMPLE 56

(3S,5R,6S,7S)-6-(4-Fluorophenyl)-3-[2-methoxy-5-(N-isopropyl-N-acetylamino)phenyl]-1-oxaspiro[4.4]nonane-7-carboxylic acid methyl ester MS: CI, m/z=484.2 (m$^+$+1). $^1$H NMR (400 MHz, CDCl$_3$) δ 4.88–4.95 (m, 1H), 4.02 (t, 1H), 3.69 (s, 3H), 3.55 (s, 3H), 3.28–3.36 (m, 1H), 3.19 (d, 1H), 2.80–3.00 (m, 1H), 2.10–2.33 (m, 3H), 1.86–1.98 (m, 3H), 1.57–1.65 (m, 3H), 0.80–0.95 (m, 6H).

EXAMPLE 57

(3S,5R,6S,7S)-6-(4-Fluorophenyl)-3-[2-methoxy-5-(N-isopropyl-N-trifluoroacetylamino)phenyl]-1-oxaspiro[4.4]nonane-7-carboxylic acid methyl ester MS: CI, m/z=438.2 (m$^+$+1), 555.2 (m$^+$+18). $^1$H NMR (400 MHz, CDCl$_3$) δ 4.72–4.77 (m, 1H), 4.00 (t, 1H), 3.65–3.75 (s+m, 4H), 3.55 (s, 3H), 3.28–3.38 (m, 1H), 3.16–3.19 (m, 1H), 2.95, 2.79 (t, 1H), 0.96–1.00 (2d, 3H), 0.84, 0.88 (2d, 3H).

EXAMPLE 58

(3S,5R,6S,7S)-6-(4-Fluorophenyl)-3-[2-methoxy-5-(N,N-dimethyl-amino)phenyl]-1-oxaspiro[4.4]nonane-7-carboxylic acid methyl ester MS: CI, m/z=428.2 (m$^+$+1), $^1$H NMR (400 MHz, CDCl$_3$) δ 7.34–7.38 (m, 2H), 6.95–7.00 (m, 2H), 6.69 (d, 1H), 6.49–6.52 (dd, 1H), 6.10 (d, 1H), 3.99 (t, 1H), 3.68–3.76 (m, 1H), 3.63 (s, 3H), 3.55 (s, 3H), 3.30–3.36 (m, 1H), 3.19 (d, 1H), 3.03–3.07 (dd, 1H), 2.70 (s, 6H), 2.25–2.34 (m, 1H), 2.12–2.20 (m, 2H), 1.92–1.98 (m, 3H).

EXAMPLE 59

(3S,5R,6S,7S)-6-(4-Fluorophenyl)-3-[2-methoxy-5-(N-methylamino)phenyl]-1-oxaspiro[4.4]nonane-7-carboxylic acid methyl ester MS: CI, m/z=414.2 (m$^+$+1), $^1$H NMR (400 MHz, CDCl$_3$) δ 7.34–7.37 (m, 2H), 6.96–6.99 (m, 2H), 6.65 (d, 1H), 6.34–6.37 (dd, 1H), 5.89 (d, 1H), 3.99 (t, 1H), 3.65–3.71 (m, 1H), 3.63 (s, 3H), 3.55 (s, 3H 3.28–3.36 (m, 1H), 3.22–3.27 (broad, 1H), 3.17, 3.20 (d, 1H), 3.04–3.08 (dd, 1H), 2.66 (s, 3H), 2.25–2.33 (m, 1H), 2.10–2.19 (m, 2H), 1.87–1.96 (m, 3H).

EXAMPLE 60

(3S,5R,6S,7S)-6-(4-Fluorophenyl)-3-[2-methoxy-5-(N-methyl-N-isopropylamino)phenyl]-1-oxaspiro[4.4]nonane-7-carboxylic acid methyl ester MS: CI, m/z=456.2 (m$^+$+1). $^1$H NMR (400 MHz, CDCl$_3$) δ 3.98 (t, 1H), 3.59–3.72 (s+m, 4H), 3.54 (s, 3H), 3.30–3.38 (m, 1H), 3.18 (d, 1H), 3.04 (t, 1H), 2.50 (s, 3H), 2.26–2.33 (m, 1H), 2.10–2.18 (m, 2H), 1.88–1.95 (m, 3H), 0.95–1.07 (m, 6H).

EXAMPLE 61

(3S,5R,6S,7S)-6-(4-Fluorophenyl)-3-[2-methoxy-5-(N-methyl-N-(1-methylimidazole-4-sulfonyl)amino)phenyl]-1-oxaspiro[4.4]nonane-7-carboxylic acid methyl ester MS: CI, m/z=558.2 (m$^+$+1), $^1$H NMR (400 MHz, CDCl$_3$) δ 4.00 (t, 1H), 3.65 (s, 3H), 3.57 (s, 3H), 3.16–3.22 (s+m, 4H), 2.90 (t, 1H), 2.22–2.32 (m, 1H), 2.05–2.15 (m, 2H), 1.84–1.95 (m, 3H).

The title compounds of Examples 62 through 65 were prepared according to the procedures described in Scheme 13 and herein.

EXAMPLE 62

(5R,6S,7S)-6-(4-Fluorophenyl)-3-(5-cyano-2-isopropoxy-phenyl)-1-oxaspiro[4.4]non-3-ene-7-carboxylic acid methyl ester $^1$H NMR (400 MHz, CD$_3$OD): δ 1.29 (d, 3H), 1.32 (d, 3H), 1.94–2.38 (2 m's, 4H), 3.48 (m, 1H), 3.57 (s, 3H), 4.08 (dd, 1H),4.69 (dd, 114), 6.38 (s, 1H), 6.92 (t, 2H), 7.08 (d, 1H), 7.31 (m, 2H), 7.41 (d, 1H), 7.53 (dd, 1H); Mass spectrum: 436 (M+1), 453 (M+NH$_3$)

EXAMPLE 63

(5R,6S,7S)-6-(4-Fluorophenyl)-3-[2-isopropoxy-5-(2-methyl-1,3,4-oxadiazol-5-yl)-phenyl]-1-oxaspiro[4.4]non-3-ene-7-carboxylic acid methyl ester $^1$H NMR (400 MHz, CD$_3$OD): δ 1.30 (d, 3H), 1.32 (d, 3H), 1.95–2.37 (2m's, 4H), 2.58 (s, 3H), 3.48 (m, 1H), 3.57 (s, 3H), 4.12 (dd, 1H), 6.40 (m, 1H), 6.92 (t, 2H), 7.11 (d, 1H), 7.32 (m, 2H), 7.68 (d, 1H), 7.82 (dd, 1H). Mass spectrum: 493 (M+1)

EXAMPLE 64

(5R,6S,7S)-6-(4-fluorophenyl)-3-[2-isopropoxy-5-(1,2,4-oxadiazol-3-yl)-phenyl]-1-oxaspiro[4.4]non-3-ene-7-carboxylic acid methyl ester $^1$H NMR (400 MHz, CD$_3$OD): δ 1.29 (d, 3H), 1.32 (d, 3H), 1.93–2.37 (2m's, 4H), 3.48 (m, 1H), 3.57 (s, 3H), 4.14 (dd, 1H), 4.68–4.77 (m, 2H), 6.38 (m, 1H), 6.92 (t, 2H), 7.09 (d, 1H), 7.32 (m, 2H), 7.75 (d, 1H), 7.92 (dd, 1H), 9.20 (s, 1H). Mass spectrum: 479 (M+1)

EXAMPLE 65

(5R,6S,7S)-6-(4-fluorophenyl)-3-[2-isopropoxy-5-(5-methyl-1,2,4-oxadiazol-3-yl)-phenyl]-1-oxaspiro[4.4]non-3-ene-7-carboxylic acid methyl ester $^1$H NMR (400 MHz, CD$_3$OD): δ 1.29 (d, 3H), 1.32 (d, 3H), 1.95–2.36 (2 m's, 4H), 2.61 (s, 3H), 3.49 (m, 1H), 3.57

(s, 3H), 4.12 (dd, 1H), 4.70 (septet, 1H), 4.73 (dd, 1H), 6.37 (m, 1H), 6.92 (t, 2H), 7.07 (d, 1H), 7.32 (m, 2H), 7.78 (d, 1H), 7.86 (dd, 1H).

The title compounds of Examples 66 and 67 were prepared by hydrogenation of the appropriate intermediates from Examples 62 and 63, respectively, according to the procedure given in Example 6, Step G.

EXAMPLE 66

(3S,5R,6S,7S)-6-(4-Fluorophenyl)-3-(5-cyano-2-isopropoxy-phenyl)-1-oxaspiro[4.4]nonane-7-carboxylic acid methyl ester $^1$H NMR (400 MHz, CD$_3$OD): δ 1.28 (d, 3H), 1.30 (d, 3H), 1.88–2.00 (m, 3H), 2.15–2.30 (m, 3H), 3.18 (t, 1H), 3.53 (s, 3H), 3.65 (m, 1H), 4.06 (t, 1H), 4.67 (s, 1H), 6.91 (d, 1H), 6.96–7.02 (m, 3H), 7.34 (m, 2H), 7.42 (dd, 1H). Mass spectrum: 438 (M+1), 455 (M+NH$_3$)

EXAMPLE 67

(3S,5R,6S,7S)-6-(4-Fluorophenyl)-3-[2-isopropoxy-5-(2-methyl-1,3,4-oxadiazol-5-yl)-phenyl]-1-oxaspiro[4.4]nonane-7-carboxylic acid methyl ester $^1$H NMR (400 MHz, CD$_3$OD): δ 1.29 (d, 3H), 1.31 (d, 3H), 1.90–2.04 (m, 3H), 2.18–2.32 (m, 3H), 2.61 (s, 3H), 3.16 (t, 1H), 3.53 (s, 3H), 3.71 (m, 1H), 4.07 (t, 1H), 4.69 (septet, 1H), 6.95 (t, 2H), 7.01 (d, 1H), 7.30 (d, 1H), 7.36 (m, 2H), 7.73 (dd, 1H). Mass spectrum: 495 (M+1)

EXAMPLE 68

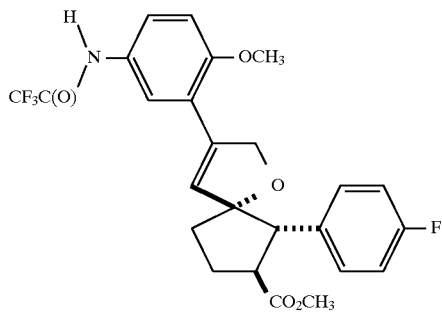

(5R,6S,7S)-6-(4-Fluorophenyl)-3-(2-methyloxy-5-(2,2,2-trifluoroacetamido)phenyl)-1-oxaspiro[4.4]non-3-ene-7-carboxylic acid methyl ester Step A: N-(3-bromo-4-methoxyphenyl)-2,2,2-trifluoroacetamide.

A solution of 3-bromo-4-methoxyaniline (2.50 g, 12.4 mmol) and triethylamine (1.74 mL, 12.4 mmol) in methylene chloride (25 mL) was cooled to 0° C. and trifluoroacetic anhydride (1.75 mL, 2.60 g, 12.4 mmol) was added dropwise over 10 min. Once the addition was complete, the ice bath was removed and the mixture was stirred at room temperature for 1 h. The reaction mixture was partitioned between 50 mL of dichloromethane and 50 mL of water. The aqueous layer was extracted with 50 mL of ethyl acetate. The combined organic layers were washed with 50 mL of brine, dried over sodium sulfate, and evaporated to give a white solid. The crude material was purified by flash column chromatography, eluting with 1.0 L of 5% ethyl acetate/hexane, 1.0 L of 7% of ethyl acetate/hexane and 1.0 L of 10% of ethyl acetate/hexane to obtain N-(3-bromo-4-methoxyphenyl)-2,2,2-trifluoroacetamide (3.42 g, 93%) as a white solid. $^1$H NMR (400 MHz, CDCl$_3$): δ 7.76 (d, 1H, J=3 Hz), 7.50 (dd, 1H, J=9 ,3 Hz), 6.89 (d, 1H, J=9 Hz), 3.89 (s, 3H).

Step B: (5R,6S,7S)-6-(4-Fluorophenyl)-3-(2-methyloxy-5-(2-trifluoroacetamido)phenyl)-1-oxaspiro[4.4]non-3-ene-7-carboxylic acid methyl ester The title compound was prepared by using the procedure given in Example 6, Step F d), replacing 2-bromo-4-(5-(trifluoromethyl)tetrazol-1-yl)anisole with N-(3-bromo-4-methoxyphenyl)-2,2,2-trifluoroacetamide (from Step A above). $^1$H NMR (400 MHz, CDCl$_3$): δ 7.71 (bs, 1H), 7.46 (dd, 1H, J=9, 3 Hz), 7.27 (dd, 2H, J=9, 6 Hz), 6.98 (d, 1H, J=3 Hz), 6.89 (t, 2H, J=9 Hz), 6.87 (d, 1H, J=9 Hz), 6.35 (t, 1H, J=2 Hz), 4.72 (dd, 1H, J=12, 2 Hz), 4.08 (dd, 1H, J=12, 2 Hz), 3.84 (s, 3H), 3.59 (s, 3H), 3.46 (dt, 1H, J=11, 8 Hz), 3.30 (d, 1H, J=11 Hz), 2.41–2.22 (m, 2H), 2.33–1.92 (m, 2H). Mass spectrum (NH3CI): m/e=511 (M+NH$_3$+1).

EXAMPLE 69

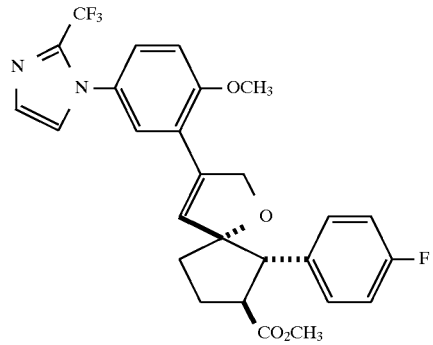

(5R,6S,7S)-6-(4-Fluorophenyl)-3-(2-methoxy-5-(2-(trifluoromethyl)imidazol-1-yl)phenyl)-1-oxaspiro[4.4]non-3-ene-7-carboxylic acid methyl ester Step A: 1-(3-Bromo-4-methoxyphenyl)-2-(trifluoromethyl)imidazole Triphenylphosphine (2.1 g, 8.0 mmol) was added in portions to a suspension of N-(3-bromo-4-methoxyphenyl)-2,2,2-trifluoroacetamide (2.0 g, 6.7 mmol) in 40 mL of carbon tetrachloride at 80° C., and stirring was continued at 80° C. overnight. An additional portion of triphenylphosphine (2.1 g, 8.0 mmol) was added and stirring was continued for 2.5 h at 80° C. After cooling to room temperature, the mixture was concentrated under reduced pressure. The residue was treated with 50 mL of boiling hexane and filtered. The undissolved material was treated with 100 mL of boiling hexane and filtered. The combined filtrates were concentrated. The resulting residue was treated with hexane at room temperature and filtered. Concentration of the filtrate yielded 2.95 g of brown oil. NMR indicated that this crude material contained 1.83 g (5.78 mmol) of the intermediate chloroimidate.

Aminoacetaldehyde diethyl acetal (2.52 mL, 17.3 mmol) was added dropwise to an ice cold solution of the crude chloroimidate in 20 mL of THF. After 30 min at 0° C., the mixture was stirred for 2.5 h with slow warming to 25° C. The mixture was concentrated in vacuo, and the residue was dissolved in 55 mL of acetic acid and heated at reflux for 1.5 h. After cooling to room temperature, the acetic acid was removed in vacuo. The residue was partitioned between 100 mL of ethyl acetate and 50 mL of 2.5N aq. sodium hydroxide, and the aqueous layer was then extracted with 2×100 mL of ethyl acetate. The combined ethyl acetate layers were washed with 100 mL of brine, dried over sodium sulfate, and evaporated. Flash column chromatography on 150 g of silica gel eluting with 2 L of 10% ethyl acetate/hexane followed by 1 L of 20% of ethyl acetate/hexane yielded 1-(3bromo-4-methoxyphenyl)-2-(trifluoromethyl) imidazole (1.22 g, 65% yield) as amber crystals. ¹H NMR (400 MHz, CDCl₃): δ 7.58 (d, 1H, J=3 Hz), 7.31 (dd, 1H, J=9, 3 Hz), 7.21 (d, 1H, J=1 Hz), 7.21 (d, 1H, J=1 Hz), 6.98 (d, 1H, J=9 Hz), 3.97 (s, 3H). Mass spectrum (NH₃Cl): m/e=321 (M+1).

Step B: (5R,6S,7S)-6-(4-Fluorophenyl)-3-(2-methoxy-5-(2-(trifluoromethyl)imidazol-1-yl)phenyl)-1-oxaspiro[4.4]non-3-ene-7-carboxylic acid methyl ester The title compound was prepared by using the procedure given of Example 6, Step F d), replacing 2-bromo-4-(5-(trifluoromethyl)tetrazol-1-yl)anisole with 1-(3-bromo-4-methoxy-phenyl)-2-(trifluoromethyl)imidazole (from Step A above). ¹H NMR (400 MHz, CDCl₃): δ 7.27 (dd, 2H, J=9, 6 Hz), 7.20 (dd, 1H, J=9, 2 Hz), 7.18 (d, 1H, J=1 Hz), 7.07 (d, 1H, J=1 Hz), 6.93 (d, 1H, J=9 Hz), 6.89 (t, 2H, J=9 Hz), 6.84 (d, 1H, J=2 Hz), 6.36 (t, 1H, J=2 Hz), 4.71 (dd, 1H, J=12, 2 Hz), 4.05 (dd, 1H, J=12, 2 Hz), 3.90 (s, 3H), 3.59 (s, 3H), 3.46 (dt, 1H, J=11, 8 Hz), 3.32 (d, 1H, J=11 Hz), 2.41–2.21 (m, 2H), 2.14–1.94 (m, 2H). Mass spectrum (NH₃Cl): m/e=517 (M+1).

EXAMPLE 70

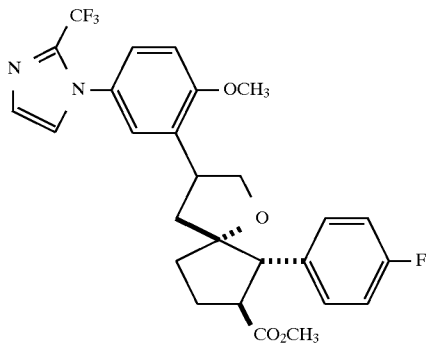

(3S,5R,6S,7S)-6-(4-Fluorophenyl)-3-(2-methoxy-5-(2-(trifluoromethyl)imidazol-1-yl)phenyl)-1-oxaspiro[4.4]nonane-7-carboxylic acid methyl ester The title compound was prepared according to the procedure of Example 6, Step G, substituting (5R,6S,7S)-6-(4-fluorophenyl)-3-(2-methoxy-5-(2-(trifluoromethyl) imidazol-1-yl)phenyl)-1-oxaspiro[4.4]non-3-ene-7-carboxylic acid methyl ester for methyl[5-(RS),6-(SR),7-(SR)]-6-(4-fluorophenyl)-3-(2-methoxy-5-((5-trifluoromethyl)tetrazol-1-yl)phenyl)-1-oxaspiro[4.4]non-3-ene-7 -carboxylate (from Example 69, Step B). ¹H NMR (400 MHz, CDCl₃): δ 7.32 (dd, 2H, J=9, 6 Hz), 7.20 (d, 1H, J=1 Hz), 7.10 (dd, 1H, J=9, 3 Hz), 6.97 (d, 1H, J=1 Hz), 6.90 (t, 2H, J=9 Hz), 6.81 (d, 1H, J=9 Hz), 6.62 (d, 1H, J=3 Hz), 4.07 (t, 1H, J=8 Hz), 3.78 (s, 3H), 3.78–3.67 (m, 1H), 3.56 (s, 3H), 3.38–3.30 (m, 1H), 3.20 (d, 1H, J=11 Hz), 3.06 (t, 1H, J=8 Hz), 2.36–2.27 (m, 1H), 2.25–2.16 (m, 2H), 2.00–1.87 (m, 3H). Mass spectrum (NH₃Cl): m/e=519 (M+1).

EXAMPLE 71

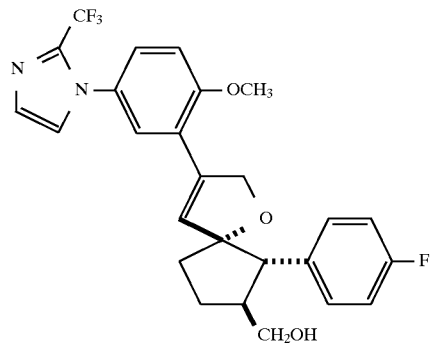

(5R,6S,7S)-(6-(4-Fluorophenyl)-3-(2-methoxy-5-(2-(trifluoromethyl)imidazol-1-yl)phenyl)-1-oxaspiro [4.4]non-3-ene-7-yl)methanol The title compound was prepared according to the procedure of Example 10, Step A, substituting (3S,5R,6S,7S)-6-(4-fluorophenyl)-3-(2-methoxy-5-(2-(trifluoromethyl) imidazol-1-yl)phenyl)-1-oxaspiro[4.4]nonane-7-carboxylic acid methyl ester for methyl[3-(S),5-(R),6-(S),7-(S)]-6-(4-fluorophenyl)-3-(2-methoxy-5-((5-trifluoromethyl)tetrazol-1-yl)phenyl)-1-oxaspiro[4.4]nonane-7-carboxylate (from Example 70). ¹H NMR (400 MHz, CDCl₃): δ 7.27 (dd, 2H, J=9, 6 Hz), 7.21–7.16 (m, 3H), 7.07 (s, 1H), 6.92 (d, 1H, J=9 Hz), 6.91 (t, 2H, J=9 Hz), 6.84 (d, 1H, J=2 Hz), 6.33 (t, 1H, J=2 Hz), 4.71 (dd, 1H, J=12, 2 Hz), 4.04 (dd, 1H, J=12, 2 Hz), 3.89 (s, 3H), 3.66 (dd, 1H, J=11, 4 Hz), 3.52 (dd, 1H, J=11, 5 Hz), 2.82–2.74 (m, 2H), 2.24–2.03 (m, 3H), 1.70–1.61 (m, 1H). Mass spectrum (NH₃Cl): m/e=489 (M+1).

EXAMPLE 72

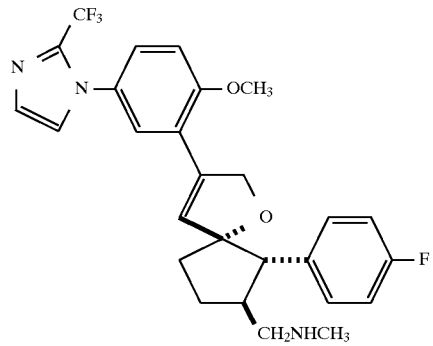

(5R,6S,7S)-(6-(4-Fluorophenyl)-3-(2-methoxy-5-(2-(trifluoromethyl)imidazol-1-yl)phenyl)-1-oxaspiro [4.4]non-3-ene-7-ylmethyl)methylamine Step A: (5R,6S,7S)-6-(4-Fluorophenyl)-3-(2-methoxy-5-(2-(trifluoromethyl)imidazol-1-yl)phenyl)-1-oxaspiro[4.4]non-3,7-carboxyaldehyde The title compound was prepared according to the procedure of Example 10, Step B, first paragraph replacing[3-(S),5-(R),6-(S),7-(S)]-6-(4-fluorophenyl)-3-(2-methoxy-5-((5-trifluoromethyl)tetrazol-1-yl)phenyl)-1-oxaspiro[4.4] nonane-7-methanol with (5R,6S,7S)-(6-(4-fluorophenyl)-3-(2-methoxy-5-(2-(trifluoromethyl)imidazol-1-yl)phenyl)-1-oxaspiro[4.4]non-3-ene-7-yl)methanol (from Example 70). ¹H NMR (400 MHz, CDCl₃): δ 9.66 (d, 1H, J=2 Hz), 7.29

(dd, 2H, J=9, 6 Hz), 7.23–7.18 (m, 1H), 7.19 (d, 1H, J=1 Hz), 7.08 (d, 1H, J=1 Hz), 6.93 (d, 1H, J=9 Hz), 6.92 (t, 2H, J=9 Hz), 6.85 (d, 1H, J=3 Hz), 6.35 (t, 1H, J=2 Hz), 4.73 (dd, 1H, J=12, 2 Hz), 4.08 (dd, 1H, J=12, 2 Hz), 3.90 (s, 3H), 3.56–3.46 (m, 1H), 3.28 (d, 1H, J=11 Hz), 2.32–2.23 (m, 1H), 2.16–2.02 (m, 3H). Mass spectrum (NH$_3$CI): m/e=487 (M+1).

Step B: (5R,6S,7S)-(6-(4-Fluorophenyl)-3-(2-methoxy-5-(2-(trifluoromethyl)imidazol-1-yl)phenyl)-1-oxaspiro[4.4]non-3-ene-7-ylmethyl)methylamine The title compound was prepared according to the procedure of Example 10, Step B (second paragraph) replacing the crude aldehyde with (5R,6S,7S)-6-(4-Fluorophenyl)-3-(2-methoxy-5-(2-(trifluoromethyl)imidazol-1-yl)phenyl)-1-oxaspiro[4.4]non-3-7-carboxaldehyde (from Step A above). $^1$H NMR (400 MHz, CDCl$_3$): δ 7.27 (dd, 2H, J=9, 6 Hz), 7.19 (dd, 1H, J=9, 3 Hz), 7.18 (d, 1H, J=1 Hz), 7.06 (d, 1H, J=1 Hz), 6.92 (t, 2H, J=9 Hz), 6.91 (d, 1H, J=9 Hz), 6.83 (d, 1H, J=3 Hz), 6.32 (t, 1H, J=2 Hz), 4.69 (dd, 1H, J=12, 2 Hz), 3.98 (dd, 1H, J=12,2 Hz), 3.88 (s, 3H), 2.92–2.81 (m, 1H), 2.73 (dd, 1H, J=12, 5 Hz), 2.66 (d, 1H, J=12 Hz), 2.59 (dd, 1H, J=12, 9 Hz), 2.47 (s, 3H), 2.36–2.06 (m, 3H), 1.63–1.52 (m, 1H). Mass spectrum (NH$_3$CI): m/e=502 (M+1).

EXAMPLE 73

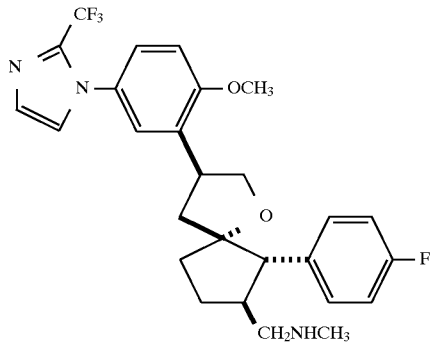

(3S,5R,6S,7S)-(6-(4-Fluorophenyl)-3-(2-methoxy-5-(2-(trifluoromethyl)imidazol-1-yl)phenyl)-1-oxaspiro[4.4]nonane-7-ylmethyl)methylamine The title compound was prepared according to the procedure of Example 6, Step G, substituting (5R,6S,7S)-(6-(4-fluorophenyl)-3-(2-methoxy-5-(2-(trifluoromethyl) imidazol-1-yl)phenyl)-1-oxaspiro[4.4]non-3-ene-7-ylmethyl)methylamine (from Example 72) for methyl[3-(SR),5-(RS),6-(SR),7-(SR)]-6-(4-fluorophenyl)-3-2-methoxy-5-((5-trifluoromethyl)tetrazol-1-yl)phenyl)-1-oxaspiro[4.4]nonane-7-carboxylate. $^1$H NMR (400 MHz, CDCl$_3$): δ 7.31 (dd, 2H, J=9, 6 Hz), 7.20( d, 1H, J=1 Hz), 7.09 (dd, 1H, J=9, 3 Hz), 6.97 (d, 1H, J=1 Hz), 6.90 (t, 2H, J=9 Hz), 6.81 (d, 1H, J=9 Hz), 6.63 (d, 1H, J=3 Hz), 4.06 (t, 1H, J=8 Hz), 3.78 (s, 3H), 3.75–3.66 (m, 1H), 2.98 (t, 1H, J=8 Hz), 2.71–2.59 (m, 1H), 2.56 (dd, 1 H, J=11, 5 Hz), 2.52 (d, 1H, J=11 Hz), 2.43 (dd, 1H, J=11, 9 Hz), 2.33 (s, 3H), 2.25–2.12 (m, 3H), 1.93–1.83 (m, 2H), 1.53–1.42 (m, 1 H). Mass spectrum (ESI): m/e=504 (M+1).

EXAMPLE 74

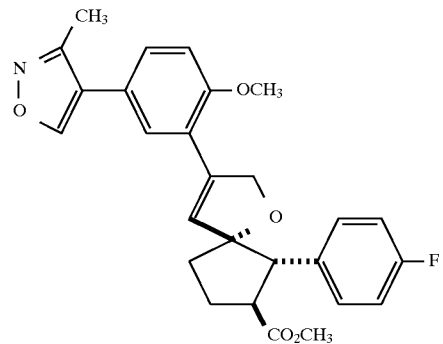

(5R,6S,7S)-6-(4-Fluorophenyl)-3-(2-methoxy-5-(3-methylisoxazol-4-yl)phenyl)-1-oxaspiro[4.4]non-3-ene-7-carboxylic acid methyl ester Step A: 2-Bromo-1-methoxy-4-(2-methoxyvinyl)benzene A suspension of (methoxymethyl)triphenylphosphonium chloride (4.78 g, 14.0 mmol) and potassium tert-butoxide (1.46 g, 13.02 mmol) in THF (14 mL) was stirred for 1 h at room temperature. 3-Bromo-4-methoxybenzaldehyde (2.0 g, 9.3 mmol) was added, and the mixture was stirred overnight at room temperature. Saturated aqueous ammonium chloride (10 mL) was added. The mixture was partitioned between 100 mL of ethyl acetate and 40 mL of water. The aqueous was extracted with 2×50 mL of ethyl acetate. The combined organic layers were washed with 40 mL of saturated aqueous sodium bicarbonate followed by 40 mL of brine, dried over sodium sulfate, and evaporated. Flash chromatography on 120 g silica gel, eluting with 3 L of hexane and 1 L of 10% of ethyl acetate/hexane gave a 1:1 mixture of the E- and Z-isomers of 2-bromo-1-methoxy-4-(2-methoxyvinyl)benzene as 1.87 g (87% yield) of colorless oil. $^1$H NMR (400 MHz, CDCl$_3$) for the 1:1 mixture of E- and Z-isomers: δ 7.83 and 7.43 (two d, 1H, J=2 Hz); 7.44 and 7.11 (two dd, 1H, J=9, 2 Hz); 6.93 and 5.71 (two d, 1H, J=13 Hz); 6.82 and 6.81 (two d, 1H, J=9 Hz); 6.08 and 5.11 (two d, 1H, J=7 Hz); 3.88, 3.87, 3.78, and 3.67 (four s, 6H). Mass spectrum (NH$_3$CI): m/e=243 (M+1).

Step B: 4-(3-Bromo-4-methoxyphenyl)-5-methoxy-3-methyl-4,5-dihydroisoxazole

Triethylamine (0.050 mL, 0.36 mmol) was added in portions to a mixture of 2-bromo-1-methoxy-4-(2-methoxyvinyl)benzene (500 mg, 2.06 mmol, 1:1 ratio of E- and Z-isomers), phenylisocyanate (0.489 mL, 4.5 mmol), and nitroethane (0.180 mL, 2.5 mmol) in dry toluene (2.0 mL) at room temperature. After stirring at room temperature for 5 h followed by 1 h at 100° C. for 1 h, the mixture was allowed to stand overnight at room temperature. Water (6 mL) was then added and stirring was continued at room temperature for 4 h. The mixture was filtered, the layers of the filtrate were separated, and the aqueous layer was extracted with 2×30 mL of toluene. The combined organic layers were dried over sodium sulfate and evaporated. Flash column chromatography on 50 g of silica gel eluting with 2 L of 10% of ethyl acetate/hexane yielded 4-(3-bromo-4-methoxyphenyl)-5-methoxy-3-methyl-4,5-dihydroisoxazole as 0.28 g of yellow oil containing some remaining impurity. $^1$H NMR (400 MHz, CDCl$_3$): δ 7.33 (d, 1H, J=2 Hz), 7.03(dd, 1H, J=9, 2 Hz), 6.87 (d, 1H, J=9 Hz), 5.15 (d, 1H, J=1 Hz), 3.89 (s, 3H), 3.88 (s, 1H), 3.47 (s, 3H), 1.83 (s, 3H). Mass spectrum (NH$_3$CI): m/e=300 (M+1).

85

Step C: 4-(3-Bromo-4-methoxyphenyl)-3-methylisoxazole.

A solution of 4-(3-bromo-4-methoxyphenyl)-5-methoxy-3-methyl-4,5-dihydroisoxazole (260 mg, 0.87 mmol) in 15 mL of a 5:1 mixture of ethanol and 12N aqueous HCl was heated at reflux overnight. After cooling to room temperature, the reaction was concentrated to a small volume in vacuo. Saturated aqueous sodium bicarbonate (50 mL) was added and the mixture was extracted with 3×50 mL of ethyl acetate. The combined ethyl acetate layers were washed with 50 mL of brine, dried over sodium sulfate, and evaporated. The crude residue was subjected to flash chromatography on 25 g of silica gel eluting with 500 mL of 20% of diethyl ether/hexane to give 4-(3-bromo-4-methoxyphenyl)-3-methylisoxazole (158 mg, 68% yield) as a white solid. $^1$H NMR (400 MHz, CDCl$_3$): δ 8.40 (s, 1H), 7.57 (d, 1H, J=2 Hz), 7.29 (dd, 1H, J=9, 2 Hz), 6.86 (d, 1H, J=9 Hz), 3.94 (s, 3H), 2.40 (s, 3H). Mass spectrum (ESI): m/e=268 (M+1).

Step D: (5R,6S,7S)-6-(4-Fluorophenyl)-3-(2-methoxy-5-(3-methylisoxazol-4-yl)phenyl)-1-oxaspiro[4.4]non-3-ene-7-carboxylic acid methyl ester The title compound was prepared according to the procedure of Example 6, Step F d), replacing 2-bromo-4-(5-(trifluoromethyl)tetrazol-1-yl)anisole with 4-(3-bromo-4-methoxyphenyl)-3-methylisoxazole (from Step C above). $^1$H NMR (400 MHz, CDCl$_3$): δ 8.32 (s, 1H), 7.28 (dd, 2H, J=9, 6 Hz), 7.20 (dd, 1H, J=9, 2 Hz), 6.92 (d, 1H, J=9 Hz), 6.89 (t, 2H, J=9 Hz), 6.83 (d,1H J=3 Hz), 6.32 (t, 1H, J=2 Hz), 4.75 (dd, 1H, J=12, 2 Hz), 4.09 (dd, 1H, J=12, 2 Hz), 3.84 (s, 3H), 3.59 (s, 3H), 3.47 (dt, 1H, J=11, 8 Hz), 3.31 (d, 1H, J=11 Hz), 2.44–2.22 (m, 2H), 2.33 (s, 3H), 2.14–1.94 (m, 2 H). Mass spectrum (NH$_3$Cl): m/e=464 (M+1).

EXAMPLE 75

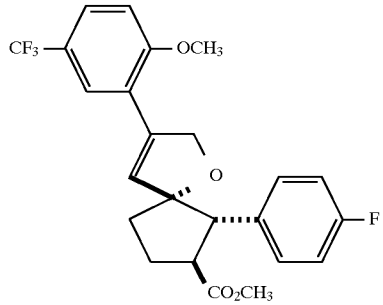

(5R,6S,7S)-6-(4-Fluorophenyl)-3-(2-methoxy-5-(trifluoromethyl)phenyl)-1-oxaspiro[4.4]non-3-ene-7-carboxylic acid methyl ester The title compound was prepared according to the procedure of Example 6, Step F d), replacing 2-bromo-4-(5-(trifluoromethyl)tetrazol-1-yl)anisole with 2-bromo-4-(trifluoromethyl)anisole (prepared according to the general procedure given in: J. Alexander, Org. Prep. Proced. Int., 1986, 18, 213–215). $^1$H NMR (400 MHz, CDCl$_3$): δ 7.46 (dd, 1H, J=9, 2 Hz), 7.27 (dd, 2H, J=9, 6 Hz) 7.10 (d, 1H, J=2 Hz) 6.91 (d, 1H, J=9 Hz), 6.90 (t, 2H, J=9 Hz), 6.33 (t, 1H, J=2 Hz), 4.75 (dd, 1H, J=12, 2 Hz), 4.11 (dd, 1H, J=12, 2 Hz), 3.87 (s, 3H), 3.59 (s, 3H), 3.46 (dt, 1H, J=12, 8 Hz), 3.31 (d, 1H, J=12 Hz), 2.42–2.21 (m, 2H), 2.14–1.94 (m, 2H). Mass spectrum (NH$_3$Cl): m/e=451 (M+1).

86

EXAMPLE 76

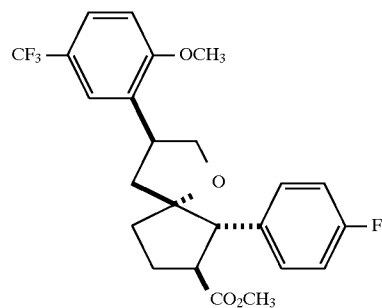

(3S,5R,6S,7S)-6-(4-Fluorophenyl)-3-(2-methoxy-5-(trifluoromethyl)phenyl)-1-oxaspiro[4.4]nonane-7-carboxylic acid methyl ester The title compound was prepared according to the procedure of Example 6, Step G, substituting (5R,6S,7S)-6-(4-fluorophenyl)-3-(2-methoxy-5-(trifluoromethyl)phenyl)-1-oxaspiro[4.4]non-3-ene-7-carboxylic acid methyl ester (from Example 75) for methyl[3-(SR),5-(RS),6-(SR),7-(SR) ]-6-(4-fluorophenyl)-3-2-methoxy-5-((5-trifluoromethyl) tetrazol-1-yl)phenyl)-1-oxaspiro[4.4]-nonane-7-carboxylate. $^1$H NMR (400 MHz, CDCl$_3$): δ 7.40–7.33 (m, 3H), 7.01 (t, 2H, J=9 Hz), 6.91 (d, 1H, J=2Hz), 6.81 (d, 1H, J=9 Hz), 4.04 (t, 1H, J=8 Hz), 3.76–3.65 (m, 1H), 3.74 (s, 3H), 3.58 (s, 3 H), 3.40–3.31 (m, 1H), 3.22 (d, 1H, 11 Hz), 3.06 (dd, 1H, J=10, 8 Hz), 2.37–2.28 (m, 1H), 2.23–2.15 (m, 2H), 2.02–1.91 (m, 3H). Mass spectrum (NH$_3$Cl): m/e=453 (M+1).

EXAMPLE 77

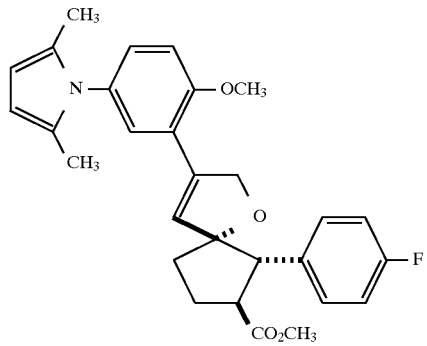

(5R,6S,7S)-6-(4-Fluorophenyl)-3-(2-methoxy-5-(2,5-dimethylpyrrol-1-yl)phenyl)-1-oxaspiro[4.4]non-3-ene-7-carboxylic acid methyl ester Step A: 1-(3-Bromo-4-methoxyphenyl)-2,5-dimethylpyrrole.

Using the general procedure described by S. P. Bruekelman, S. E. Leach, G. D. Meakins, and M. D. Tirel (J. Chem. Soc., Perkin Trans. 1, 1984, 2801–2807), acetic acid (0.50 mL, 0.52 g, 8.7 mmol) and sodium acetate trihydrate (70 mg, 0.51 mmol) were added to a solution of 2,5-hexanedione (8.0 mL, 7.8 g, 68 mmol) and 3-bromo-4-methoxyaniline (see Y. -Y. Lui, M. Minich, J. Labelled Compounds and Radiopharmaceuticals, 1981, 18, 791–797) in 40 mL of toluene. The mixture was heated to reflux for 2 h in a flask connected to a Dean-Stark trap. After cooling the mixture to room temperature, ethyl acetate (20 mL) was added and the solution was washed with 25 mL. each of water, saturated aqueous sodium bicarbonate, and saturated aqueous sodium chloride. The organic layer was dried (sodium sulfate), decanted, and evaporated to give brown crystals. Recrystallization from 20 mL of warm hexane cooled to 0° C. yielded 8.17 g of tan crystals (67% yield). $^1$H NMR (400 MHz, CDCl$_3$): δ 7.42 (d, 1H, J=2 Hz), 7.14 (dd, 1H, J=9, 2 Hz), 6.96 (d, 1H, J=9 Hz), 5.87 (s, 2H), 3.95 (s, 3H), 2.02 (s, 6H). Mass spectrum (NH$_3$CI): m/e=280 (M+1).

Step B: (5R,6S,7S)-6-(4-Fluorophenyl)-3-(2-methoxy-5-(2,5-dimethylpyrrol-1-yl)phenyl)-1-oxaspiro[4.4]non-3-ene-7-carboxylic acid methyl ester The title compound was prepared according to the procedure of Example 6, Step F d), replacing 2-bromo-4-(5-(trifluoromethyl)tetrazol-1-yl)anisole with 1-(3-bromo-4-methoxyphenyl)-2,5-dimethylpyrrole (from Step A above). $^1$H NMR (400 MHz, CDCl$_3$): δ 7.27 (dd, 2H, J=9, 6 Hz), 7.06 (dd, 1H, J=9, 2 Hz) 6.92 (d, 1H, J=9 Hz), 6.88 (t, 2H, J=9 Hz), 6.69 (d, 1H, J=2 Hz), 6.34 (t, 1H, J=Hz), 5.87 (s, 2H), 4.71 (dd, 1H, J=12, 2 Hz), 4.02 (dd, 1H, J=12, 2 Hz), 3.89 (s, 3H), 3.59 (s, 3H), 3.46 (dt, 1H, J=12, 9 Hz), 3.30 (d, 1 H, J=12 Hz), 2.41–2.21 (m, 2H), 2.14–2.06 (m, 1H), 2.04–1.94 (m, 1H), 1.96 (s, 6H). Mass spectrum (NH$_3$CI): m/e=476 (M+1).

EXAMPLE 78

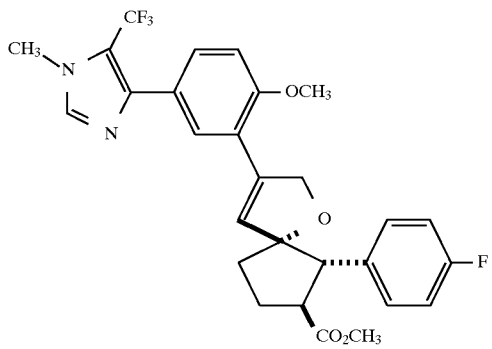

(5R,6S,7S)-6-(4-Fluorophenyl)-3-(2-methoxy-5-(5-trifluromethyl-1-methylimidazol-4-yl)phenyl)-1-oxaspiro[4.4]non-3-ene-7-carboxylic acid methyl ester Step A: 3-(3-Bromo-4-methoxyphenyl)-3-(dimethylhydrazono)-1.1.1-trifluoropropan-2-one Using the general procedure of Y. Kamitori, M. Hojo, R. Masuda, T. Fujitani, S. Ohara, and T. Yokoyama (J. Org. Chem., 1988, 53, 129–135), 1,1-dimethylhydrazine (0.140 mL, 111 mg, 1.8 mmol) was added to a solution of 3-bromo-4-methoxybenzaldehyde (1.00 g, 4.65 mmol) in 1.3 mL of dry chloroform at room temperature. After 2 h, additional 1,1-dimethylhydrazine (0.250 mL, 198 mg, 3.29 mmol) was added and the solution was stirred at room temperature for 3 h. Chloroform (10 mL) and 2,6-lutidine (2.75 mL, 2.52 g, 23.6 mmol) were added, and the solution was cooled to 0° C. before the addition of a solution of trifluoroacetic anhydride (6.6 mL, 9.8 g, 46 mmol) in chloroform (20 mL). The mixture was allowed to slowly warm to room temperature. After stirring overnight, the mixture was washed with 50 mL each of 0.2N aqueous HCl, water, and saturated aqueous sodium bicarbonate solution. The organic layer was dried (magnesium sulfate), filtered, and evaporated to give a yellow syrup which crystallized upon standing. Recrystallization from a mixture of cyclohexane (7 mL) and toluene (5 mL) warmed to 80° C. and allowed to cool to room temperature gave 755 mg (46% yield) of tan crystals. $^1$H NMR (400 MHz, CDCl$_3$): δ 7.41 (d, 1H, J=2 Hz), 7.15 (dd, 1H, J=8, 2 Hz), 6.89 (d, 1H, J=8 Hz), 3.92 (s, 3H), 3.09 (s, 6H). Mass spectrum (NH$_3$CI): m/e=353 (M+1).

Step B: 4-(3-Bromo-4-methoxyphenyl)-5-trifluoromethyl-1-methylimidazole and 5-(3-bromo-4-methoxyphenyl)-4-trifluoromethyl-1-methylimidazole Using the general procedure of S. Ohara, K. Kawasaki, Y. Kawamura, and M. Tanaka (J. Heterocyclic Chem., 1990, 27, 487–495), silica gel (EM silica gel 60, 230–400 mesh) was dried under vacuum at 180° C. for 2 h. A suspension of 1.80 g of this activated silica gel was stirred in 9 mL of dry toluene and 3-(3-bromo-4-methoxyphenyl)-3-(dimethylhydrazono)-1,1,1-trifluoropropan-2-one (250 mg 0.71 mmol) was added as a solution in 5 mL of toluene. The resulting suspension was heated to reflux for 48 h, then allowed to cool to room temperature and stirred overnight. After the addition of 95% ethanol (20 mL) the mixture was stirred for 10 min and filtered. The silica gel was stirred with 20 mL of 95% ethanol and filtered, and the process was repeated again. Evaporation of the combined filtrates gave a pale amber oil. Flash column chromatography on 15 g of silica gel eluting with 10% ethyl acetate in hexane followed by 15% ethyl acetate in hexane gave 167 mg of 4-(3-bromo-4-methoxyphenyl)-5-trifluoromethyl-1-methylimidazole and 5-(3-bromo-4-methoxyphenyl)-4-trifluoromethyl-1-methylimidazole as a 6:1 mixture as determined by NMR. This material was recrystallized from a 65° C. solution in hexane (0.75 mL) and toluene (0.15 mL) cooled to –10° C. Recrystallization again from a 65° C. solution in hexane (0.75 mL) and toluene (0.15 mL) cooled to room temperature gave 112 mg of 4-(3-bromo-4-methoxyphenyl)-5-trifluoromethyl-1-methylimidazole as white crystals. Concentration of the mother liquors yielded 48 mg of 4-(3-bromo-4-methoxyphenyl)-5-trifluoromethyl-1-methylimidazole and 5-(3-bromo-4-methoxyphenyl)-4-trifluoromethyl-1-methylimidazole as a 1:1 mixture as determined by NMR. 4-(3-Bromo-4-methoxyphenyl)-5-trifluoromethyl-1-methylimidazole: $^1$H NMR (400 MHz, CDCl$_3$): δ 7.78 (d, 1H, J=2 Hz), 7.75 (s, 1H), 7.47 (bd, 1H, J=8 Hz), 6.93 (d, 1H, J=8 Hz), 3.94 (s, 3H), 3.81 (s, 3H). Mass spectrum (ESI): m/e=335 (M+1).

Step C: (5R,6S,7S)-6-(4-Fluorophenyl)-3-(2-methoxy-5-(5-trifluoromethyl-1-methylimidazol-4-yl)phenyl)-1-oxaspiro[4.4]non-3-ene-7-carboxylic acid methyl ester The title compound was prepared according to the procedure given in Example 6, Step F d), replacing 2-bromo-4-(5-(trifluoromethyl)tetrazol-1-yl)anisole with 4-(3-bromo-4-methoxyphenyl)-5-trifluoromethyl-1-methylimidazole (from Step B above). $^1$H NMR (400 MHz, CDCl$_3$): δ 7.52 (s, 1H), 7.41 (bd, 1H, J=9 Hz), 7.27 (dd, 2H, J=9, 6 Hz), 7.09 (d, 1H, J=2 Hz), 6.90 (d, 1H, J=9 Hz), 6.88 (t, 2H, J=9 Hz), 6.32 (t, 1H, J=2 Hz), 4.77 (dd, 1H, J=12, 2 Hz), 4.12 (dd, 1H, J=12, 2 Hz), 3.86 (s, 3H), 3.80 (s, 3H), 3.58 (s, 3H), 3.46 (dt, 1H, J=11, 8 Hz), 3.30 (d, 1H, J=11 Hz), 2.41–2.21 (m, 2H), 2.13–1.92 (m, 2H). Mass spectrum (ESI): m/e=531 (M+1).

EXAMPLE 79

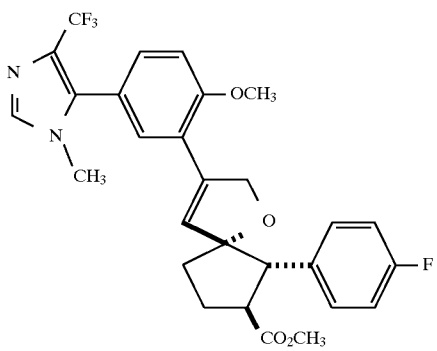

(5R,6S,7S)-6-(4-Fluorophenyl)-3-(2-methoxy-5-(4-trifluoromethyl-1-methylimidazol-5-yl)phenyl)-1-oxaspiro[4.4]non-3-ene-7-carboxylic acid methyl ester The title compound was prepared according to the procedure given in Example 6, Step F d), replacing 2-bromo-4-(5-(trifluoromethyl)tetrazol-1-yl)anisole with a 1:1 mixture of 4-(3-bromo-4-methoxyphenyl)-5-trifluoromethyl-1-methylimidazole and 5-(3-bromo-4-methoxyphenyl)-4-trifluoromethyl-1-methylimidazole (from Example 78, Step B). $^1$H NMR (400 MHz, CDCl$_3$): δ 7.64 (s, 1H), 7.28 (dd, 2H, J=9, 6 Hz), 7.18 (dd, 1H, J=9, 2 Hz), 6.95 (d, J=9 Hz), 6.89 (t, 2H, J=9 Hz), 6.81 (d, 1H, J=2 Hz), 6.32 (t, 1H, J=Hz), 4.73 (dd, 1H, J=12, 2 Hz), 4.05 (dd, 1H, J=12, 2 Hz), 3.89 (s, 3H Hz), 3.51–3.42 (m, 1H), 3.46 (s, 3H), 2.42–2.22 (m, 2H), 2.14–1.93 (m, 2H). Mass spectrum (ESI): m/e=531 (M+1).

EXAMPLE 80

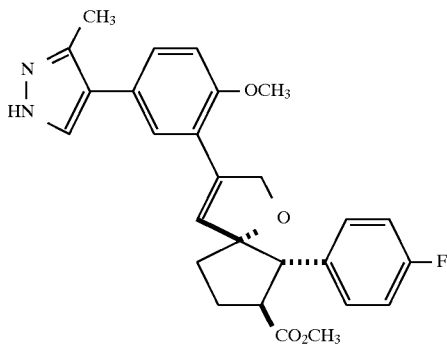

(3S,5R,6S,7S)-6-(4-Fluorophenyl)-3-(2-methoxy-5-(3-methylpyrazol-4-yl)phenyl)-1-oxaspiro[4.4]non-3-ene-7-carboxylic acid methyl ester Step A: 1-(3-Bromo-4-methoxyphenyl)-2-nitropropene Nitroethane (0.800 mL, 836 mg, 11.1 mmol) and n-butylamine (0.050 mL, 37 mg, 0.51 mmol) were added to a solution of 3-bromo-4-methoxybenzaldehyde (2.00 g, 9.30 mmol) in 2.0 mL of absolute ethanol. The solution was heated in a 95° C. oil bath for 8 h and then stirred overnight at room temperature. The ethanol was evaporated, the residue was stirred with 12 mL of 8% ether in hexane, and the supernatant was decanted. The undissolved material was stirred with 12 mL of 8% ether in hexane, and sufficient toluene was added to bring it into solution at 60° C. The crystals which separated at room temperature were recrystallized again from a solution of hexane (7 mL) and toluene (1.8 mL) at 55° C. cooled to room temperature to give 1-(3-bromo-4-methoxyphenyl)-2-nitropropene as 598 mg of yellow needles. All of the mother liquors were combined and evaporated, and the residue was purified by flash column chromatography on 85 g of silica gel eluting with 25% dichloromethane in hexane to give an additional 791 mg of 1-(3-bromo-4-methoxyphenyl)-2-nitropropene (total isolated yield of 55%). $^1$H NMR (400 MHz, CDCl$_3$): δ 8.00 (s, 1H), 7.68 (d, 1H, J=2 Hz), 7.40 (dd, 1H, J=9, 2 Hz), 6.97(d, 1H, J=9Hz), 3.96 (s, 3H), 2.47 (s, 3H). Mass spectrum (NH$_3$CI): m/e=272 (M+1).

Step B: 4-(3-Bromo-4-methoxyphenyl)-3-methyl-3-nitro-4,5-dihydro-3H-pyrazole

An ethereal solution of diazomethane (3.0 mL, 0.3M, 0.9 mmol) was added to 1-(3-bromo-4-methoxyphenyl)-2-nitropropene (250 mg, 0.92 mmol) dissolved in 2.5 mL of ether, and the solution was allowed to stand at room temperature for 28 h. Acetic acid (0.25 mL, 0.26 g, 4.4 mmol) was then added to the almost colorless solution, giving some gas evolution. After 15 min, the solution was diluted with 25 mL of ethyl acetate and washed with 10 mL of saturated aqueous sodium bicarbonate followed by 10 mL of saturated aqueous sodium chloride. The organic layer was dried (sodium sulfate), decanted, and evaporated to give 285 mg (99% yield) of a colorless oil which crystallized upon standing. $^1$H NMR (400 MHz, CDCl$_3$): δ 7.17 (d, 1H, J=2 Hz), 6.89 (dd, 1H, J=8, 2 Hz), 6.84 (d, 1H, J=8 Hz), 5.21 (dd, 1H, J=18, 8 Hz), 4.97 (dd, 1H, J=18, 6 Hz), 3.90 (s, 3H), 3.77 (dd, 1H, J=8, 6 Hz), 1.60 (s, 3H).

Step C: 4-(3-Bromo-4-methoxyphenyl)-3-methylpyrazole

A mixture of 4-(3-bromo-4-methoxyphenyl)-3-methyl-3-nitro-4,5-dihydro-3H-pyrazole (100 mg, 0.32 mmol) and 0.5 mL of water was stirred at room temperature and 2.0 mL of 40% aqueous potassium hydroxide was added. After the mixture had been sonicated for 5 min, 1.0 mL of 95% ethanol was added, followed 20 min later by another 0.5 mL of 95% ethanol. After 15 min, the solution was extracted with 2×20 mL of ether. The ether extracts were washed in succession with 10 mL of saturated aqueous sodium chloride solution, dried (sodium sulfate), decanted, and evaporated to give a white solid. Flash column chromatography on 4 g of silica gel eluting with 15–20% ethyl acetate in dichloromethane gave 80 mg of white solid (94% yield). $^1$H NMR (400 MHz, CDCl$_3$): δ 7.62 (s, 1H), 7.30 (dd, 1H, J=8, 2 Hz), 6.94 (d, 1H, J=8 Hz), 3.93 (s, 3H), 2,43 (s, 3H). Mass spectrum (NH$_3$CI): m/e=267 (M+1).

Step D: 1-(tert-Butoxycarbonyl)-4-(3-bromo-4-methoxyphenyl)-3-methylpyrazole

A solution of 4-(3-bromo-4-methoxyphenyl)-3-methylpyrazole (72 mg, 0.27 mmol) in 0.5 mL of dry tetrahydrofuran was stirred at room temperature and di-tert-butyldicarbonate (98 mg, 0.45 mmol) was added followed by triethylamine (0.085 mL, 62 mg, 0.61 mmol). After 0.5 h, 4-(dimethylamino)pyridine (10 mg, 0.082 mmol) was added, and the solution was stirred 1 h longer. The solution was diluted with 30 mL of ethyl acetate and washed with 5 mL each of 2N aqueous HCl, saturated aqueous sodium bicarbonate, and saturated aqueous sodium chloride. The organic layer was dried (sodium sulfate), decanted, and evaporated. The residue was purified by flash column chromatography on 5 g of silica gel eluting with 15% ethyl acetate in hexane to give 92 mg of a colorless film. $^1$H NMR (400 MHz, CDCl$_3$): δ 8.01 (s, 1H), 7.57 (d, 1H, J=2 Hz), 7.29 (dd, 1H, J=8, 2 Hz), 6.92 (d, 1H, J=8 Hz), 3.91 (s, 3H), 2.40 (s, 3H), 1.64 (s, 9H).

Step E: (3S,5R,6S,7S)-6-(4-Fluorophenyl)-3-(2-methoxy-5-(1-(tert-butoxycarbonyl)-3-methylpyrazol-4-yl)phenyl)-1-oxaspiro[4.4]nonane-7-carboxylic acid methyl ester The title compound was prepared according to the procedure given in Example 6, Step F d), replacing 2-bromo-4-(5 -(trifluoromethyl)tetrazol-1-yl)anisole with 1-(tert-butoxycarbonyl)-4-(3-bromo-4-methoxyphenyl)-3-methylpyrazole (from Step D above). $^1$H NMR (400 MHz, CDCl$_3$): δ 7.94 (s, 1H), 7.26 (dd, 2H, J=9, 6 Hz), 7.21 (dd, H, J=9, 2 Hz), 6.87 (t, 2H, J=9 Hz), 6.84 (d, 1H, J=2 Hz), 6.28 (t, 1H, J=2 Hz), 4.73 (dd, 1H, J=12, 2 Hz), 4.07 (dd, 1 H, J=12, 2 Hz), 3.83 (s, 3H), 3.56 (s, 3H), 3.44 (dt, 1H, J=11, 8 Hz), 3.29 (d, 1H, J=11 Hz), 2.39–2.20 (m, 2H), 2.33 (s, 3H), 2.12–1.91 (m, 2H), 1.63 (s, 9H). Mass spectrum (ESI): m/e=563 (M+1).

Step F: (3S,5R,6S,7S)-6-(4-Fluorophenyl)-3-(2-methoxy-5-(3-methylpyrazol-4-yl)phenyl)-1-oxaspiro[4.4]nonane-7-carboxylic acid methyl ester A solution of (3S,5R,6S,7S)-6-(4-fluorophenyl)-3-(2-methoxy-5-(1-(tert-butoxycarbonyl)-3-methylpyrazol-4-yl) phenyl)-1-oxaspiro[4.4]nonane-7-carboxylic acid methyl ester (12 mg, 0.021 mmol) in 2.0 mL of dichloromethane was stirred at 0° C. and 2.0 mL of trifluoroacetic acid was added. After the solution had been stirred at 0° C. for 1.5 h, toluene (5 mL) was added and the solvent was evaporated at reduced pressure. The residue was purified by flash column chormatogrpahy on 1 g of silica gel, eluting with 25% ethyl acetate in dichloromethane to give 8 mg of colorless film (80% yield). $^1$H NMR (400 MHz, CDCl$_3$): δ 7.60 (bs, 1H), 7.29 (dd, 2H, J=9, 6 Hz), 7.22 (dd, 1H, J=8, 2 Hz), 6.91 (d, 1H, J=8 Hz), 6.89 (t,,2H, J=9 Hz), 6.86 (d, 1H, J=2 Hz), 6.21 (t, 1H, J=2 Hz), 4.77 (dd, 1H, J=12, 2 Hz), 4.10 (dd, 1H, J=12, 2 Hz), 3.85 (s, 3H), 3.59 (s, 3H), 3.47 (dt, 1H, J=11, 8 Hz), 3.22 (d, 1H, J=11 Hz), 2.43–2.22 (m, 2H), 2.40 (s, 3H), 2.15–1.94 (m, 2H). Mass spectrum (NH$_3$CI): m/e=436 M+1.

EXAMPLE 81

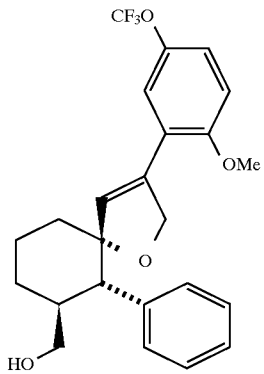

(5R,6S,7S)-6-Phenyl-3-(2-methoxy-5-(trifluoromethoxy)phenyl)-7-(hydroxymethyl)-1-oxaspiro[5.4]dec-3-ene Step A: 1-Phenyl-2-(carboxyoxazolidinone)-cyclohex-5-ene

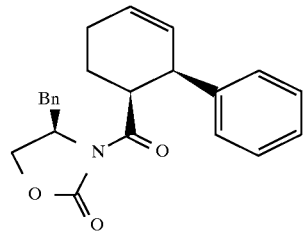

To a solution of the acryloyloxazolidinone (30.2 g, 131 mmol) in CH$_2$Cl$_2$ (600 mL) at −50° C. was added freshly distilled 1-phenyl-1,3-butadiene (34.0 g, 261 mmol). The reaction was cooled to −70° C. whereupon a solution of diethylaluminum chloride (123 mL, 1.8M in PhMe, 222 mmol, 1.7 equiv) was added. The mixture was stirred for 20 min and then added to a stirred solution of 1M aq. HCl (1.0 L). After the bubbling subsided the aqueous was extracted with CH$_2$Cl$_2$ (3×600 mL). The combined organic extracts were washed with brine (1×600 mL), dried (Na$_2$SO$_4$) and concentrated in vacuo yielding a white semisolid. The residue was triturated with hexanes (~600 mL) and the solid collected by vacuum filtration with cold hexane washes affording 34.3 g (74%) of the Diels-Alder adduct as a white solid. $^1$H NMR (CDCl$_3$, 500 MHz) δ 7.10–7.46 (m, 10H), 5.95–6.03 (m, 1H), 5.75–5.81 (m, 1H), 4.48–4.56 (m, 1H), 4.26 (br. s, 1H), 4.13 (d, 2H, J=5.2 Hz), 4.06 (ddd, 1H, J=11.9, 6.4, 2.9 Hz), 2.92 (dd, 1H, J=13.0, 2.9 Hz), 2.29–2.39 (m, 2H), 2.06–2.25 (m, 2H), 1.75–1.83 (m, 1H) ppm.

Step B: 1-(R)-Phenyl-2-(S)-carboxycyclohex-5-ene

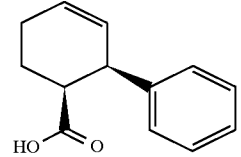

To a solution of the oxazolidinone from Step A above (15.0 g, 41.5 mmol) in THF (600 mL) and H$_2$O (200 mL) at 0° C. was added 30% H$_2$O$_2$ (38.0 mL, 332 mmoL), followed by LiOH.H$_2$O (3.50 g, 83.0 mmol). The mixture was allowed to warm to room temp. and stirred for 20 h, whereupon the mixture was quenched by addition of Na$_2$S$_2$O$_3$ (8.9 equiv, 46.0 g, 308 mmol) and H$_2$O (283 mL) at 0° C., followed by addition of 0.5N aq. NaHCO$_3$ (440 mL) and stirred for 10 min. The THF was removed in vacuo, the mixture diluted with H$_2$O (500 mL) and then extracted with CH$_2$Cl$_2$ (3×500 mL). The combined organic extracts were washed with brine, dried (Na$_2$SO$_4$) and concentrated in vacuo yielding the oxazolidone auxiliary. The aqueous layer was then acidified with 2N aq. HCl to pH=1. The aqueous layer was then extracted with EtOAc (3×500 mL). The combined organic extracts were washed with brine, dried (Na$_2$SO$_4$) and concentrated in vacuo yielding the carboxylic acid (11.4 g, 99%) as a colorless oil. $^1$H NMR (CDCl$_3$, 500 MHz) δ 7.15–7.40 (m, 5H), 5.93–6.07 (m, 1H), 5.75–5.86 (m, 1H), 3.89 (br. s, 1H), 2.96 (dd, 1H, J=15.4, 5.8 Hz), 2.26–2.35 (m, 1H), 2.13–2.23 (m, 1H), 1.75–1.88 (m, 2H) ppm.

Step C: 4-(S)-Iodo-8-(R)-phenyl-7-oxo-6-oxabicyclo[3.2.1]octane

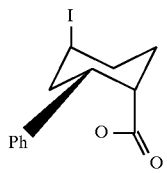

To a vigorously stirred biphasic mixture of the acid from Step B (5.50 g, 27.2 mmol) in CH$_2$Cl$_2$ (250 mL) and sat. aq. NaHCO$_3$ (250 mL) at 0° C. was added I$_2$ (8.28 g, 32.6 mmol). The mixture was stirred 30 min at 0° C. then 60 min at room temp, whereupon it was quenched by the addition of excess 0.25M Na$_2$S$_2$O$_3$. The mixture was diluted with sat. aq. NaHCO$_3$ (100 mL) and H$_2$O (200 mL) and extracted with CH$_2$Cl$_2$ (3×300 mL). The combined organic extracts were washed with brine, dried (Na$_2$SO$_4$) and concentrated in vacuo yielding the iodolactone (8.6 g) as a yellow solid which was used directly in the next step. $^1$H NMR (CDCl$_3$, 500 MHz) δ 7.23–7.41 (m, 5H), 4.86 (d, 1H, J=4.1 Hz), 4.69 (t, 1H, J=4.5 Hz), 4.20 (s, 1H), 2.94 (br. d, 1H, J=4.3 Hz), 2.45–2.55 (m, 1H), 2.01–2.26 (m, 3H) ppm.

Step D: 8-(R)-Phenyl-7-oxo-6-oxabicyclo[3.2.1]octane

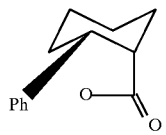

To a solution of the iodolactone from Step C (15.6 g, 49.5 mmol) in PhH (500 mL) was added nBu$_3$SnH (36.0 g, 124 mmol) and AIBN (406 mg, 2.48 mmol). The reaction mixture was heated to reflux for 1.5 h, and then left standing at room temp overnight. The reaction mixture was concentrated in vacuo. The residue was purified by column chromatography (300 g silica gel 60, 120 mm diam. column, 0–40% EtOAc/hexanes) to afford the bicyclic lactone (9.16 g, 95%) as a colorless oil. $^1$H NMR (CDCl$_3$, 500 MHz) δ 7.21–7.43 (m, 5H), 4.93 (d, 1H, J=4.5 Hz), 3.12 (s, 1H), 2.86 (br. d, 1H, J=4.1 Hz), 2.10–2.26 (m, 2H), 1.78–1.96 (m, 4H) ppm.

Step E: 1-(R)-Hydroxy-2-(R)-phenyl-3-(S)-hydroxymethylcyclohexane

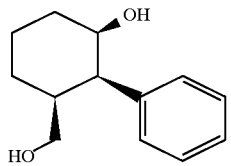

To a solution of the lactone from Step D (9.16 g, 45.3 mmol) in Et$_2$O (300 mL) at 0° C. was added LiAlH$_4$ (5.16 g, 136 mmol). The reaction mixture was maintained at 0° C. for 2 h whereupon it was quenched by sequential addition of H$_2$O (5.2 mL), 15% aq. NaOH (5.2 mL) and H$_2$O (15.6 mL). The mixture was stirred for 1 h, then had added to it sat. aq. Rochelle's salts (375 mL) and vigorously stirred 4 h. The mixture was then extracted with EtOAc (3×200 mL) and the combined organic extracts were washed with brine, dried (Na$_2$SO$_4$), and concentrated in vacuo to yield the diol (9.10 g, 99%) as a colorless oil, which was used directly in the next step. $^1$H NMR (CDCl$_3$, 500 MHz) δ 7.20–7.51 (m, 5H), 4.02–4.10 (m, 1H), 3.43 (dd, 1H, J=10.8, 5.5 Hz), 3.36 (dd, 1H, J=11.0, 6.2 Hz), 3.27 (t, 1H, J=4.9 Hz), 2.39 (br. s, 2H), 1.96–2.12 (m, 2H), 1.65–1.83 (m, 4H), 1.45–1.58 (m, 1H) ppm.

Step F: 1-(R)-Hydroxy-2-(R)-phenyl-3-(S)-t-butyl-dimethylsilyloxymethylcyclohexane

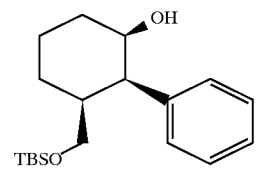

To a solution of the diol from Step E (9.10 g, 43.6. mmol) in CH$_2$Cl$_2$ (125 mL) at room temp was added iPr$_2$NEt (5.76 g, 44.6 mmol), and TBSOTf (6.70 g, 44.6 mmol). The mixture was stirred 18 h at room temp, then was concentrated in vacuo. The residue was purified by column chromatography (300 g silica gel 60, 120 mm diam. column, 10–25% EtOAc/hexanes) to afford the monosilylated alcohol (12.4 g, 87%) as a colorless oil. $^1$H NMR (CDCl$_3$, 500 MHz) δ 7.20–7.56 (m, 5H), 3.97–4.08 (m, 1H), 3.40 (dd, 1H, J=10.1, 5.3 Hz), 3.34 (dd, 1H, J=10.0, 5.9 Hz), 3.29 (t, 1H, J=4.8 Hz), 2.04–2.10 (m, 1H), 1.94–2.03 (m, 1H), 1.78–1.85 (m, 1H), 1.65–1.77 (m, 3H), 1.48–1.55 (m, 1H), 0.89 (s, 9H), –0.029 (s, 3H), –0.042 (s, 3H) ppm.

Step G: 1-Oxo-2-(R)-phenyl-3-(S)-t-butyldimethylsilyloxymethylcyclohexane

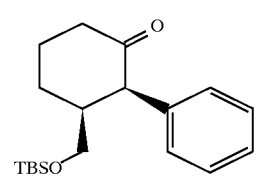

To a solution of the alcohol (12.4 g, 38.7 mmol) in CH$_2$Cl$_2$ (500 mL) was added pyridine (14.1 mL, 174 mmol) and Dess-Martin periodinane reagent (24.6 g, 58.1 mmol) at room temp. After 3 h the reaction mixture was quenched by addition of sat. aq. NaHCO$_3$ (200 mL), diluted with H$_2$O (300 mL) and extracted with EtOAc (3×300 mL). The combined organic extracts were washed with brine, dried (Na$_2$SO$_4$), and concentrated in vacuo to yield the ketone (12.3 g, 100%) as a colorless glass, which was used directly in the next step. $^1$H NMR (CDCl$_3$, 500 MHz) δ 7.20–7.41 (m, 5H), 3.83 (d, 1H, J=5.8 Hz), 3.44–3.53 (m, 2H), 2.60 (dt, 1H, J=15.1, 6.2 Hz), 2.41–2.50 (m, 1H), 2.33–2.39 (m, 1H), 2.20–2.30 (m, 1H), 1.89–2.08 (m, 3H), 0.89 (s, 9H), –0.011 (s, 3H), –0.039 (s, 3H) ppm.

Step H: 1-Oxo-2-(S)-phenyl-3-(S)-t-butyldimethylsilyloxymethyl cyclohexane

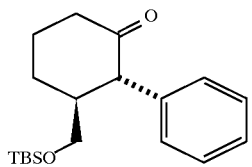

To a solution of the ketone from Step G above (12.3 g, 38.0 mmol) in MeOH (330, mL)at room temp was added 1M NaOH (110 mL) and the mixture stirred for 16 h. The reaction mixture was diluted with $H_2O$ (500 mL) and concentrated to remove the MeOH. The aqueous was then extracted with EtOAc (3×300 mL), the combined organic extracts were washed with brine, dried ($Na_2SO_4$), and concentrated in vacuo. The residue was purified by column chromatography (150 g silica gel 60, 60 mm diam. column, 5–25% EtOAc/hexanes) to afford the epimerized ketone ( 11.6 g, 94%) as a colorless glass. $^1$H NMR ($CDCl_3$, 500 MHz) δ 7.32–7.35 (m, 2H), 7.22– 7.29 (m, 1H), 7.07–7.20 (m, 2H), 3.62 (d, 1H, J=11.7 Hz), 3.38 (dd, 1H, J=9.9, 2.3 Hz), 3.19 (dd, 1H, J=9.9, 4.6 Hz), 2.55 (d, 1H, J=13.5 Hz), 2.43–2.49 (m, 1H), 2.18–2.23 (m, 1H), 2.09–2.17 (m, 1H), 1.98–2.06 (m, 1H), 1.78–1.97 (m, 2H), 0.90 (s, 9H), –0.045 (s, 3H), –0.078 (s, 3H) ppm. $^{13}$C NMR ($CDCl_3$, 500 MHz) δ 210.8, 137.1, 129.6, 128.3, 127.0, 64.7, 59.2, 47.6, 41.9, 28.7, 26.0, 25.7, 18.4, 5.50, 5.59 ppm. ESIMS m/z calcd. for $C_{19}H_{30}O_2Si$ 318.5; found 350.3[(M+H)+HCN]$^+$, 336.4[M+NH$_4$]$^+$, 319.4 [M+H]$^+$, 187.2 [M–TBSO]+.FTIR 2955, 2929, 2858, 1715, 1471, 1254, 1122, 1006, 837, 777, 699 $cm^{-1}$.

Step I: (2S, 3S)-3-t-Butyldimethylsiloxymethyl-2-phenylcyclohexanone

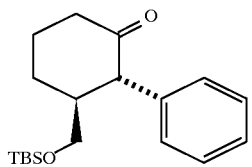

To a solution of oxalyl chloride (685 μL, 7.88 mmol) in $CH_2Cl_2$ (25 mL) at –70° C. was added dropwise dimethylsulfoxide (1.12 mL, 15.8 mmol). After 15 minutes a solution of the alcohol, (2S, 3S)-3-(t-butyldimethylsiloxy)methyl-2-phenylcyclohexanol, (1.00 g, 3.15 mmol) in $CH_2Cl_2$ (14 mL) was added. After stirring 45 mins $Et_3N$ (4.37 mL, 31.5 mmol) was added and the reaction was allowed to warm to room temperature and stirred one hour. The mixture was partitioned between water (100 mL), sat. aq. NaCl (50 mL), and $CH_2Cl_2$ (40 mL) and extracted with $CH_2Cl_2$ (4×40 mL). The combined organic extracts were washed with brine, dried ($Na_2SO_4$) and concentrated in vacuo. The residue was purified by flash column chromatography (100 g silica gel 60, 65 mm diam. column, 0–10% EtOAc/hexane) to yield the ketone (872 mg, 87.7%) as a light yellow oil. $^1$H NMR ($CDCl_3$, 500 MHz) δ 7.32–7.35 (m, 2H), 7.22–7.29 (m, 1H), 7.07–7.20 (m, 2H), 3.62 (d, 1H, J=11.7 Hz), 3.38 (dd, 1H, J=9.9, 2.3 Hz), 3.19 (dd, 1H, J=9.9, 4.6 Hz), 2.55 (d, 1H, J=13.5 Hz), 2.43–2.49 (m, 1H), 2.18–2.23 (m, 1H), 2.09–2.17 (m, 1H), 1.98–2.06 (m, 1H), 1.78–1.97 (m, 2H), 0.90 (s, 9H), –0.045 (s, 3H), –0.078 (s, 3H) ppm. $^{13}$C NMR ($CDCl_3$, 500 MHz) δ 210.8, 137.1, 129.6, 128.3, 127.0, 64.7, 59.2, 47.6, 41.9, 28.7, 26.0, 25.7, 18.4, 5.50, 5.59 ppm. ESIMS m/z calcd. for $C_{19}H_{30}O_2Si$ 318.5; found 350.3[(M+H)+HCN]$^+$, 336.4[M+NH$_4$]$^+$, 319.4[M+H]$^+$, 187.2[M–TBSO]$^+$. FTIR 2955, 2929, 2858, 1715, 1471, 1254, 1122, 1006, 837, 777, 699 $cm^{-1}$.

Step J: (1R,2S,3S)-1-(3'-acetoxy-2'-methylene)propyl-3-t-butyldimethylsiloxymethyl-1-hydroxy-2-phenyl cyclohexanol

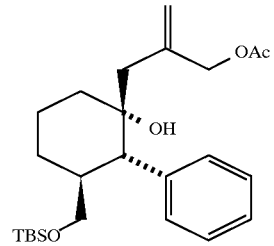

To the ketone, (2S,3S)-3-(t-butyldimethylsiloxy)methyl-2-phenylcyclohexanone, (872 mg, 2.76 mmol) in $CH_2Cl_2$ (2.2 mL) was added 3-acetoxy-2-(trimethylstannyl)methyl propene (1.78 g, 6.43 mmol) at room temperature. The solution was cooled to –10° C. and stirred for 10 minutes. After the addition of $BF_3.Et_2O$ (847 μL, 6.89 mmol), the solution was again stirred for 10 minutes. The reaction was quenched by addition of sat. aq. $NH_4Cl$ (35 mL) and partitioned between $Et_2O$ (100 mL) and $H_2O$ (25 ml) and extracted with Et2O (3×50 mL). The combined organic extracts were washed with brine, dried ($Na_2SO_4$), and concentrated in vauco. The residue was purified by column chromatography (120 g silica gel 60, 65 mm diam. column, 0–10% EtOAc/hexane) to yield the tertiary alcohol (1.11 g, 93.3%) as a light yellow oil. Protected allyl acetate: $^1$H NMR (500 MHz, $CDCl_3$) δ 7.46 (d, 1H, J=6.6 Hz), 7.35 (br. s, 1H), 7.24–7.25 (m, 2H), 7.04 (br. s, 1H) 5.10 (s, 1H), 4.87 (s, 1H), 4.49 (ABX, 2H, J=13.7 Hz), 3.24 (dd, 1H, J=9.8, 2.3 Hz), 3.07 (dd, 1H, J=9.9, 5.9 Hz), 2.42 (d, 1H, J=11.7 Hz), 2.14–2.19 (m, 1H), 1.88–1.94 (m, 8H), 1.65–1.82 (m, 2H), 1.24–1.44 (m, 2H), 0.84 (s, 9H), –0.12 (s, 3H), –0.16 (s, 3H) ppm. $^{13}$C NMR (500 MHz, $CDCl_3$) δ 170.7, 140.9, 140.5, 132.5, 128.4, 127.7, 127.4, 126.5, 115.8, 72.7, 67.6, 66.0, 55.2, 45.7, 39.9, 36.7, 29.7, 26.0, 20.9, 20.8, 18.4, –5.53, –5.56 ppm. ESIMS (m/z calcd for $C_{25}H_{40}O_4Si$ 432.3; found 450.4[M+NH$_4$]$^+$, 433.5[M+H]$^+$, 415.4[(M+H)–H$_2$O]$^+$ .283.3[(M–H$_2$O)–TBSO],223.3[(M–H$_2$O, TBSO)–AcO]$^+$. FTIR 3507, 2932, 2857, 1732, 1471, 1386, 1253, 1111, 1032, 838, 776, 702 $cm^{-1}$. An amount of the t-butyldimethylsilyl ether is cleaved under certain conditions to afford the primary alcohol. Unprotected allyl acetate: $^1$H NMR (500 MHz, $CDCl_3$) δ 7.51 (d, 1H, 7.5 Hz), 7.381 (m, 1H), 7.26–7.28 (m, 2H), 7.092 (br. s, 1H), 5.12 (t, 1H, J=1.6 Hz), 4.87 (s, 1H), 4.48 (ABX, 2H, J=13.8 Hz) 3.34 (dd, 1H, J=10.9, 1.8 Hz), 3.18 (m, 1H), 2.41 (d, 1H, J=11.9 Hz), 2.22–2.30 (m, 1H), 1.97 (d, 3H, J=1.6 Hz), 1.88–1.94 (m, 4H), 1.70–1.87 (m, 2H), 1.27–1.39 (m, 2H). FTIR 3455, 2933, 1730, 1233, 1033 $cm^{-1}$.

Reprotection to form the TBS ether

To a solution of the alcohol, (1R,2S,3S)-1-(3'-acetoxy-2'-methylene)propyl-1-hydroxy-3-hydroxymethyl-2-phenyl cyclohexanol, (120 mg, 0.38 mmol) in $CH_2Cl_2$ (4 mL) at –70° C. was added 2,6-lutidine (53.3 μL, 0.38 mmol) followed by t-butyldimethylsilyl trifluoromethane sulfonate (105 μL, 0.46 mmol). After 2 hours, 2,6-lutidine (18.0 μL, 0.13 mmol) and t-butyldimethylsilyl trifluoromethane sulfonate (35 μL, 0.15 mmol) were again added. The solution was stirred 1 hour, quenched by addition of sat. aq. $NaHCO_3$ (20 mL), and extracted with $CH_2Cl_2$ (4×20 mL). The combined organic extracts were washed with brine, dried (Na₂SO₄), and concentrated in vauco. The residue was purified by column chromatography (5 g silica gel 60, 35 mm diam. column, 0–2.5% MeOH/CH₂Cl₂) yielding the tertiary alcohol ( 120 mg, 74%) as a faint yellow oil. Reprotection to form the TIPS ether (1R,2S,3S)-1-(3'-acetoxy-2'-methylene)propyl-1-hydroxy-3-triisopropylsiloxymethy-2-phenyl cyclohexanol

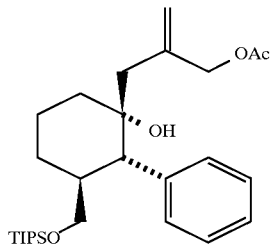

To a solution of the alcohol, (1S,2S,3S)-1-(3'-acetoxy-2'-methylene)propyl-3-hydroxymethyl-2-phenyl cyclohexanol, (620 mg, 1.96 mmol) in CH₂Cl₂ (19 mL) at −70° C. was added 2,6-lutidine (342 μL, 2.94 mmol) followed by triisopropyl triflate (685 μL, 2.55 mmol). The solution was stirred for 10 minutes and then quenched with sat. aq. NaHCO₃ (20 mL). The mixture was washed with CH₂Cl₂ (4×20 mL), and the combined organic extracts were washed with brine, dried (Na₂SO₄), and concentrated in vauco. The residue was purified by column chromatography (50 g silica gel 60, 44 mm diam. column, 0–10% EtOAc/hexane) yielding the silyl ether (851 mg, 91%) as a faint yellow oil. ¹H NMR (CDCl₃, 500 MHz) δ 7.44 (d, 1H, 7.3 Hz), 7.34 (s, 1H), 7.25 (m, 2H), 7.06 (br. s, 1H), 5.10 (s, 1H), 4.88 (s, 1H), 4.49 (ABX, 2H, J=13.7 Hz), 3.35 (dd, 1H, J=9.6, 1.9 Hz), 3.19 (dd, 1H, J=9.6, 5.5 Hz), 2.47 (d, 1H, J=11.7 Hz), 2.31–2.23 (m, 1H), 1.87–2.02 (m, 8H), 1.73–1.82 (m, 1H, J=13.4, 3.4 Hz), 1.66–1.70 (m, 1H), 1.40–1.48 (dd, 1H, J=13.0, 4.1), 1.27–1.33 (dt, 1H, J=13.3, 4.2 Hz), 1.07 (s, 3H), 0.94 (d, 18H, J=3.9 Hz) ppm. ¹³C NMR (CDCl₃, 500 MHz) δ 170.8, 140.9, 140.4, 132.6, 128.4, 127.8, 127.3, 126.5, 115.8, 72.7, 67.7, 66.3, 55.1, 45.7, 40.2, 36.6, 29.8, 21.0, 20.9, 18.1, 18.0, 12.0 ppm. ESIMS m/z calcd for C₂₈H₄₆O₄Si 474.3; found 492.5[M+NH₄]⁺, 475.5[M+H]⁺, 457.5[M−H₂O]⁺, 413.6[M−H, HOAc]⁺, 301.4[M−TIPSO]⁺, 283.4[(M−H₂O)−TIPSO]⁺, 223.3[(M−H₂O, TIPS)−AcO]⁺. FRIR 3508, 2942, 2866, 1732, 1463, 1383, 1232, 1114, 1032, 883, 775, 702, 680 cm⁻¹.

Step K: (5R,6S,7S)-6-Phenyl-3-methylene-7-(t-butyldimethylsilyloxymethyl)-1-oxaspiro[5.4]decane

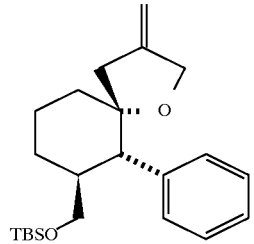

To a solution of the acetate, (1R,2S,3S)-1-(3'-acetoxy-2'-methylene)propyl-3-t-butyldimethylsiloxymethyl-1-hydroxy-2-phenyl cyclohexanol, (575 mgs, 1.33 mmol) in THF (12 mL) at −5° C. that had been degassed with argon (3×) was added lithium bis(trimethylsilyl)amide (1.47 mL, 1.47 mmol; 1.0M in THF). After stirring 10 minutes, ZnCl₂ (2.94 mL, 1.47 mmol; 0.5M in THF) was added and the mixture allowed to warm to room temp and stirred 30 mins. Pd(PPh₃)₄ (76 mgs, 0.067 mmol) was added to the reaction, and the solution was degassed again prior to being refluxed at 70° C. for 16 hours. The reaction was quenched with sat. aq. NH₄Cl (30 mL), diluted with water (100 mL), and extracted with EtOAc (3×75 mL). The combined organic extracts were washed with sat. aq. NaHCO₃, brine, dried (Na₂SO₄) and concentrated in vacuo. The residue was purified by column chromatography (45 g silica gel 60, 40 mm diam. column, 25–50% CH₂Cl₂/hexanes) to yield the 1R spiro olefin (402 mg, 82%) as a colorless oil. ¹H NMR (CDCl₃, 500 MHz) δ 7.19–7.28 (m, 5H), 4.69 (d, 2H, J=11.5 Hz), 4.19 (d, 2H, J=13.1 Hz), 4.24 (d, 1H, J=12.6 Hz), 3.23 (dd, 1H, J=9.8, 2.0 Hz), 3.05 (dd, 1H, J=9.8, 5.7 Hz), 2.53 (d, 1H, J=11.4 Hz), 2.17–2.22 (m, 1H), 2.09 (d, 1H, J=15.5 Hz), 1.91–1.94 (m, 2H), 1.78–1.86 (m, 1H), 1.66 (d, 1H, J=13.3 Hz), 1.36–1.44 (m, 1H), 1.25–1.32 (m, 1H), 0.86 (s, 9H), −0.11 (s, 3H), −0.15 (s, 3H) ppm. ESIMS m/z calcd for C₂₃H₃₆O₂Si 372.6; found 373.2 [M+H]⁺, 241.1 [M−TBSO]⁺, 223.1 [(M−TBSO)−H₂O]⁺. FTIR 2929, 2857, 1667, 1471, 1252, 1116 1052, 8812, 836, 775, 703 cm⁻¹.

Step K': (5R,6S,7S)-6-Phenyl-3-methylene-7-(triisopropylsilyloxymethyl)-1-oxaspiro[5.4]decane

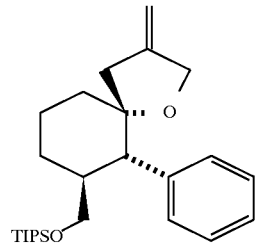

To a solution of the acetate, (1R,2S,3S)-1-(3'-acetoxy-2'-methylene)propyl-1-hydroxy-3-triisopropylsiloxymethyl-2-phenyl cyclohexanol, (300 mg, 0.63 mmol) in THF (6 mL) at −5° C. that had been degassed with argon (3×) was added lithium bis(trimethylsilyl)amide (695 μL, 0.69 mmol; 1.0M in THF). After 10 minutes, ZnCl₂ (1.39 mL, 0.69 mmol; 0.5M in THF) was added and the mixture was allowed to warm to room temp and stirred 30 mins. Pd₂(dba)₃ (29 mg, 0.032 mmol) and P(2-fur)₃ (29 mg, 0.126 mmol) were added together and the solution was degassed a final time prior to being refluxed at 70° C. for 4 hours. The reaction was quenched with sat. aq. NH₄Cl (10 mL), diluted with water (50 mL), and extracted with EtOAc (3×50 mL). The combined organic extracts were washed with sat. aq. NaHCO₃, brine, dried (Na₂SO₄) and concentrated in vacuo. The residue was purified by column chromatography (34 g silica gel 60,; 25, 50, 100% CH₂Cl₂/hexane) to yield a colorless oil as a single diastereomer (200 mg, 76%). ¹H NMR (CDCl₃, 500 MHz) δ 7.15–7.40 (m, 5H), 4.69 (d, 2H, J=12.4 Hz), 4.24 (d, 2H, J=12.6 Hz), 4.18 (d, 1H, 12.8 Hz), 3.34 (dd, 1H, 9.6, 2.3 Hz), 3.18 (dd, 1H, 9.6, 4.1), 2.56 (d, 1H, J=11.9 Hz), 2.3 (d, 1H, J=15.4 Hz), 2.17–2.23 (m, 1H), 2.09 (d, 1H, J=15.3 Hz), 1.90–1.98 (m, 2H), 1.81 (qt, 1H, J=13.2, 3.4 Hz), 1.65–1.71 (m, 1H), 1.42–1.52 (m, 1H), 1.30 (dt, 1H, J=13.4, 3.1 Hz), 1.01 (s, 21H) ppm. ¹³C NMR (CDCl₃, 500 MHz) δ 148.6, 140.8, 127.6, 126.2, 115.1, 103.8, 84.8, 70.2, 66.3, 53.0, 42.7, 41.4, 36.8, 29.7, 21.4, 18.1, 12.0 ppm. FTIR 2941, 2865, 1731, 1669, 1463, 1382, 1118, 1051, 882, 787, 703, 681 cm⁻¹.

Step L: (5R,6S,7S)-6-Phenyl-7-(t-butyldimethylsilyloxymethyl)-1-oxaspiro[5.4]deca-3-none

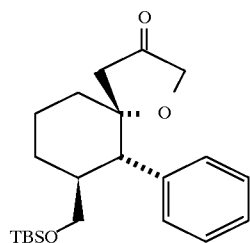

To a solution of olefin (301 mg, 0.81 mmol) in $(CH_3)_2CO$ (3.0 mL) and $H_2O$ (1.5 mL) that had been stirred for 10 minutes was added $OsO_4$ (3.0 mL; 2.5% (w/v) in t-butanol) at room temperature. After 10 mins, N-methylmorpholine-N-oxide (153 mg, 1.29 mmol) was added and the reaction mixture stirred 2 h, whereupon it was quenched by addition of $NaHSO_3$ (600 mg) and stirred for 30 mins. The reaction mixture was then diluted with water (50 mL) and extracted with $CH_2Cl_2$ (3×50 mL). The combined organic extracts were washed with brine, dried ($Na_2SO_4$), and concentrated in vacuo. The brown oil (310 mg) was used directly in the next step.

To a solution of crude diol (310 mg) in THF:$H_2O$ (12 mL, 4:1) at room temperature was added $NaIO_4$ (321 mg, 1.50 mmol). After stirring for 18 hours, the reaction suspension was diluted with water (50 mL) and extracted with EtOAc (3×50 mL). The combined organic extracts were washed with brine, dried ($Na_2SO_4$), and concentrated in vacuo. The residue was purified by column chromatography ( 30 g silica gel 60, 0–1–2.5% MeOH/$CH_2Cl_2$) to afford the ketone (84 mg 27%) as a colorless oil. In addition the 3-hydroxymethyl-1-spiroketone (151 mg, 73%) was isolated as a colorless glass. This alcohol was immediately resilylated under standard conditions (TBSOTf, 2,6-lutidine, $CH_2Cl_2$) in >95% yield. $^1$HNMR (CDCl$_3$, 500 MHz) δ 7.20–7.36 (m, 5H), 3.90 (s, 2H), 3.26 (dd, 1H, J=9.8, 2.3 Hz), 3.10 (dd, 1H, J=9.6, 5.3 Hz), 2.62 (d, 1H, J=11.7 Hz), 2.30 (d, 2H, J=18.1 Hz), 2.07 (d, 1H, J=18.0 Hz), 2.00 (d, 1H, J=13.0 Hz), 1.84–1.96 (m, 1H), 1.66–1.74 (m, 1H), 1.38–1.50 (m, 2H), 0.85 (s, 9H), −0.11 (s, 3H), −0.16 (s, 3H) ppm. Alternate procedure utilizing ozonolysis conditions without cleaving the silyl ether: To a cooled (−78° C.) solution of the allylic ether (244 mg, 0.66 mmol) in $CH_2Cl_2$ (2.5 mL) and MeOH (2.5 mL) was bubbled a mixture of ozone and oxygen for 15 seconds. The solution was purged with nitrogen, and dimethyl sulfide (600 uL) was added and the reaction solution was stirred at room temperature for 3 hours. The solvent was removed in vacuo and the residue partitioned between EtOAc (100 mL) and $H_2O$ (100 mL), extracted with EtOAc (3×100 mL) and the combined organic extracts were washed with brine, dried ($Na_2SO_4$), and concentrated in vacuo. The residue was purified by column chromatography (20 g silica gel 60, 18 mm diam. column, 5–25% EtOAc/hexanes) to afford the ketone (206 mg, 82%) as a colorless oil.

Step L': (5R,6S,7S)-6-Phenyl-7-(triisopropylsilyloxymethyl)-1-oxaspiro[5.4]deca-3-none

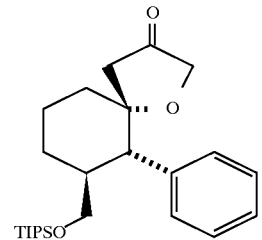

To a solution of olefin (310 mg, 0.75 mmol) in $(CH_3)_2CO$ (3.0 mL) and $H_2O$ (1.5 mL) that had been stirred for 10 minutes was added $OsO_4$ (3.0 mL; 2.5% (w/v) in t-butanol) at room temperature. After 10 mins, N-methylmorpholine-N-oxide (140 mg, 1.21 mmol) was added and the reaction mixture stirred 2.5 h, whereupon it was quenched by addition of $NaHSO_3$ (600 mg) and stirred for 30 mins. The reaction mixture was then diluted with water (50 mL) and extracted with $CH_2Cl_2$ (3×50 mL). The combined organic extracts were washed with brine, dried ($Na_2SO_4$), and concentrated in vacuo. The brown oil (310 mg) was used directly in the next step.

To a solution of crude diol (310 mg) in THF:$H_2O$ (17 mL, 4:1) at room temperature was added $NaIO_4$ (295 mg, 1.38 mmol). After stirring for 18 hours, the reaction suspension was diluted with water (50 mL) and extracted with EtOAc (3×50 mL). The combined organic extracts were washed with brine, dried ($Na_2SO_4$), and concentrated in vacuo. The residue was purified by column chromatography (30 g silica gel 60, 0–1–2.5% MeOH/$CH_2Cl_2$) to afford the ketone (258 mg, 83%) as a colorless oil. $^1$H NMR (CDCl$_3$, 500 MHz) δ 7.21–7.28 (m, 5H), 3.90 (s, 2H), 3.38 (dd, 1H, J=9.6, 2.5 Hz), 3.21 (dd, 1H, J=9.6, 5.0 Hz), 2.66 (d, 1H, J=11.7 Hz), 2.30–2.36 (m, 2H), 2.08 (d, 1H, J=18.1 Hz), 1.85–2.04 (m, 3H), 1.69–1.73 (m, 1H), 1.53 (m, 1H), 1.43 (td, 1H, J=13.5, 3.8 Hz), 0.95 (d, 21H, J=4.5 Hz) ppm. $^{13}$C NMR 215.79, 139.55, 128.09, 126.87, 83.88, 70.13, 66.03, 53.05, 47.11, 40.28, 36.94, 29.38, 21.26, 18.07, 18.05, 11.98 ppm. FTIR 2940, 2865, 1762, 1462, 1287, 1120, 1068, 883, 771, 704, 680 cm$^{-1}$.

Step M: (5R,6S,7S)-6-Phenyl-3-(trifluoromethylsulfonyloxy)-7-(t-butyldimethylsilyloxymethyl)-1-oxaspiro[5.4]dec-3-ene

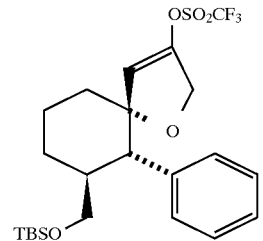

To a solution of the ketone (300 mg, 0.805 mmol) in THF (10 mL) at −70° C. under Ar was added dropwise NaHMDS (1.77 mL, 1.77 mmol, 1M in THF). After stirring 30 mins, 5-chloro-2-N-bis(trifluoromethylsulfonyl)pyridine (from Example 6, Step D) (506 mg, 1.29 mmol) was added and the mixture warmed to −20° C. and stirred for 16 h. The reaction mixture was quenched by addition of sat. aq. NH$_4$Cl (25 mL), diluted with $H_2O$ (50 mL) and extracted with EtOAc (3×50 mL). The combined organic extracts were washed with brine, dried (Na₂SO₄), and concentrated in vacuo. The residue was purified by column chromatography ( 40 g silica gel 60, 35 mm col. diam., 2.5–5% EtOAc/hexanes) to afford the ketone (297 mg, 73%) as a colorless oil. $^1$H NMR (CDCl₃, 500 MHz) δ 7.01–7.40 (m, 5H), 5.52 (s, 1H), 4.48 (dd, 1H, J=11.9, 1.6 Hz), 4.20 (dd, 1H, J=11.9, 1.8 Hz), 3.29 (dd, 1H, J=10.1, 2.3 Hz), 3.11 (dd, 1H, J=9.8, 5.5 Hz), 2.61 (d, 1H, J=11.6 Hz), 2.18–2.30 (m, 1H), 1.80–2.02 (m, 3H), 1.69–1.78 (m, 1H), 1.55–1.65 (m, 1H), 1.36–1.50 (m, 1H), 0.85 (s, 9H), −0.12 (s, 3H),−0.17 (s, 3H) ppm.

Step N: (5R,6S,7S)-6-Phenyl-3-(trimethylstannyl)-7-(t-butyl-dimethylsilyloxymethyl)-1-oxaspiro[5.4]dec-3-ene

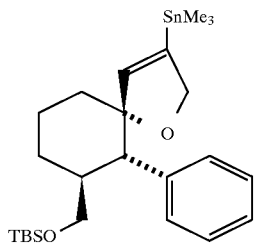

To a solution of enol triflate (40 mg, 079 mmol) in dioxane (1.5 mL) was added LiCl (10 mg, 0.237 mmol). The solution was degassed (3×) with argon prior to the addition of Pd(PPh₃)₄ (2.0 mg, 0.002 mmol). To this reaction was then added (Me₃Sn)₂ (52 mg, 0.158 mmol) and the solution was refluxed at 100° C. for 3 hours. The reaction was quenched with sat. aq. NaHCO₃ (5 mL), diluted with H₂O (10 mL), and extracted with EtOAc (3×25 mL). The combined organic extracts were washed with brine, dried (Na₂SO₄), and concentrated in vacuo. The residue was purified by column chromatography (5 g silica gel 60, 8 mm diam. column, 2.5% EtOAc/hexanes) to afford the vinyl stannane (26 mg, 63%) as a colorless glass. $^1$H NMR (500 MHz, CDCl₃) δ 6.97–7.23 (m, 5H), 5.48 (t, 1H, J=2.4 Hz), 4.53 (dd, 1H, J=12.3, 2.3 Hz), 4.14 (dd, 1H, J =12.6, 2.3 Hz), 3.32 (dd, 1H, J=9.8, 2.6 Hz), 3.14 (dd, 1H, J=9.9, 6.2 Hz), 2.54 (d, 1H, J=11.6 Hz), 2.23–2.32 (m, 1H), 1.93–2.00 (m, 1H), 1.78–1.89 (m, 1H), 1.68–1.76 (m, 1H), 1.56–1.63 (m, 1H), 1.30–1.44 (m, 2H), 0.84 (s, 9H), −0.071 (s, 9H), −0.12 (s, 3H), −0.17 (s, 3H) ppm.

Step O: (5R,6S,7S)-6-Phenyl-3-(2-methoxy-5-(trifluoromethoxy)phenyl)-7-(t-butyldimethylsilyloxymethyl)-1-oxaspiro[5.4]dec-3-ene

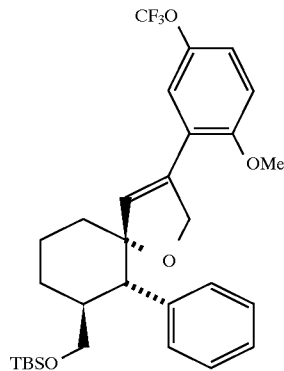

To a solution of the vinyl stannane (14.0 mg, 0.027 mmol) and 1-bromo-2-methoxy-5-trifluoromethoxy benzene (15.0 mg, 0.054 mmol) in PhMe (1.0 mL), degassed with Ar (3×) at room temperature was added PdCl₂(PPh₃)₂ (1.0 mg, 0.001 mmol). The reaction mixture was heated to 100° C. for 1 h, whereupon it was quenched by addition of sat. aq. NaHCO₃ (5 mL), diluted with H₂O (10 mL) and extracted with EtOAc (3×20 mL). The combined organic extracts were washed with brine, dried (Na₂SO₄), and concentrated in vacuo. The residue was purified by preparative chromatography (1000 µM silica gel plate, 5% EtOAc/hexanes) to afford the coupled adduct (6.3 mg, 43%) as a colorless glass. $^1$H NMR (500 MHz, CDCl₃) δ 6.93–7.22 (m, 6H), 6.74 (d, 1H, J=8.7 Hz), 6.62 (s, 1H), 6.03 (s, 1H), 4.88 (d, 1H, J=11.2 Hz), 4.44 (d, 1H, J=11.5 Hz), 3.74 (s, 3H), 3.33 (d, 1H, J=9.6 Hz), 3.15 (dd, 1H, J=9.4, 6.0 Hz), 2.60 (d, 1H, J=11.7 Hz), 2.23–2.37 (m, 1H), 1.82–2.02 (m, 2H), 1.51–1.80 (m, 3H), 1.30–1.47 (m, 2H), 0.86 (s, 9H), −0.10 (s, 3H), −0.15 (s, 3H) ppm.

Step P: (5R,6S,7S)-6-Phenyl-3-(2-methoxy-5-(trifluoromethoxy)phenyl)-7-(hydroxymethyl)-1-oxaspiro[5.4]dec-3-ene

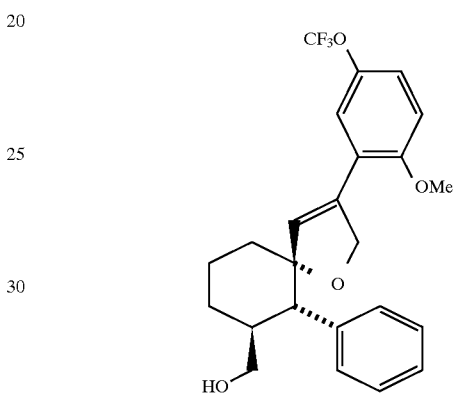

The silyl ether (6.2 mg, 0.011 mmol) had added to it a solution mixture (1 mL) containing THF/pyridine/95% HF-pyridine complex 5:1:0.5at room temperature. After stirring for 2 h the reaction mixture was quenched by addition of H₂O (20 mL) and sat. NaHCO₃ (20 mL). The mixture was extracted with EtOAc (3×25 mL) and the combined organic extracts were washed with brine, dried (Na₂SO₄), and concentrated in vacuo. The residue was purified by preparative chromatography (1000 µM silica gel plate, 25% EtOAc/hexanes) to afford the 3-hydroxymethyl adduct (3.1 mg, 65%) as a colorless oil. $^1$H NMR (CDCl₃, 500 MHz) δ 6.95–7.22 (m, 6H), 6.74 (d, 1H, J=8.9 Hz), 6.61 (d, 1H, J=2.1 Hz), 6.03 (s, 1H), 4.88 (dd, 1H, J=11.7, 1.4 Hz), 4.46 (d, 1H, J=11.7 Hz), 3.74 (s, 3H), 3.41 (dd, 1H, J=10.9, 2.9 Hz), 3.15 (dd, 1H, J=10.8, 5.9 Hz), 2.64 (d, 1H, J=11.9 Hz), 2.25–2.40 (m, 1H), 1.82–2.06 (m, 2H), 1.53–1.81 (m, 3H), 1.31–1.48 (m, 3H) ppm.

Examples 82 through 89 were prepared by alkylation, acylation or sulfonylation of commercially available benzoic acid,aniline or phenol derivatives by the standard procedures discussed above. When necessary, the bromine substituent was installed by bromination under standard conditions (such as Fe/bromine if a nitro precursor to an aniline derivative is brominated). For the formation of imidazo-1-yl aryl subunits, a chlorinated intermediate of the type generated in Example 6, step F(b) is treated with 2,2-diethoxyethylamine, followed by acetic acid. The aryl bromides were coupled to the 1-oxaspiro[4.4]non-3-ene framework using the conditions given in Example 6, step F(d).

EXAMPLE 82

(5R,6S,7S)-6-(4-Fluorophenyl)-3-(2-methoxy-5-fluoro)phenyl-1-oxaspiro[5.4]non-3-ene-7-carboxylic acid methyl ester

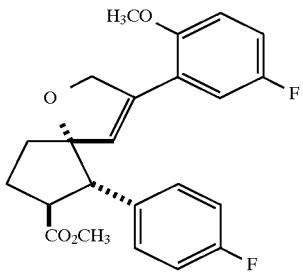

Mass spectrum (CI): m/e=401 (M+1).

EXAMPLE 83

(5R,6S,7S)-6-(4-Fluorophenyl)-3-(2-isopropoxy-5-fluoro)phenyl-1-oxaspiro[5.4]non-3-ene-7-carboxylic acid methyl ester

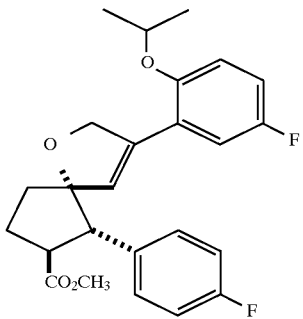

Mass spectrum (CI): m/e=429 (M+1).

EXAMPLE 84

(5R,6S,7S)-6-(4-Fluorophenyl)-3-(2-isopropyl-5-(N-trifluoroacetyl-N-methyl)amino)phenyl-1-oxaspiro[5.4]non-3-ene-7-carboxylic acid methyl ester

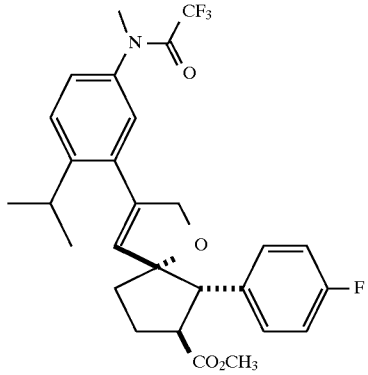

Mass spectrum (CI): m/e=537 (M+NH$_4^+$).

EXAMPLE 85

(5R,6S,7S)-6-(4-Fluorophenyl)-3-(2-isopropyl-5-(5-(trifluoromethyl)tetrazol-1-yl)phenyl-1-oxaspiro[5.4]non-3-ene-7-carboxylic acid methyl ester

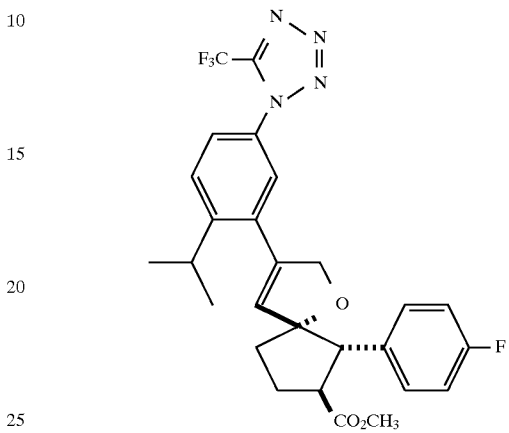

Mass spectrum (CI): m/e=530 (M+1).

EXAMPLE 86

(5R,6S,7S)-6-(4-Fluorophenyl)-3-(2-isopropyl-5-(2-(trifluoromethyl)imidazol-1-yl)phenyl-1-oxaspiro[5.4]non-3-ene-7-carboxylic acid methyl ester

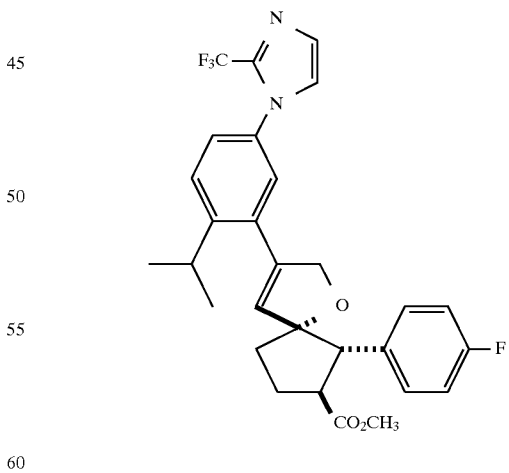

Mass spectrum (CI): m/e=529 (M+1).

EXAMPLE 87

(3S,5R,6S,7S)-6-(4-Fluorophenyl)-3-(2-methoxy-5-(N-(dimethylaminosulfonyl)-N-methyl)amino)phenyl-1-oxaspiro[5.4]nonane-7-carboxylic acid methyl ester

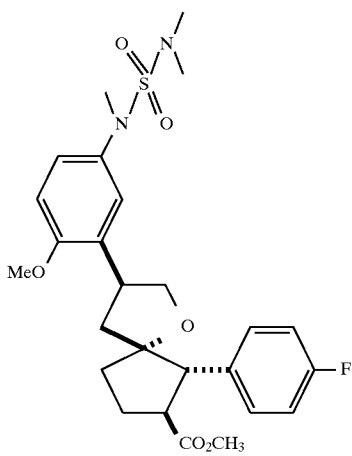

Mass spectrum (CI): m/e=521 (M+1).

EXAMPLE 88

(5R,6S,7S)-6-(4-Fluorophenyl)-3-(2-methoxy-5-(dimethylaminocarbonyl))-phenyl-1-oxaspiro[5.4]non-3-ene-7-carboxylic acid methyl ester

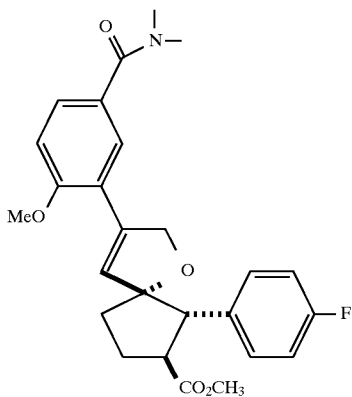

Mass spectrum (CI): m/e=454 (M+1).

EXAMPLE 89

(5R,6S,7S)-6-(4-Fluorophenyl)-3-(2-trifluoromethoxy-5-(N-(methanesulfonyl)-N-methyl)amino)phenyl-1-oxaspiro[5.4]non-3-ene-7-carboxylic acid methyl ester

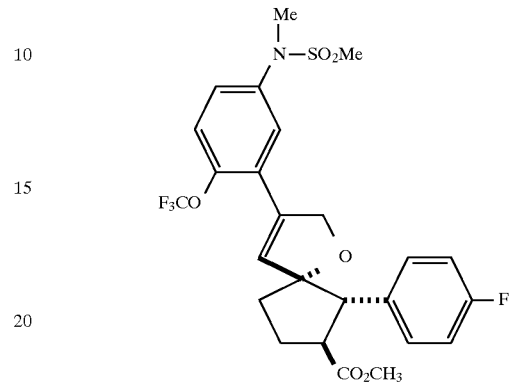

Mass spectrum (CI): m/e=544 (M+1).

Examples 90 through 96 were prepared by hydrogenation of the appropriate precursors (given in Example 38 and Examples 82–89), according to the procedures given in Example 6, step G or. Example 13.

EXAMPLE 90

(3S,5R,6S,7S)-6-(4-Fluorophenyl)-3-(2-methoxy-5-fluoro)phenyl-1-oxaspiro[5.4]nonane-7-carboxylic acid methyl ester

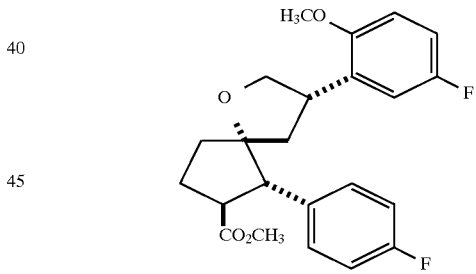

Mass spectrum (CI): m/e=403 (M+1).

EXAMPLE 91

(3S,5R,6S,7S)-6-(4-Fluorophenyl)-3-(2-isopropoxy-5-fluoro)phenyl-1-oxaspiro[5.4]nonane-7-carboxylic acid methyl ester

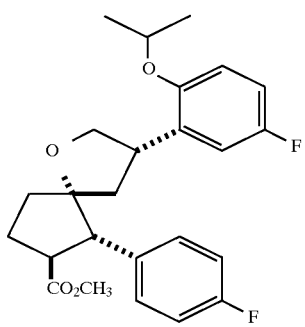

Mass spectrum (CI): m/e=431 (M+1).

EXAMPLE 92

(3S,5R,6S,7S)-6-(4-Fluorophenyl)-3-(2-methoxy-5-(N-(methanesulfonyl)-N-methyl)amino)phenyl-1-oxaspiro[5.4]nonane-7-carboxylic acid methyl ester

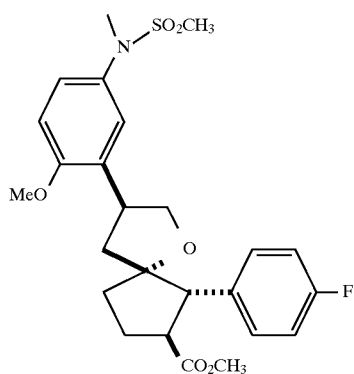

Mass spectrum (CI): m/e=509 (M+NH$_4^+$).

EXAMPLE 93

(3S,5R,6S,7S)-6-(4-Fluorophenyl)-3-(2-isopropyl-5-(N-trifluoroacetyl-N-methyl)amino)phenyl-1-oxaspiro[5.4]nonane-7-carboxylic acid methyl ester

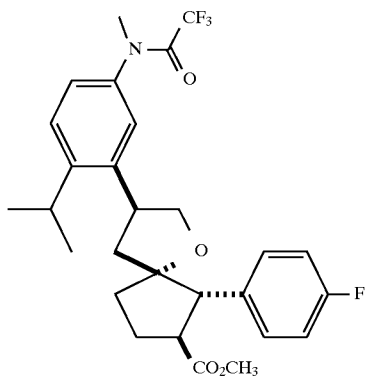

Mass spectrum (CI): m/e=522 (M+1).

EXAMPLE 94

(3S,5R,6S,7S)-6-(4-Fluorophenyl)-3-(2-isopropyl-5-(5-(trifluoromethyl)tetrazol-1-yl)phenyl-1-oxaspiro[5.4]nonane-7-carboxylic acid methyl ester

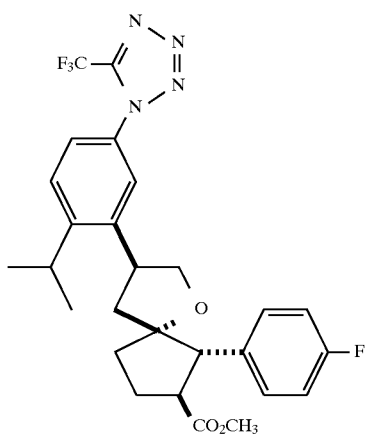

Mass spectrum (CI): m/e=533 (M+1).

EXAMPLE 95

(3S,5R,6S,7S)-6-(4-Fluorophenyl)-3-(2-methoxy-5-(dimethylaminocarbonyl))phenyl-1-oxaspiro[5.4]nonane-7-carboxylic acid methyl ester

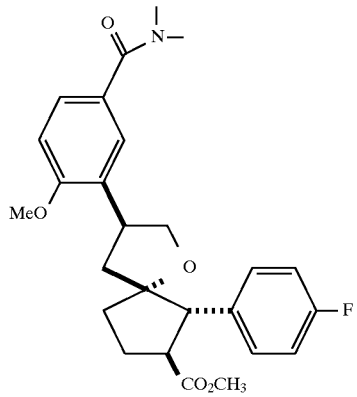

Mass spectrum (CI): m/e=456 (M+1).

EXAMPLE 96

(3S,5R,6S,7S)-6-(4-Fluorophenyl)-3-(2-trifluoromethoxy-5-(N-(methanesulfonyl)-N-methyl)amino)phenyl-1-oxaspiro[5.4]nonane-7-carboxylic acid methyl ester

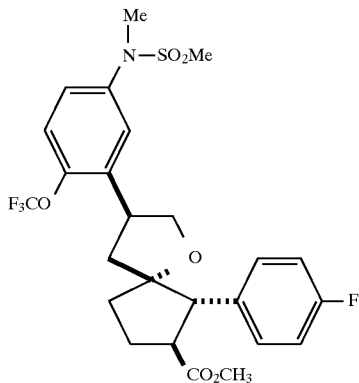

Mass spectrum (CI): m/e 545 (M+1).

EXAMPLE 97

(5R,6S,7S)-6-(4-Fluorophenyl)-3-(2-isopropoxy-5-fluoro)phenyl-7-(hydroxymethyl)-1-oxaspiro[5.4]non-3-ene

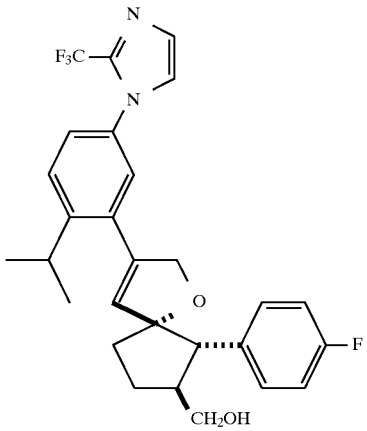

The title compound was prepared by reduction of (5R,6S,7S)-6-(4-fluorophenyl)-3-(2-isopropoxy-5-fluoro)phenyl-1-oxaspiro[5.4]non-3-ene-7-carboxylic acid methyl ester from Example 83 above under the conditions given in Example 10, step A. Mass spectrum (CI): m/e=401 (M+1).

EXAMPLE 98

(5R,6S,7S)-6-(4-Fluorophenyl)-3-(2-isopropyl-5-(2-(trifluoromethyl)imidazol-1-yl)phenyl-7-(hydroxymethyl)-1-oxaspiro[5.4]non-3-ene The title compound was prepared by reduction of (5R,6S,7S)-6-(4-fluorophenyl)-3-(2-isopropyl-5-(2-(trifluoromethyl)imidazol-1-yl)phenyl-1-oxaspiro[5.4]non-3-ene-7-carboxylic acid methyl ester from Example 86 above under the conditions given in Example 10, step A. Mass spectrum (CI): m/e=501 (M+1).

Examples 99 through 116 were prepared by alkylation, acylation or sulfonylation of commercially available benzoic acid, aniline or phenol derivatives by the standard procedures discussed above. When necessary, the bromine substituent was installed by bromination under standard conditions (such as Fe/bromine if a nitro precursor to an aniline derivative is brominated). For the formation of imidazo-1-yl aryl subunits, a chlorinated intermediate of the type generated in Example 6, step F(b) is treated with 2,2-diethoxyethylamine, followed by acetic acid. The aryl bromides were coupled to the 1-oxaspiro[4.4]non-3-ene framework using the conditions given in Example 6, step F(d), and the ester moiety was reduced according to the procedure given in Example 10, step A.

EXAMPLE 99

(5R,6S,7S)-6-(4-Fluorophenyl)-3-(2-isopropyl-5-(5-(trifluoromethyl)tetrazol-1-yl)phenyl-7-(hydroxymethyl)-1-oxaspiro[5.4]non-3-ene

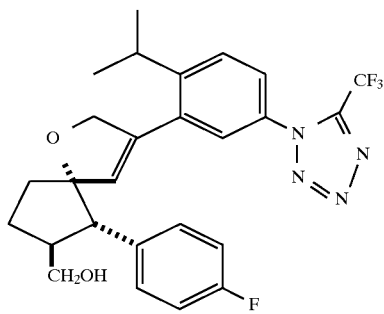

EXAMPLE 100

(5R,6S,7S)-6-(4-Fluorophenyl)-3-(2-isopropoxy-5-chloro)phenyl-7-(hydroxymethyl)-1-oxaspiro[5.4]non-3-ene

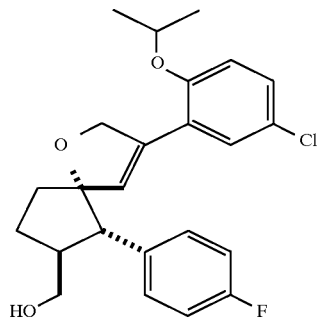

Mass spectrum (CI): m/e=417 (M+1).

EXAMPLE 101

(5R,6S,7S)-6-(4-Fluorophenyl)-3-(2,5-dichloro)phenyl-7-(hydroxymethyl)-1-oxaspiro[5.4]non-3-ene

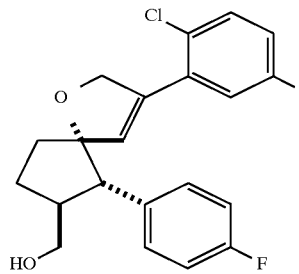

EXAMPLE 102

(5R,6S,7S)-6-(4-Fluorophenyl)-3-(2-fluoro-5-trifluoromethyl)phenyl-7-(hydroxymethyl)-1-oxaspiro[5.4]non-3-ene

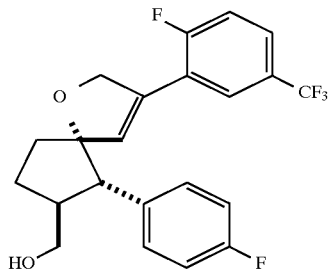

Mass spectrum-(CI): m/e=411 (M+1).

EXAMPLE 103

(5R,6S,7S)-6-(4-Fluorophenyl)-3-(2-isopropoxy-5-isopropyl)phenyl-7-(hydroxymethyl-1-oxaspiro[5.4]non-3-ene

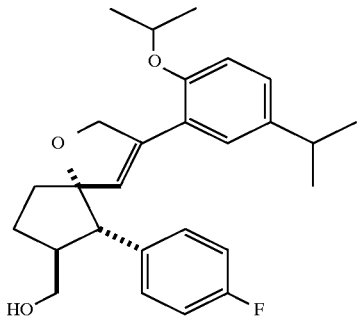

Mass spectrum (CI): m/e=425 (M+1).

EXAMPLE 104

(5R,6S,7S)-6-(4-Fluorophenyl)-3-(2-isopropoxy-5-methyl)phenyl-7-(hydroxymethyl)-1-oxaspiro[5.4]non-3-ene

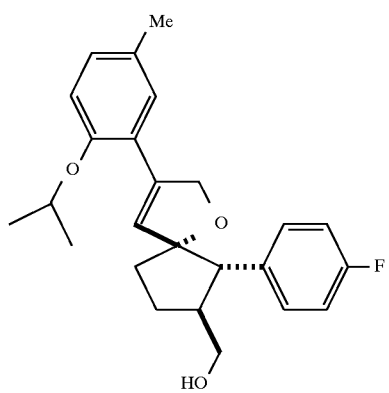

Mass spectrum (CI): m/e=397 (M+1).

EXAMPLE 105

(5R,6S,7S)-6-(4-Fluorophenyl)-3-(2-methyl-5-chloro)phenyl-7-(hydroxymethyl)-1-oxaspiro[5.4]non-3-ene

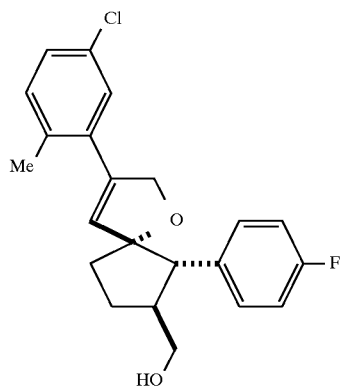

Mass spectrum (CI): m/e=373 (M+1).

EXAMPLE 106

(5R,6S,7S)-6-(4-Fluorophenyl)-3-(2-chloro-5-methyl)phenyl-7-(hydroxymethyl)-1-oxaspiro[5.4]non-3-ene

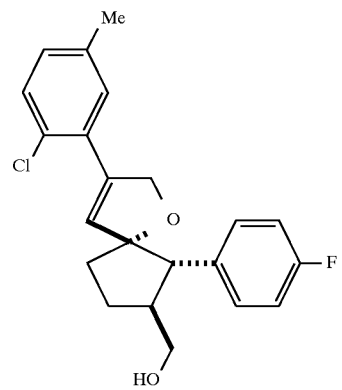

Mass spectrum (CI): m/e=373 (M+1).

EXAMPLE 107

(5R,6S,7S)-6-(4-Fluorophenyl)-3-(2-methoxy-5-methyl)phenyl-7-(hydroxymethyl)-1-oxaspiro[5.4]non-3-ene

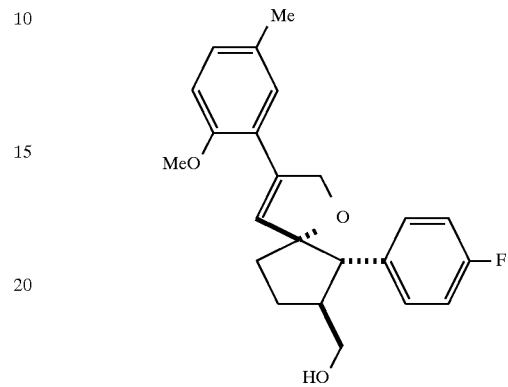

Mass spectrum (CI): m/e=369 (M+1).

EXAMPLE 108

(5R,6S,7S)-6-(4-Fluorophenyl)-3-(2-cyclopropylmethyl-5-fluoro)phenyl-7-(hydroxymethyl)-1-oxaspiro[5.4]non-3-ene

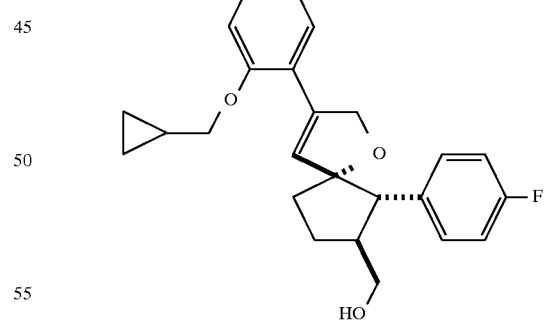

Mass spectrum (CI): m/e=413 (M+1).

EXAMPLE 109

(5R,6S,7S)-6-(4-Fluorophenyl)-3-(2-isopropyl-5-methyl)phenyl-7-(hydroxymethyl)-1-oxaspiro[5.4]non-3-ene

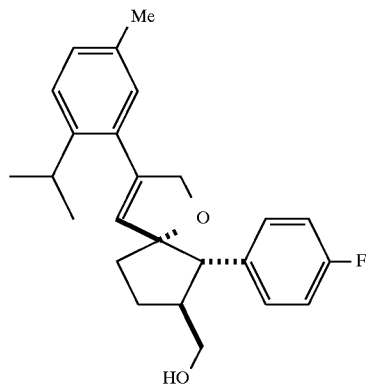

Mass spectrum (CI): m/e=381 (M+1).

EXAMPLE 110

(5R,6S,7S)-6-(4-Fluorophenyl)-3-(2-methoxy-5-isopropyl)phenyl-7-(hydroxymethyl)-1-oxaspiro[5.4]non-3-ene

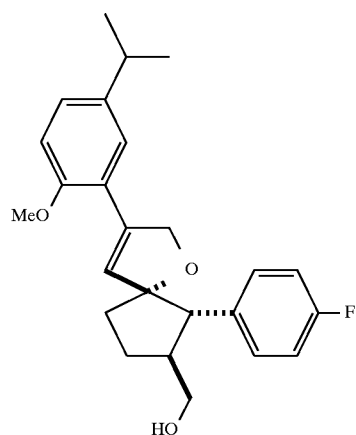

Mass spectrum (CI): m/e=365 (M−OCH₃).

EXAMPLE 111

(5R,6S,7S)-6-(4-Fluorophenyl)-3-(2-fluoro-5-methyl)phenyl-7-(hydroxymethyl)-1-oxaspiro[5.4]non-3-ene

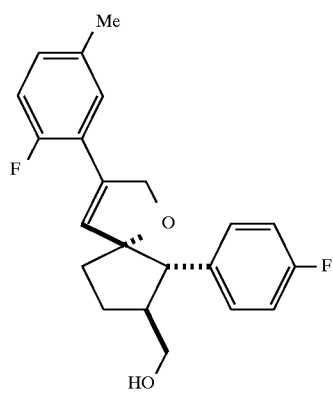

Mass spectrum (CI): m/e=357 (M+1).

EXAMPLE 112

(5R,6S,7S)-6-(4-Fluorophenyl)-3-(2-cyclobutyloxy-5-fluoro)phenyl-7-(hydroxymethyl)-1-oxaspiro[5.4]non-3-ene

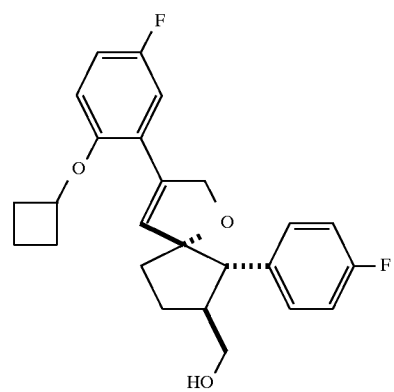

Mass spectrum (CI): m/e=411 (M−1).

EXAMPLE 113

(5R,6S,7S)-6-(4-Fluorophenyl)-3-(2-methoxy-5-((N,N-dimethylamino)carbonylmethyl)phenyl-7-(hydroxymethyl)-1-oxaspiro[5.4]non-3-ene

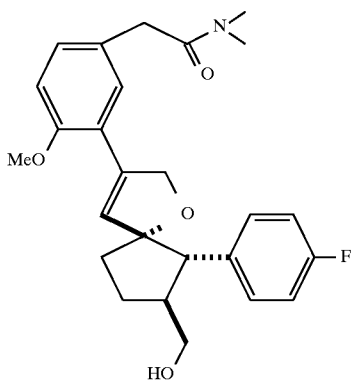

Mass spectrum (CI): m/e=440 (M+1).

EXAMPLE 114

(5R,6S,7S)-6-(4-Fluorophenyl)-3-(2-trifluoromethoxy-5-(N-(methanesulfonyl)-N-methylamino)phenyl-7-(hydroxymethyl)-1-oxaspiro[5.4]non-3-ene

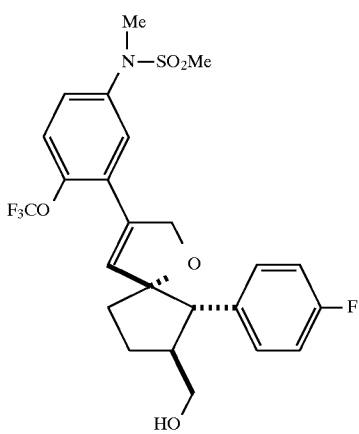

Mass spectrum (CI): m/e=533 (M+NH$_4^+$).

EXAMPLE 115

(5R,6S,7S)-6-(4-Fluorophenyl)-3-(2-trifluoromethoxy-5-(N-(3,5-dimethylisoxazol-4-ylcarbonyl)-N-methylamino)phenyl-7-(hydroxymethyl)-1-oxaspiro[5.4]non-3-ene

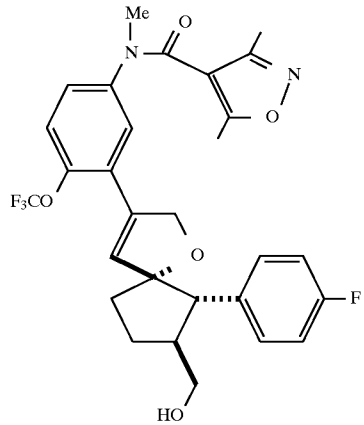

Mass spectrum (CI): m/e=561 (M+1).

EXAMPLE 116

(5R,6S,7S)-6-(4-Fluorophenyl)-3-(2-trifluoromethoxy-5-(N-(5-methylisoxazol-3-ylcarbonyl)-N-methylamino)phenyl-7-(hydroxymethyl)-1-oxaspiro[5.4]non-3-ene

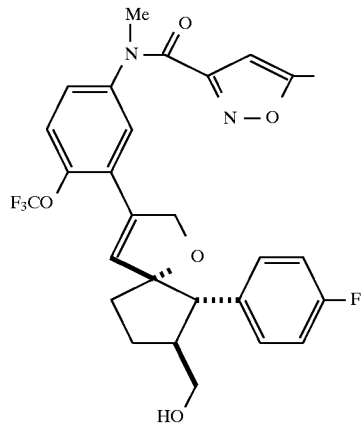

Mass spectrum (CI): m/e=547 (M+1).

Examples 117 through 120 were prepared from (5R,6S,7S)-6-(4-fluorophenyl)-3-(2-isopropyl-5-(5-(trifluoromethyl)tetrazol-1-yl)phenyl-7-(hydroxymethyl)-1-oxaspiro[5.4]non-3-ene through formation of the aldehyde and reductive amination with commercially available amines according to the procedures given in Example 10, steps A and B.

EXAMPLE 117

(5R,6S,7S)-6-(4-Fluorophenyl)-3-(2-isopropyl-5-(5-(trifluoromethyl)tetrazol-1-yl)phenyl-7-(N,N-dimethylaminomethyl)-1-oxaspiro[5.4]non-3-ene

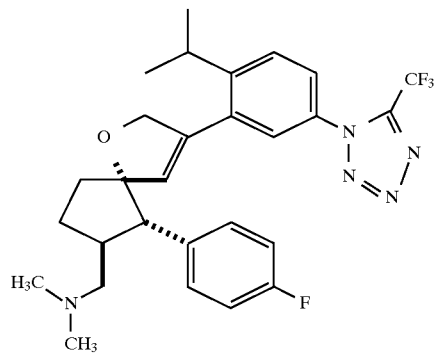

Mass spectrum (CI): m/e=530 (M+1).

EXAMPLE 118

(5R,6S,7S)-6-(4-Fluorophenyl)-3-(2-isopropyl-5-(5-(trifluoromethyl)tetrazol-1-yl)phenyl-7-(pyrrolidin-1-ylmethyl)-1-oxaspiro[5.4]non-3-ene

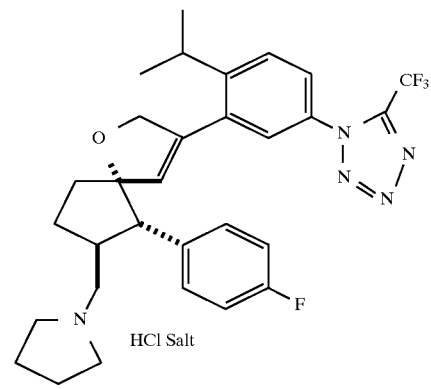

Mass spectrum (CI): m/e=556 (M+1).

EXAMPLE 119

(5R,6S,7S)-6-(4-Fluorophenyl)-3-(2-isopropyl-5-(5-(trifluoromethyl)tetrazol-1-yl)phenyl-7-(morpholin-1-ylmethyl)-1-oxaspiro[5.4]non-3-ene

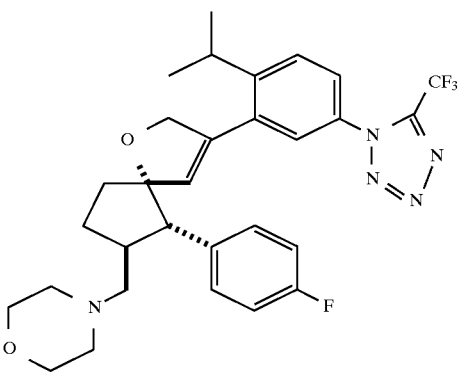

Mass spectrum (CI): m/e=572 (M+1).

EXAMPLE 120

(5R,6S,7S)-6-(4-Fluorophenyl)-3-(2-isopropyl-5-(5-(trifluoromethyl)tetrazol-1-yl)phenyl-7-(N-(2-fluoroethyl)aminomethyl)-1-oxaspiro[5.4]non-3-ene

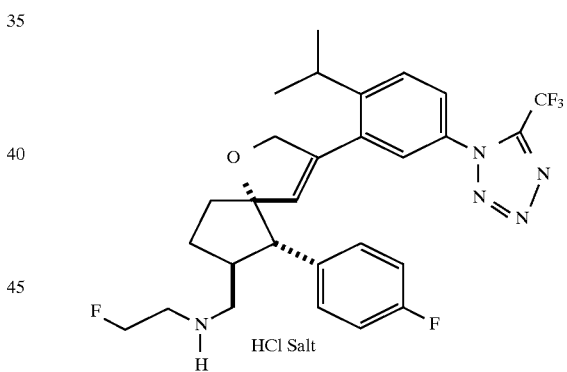

Mass spectrum (CI): m/e=548 (M+1).

EXAMPLE 121

(5R,6S,7S)-6-(4-Fluorophenyl)-3-(2-isopropyl-5-(5-(trifluoromethyl)tetrazol-1-yl)phenyl-7-(N-cyclopropylaminomethyl)-1-oxaspiro[5.4]non-3-ene

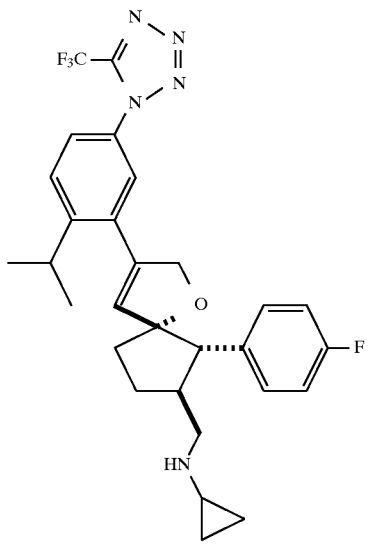

The title compound was prepared from (5R,6S,7S)-6-(4-fluorophenyl)-3-(2-isopropyl-5-(5-(trifluoromethyl)tetrazol-1-yl)phenyl-7-(hydroxymethyl)-1-oxaspiro[5.4]non-3-ene by the procedures given in Example 10, steps A and B. Mass spectrum (CI): m/e=542 (M+1).

Examples 122 through 125 were prepared from (5R,6S,7S)-6-(4-fluorophenyl)-3-(2-isopropyl-5-(2-(trifluoromethyl)imidazol-1-yl)phenyl-7-(hydroxymethyl)-1-oxaspiro[5.4]non-3-ene through formation of the aldehyde and reductive amination with commercially available amines according to the procedures given in Example 10, steps A and B.

EXAMPLE 122

(5R,6S,7S)-6-(4-Fluorophenyl)-3-(2-isopropyl-5-(2-(trifluoromethyl)imidazol-1-yl)phenyl-7-(methylaminomethyl)-1-oxaspiro[5.4]non-3-ene

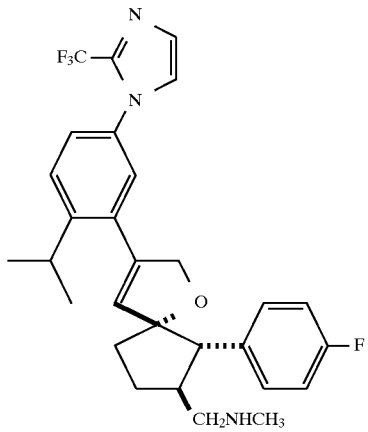

Mass spectrum (CI): m/e=514 (M+1).

EXAMPLE 123

(5R,6S,7S)-6-(4-Fluorophenyl)-3-(2-isopropyl-5-(2-(trifluoromethyl)imidazol-1-yl)phenyl-7-(N-(2,2,2-trifluoroethyl)aminomethyl)-1-oxaspiro[5.4]non-3-ene

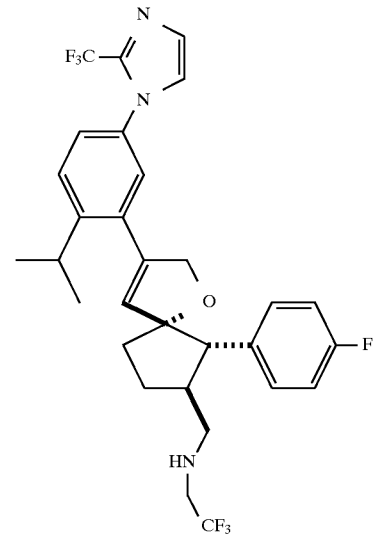

Mass spectrum (CI): m/e=582 (M+1).

EXAMPLE 124

(5R,6S,7S)-6-(4-Fluorophenyl)-3-(2-isopropyl-5-(2-(trifluoromethyl)imidazol-1-yl)phenyl-7-(morpholin-4-ylmethyl)-1-oxaspiro[5.4]non-3-ene

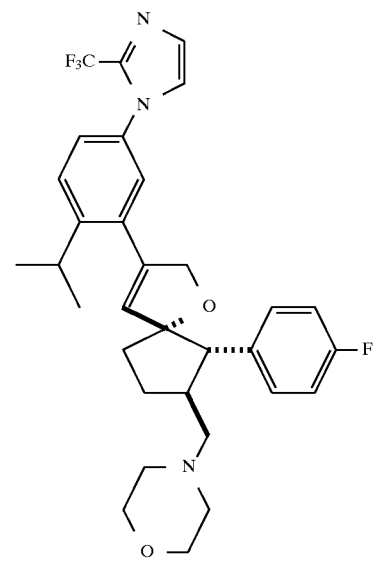

Mass spectrum (CI): m/e=570 (M+1).

EXAMPLE 125

(5R,6S,7S)-6-(4-Fluorophenyl)-3-(2-isopropyl-5-(2-(trifluoromethyl)imidazol-1-yl)phenyl-7-(pyrrolidin-1-ylmethyl)-1-oxaspiro[5.4]non-3-ene

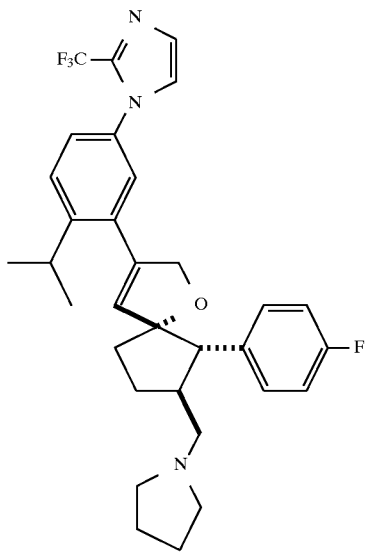

Mass spectrum (CI): m/e=554 (M+1).

Examples 126 through 131 were prepared by hydrogenation of the appropriate precursors (given in Example 97 and Examples 99–103), according to the procedures given in Example 6, step G or Example 13.

EXAMPLE 126

(3S,5R,6S,7 S)-6-(4-Fluorophenyl)-3-(2-isopropyl-5-(5-(trifluoromethyl)tetrazol-1-yl)phenyl-7-(hydroxymethyl)-11-oxaspiro[5.4]nonane

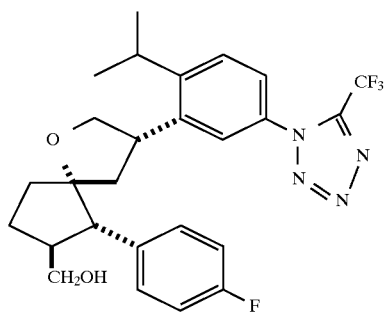

Mass spectrum (CI): m/e=522 (M+NH$_4^+$).

EXAMPLE 127

(3S,5R,6S,7S)-6-(4-Fluorophenyl)-3-(2-isopropoxy-5-fluoro)phenyl-7-(hydroxymethyl-1-oxaspiro[5.4]nonane

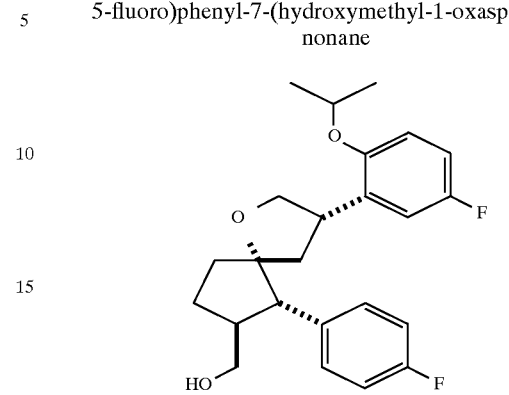

Mass spectrum (CI): m/e=403 (M+1).

EXAMPLE 128

(3S,5R,6S,7S)-6-(4-Fluorophenyl)-3-(2-isopropoxy)phenyl-7-(hydroxymethyl)-1-oxaspiro[5.4]nonane

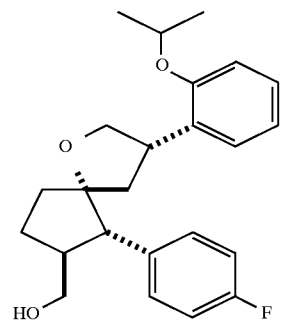

Mass spectrum (CI): m/e=385 (M+1).

EXAMPLE 129

(3S,5R,6S,7S)-6-(4-Fluorophenyl)-3-phenyl-7-(hydroxymethyl)-1-oxaspiro[5.4]nonane

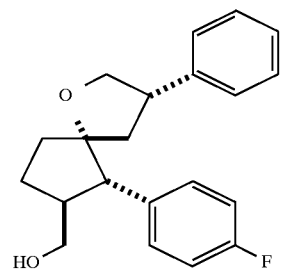

Mass spectrum (CI): m/e=327 (M+1).

EXAMPLE 130

(3S,5R,6S,7S)-6-(4-Fluorophenyl)-3-(2-fluoro-5-trifluoromethyl)phenyl-7-(hydroxymethyl)-1-oxaspiro[5.4]nonane

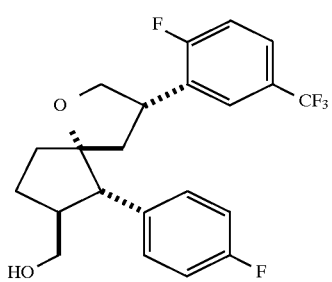

Mass spectrum (CI): m/e=413 (M+1).

EXAMPLE 131

(3S,5R,6S,7S)-6-(4-Fluorophenyl)-3-(2-isoproxy-5-isopropyl)phenyl-7-(hydroxymethyl)-1-oxaspiro[5.4]nonane

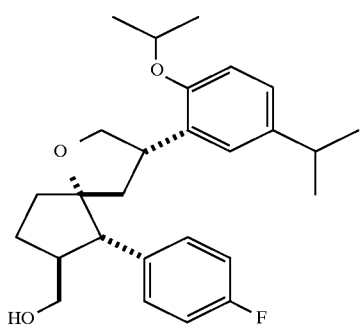

Mass spectrum (CI): m/e=427 (M+1).

Examples 132 through 143 were prepared by hydrogenation of the appropriate precursors (given in Example 96, Example 98 and Examples 104–116), according to the procedures given in Example 6, step G or Example 13.

EXAMPLE 132

(3S,5R,6S,7S)-6-(4-Fluorophenyl)-3-(2-methoxy-5-(N-(2,2,2-trifluoroethyl)-N-isopropyl)amino)phenyl-7-(hydroxymethyl)-1-oxaspiro[5.4]nonane

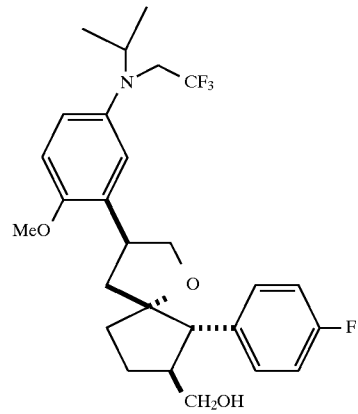

Mass spectrum (CI): m/e=496 (M+1).

EXAMPLE 133

(3S,5R,6S,7S)-6-(4-Fluorophenyl)-3-(2-trifluoromethoxy-5-(N-(methanesulfonyl)-N-methyl)amino)phenyl-7-(hydroxymethyl)-1-oxaspiro[5.4]nonane

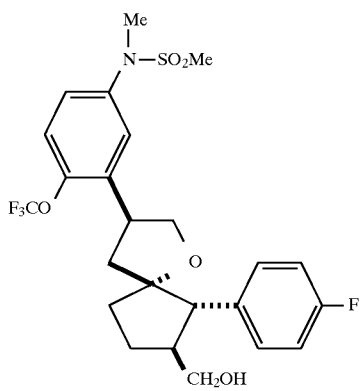

Mass spectrum (CI): m/e=535 (M+NH$_4^+$).

EXAMPLE 134

(3S,5R,6S,7S)-6-(4-Fluorophenyl)-3-(2-isopropoxy-5-methyl)phenyl-7-(hydroxymethyl)-1-oxaspiro[5.4]nonane

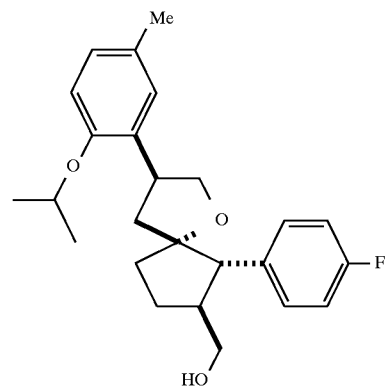

Mass spectrum (CI): m/e=399 (M+1).

EXAMPLE 135

(3S,5R,6S,7S)-6-(4-Fluorophenyl)-3-(3-methyl)phenyl-7-(hydroxymethyl)-1-oxaspiro[5.4]nonane

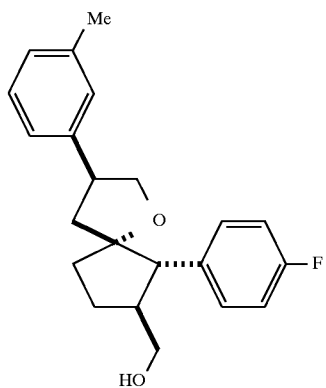

Mass spectrum (CI): m/e=341 (M+1).

EXAMPLE 136

(3S,5R,6S,7S)-6-(4-Fluorophenyl)-3-(2-methyl)phenyl-7-(hydroxymethyl)-1-oxaspiro[5.4]nonane

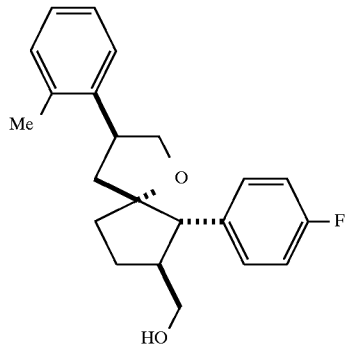

Mass spectrum (CI): m/e=341 (M+1).

EXAMPLE 137

(3S,5R,6S,7S)-6-(4-Fluorophenyl)-3-(2-methoxy-5-methyl)phenyl-7-(hydroxymethyl-1-oxaspiro[5.4]nonane

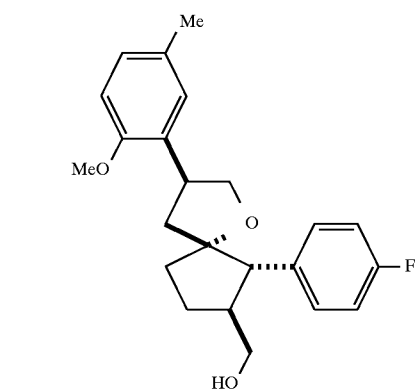

Mass spectrum (CI): m/e=371 (M+1).

EXAMPLE 138

(3S,5R,6S,7S)-6-(4-Fluorophenyl)-3-(2-cyclopropylmethyl-5-fluoro)phenyl-7-(hydroxymethyl)-1-oxaspiro[5.4]nonane

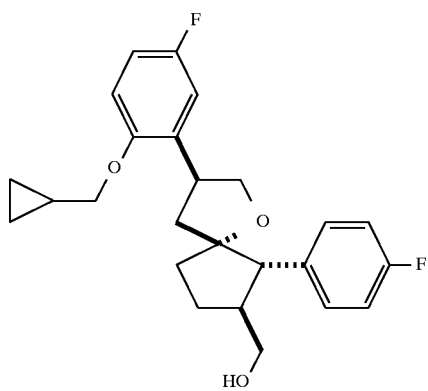

Mass spectrum (CI): m/e=415 (M+1).

EXAMPLE 139

(3S,5R,6S,7S)-6-(4-Fluorophenyl)-3-(2-isopropyl-5-methyl)phenyl-7-(hydroxymethyl)-1-oxaspiro[5.4]nonane

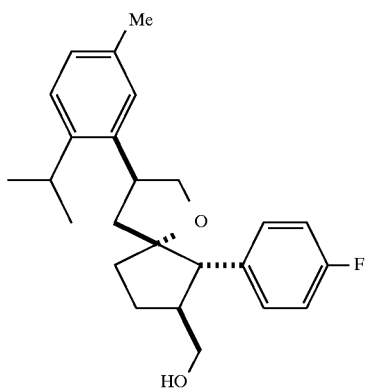

Mass spectrum (CI): m/e=383 (M+1).

EXAMPLE 140

(3S,5R,6S,7S)-6-(4-Fluorophenyl)-3-(2-fluoro-5-methyl)phenyl-7-(hydroxymethyl)-1-oxaspiro[5.4]nonane

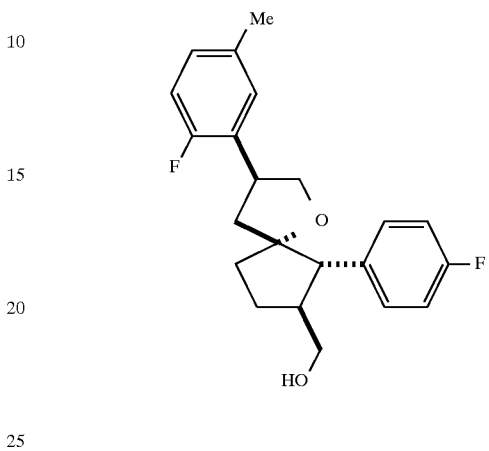

Mass spectrum (CI): m/e=359 (M+1).

EXAMPLE 141

(3S,5R,6S,7S)-6-(4-Fluorophenyl)-3-(2-methoxy-5-isopropyl)phenyl-7-(hydroxymethyl)-1-oxaspiro[5.4]nonane

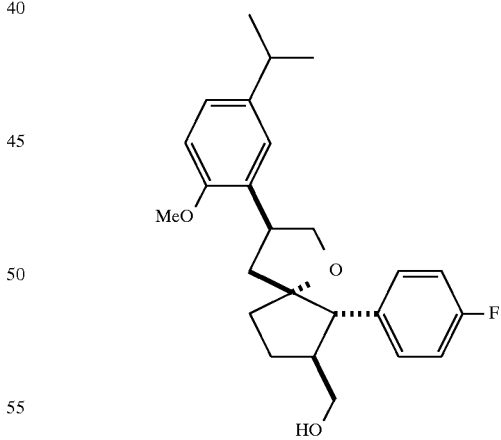

Mass spectrum (CI): m/e=399 (M+1).

EXAMPLE 142

(3S,5R,6S,7S)-6-(4-Fluorophenyl)-3-(2-cyclobutyloxy-5-fluoro)phenyl-7-(hydroxymethyl)-1-oxaspiro[5.4]nonane

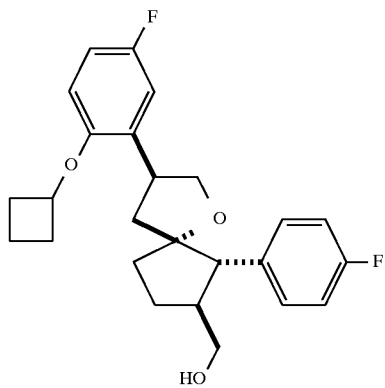

Mass spectrum (CI): m/e=415 (M+1).

EXAMPLE 143

(3S,5R,6S,7S)-6-(4-Fluorophenyl)-3-(2-methoxy-5-((N,N-dimethylamino)carbonylmethyl)phenyl-7-(hydroxymethyl)-1-oxaspiro[5.4]nonane

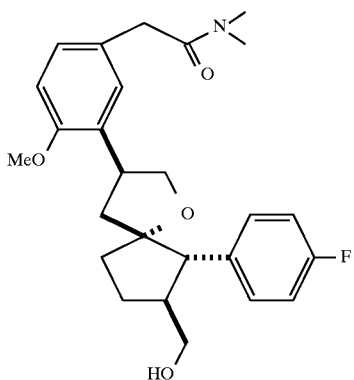

Examples 144 through 150 were prepared from (3S,5R,6S,7S)-6-(4-fluorophenyl)-3-(2-isopropyl-5-(5-(trifluoromethyl)tetrazol-1-yl)phenyl-7-(hydroxymethyl)-1-oxaspiro[5.4]nonane or (3S,5R,6S,7S)-6-(4-fluorophenyl)-3-(2-isopropoxy-5-fluoro)phenyl-7-(hydroxymethyl)-1-oxaspiro[5.4]nonane through formation of the aldehyde and reductive amination with commercially available amines according to the procedures given in Example 10, steps A and B.

EXAMPLE 144

(3S,5R,6S,7S)-6-(4-Fluorophenyl)-3-(2-isopropyl-5-(5-(trifluoromethyl)tetrazol-1-yl)phenyl-7-(aminomethyl)-1-oxaspiro[5.4]nonane

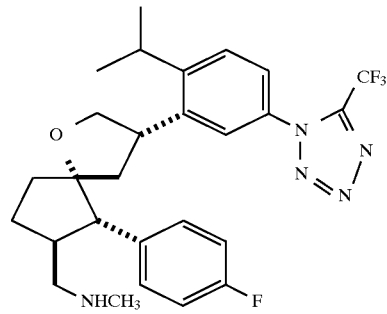

Mass spectrum (CI): m/e=518 (M+1).

EXAMPLE 145

(3S,5R,6S,7S)-6-(4-Fluorophenyl)-3-(2-isopropoxy-5-fluoro)phenyl-7-(N,N-dimethylaminomethyl)-1-oxaspiro[5.4]nonane

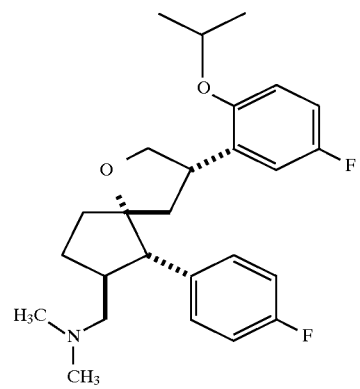

Mass spectrum (CI): m/e=430 (M+1).

EXAMPLE 146

(3S,5R,6S,7S)-6-(4-Fluorophenyl)-3-(2-isopropoxy-5-fluoro)phenyl-7-(pyrrolidin-1-ylmethyl)-1-oxaspiro[5.4]nonane

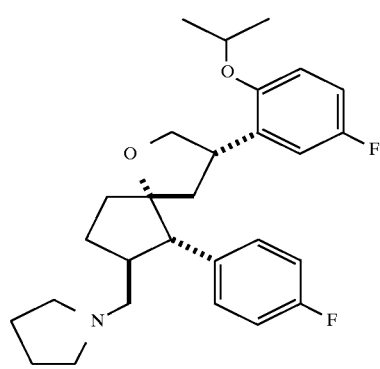

Mass spectrum (CI): m/e=456 (M+1).

EXAMPLE 147

(3S,5R,6S,7S)-6-(4-Fluorophenyl)-3-(2-isopropoxy-5-fluoro)phenyl-7-(N-(2,2-trifluoroethyl)aminomethyl)-1-oxaspiro[5.4]nonane

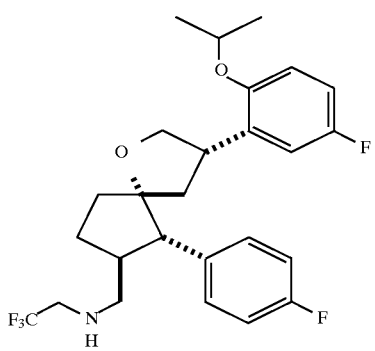

Mass spectrum (CI): m/e=484 (M+1).

EXAMPLE 148

(3S,5R,6S,7S)-6-(4-Fluorophenyl)-3-(2-isopropoxy-5-fluoro)phenyl-7-(N-(2,2-trifluoroethyl)-N-methylaminomethyl)-1-oxaspiro[5.4]nonane

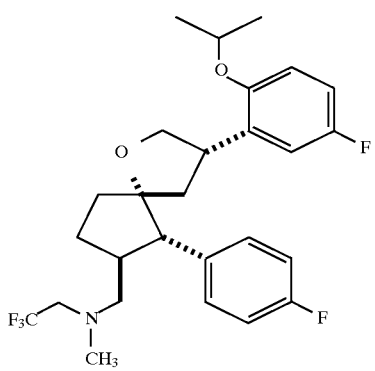

Mass spectrum (CI): m/e=484 (M+1).

EXAMPLE 149

(3S,5R,6S,7S)-6-(4-Fluorophenyl)-3-(2-isopropoxy-5-fluoro)phenyl-7-(N-(cyclopropyl)aminomethyl)-1-oxaspiro[5.4]nonane

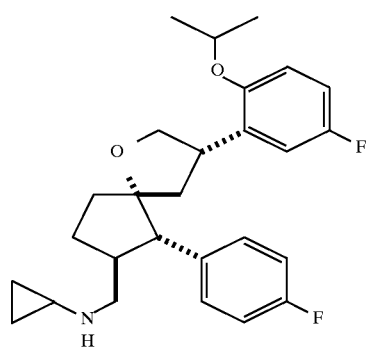

Mass spectrum (CI): m/e=498 (M+1).

EXAMPLE 150

(3S,5R,6S,7S)-6-(4-Fluorophenyl)-3-(2-isopropoxy-5-fluoro)phenyl-7-(N-(cyclopropyl)-N-methylaminomethyl-1-oxaspiro[5.4]nonane

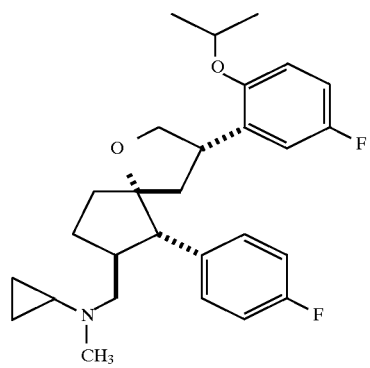

Mass spectrum (CI): m/e=456 (M+1).

Examples 151 and 152 were prepared from (3S,5R,6S,7S)-6-(4-fluorophenyl)-3-(2-isopropoxy-5-fluoro)phenyl-7-(hydroxymethyl)-1-oxaspiro[5.4]nonane through formation of the aldehyde and reductive amination with commercially available amines according to the procedures given in Example 10, steps A and B.

EXAMPLE 151

(3S,5R,6S,7S)-6-(4-Fluorophenyl)-3-(2-isopropoxy-5-fluoro)phenyl-7-(morpholin-4-ylmethyl)-1-oxaspiro[5.4]nonane

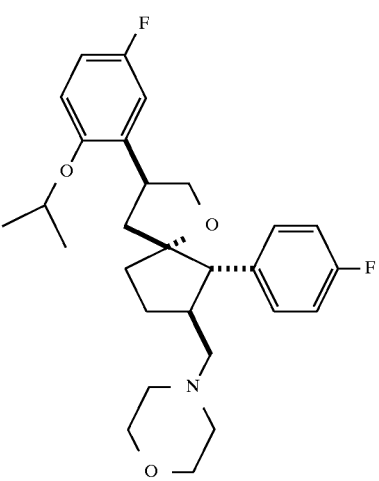

Mass spectrum (CI): m/e=472 (M+1).

EXAMPLE 152

(3S,5R,6S,7S)-6-(4-Fluorophenyl)-3-(2-isopropoxy-5-fluoro)phenyl-7-(2-(fluoroethyl)aminomethyl)-1-oxaspiro[5.4]nonane

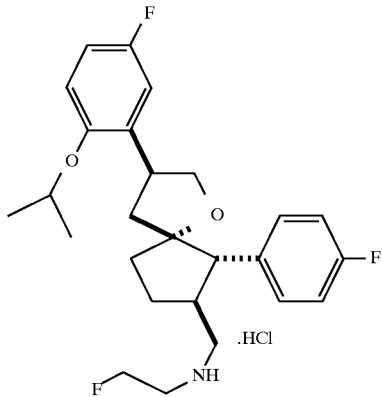

Mass spectrum (CI): m/e=397 (M+1).

EXAMPLE 153

(5R,6S,7S)-6-(4-Fluorophenyl)-3-(5-cyano-2-isopropoxy-phenyl)-1-oxaspiro[4.4]non-3-ene-7-methanol The title compound was prepared following the procedure described in Example 6, Step F(d) using 3-bromo-4-isopropoxybenzonitrile and (5R,6S,7S)-6-(4-fluorophenyl)-3-(trimethylstannyl)-1-oxaspiro[4.4]non-3-ene-7-methanol as substrates for the cross-coupling reaction. 400 MHz $^1$H NMR (CD$_3$OD): δ 1.28 (s, 3H), 1.31 (s, 3H), 1.70 (m, 1H), 2.18 (m, 2H), 2.72 (m, 1H), 2.82 (d, 1H), 3.37 (dd, 1H), 3.55 (dd, 1H), 4.05 (dd, 1H), 4.67 (dd, 1H), 4.70 (m, 1H), 6.35 (m, 1H), 6.92 (t, 2H), 7.07 (d, 1H), 7.30 (m, 2H), 7.38 (d, 1H), 7.52 (dd, 1H); Mass spec (NH$_3$/CI): 408 (M+1); 425 (M+NH$_3$).

EXAMPLE 154

(5R,6S,7S)-7-(Dimethylamino)-6-(4-fluorophenyl)-3-(5-cyano-2-isopropoxy-phenyl)-1-oxaspiro[4.4]non-3-ene Step A: (5R,6S,7S)-6-(4-fluorophenyl)-3-(5-cyano-2-isopropoxyphenyl)-1-oxaspiro[4.4]non-3-ene-7-carboxylic acid (5R,6S,7S)-6-(4-Fluorophenyl)-3-(5-cyano-2-isopropoxyphenyl)-1-oxaspiro[4.4]non-3-ene-7-carboxylic acid methyl ester(128 mg, 0.294 mmol) was taken up in THF(2 mL) and methanol (2 mL) and treated with 2.5N NaOH (0.4 mL, 1.0 mmol) for 6 hours at room temperature. 2N Hydrochloric acid (5 mL) was then added, and the product extracted with ethyl acetate (2×30 mL). The combined extracts were washed with saturated brine solution, dried (MgSO$_4$), and evaporated to afford the title compound; yield 124 mg.

Step B: (5R,6S,7S)-7-(benzyloxycarbonylamino)-6-(4-fluorophenyl)3-(5-cyano-2-isopropoxy-phenyl)-1-oxaspiro[4.4]non-3-ene To a solution of (5R,6S,7S)-6-(4-fluorophenyl)-3-(5-cyano-2-isopropoxy-phenyl)-1-oxaspiro[4.4]non-3-ene-7-carboxylic acid (128 mg, 0.304 mmol) in toluene (2 mL) were added N,N,-diisopropylethylamine (64 μL, 0.367 mmol) followed by diphenylphosphoryl azide (73 μl, 0.339 mmol). The mixture was stirred for 30 minutes at room temperature and then for 1 hour at 100° C. Benzyl alcohol (63 μL, 0.609 mmol) was then added, and the mixture was stirred for 18 hours at 100° C. The cooled mixture was diluted with ethyl acetate (30 mL), washed with saturated sodium hydrogencarbonate solution, saturated brine solution, dried (Na$_2$SO$_4$), and evaporated. Silica gel chromatography eluting with 30% ethyl acetate/hexane afforded the title compound; yield 49 mg. The 400 MHz NMR spectrum in CD$_3$OD was in accord with the desired structure.

Step C: (5R,6S,7S)-7-amino-6-(4-fluorophenyl)-3-(5-cyano-2-isopropoxy-phenyl)-1-oxaspiro[4.4]non-3-ene Hydrogenolysis of the title compound from Step C (49 mg) in methanol (2 mL) in the presence of 10% palladium-on-charcoal (20 mg) for 1 hour afforded the desired title compound; yield 34 mg Step D: (5R,6S,7S)-7-(dimethylamino)-6-(4-fluorophenyl)-3-(5-cyano-2-isopropoxy-phenyl-1-oxaspiro[4.4]non-3-ene (5R,6S,7S)-7-Amino-6-(4-fluorophenyl)-3-(5-cyano-2-isopropoxy-phenyl)-1-oxaspiro[4.4]non-3-ene (17.7 mg, 0.045 mmol) was taken up in acetonitrile (0.72 mL). Water (0.2 mL) and 37% formaldehyde (33 μL) were added followed by a solution of sodium cyanoborohydride (11.2 mg, 0.178 mmol) in acetonitrile (0.2 mL). The reaction mixture was stirred for 1 hour at room temperature with occasional addition of 20% acetic acid/acetonitrile to maintain the pH of the reaction at ~7. The mixture was evaporated, and the residue was partitioned between ethyl acetate and 2.5N NaOH. The organic layer was washed with saturated brine solution and evaporated. Pure title compound (12.3 mg) was obtained by silica gel chromatography eluting with 5–10% methanol/methylene chloride. 400 MHz $^1$H-NMR (CD$_3$OD): δ 1.28 (d, 3H), 1.31 (d, 3H), 2.28 (s, 6H), 3.17 (d, 1H), 3.68 (m, 1H), 4.10 (dd, 1H), 4.65–4.75 (m, 2H), 6.32 (m, 1H), 6.96 (t, 2H), 7.08 (d, 1H), 7.38 (m, 3H), 7.53 (dd, 1H).

EXAMPLE 155

(3S,5R,6S, 7S)-6-(4-Fluorophenyl)-3-(5-cyano-2-isopropoxy-phenyl)-7-(pyrrolidin-1-yl)methyl)-1-oxaspiro[4.4]nonane hydrochloride Step A: (3S,5R,6S, 7S)-6-(4-Fluorophenyl)-3-(5-cyano-2-isopropoxy-phenyl)-1-oxaspiro[4.4]nonane-7-methanol The title compound was prepared by hydrogenation of (5R, 6S, 7S)-6-(4-fluorophenyl)-3-(5-cyano-2-isopropoxy-phenyl)-1-oxaspiro[4.4]non-3-ene-7-methanol (78 mg) in methanol (4 mL) over 10% palladium-on-charcoal (20 mg) at 50 psi for 90 minutes. Purification was achieved by means of silica gel chromatography eluting with 10% acetone/methylene chloride; yield 35 mg.

Step B: (3S,5R,6S,7S)-6-(4-Fluorophenyl)-7-(methanesulfonyloxy)-3-(5-cyano-2-isopropoxy-phenyl)-1-oxaspiro[4.4]nonane To a solution of (5R,6S,7S)-6-(4-fluorophenyl)-3-(5-cyano-2-isopropoxy-phenyl)-1-oxaspiro[4.4]nonane-7-methanol (35 mg, 0.085 mmol) in methylene chloride (1 mL) were added triethylamine (24 μL, 0.172 mmol) and methanesulfonic anhydride (22 mg, 0.126 mmol). The reaction mixture was stirred for 2 hours at room temperature, diluted with methylene chloride, washed with water, 2N hydrochloric acid, saturated sodium hydrogencarbonate solution, saturated brine solution, dried (Na$_2$SO$_4$), and evaporated. The product was used without further purification in Step C.

Step C: (3S,5R,6S,7S)-6-(4-Fluorophenyl)-7-(iodomethyl)-3-(5-cyano-2-isopropoxy-phenyl)-1-oxaspiro[4.4]nonane The methanesulfonate from Step B was dissolved in acetone (2 mL). Sodium iodide (25 mg, 0.167 mmol) was added, and the mixture was heated at reflux temperature until TLC indicated disappearance of starting material. The cooled reaction mixture was evaporated, the residue taken up in methylene chloride, washed with water, 10% sodium thiosulfate solution, saturated brine solution, dried ($Na_2SO_4$), and evaporated. The title compound was obtained pure by silica gel chromatography eluting with 15% diethyl ether/hexane; yield 35 mg.

Step D: (3S,5R,6S,7S)-6-(4-Fluorophenyl)-3-(5-cyano-2-isopropoxy-phenyl)-7-(pyrrolidin-1-yl)methyl)-1-oxaspiro[4.4]nonane hydrochloride A mixture of (3S,5R,6S,7S)-6-(4-fluorophenyl)-7-(iodomethyl)-3-(5-cyano-2-isopropoxy-phenyl)-1-oxaspiro[4.4]nonane (35 mg, 0.067 mmol), N,N-diisopropylethylamine (42 μL, 0.241 mmol), and pyrrolidine (16 μL, 0.192 mmol) in acetonitrile (1.5 mL) was stirred for 2 hours at 80° C. The cooled mixture was evaporated, the residue taken up in ethyl acetate, washed with water, saturated brine solution, dried ($MgSO_4$), and evaporated. Silica gel chromatography eluting with 3–5% methanol/methylene chloride afforded pure title compound; yield 19 mg (61%). 400 MHz $^1$H NMR ($CD_3OD$): δ 1.27 (s, 3H), 1.30 (s, 3H), 3.11 (t, 1H), 3.63 (m, 1H), 4.03 (t, 1H), 4.67 (m, 1H); Mass spec ($NH_3$/CI): 463 (M+1)

EXAMPLE 156

(3S,5R,6S,7S)-6-(4-fluorophenyl)-3-(2-methylthio-5-(5-(trifluoromethyl)tetrazol-1-yl)phenyl)-1-oxaspiro[4.4]non-3-ene-7-methanol Step A: 2-bromo-4-nitro-benzene-o-ethylxanthate The title compound was prepared from commercially available 2-bromo-4-nitroaniline (5.0 g, 23.0 mmol), according the procedure of (J. Org. Chem., 1990, 55, 2738), to give 2.36 g of the title compound as a red oil.

Step B: 2-bromo-4-nitro-methylthioanisole

To a solution of 2-bromo-4-nitro-benzene-o-ethylxanthate (1.84 g, 5.71 mmol) in 20 mL of MeOH was added sodium methoxide (925 mg, 17.1 mmol) and the reaction mixture heated at 80° C. for 10 minutes. Half of the reaction mixture was treated with methyl iodide (0.35 mL, 5.7 mmol) and stirred for 18 h at rt. The reaction mixture was diluted with EtOAc, washed with 1$\underline{N}$ HCl, $H_2O$, brine, dried over $Na_2SO_4$, filtered, and conc. to give 1.21 g of solid. Purification by flash chromatograpy on silica gel eluding with 2% EtOAc/hexanes afforded 450 mg of the title compound. $^1$H NMR (400 Mhz, $CDCl_3$): δ 2.54 (s, 3H), 7.18 (d, 1H), 8.15 (dd, 1H), 8.38 (dd 1H)

Step C: 2-bromo-4-amino-methylthioanisole

To a solution of 2-bromo-4-nitro-methylthioanisole (450 mg, 1.81 mmol) in 45 mL of MeOH was added a suspension of copper(11) acetate (85 mg, 0.47 mmol) in 9 mL of MeOH. Sodium borohydride (300 mg, 7.9 mmol) was added as a solid over 0.5 h. The reaction was diluted with $Et_2O$, washed with $NaHCO_3$, dried with $Na_2SO_4$, filtered, and conc. to give 387 mg of the title compound. MS:m/e=218 (M+1) $^1$H NMR (400 Mhz, $CDCl_3$): δ 2.35 (s, 3H), 6.62 (dd, 1H), 6.94 (d, 1H), 7.08 (d, 1H)

Step D: 2-bromo-4-(5-(trifluoromethyl)tetrazol-1-yl) methylthioanisole

The title compound was prepared according to the procedure of Example 6, Step F, b,c replacing 2-bromo-4-aminoanisole with 2-bromo-4-amino-methylthioanisole. Purification by flash chromatograpy on silica gel eluding with 5% EtOAc/hexanes afforded 129 mg of the title compound. $^1$H NMR (400 Mhz, $CDCl_3$): δ 2.55 (s, 3H), 7.25 (d, 1H), 7.42 (dd, 1H), 7.67 (dd, 1H)

Step E: (3S,5R,6S,7S)-6-(4-fluorophenyl)-3-(2-methylthio-5-(5-(trifluoromethyl)tetrazol-1-yl)phenyl)-1-oxaspiro[4.4]non-3-ene-7-methanol To a solution of (5RS,6SR,7SR)-6-(4-fluorophenyl)-3-(2-trimethylstannyl)-1-oxaspiro[4.4]non-3-ene-7-methanol (257 mg, 0.625 mmol) in 8 mL of toluene was added 2-bromo-4-(5-trifluoromethyl)tetrazol-1-yl) methylthioanisole (212 mg, 0.625 mmol) prepared as described in step D, and bis-triphenylphosphine dichloride (13 mg, 0.019 mmol) and the mixture was heated at 100° C. for 18 h. The reaction mixture was conc. to give 461 mg of crude product. Purification by flash chromatograpy on silica gel eluding with 10% acetone/hexanes afforded 199 mg of the title compound. MS:m/e=507 (M+1) $^1$H NMR (400 MHz, $CD_3OD$): δ 2.50 (s, 3H), 3.55 (dd, 2H), 4.05 (dd, 2H), 4.65 (dd, 2H), 6.95 (t, 2H), 7.09 (s, 1H), 7.35 (t, 2H), 7.45 (s, 2H)

EXAMPLE 157

(3S,5S,6S,7S)-6-(4-fluorophenyl)-3-(2-methylthio-5-(5--(trifluoromethyl)tetrazol-1-yl)phenyl)-1-oxaspiro[4.4]nonane-7-methanol To a solution of (3S,5R,6S,7S)-6-(4-fluorophenyl)-3-(2-methylthio-5-(5-(trifluoromethyl)tetrazol-1-yl)phenyl)-1-oxaspiro[4.4]non-3-ene-7-methanol (183 mg, 0.361 mmol; from Example 156, step E) in 6 mL of MeOH was added 90 mg of platinum oxide and the mixture hydrogenated at 40 psi for 6 h. The reaction was filtered free of catalyst and conc. to give 176 mg of crude solid. Purification by flash chromatography on silica gel eluting with 10% acetone/hexanes gave 122 mg (66%) of the title compound. MS: m/e=509 (M+1) $^1$H NMR (400 MHz, $CD_3OD$): δ 2.53 (s, 3H), 3.47 (dd, 2H), 3.85 (q, 2H), 4.10 (t, 2H), 6.63 (d, 1H), 6.80 (t, 2H), 7.35 (m, 4H)

EXAMPLE 158

(3S,5R,6S,7S)-7-(1-(Pyrrolidinyl)methyl)-6-(4-fluorophenyl)-3-(2-methylthio-5-(5-(trifluoromethyl) tetrazol-1-yl)phenyl)-1-oxaspiro[4.4]nonane hydrochloride To a solution of (3S,5R,6S,7S)-6-(4-fluorophenyl)-3-(2-methylthio-5-(5-(trifluoromethyl)tetrazol-1-yl)phenyl)-1-oxaspiro[4.4]nonane-7-iodomethane (30 mg, 0.049 mmol) in 1.5 mL of MeCN was added DIPEA (34 uL, 0.196 mmol) and pyrrolidine (13 uL, 0.147 mmol) and the mixture heated for 1 h at 80° C. The reaction mixture was diluted with EtOAc, washed with $H_2O$, brine, dried, and conc. to give 27 mg of crude solid. Purification by flash chromatography on silica gel eluting with 5% MeOH/$CH_2Cl_2$ gave 22 mg of solid which was treated with 1.0M HCl/$Et_2O$ to give 24 mg of the title compound as the hydrochloride salt. MS:m/e= 562(M+1) $^1$H NMR (400 MHz, $CD_3OD$): δ 2.53 (s, 3H), 3.15 (t, 1H), 3.85 (q, 1H), 4.10 (t, 1H), 6.62 (d, 1H), 6.82 (t, 2H), 7.35 (m, 4H)

EXAMPLE 159

(3S,5R,6S,7S)-6-(4-fluorophenyl)-3-(2-methylthio-5-(5-(trifluoromethyl)imidazol-1-yl)phenyl)-1-oxaspiro[4.4]non-3-ene-7-methanol To a solution of (5RS,6SR,7SR)-6-(4-fluorophenyl)-3-(2-trimethylstannyl)-1-oxaspiro[4.4]non-3-ene-7-methanol (244 mg, 0.593 mmol) in 8 mL of toluene was added 2-bromo-4-(5-trifluoromethyl) imidazol-1-yl)

methylthioanisole (200 mg, 0.593 mmol), (prepared as described in Example 69, Step A, replacing N-(3-bromo-4-methoxyphenyl)-2,2,2-trifluoroacetamide with N-(3-bromo-4-methylthiophenyl)-2,2,2-trifluoroacetamide), tetrakis (triphenylphosphine)palladium(0) 20 mg, and the mixture was heated at 100° C. for 10 h. The reaction mixture was conc. to dryness to give 432 mg of crude product. Purification by flash chromatography on silica gel eluting with 10% acetone/hexanes gave 192 mg of the title compound. MS:m/e=505(M+1) $^1$H NMR (400 MHz, CD$_3$OD): δ 2.45 (s, 3H), 2.70 (m, 1H), 2.84 (d, 1H), 3.55 (dd, 1H), 4.00 (dd, 1H), 4.65 (dd, 1H), 6.15 (t, 1H), 6.85 (d, 1H), 6.95 (t, 2H), 7.35 (m, 4H)

EXAMPLE 160

(3S,5R,6S,7S)-6-(4-fluorophenyl)-3-(2-methylthio-5-(5-(trifluoromethyl)imidazol-1-yl)phenyl)-1-oxaspiro[4.4]nonane-7-methanol The title compound was prepared according to the procedure of Example 157 replacing (3S,5R,6S,7S)-6-(4-fluorophenyl)-3 -(2-methylthio-5-(5-(trifluoromethyl) tetrazol-1-yl)phenyl)-1-oxaspiro[4.4]non-3-ene-7-methanol with (3S,5R,6S,7S)-6-(4-fluorophenyl)-3-(2-methylthio-5-(5-(trifluoromethyl)imidazol-1-yl)phenyl)-1-oxaspiro[4.4]non-3-ene-7-methanol. MS:m/e=507(M+1) $^1$H NMR (400 MHz, CD$_3$OD): δ 2.50 (s, 3H), 2.20 (d, 1H), 3.10 (t, 1H), 3.49 (dd, 1H), 4.05 (t, 1H), 6.45 (s, 1H), 6.81 (t, 2H), 7.32 (m, 6H)

EXAMPLE 161

(3S,5R,6S,7S)-7-(1-(morpholinyl)methyl)-6-(4-fluorophenyl)-3-(2-methylthio-5-(5-(trifluoromethyl) imidazol-1-yl)phenyl)-1-oxaspiro[4.4]nonane hydrochloride The title compound was prepared according to the procedure of Example 158 replacing (3S,5R,6S,7S)-6-(4-fluorophenyl)-3-(2-methylthio-5-(5-(trifluoromethyl) tetrazol-1-yl)phenyl)-1-oxaspiro[4.4]nonane-7-iodomethane with (3S,5R,6S,7S)-6-(4-fluorophenyl)-3-(2-methylthio-5-(5-(trifluoromethyl)imidazol-1-yl)phenyl)-1-oxaspiro[4.4]nonane-7-iodomethane and replacing pyrrolidine with morpholine. MS:m/e=576(M+1) $^1$H NMR (400 MHz, CD$_3$OD): δ 2.61 (d, 1H), 3.12 (t, 1H), 3.84 (q, 1H), 4.05 (t, 1H), 6.47 (s, 1H), 6.83 (t, 2H), 7.17 (dd, 1H), 7.26 (d, 1H), 7.33 (m, 4H)

EXAMPLE 162

(3S,5R,6S,7S)-7-(morpholinyl)methyl)-6-(4-fluorophenyl)-3-(2-methylthio-5-(5-(trifluoromethyl) imidazol-1-yl)phenyl)-1-oxaspiro[4.4]nonane hydrochloride The title compound was prepared according to the procedure of Example 158 replacing pyrrolidine with morpholine. MS:m/e=578(M+1) $^1$H NMR (400 MHz, CD$_3$OD): δ 2.52 (s, 3H), 2.63 (d, 1H), 3.16 (t, 1H), 3.83 (q, 1H), 4.08 (t, 1H), 6.63 (s, 1H), 6.81 (t, 2H), 7.33 (m, 4H)

EXAMPLE 163

(3R,5R,6S,7S)-6-(4-fluorophenyl)-3-(2-methylthio-5-(5-(trifluoromethyl)tetrazol-1-yl)phenyl)-1-oxaspiro[4.4]nonane-7-carboxylic acid methyl ester (Compound A)

(3S,5R,6S,7S)-6-(4-fluorophenyl)-3-(2-methylthio-5-(5-(trifluoromethyl)tetrazol-1-yl)phenyl)-1-oxaspiro[4.4]nonane-7-carboxylic acid methyl ester (Compound B)

To a solution of (5R,6S,7S)-6-(4-fluorophenyl)-3-(2-methylthio-5-(5-(trifluoromethyl)tetrazol-1-yl)phenyl)-1-oxaspiro[4.4]non-3-ene-7-carboxylic acid methyl ester (50 mg, 0.094 mmol) in 1.5 mL of MeOH was added p-TsOH (5 mg, 0.026 mmol) and 10% Pd/C (5 mg, 0.26 mmol) and the mixture heated at 60° C. for 2.5 h. The mixture was filtered free of catalyst, and conc. to dryness. The solid was partitioned between CH$_2$Cl$_2$ and H$_2$O, the organic layer washed with H$_2$O, dried Na$_2$SO$_4$, and conc. to give 47 mg of solid. Purification by flash chromatography on silica gel eluting with 10% EtOAc/hexanes gave 24 mg of a faster moving product and 13 mg of a slower moving product. The faster moving product (24 mg, 0.045 mmol) was treated with TFA (750 uL) and triethylsilane (22 uL, 0.135 mmol) at rt for 2 h and 60° C. for 5 min., conc. and coeevaporated with toluene to give 27 mg of solid. The slower moving product was treated the same as above to give 13 mg of solid. Both the higher and slower moving products were combined and purified by flash chromatography on silica gel eluting with 10% EtOAc/hexanes to give 2 mg of the faster moving product (Compound A) and 11 mg of the slower moving product (Compound B).

(Compound A): (3R-isomer) (MS:m/e=536(M+1) $^1$H NMR (400 MHz, CD$_3$OD): δ 2.45 (s, 3H), 2.97 (q, 1H), 3.16 (d, 1H), 3.52 (s, 3H), 3.64 (t, 1H), 3.74 (t, 1H), 7.07 (t, 2H), 7.44 (m, 5H)

(Compound B): (3S-isomer) (MS:m/e=536(M+1) $^1$H NMR (400 MHz, CD$_3$OD): δ 2.53 (s, 3H), 2.21 (m, 2H), 3.52 (s, 3H), 3.85 (q, 1H), 4.10 (t, 1H), 6.63 (d, 1H), 6.80 (t, 2H), 7.34 (m, 4H)

EXAMPLE 164

(3S,5R,6S,7S)-6-(4-fluorophenyl)-3-(2-methylthio-5-(5-(trifluoromethyl)tetrazol-1-yl)phenyl)-1-oxaspiro[4.4]non-3-ene-7-carboxylic acid methyl ester The title compound was prepared according to the procedure of Example 156, step E, replacing (5RS,6SR,7SR)-6-(4-fluorophenyl)-3-(2-trimethylstannyl)-1-oxaspiro[4.4]non-3-ene-7-methanol with (5RS,6SR,7SR)-6-(4-fluorophenyl)-3-(2-trimethystannyl)-1-oxaspiro[4.4]non-3-ene-7-carboxylic acid methyl ester. MS:m/e=535(M+1) $^1$H NMR (400 MHz, CD$_3$OD): δ 2.50 (s, 3H), 3.56 (s, 3H), 4.07 (dd, 1H), 4.69 (dd, 1H), 6.25 (t, 1H), 6.94 (t, 2H), 7.09 (s, 1H), 7.36 (m, 2H), 7.47 (s, 2H)

EXAMPLE 165

(3S,5R,6S,7S)-6-(4-fluorophenyl)-3-(2-methylthio-5-(5-(trifluoromethyl)tetrazol-1-yl)phenyl)-1-oxaspiro[4.4]non-3-ene-7-carboxylic acid methyl ester Step A: 2-bromo-4-nitro-isopropylthioanisole The title compound was prepared as described in Example 156, Step B, replacing methyl iodide with isopropyl iodide. $^1$H NMR (400 Mhz, CDCl$_3$): δ 1.44 (d, 6H), 3.58 (m, 1H), 7.27 (d, 1H), 8.12 (dd, 1H), 8.39 (dd, 1H)

Step B: 2-bromo-4-amino-isopropylthioanisole

The title compound was prepared as described in Example 156, Step C, replacing 2-bromo-4-nitro-methylthioanisole with 2-bromo-4-nitro-isopropylthioanisole. $^1$H NMR (400 Mhz, CD$_3$OD): δ 1.19 (d, 6H), 3.23 (m, 1H), 6.57 (m, 1H), 6.95 (d 1H), 7.25 (d, 1H)

Step C: 2-bromo-4-(5-(trifluoromethyl)tetrazol-1-yl) isopropyl thioanisole

The title compound was prepared as described in Example 6, Step F, b,c, replacing 2-bromo-4-aminoanisole with 2-bromo-4-amino-isopropylthioanisole. Purification by flash chromatograpy on silica gel eluding with 5% EtOAc/hexanes afforded 120 mg of the title compound. ¹H NMR (400 Mhz, CDCl₃): δ 1.43 (d, 6H), 3.57 (m, 1H), 7.40 (d, 2H), 7.70 (d, 1H)

Step D: (3S,5R,6S,7S)-6-(4-fluorophenyl)-3-(2-isopropylthio-5-(5-(trifluoromethyl)tetrazol-1-yl)phenyl)-1-oxaspiro[4.4]non-3-ene-7-carboxylic acid methyl ester The title compound was prepared according to the procedure of Example 164 replacing 2-bromo-4-(5-trifluoromethyl)tetrazol-1-yl)methylthioanisole with 2-bromo-4-(5-trifluoromethyl)tetrazol-1-yl) isopropylthioanisole prepared as described in step C. MS:m/e=563(M+1) ¹H NMR (400 MHz, CD₃OD): δ 1.25 (t, 6H), 3.55 (s, 3H), 4.23 (m, 1H), 4.69 (m, 1H), 6.15 (m, 1H), 6.97 (t, 2H), 7.21 (d, 1H), 7.36 (m, 2H), 7.45 (dd, 1H), 7.58 (d, 1H)

EXAMPLE 166

(3S,5R,6S,7S)-6-(4-fluorophenyl)-3-(2-methylthio-5-(5-(trifluoromethyl)tetrazol-1-yl)phenyl)-1-oxaspiro[4.4]non-4-ene-7-carboxylic acid methyl ester To a solution of (3S,5R,6S,7S)-6-(4-fluorophenyl)-3-(2-methylthio-5-(5-(trifluoromethyl)tetrazol-1-yl)phenyl)-1-oxaspiro[4.4]non-3-ene-7-carboxylic acid methyl ester in 2 mL of MeOH was added 0.4 mL of AcOH, 26 mg of 20% Pd(OH)₂/C and the mixture hydrogenated at 40 psi for 24 h. The catalyst was removed by filtration and conc. to give 23 mg. of solid. Purification by flash chromatography on silica gel eluting with 15% EtOAc/hexanes gave 4.6 mg of the title compound. MS:m/e=535(M+1) ¹H NMR (400 MHz, CD₃OD): δ 2.45 (s, 3H), 2.93 (dd, 1H), 3.08 (dd, 1H), 3.23 (d, 1H), 6.77 (s, 1H), 6.95 (t, 2H), 7.02 (d, 1H), 7.36 (m, 3H)

EXAMPLE 167

(3S,5R,6S,7S)-6-(4-fluorophenyl)-3-(2-methylthio-5-(5-(trifluoromethyl)imidazol-1-yl)phenyl)-1-oxaspiro[4.4]non-3-ene-7-carboxylic acid methyl ester The title compound was prepared according to the procedure of Example 164 replacing 2-bromo-4-(5-trifluoromethyl)tetrazol-1-yl)methylthioanisole with 2-bromo-4-(5-trifluoromethyl)imidazol-1-yl) methylthioanisole, (prepared as described in Example 69, Step A, replacing N-(3-bromo-4-methoxyphenyl)-2,2,2-trifluoroacetamide with N-(3-bromo-4-methylthiophenyl)-2,2,2-trifluoroacetamide). MS:m/e=533(M+1) ¹H NMR (400 MHz, CD₃OD): δ 2.45 (s, 3H), 3.57 (s, 3H), 4.05 (m, 1H), 4.69 (m, 1H), 6.20 (t, 1H), 6.87 (d, 1H), 6.94 (t, 2H), 7.22 (s, 1H), 7.34 (m, 2H), 7.42 (s, 1H).

EXAMPLE 168

(3S,5R,6S,7S)-6-(4-fluorophenyl)-3-(2-isopropylthio-5-(5-(trifluoromethyl)imidazol-1-yl)phenyl)-1-oxaspiro[4.4]non-3-ene-7-carboxylic acid methyl ester The title compound was prepared according to the procedure of Example 165, step D replacing 2-bromo-4-(5-trifluoromethyl)tetrazol-1-yl)isopropylthioanisole with 2-bromo-4-(5-trifluoromethyl)imidazol-1-yl) isopropylthioanisole, (prepared as described in Example 69, Step A, replacing N-(3-bromo-4-methoxyphenyl)-2,2,2-trifluoroacetamide with N-(3-bromo-4-isopropylthiophenyl) -2,2,2-trifluoroacetamide). MS:m/e=561(M+1) ¹H NMR (400 MHz, CD₃OD): δ 1.22 (t, 6H), 3.55 (s, 3H), 4.23 (dd, 1H), 4.71 (dd, 1H), 6.12 (d, 1H), 6.95 (t, 2H), 7.03 (d, 1H), 7.30 (dd, 1H), 7.37 (s, 1H), 7.51 (d, 1H)

EXAMPLE 169

(3S,5R,6S,7S)-6-(4-fluorophenyl)-3-(2-isopropylthio-5-(5-(trifluoromethyl)tetrazol-1-yl) phenyl)-1-oxaspiro[4.4]nonane-7-carboxylic acid methyl ester The title compound was prepared according to the procedure of Example 166 and was hydrogenated for 72 h instead of 24 h. MS:m/e=591(M+1) ¹H NMR (400 MHz, CD₃OD): δ 3.14 (t, 1H), 3.23 (d, 1H), 3.54 (s, 3H), 4.10 (t, 1H), 6.96 (m, 3H), 7.18 (d, 1H), 7.37 (m, 4H)

EXAMPLE 170

(3S,5R,6S,7S)-6-(4-fluorophenyl)-3-(2-methylthio-5-(5-(trifluoromethyl)imidazol-1-yl)phenyl)-1-oxaspiro[4.4]nonane-7-carboxylic acid methyl ester The title compound was prepared according to the procedure of Example 157 replacing (3S,5R,6S,7S)-6-(4-fluorophenyl)-3-(2-methylthio-5-(5-(trifluoromethyl) tetrazol-1-yl)phenyl)-1-oxaspiro[4.4]non-3-ene-7-methanol with (3S,5R,6S,7S)-6-(4-fluorophenyl)-3-(2-methylthio-5-(5-(trifluoromethyl)imidazol-1-yl)phenyl)-1-oxaspiro[4.4] non-3-ene-7-carboxylic acid methyl ester. MS:m/e=535(M+1) ¹H NMR (400 MHz, CD₃OD): δ 2.48 (s, 3H), 3.14 (t, 1H), 3.21 (d, 1H), 3.53 (s, 3H), 3.87 (q, 1H), 4.08 (t, 1H), 6.44 (d, 1H), 6.83 (t, 2H), 7.17 (dd, 1H), 7.27 (d, 1H), 7.33 (m, 3H)

EXAMPLE 171

(3S,5R,6S,7S)-6-(4-fluorophenyl)-3-(2-isopropylthio-5-(5-(trifluoromethyl)imidazol-1-yl) phenyl)-1-oxaspiro[4.4]nonane-7-carboxylic acid methyl ester The title compound was prepared according to the procedure of Example 157 replacing (3S,5R,6S,7S)-6-(4-fluorophenyl)-3-(2-methylthio-5-(5-(trifluoromethyl) tetrazol-1-yl)phenyl)-1 -oxaspiro[4.4]non-3-ene-7-methanol with (3S,5R,6S,7S)-6-(4-fluorophenyl)-3-(2-isopropylthio-5-(5-(trifluoromethyl)imidazol-1-yl)phenyl)-1-oxaspiro [4.4]non-3-ene-7-carboxylic acid methyl ester. MS:m/e=563 (M+1) ¹H NMR (400 MHz, CD₃OD): δ 1.28 (t, 6H), 3.12 (t, 1H), 3.20 (d, 1H), 3.52 (s, 3H), 4.05 (t, 1H), 4.12 (q, 1H), 6.46 (d, 1H), 6.82 (t, 2H), 7.14(dd, 1H), 7.32 (m, 3H), 7.51 (d, 1H)

EXAMPLE 172

(3S,5R,6S,7S)-6-(4-fluorophenyl)-3-(2-isopropylthio-5-(5-(trifluoromethyl)imidazol-1-yl) phenyl)-1-oxaspiro[4.4]nonane-7-carboxylic acid methyl ester The title compound was prepared according to the procedure of Example 157 replacing (3S,5R,6S,7S)-6-(4-fluorophenyl)-3-(2-methylthio-5-(5-(trifluoromethyl) tetrazol-1-yl)phenyl)-1-oxaspiro[4.4]non-3-ene-7-methanol with (3S,5R,6S,7S)-6-(4-fluorophenyl)-3-(2-isopropylthio-5-(5-(trifluoromethyl)tetrazol-1-yl)phenyl)-1-oxaspiro[4.4] non-3-ene-7-carboxylic acid methyl ester. MS:m/e=565(M+1) ¹H NMR (400 MHz, CD₃OD): δ 1.33 (t, 6H), 3.18 (t, 1H), 3.23 (d, 1H), 3.53 (s, 3H), 4.07 (m, 2H), 6.64 (d, 1H), 6.80 (t, 2H), 7.33 (m, 3H), 7.58 (d, 1H)

Examples 173 through 200 were prepared from methyl [5-(RS), 6-(SR), 7-(SR)]-6-(4-fluorophenyl)-3-(trimethylstannyl)-1-oxaspiro-[4,4]non-3-ene-7-carboxylate by the general procedure given in Example 6, Step F(d), using aryl bromides that are either commercially available or were prepared by literature procedures.

EXAMPLE 173

Methyl[3-(S),5-(R),6-(S),7-(S)]-6-(4-fluorophenyl)-3-(2-methoxy-5-((5-trifluoromethyl)tetrazol-1-yl) phenyl)-1-oxaspiro[4.4]nonane-7-ylmethyl) methylamine $^1$H-NMR (500 MHz, CDCl$_3$) δ 1.60–2.40 (m, 8H), 2.62 (s, 3H), 2.83–3.07 (m, 6H), 3.74–3.84 (m, 4H), 3.83 (s, 3H), 4.08 (t, 1H), 6.72 (d, 1H, J=2.3 Hz), 6.91–6.95 (m, 3H), 7.23–7.34 (m, 3H). Mass Spectrum (NH$_3$—CI): m/z 506 (M+1).

EXAMPLE 174

(5R,6S,7S)-6-(4-Fluorophenyl)-3-(2-methoxy-5-(2-(trifluoromethyl)triazol-1-yl)phenyl)-1-oxaspiro[4.4] non-3-ene-7-carboxylic acid methyl ester $^1$H-NMR (500 MHz, CDCl$_3$) δ 1.97–2.41 (m, 4H), 3.32 (d, 1H, J=11.5 Hz), 3.44–3.50 (m, 1H), 3.59 (s, 3H), 3.81 (d, 1H, J=10.5 Hz), 3.93 (s, 3H), 4.06 (dd, 1H, J=2.1 & 11.7 Hz), 4.71 (dd, 1H, J=1.8 & 11.6 Hz), 6.39 (t, 1H, J=1.9 Hz), 6.84 (d, 1H, J=2.7 Hz), 6.88–6.92 (m, 2H), 6.98 (d, 1H, J=8.7), 7.26–7.28 (m, 2H), 8.27 (s, 1H). Mass Spectrum (NH$_3$—CI): m/z 518 (M+1).

EXAMPLE 175

(5R,6S,7S)-6-(4-Fluorophenyl)-3-(2-methoxy-5-(2-(trifluoromethyl)triazol-1-yl)phenyl)-1-oxaspiro[4.4] nonane-7-hydroxymethyl $^1$H-NMR (500 MHz, CDCl$_3$) δ 1.56–1.65 (m, 2H), 1.80–1.92 (m, 2H), 2.13–2.21 (m, 3H), 2.62–2.71 (m, 2H), 3.05 (t, 1H, J=8.7 Hz), 3.48–3.76 (m, 3H), 3.81 (s, 3H), 4.11 (t, 1H, J=7.8 Hz), 6.64–7.34 (m, 7H), 8.20 (s, 1H). Mass Spectrum (NH$_3$—CI): m/z 492 (M+1).

EXAMPLE 176

(5R,6S,7S)-6-(4-Fluorophenyl)-3-(2-methoxy-5-(triazol-1-yl)phenyl)-1-oxaspiro[4.4]nonane-7-hydroxymethyl $^1$H-NMR (500 MHz, CDCl$_3$) δ 1.62–2.87 (m, 8H), 3.13 (t, 1H, J=8.5 Hz), 3.46–3.76 (m, 3H), 3.78 (s, 3H), 3.89 (d, 1H, J=4.8 Hz), 4.10 (t, 1H, J=7.8 Hz), 6.68–7.35 (m, 7H), 8.26 (s, 1H). Mass Spectrum (NH$_3$—CI): m/z 424 (M+1).

EXAMPLE 177

(5R,6S,7S)-6-(4-Fluorophenyl)-3-(2-(N,N-dimethylamino)-5-(2-(trifluoromethyl)tetrazol-1-yl) phenyl)-1-oxaspiro[4.4]non-3-ene-7-carboxylic acid methyl ester $^1$H-NMR (500 MHz, CDCl$_3$) δ 1.99–2.43 (m, 3H), 2.46 (s, 6H), 2.93 (d, 1H, J=10.7 Hz),3.34 (d, 1H, J=11.7 Hz), 3.44–3.48 (m, 1H), 3.51 (s, 3H), 4.42 (dd, 1H, J=2.1 & 12.6 Hz), 4.62 (dd, 1H, J=2.1 & 12.6 Hz), 6.03 (t, 1H, J=2.0 Hz), 6.68–7.34 (m, 7H). Mass Spectrum (NH$_3$—CI): m/z 532 (M+1).

EXAMPLE 178

(5R,6S,7S)-6-(4-Fluorophenyl)-3-(2-isopropoxy-5-(2-(trifluoromethyl)tetrazol-1-yl)phenyl)-1-oxaspiro [4.4]non-3-ene-7-carboxylic acid methyl ester $^1$H-NMR (500 MHz, CDCl$_3$) δ 1.38–1.41 (m, 6H), 1.54–1.58 (m, 1H), 1.98–2.42 (m, 4H), 3.32 (d, 1H, J=11.7 Hz), 3.45–3.51 (m, 1H), 3.61 (s, 3H), 4.13 (dd, 1H, J=2.3 & 11.9 Hz), 4.64–4.69 (m, 1H), 4.74 (dd, 1H, J=1.8 & 11.9 Hz), 6.32–7.30 (m, 7H). Mass Spectrum (NH$_3$—CI): m/z 547 (M+1).

EXAMPLE 179

(5R,6S,7S)-6-(4-Fluorophenyl)-3-(2-isopropoxy-5-(2-(trifluoromethyl)imidazol-1-yl)phenyl)-1-oxaspiro[4.4]non-3-ene-7-carboxylic acid methyl ester $^1$H-NMR (500 MHz, CDCl$_3$) δ 1.35–1.39 (m, 6H), 1.97–2.39 (m, 4H), 3.31 (d, 1H, J=11.7 Hz), 3.45–3.51 (m, 1H), 3.56–3.60 (m, 4H), 3.60 (s, 3H), 4.11 (dd, 1H, J=1.6 & 11.9 Hz), 4.59–4.64 (m, 1H), 4.74 (dd, 1H, J=1.1 & 11.9 Hz), 6.29 (br s, 1H), 6.89–7.30 (m, 8H). Mass Spectrum (NH$_3$—CI): m/z 545 (M+1).

EXAMPLE 180

(5R,6S,7S)-6-(4-Fluorophenyl)-3-(2-methoxy-5-(2-(methyl)triazol-1-yl)phenyl)-1-oxaspiro[4.4]non-3-ene-7-carboxylic acid methyl ester $^1$H-NMR (500 MHz, CDCl$_3$) δ 1.97–2.30 (m, 3H), 2.30–2.39 (m, 5H), 2.34 (s, 3H), 3.33 (d, 1H, J=11.6 Hz), 3.44–3.49 (m, 1H), 3.59 (s, 3H), 3.91 (s, 3H), 4.09 (dd, 1H, J=2.1 & 11.9 Hz), 4.73 (dd, 1H, J=1.9 & 11.7 Hz), 6.38 (br s, 1H), 6.75–7.30 (m, 6H), 8.12 (s, 1H).

EXAMPLE 181

(5R,6S,7S)-6-(4-Fluorophenyl)-3-(2-(N,N-dimethylamino)-5-(2-(trifluoromethyl)tetrazol-1-yl) phenyl)-1-oxaspiro[4.4]nonane-7-carboxylic acid methyl ester $^1$H-NMR (500 MHz, CDCl$_3$) δ 1.81–2.02 (m, 3H), 2.21–2.42 (m, 3H), 2.73 (s, 6H), 3.17 (t, 1H, J=8.2 Hz), 3.22 (d, 1H, J=11.4 Hz), 3.34–3.40 (m, 1H), 3.57 (s, 3H), 3.92–3.99 (m, 1H), 4.11 (t, 1H, J=8.2 Hz), 6.43–7.32 (m, 7H). Mass Spectrum (NH$_3$—CI): m/z 534 (M+1).

EXAMPLE 182

(5R,6S,7S)-6-(4-Fluorophenyl)-3-(2-isopropoxy-5-(2-(trifluoromethyl)tetrazol-1-yl)phenyl)-1-oxaspiro [4.4]nonane-7-carboxylic acid methyl ester $^1$H-NMR (500 MHz, CDCl$_3$) δ 1.27–1.42 (m, 6H), 1.86–2.00 (m, 3H), 2.21–2.34 (m, 3H), 3.08 (t, 1H, J=8.4 Hz), 3.22 (d, 1H, J=11.2 Hz), 3.31–3.37 (m, 1H), 3.57 (s, 3H), 3.74–3.78 (m, 1H), 4.17 (t, 1H, J=8.0 Hz), 4.59–4.64 (m, 1H), 6.72–7.32 (m, 7H). Mass Spectrum (NH$_3$—CI): m/z 549 (M+1).

EXAMPLE 183

(5R,6S,7S)-6-(4-Fluorophenyl)-3-(2-isopropoxy-5-(2-(trifluoromethyl)imidazol-1-yl)phenyl)-1-oxaspiro[4.4]nonane-7-carboxylic acid methyl ester $^1$H-NMR (500 MHz, CDCl$_3$) δ 1.32 (d, 3H, J=6.1 Hz), 1.35 (d, 3H, J=6.1 Hz), 1.86–2.34 (m, 6H), 3.02 (t, 1H, J=8.6

Hz), 3.22 (d, 1H, J=11.2 Hz), 3.32–3.35 (m, 1H), 3.58 (s, 3H), 3.72–3.76 (m, 1H), 4.15 (t, 1H, J=7.7 Hz), 4.53–4.58 (m, 1H), 6.64–7.34 (m, 9H). Mass Spectrum (NH₃—CI): m/z 547 (M+1).

EXAMPLE 184

(5R,6S,7S)-6-(4-Fluorophenyl)-3-(2-methoxy-5-(2-(methyl)triazol-1-yl)phenyl)-1-oxaspiro[4.4]nonane-7-carboxylic acid methyl ester ¹H-NMR (400 MHz, CDCl₃) δ 1.86–2.36 (m, 9H), 2.24 (s, 3H), 3.01–3.39 (m, 3H), 3.54 (s, 3H), 3.64–3.78 (m, 4H), 3.75 (s, 3H), 4.07 (t, 1H, J=7.9 Hz), 6.57–7.32 (m, 7H), 8.03 (s, 1H). Mass Spectrum (NH₃—CI): m/z 466 (M+1).

EXAMPLE 185

(5R,6S,7S)-6-(4-Fluorophenyl)-3-(2-methoxycarbonyl-5-(triazol-1-yl)phenyl)-1-oxaspiro[4.4]non-3-ene-7-carboxylic acid methyl ester ¹H-NMR (500 MHz, CDCl₃) δ 1.98–2.43 (m, 4H), 3.34 (d, 1H, J=11.7 Hz), 3.46–3.51 (m, 1H), 3.61 (s, 3H), 3.82 (s, 3H), 4.02 (dd, 1H, J=1.3 & 12.2 Hz), 4.71 (dd, 1H, J=1.2 & 11.9 Hz), 5.72 (s, 1H), 6.84–8.56 (m, 9H). Mass Spectrum (NH₃—CI): m/z 478 (M+1).

EXAMPLE 186

(5R,6S,7S)-6-(4-Fluorophenyl)-3-(2-methoxycarbonyl-5-(2-(trifluoromethyl)tetrazol-1-yl)phenyl)-1-oxaspiro[4.4]non-3-ene-7-carboxylic acid methyl ester ¹H-NMR (500 MHz, CDCl₃) δ 1.98–2.41 (m, 4H), 3.33 (d, 1H, J=11.4 Hz), 3.44–3.50 (m, 1H), 3.60 (s, 3H), 3.84 (s, 3H), 4.03 (dd, 1H, J=1.3 & 11.9 Hz), 4.70 (dd, 1H, J=1.0 & 11.9 Hz), 5.79 (s, 1H), 6.94–7.96 (m, 7H). Mass Spectrum (NH₃—CI): m/z 547 (M+1).

EXAMPLE 187

(5R,6S,7S)-6-(4-Fluorophenyl)-3-(2-cyclopentoxy-5-(2-(trifluoromethyl)tetrazol-1-yl)phenyl)-1-oxaspiro[4.4]non-3-ene-7-carboxylic acid methyl ester ¹H-NMR (500 MHz, CDCl₃) δ 1.57–2.42 (m, 13H), 3.32 (d, 1H, J=11.7 Hz), 3.44–3.50 (m, 1H), 3.60 (s, 3H), 4.15 (dd, 1H, J=2.3 & 11.9 Hz), 4.75 (dd, 1H, J=1.9 & 11.9 Hz), 4.87–4.89 (m, 1H), 6.32 (t, 1H, J=2.1 Hz), 6.91 (t, 1H, J=8.7 Hz), 7.00 (d, 1H, J=8.9 Hz), 7.05 (d, 1H, J=2.8 Hz), 7.26–7.30 (m, 3H). Mass Spectrum (NH₃—CI): m/z 573 (M+1).

EXAMPLE 188

(5R,6S,7S)-6-(4-Fluorophenyl)-3-(2-cyclopentoxy-5-(2-(trifluoromethyl)imidazol-1-yl)phenyl)-1-oxaspiro[4.4]non-3-ene-7-carboxylic acid methyl ester ¹H-NMR (500 MHz, CDCl₃) δ 1.70–2.41 (m, 13H), 3.31 (d, 1H, J=11.7 Hz), 3.44–3.50 (m, 1H), 3.59 (s, 3H), 4.13 (dd, 1H, J=2.3 & 11.9 Hz), 4.75 (dd, 1H, J=1.8 & 11.9 Hz), 4.83–4.85 (m, 1H), 6.28 (t, 1H, J=2.1 Hz), 6.89–6.93 (m, 3H), 7.07 (d, 1H, J=0.9 Hz), 7.15 (dd, 1H, J=2.5 & 8.7 Hz), 7.19 (d, 1H, J=0.9 Hz), 7.26–7.30 (m, 2H). Mass Spectrum (NH₃—CI): m/z 571 (M+1).

EXAMPLE 189

(5R,6S,7S)-6-(4-Fluorophenyl)-3-(2-methoxycarbonyl-5-(triazol-1-yl)phenyl)-1-oxaspiro[4.4]nonane-7-carboxylic acid methyl ester ¹H-NMR (500 MHz, CDCl₃) δ 1.84–2.50 (m, 6H), 3.23 (d, 1H, J=11.4 Hz), 3.35–3.44 (m, 2H), 3.56 (s, 3H), 3.92 (s, 3H), 4.06–4.29 (m, 2H), 6.67 (d, 1H, J=1.8 Hz), 6.86 (t, 2H, J=8.5 Hz), ), 7.17 (dd, 1H, J=1.1 & 8.2 Hz), 7.27–7.30 (m, 2H), 7.88 (d, 1H, J=8.5 Hz), 8.31 (s, 1H), 8.58 (s, 1H). Mass Spectrum (NH₃—CI): m/z 480 (M+1).

EXAMPLE 190

(5R,6S,7S)-6-(4-Fluorophenyl)-3-(2-methoxycarbonyl-5-(2-(trifluoromethyl)tetrazol-1-yl)phenyl)-1-oxaspiro[4.4]nonane-7-carboxylic acid methyl ester ¹H-NMR (500 MHz, CDCl₃) δ 1.81–2.49 (m, 6H), 3.21 (d, 1H, J=11.4 Hz), 3.32–3.42 (m, 2H), 3.55 (s, 3H), 3.95 (s, 3H), 4.09–4.14 (m, 1H), 4.21–4.25 (m, 1H), 6.72–6.76 (m, 3H), 7.24–7.30 (m, 3H), 7.90 (d, 1H, J=8.2 Hz). Mass Spectrum (NH₃—CI): m/z 549 (M+1).

EXAMPLE 191

(5R,6S,7S)-6-(4-Fluorophenyl)-3-(2-cyclopentoxy-5-(2-(trifluoromethyl)tetrazol-1-yl)phenyl)-1-oxaspiro[4.4]nonane-7-carboxylic acid methyl ester ¹H-NMR (500 MHz, CDCl₃) δ 1.64–2.38 (m, 14H), 3.08 (t, 1H, J=8.4 Hz), 3.22 (d, 1H, J=11.2 Hz), 3.31–3.36 (m, 1H), 3.57 (s, 3H), 3.68–3.75 (m, 1H), 4.15 (t, 1H, J=7.8 Hz), 4.81 (t, 1H, J=5.7 Hz), 6.72 (d, 1H, J=2.5 Hz), 6.87–6.92 (m, 3H), 7.21 (dd, 1H, J=2.5 & 8.7 Hz), 7.29–7.32 (m, 2H). Mass Spectrum (NH₃—CI): m/z 575 (M+1).

EXAMPLE 192

(5R,6S,7S)-6-(4-Fluorophenyl)-3-(2-cyclopentoxy-5-(2-(trifluoromethyl)imidazol-1-yl)phenyl)-1-oxaspiro[4.4]nonane-7-carboxylic acid methyl ester ¹H-NMR (500 MHz, CDCl₃) δ 1.63–2.37 (m, 14H), 3.03 (t, 1H, J=8.5 Hz), 3.21 (d, 1H, J=11.2 Hz), 3.31–3.37 (m, 1H), 3.57 (s, 3H), 3.66–3.73 (m, 1H), 4.13 (t, 1H, J=7.8 Hz), 4.75–4.78 (m, 1H), 6.64 (d, 1H, J=2.5 Hz), 6.80 (d, 1H, J=8.7 Hz), 6.89–6.92 (m, 2H), 6.98 (d, 1H, J=0.9 Hz), 7.06 (dd, 1H, J=2.5 & 8.5 Hz), 7.20 (d, 1H, J=0.9 Hz), 7.30–7.33 (m, 2H). Mass Spectrum (NH₃—CI): m/z 573 (M+1).

EXAMPLE 193

(5R,6S,7S)-6-(4-Fluorophenyl)-3-(2-methoxy-5-(2-(trifluoromethyl)triazol-1-yl)phenyl)-1-oxaspiro[4.4]non-3-ene-7-hydroxymethyl ¹H-NMR (500 MHz, CDCl₃) δ 1.27 (br s, 1H), 1.65–1.71 (m, 2H), 2.06–2.23 (m, 3H), 2.77–2.83 (m, 2H), 3.51–3.72 (m, 2H), 3.92 (s, 3H), 4.04 (dd, 1H, J=2.0 & 11.9 Hz), 4.71 (dd, 1H, J=1.6 & 11.7 Hz), 6.36 (s, 1H), 6.83 (d, 1H, J=2.5 Hz), 6.92 (t, 1H, J=8.7 Hz), 6.97 (d, 1H, J=8.7 Hz), 7.19 (dd, 1H, J=2.5 & 8.7 Hz), 7.28–7.30 (m, 2H), 8.27 (s, 1H). Mass Spectrum (NH₃—CI): m/z 490 (M+1).

EXAMPLE 194

(5R,6S,7S)-6-(4-Fluorophenyl)-3-(2-methoxy-5-(2-(trifluoromethyl)triazol-1-yl)phenyl)-1-oxaspiro[4.4]nonane-7-ylmethyl)(1-fluoroethyl)amine ¹H-NMR (500 MHz, CDCl₃) δ 1.46–2.83 (m, 13H), 3.01 (t, 1H, J=8.7 Hz), 3.68–3.76 (m, 1H), 3.81 (s, 3H), 4.09 (t, 1H, J=7.7 Hz), 4.38 (t, 1H, J=4.8 Hz), 4.48 (t, 1H, J=4.6 Hz), 6.63 (d, 1H, J=2.3 Hz), 6.86 (d, 1H, J=8.7 Hz), 6.92 (t, 1H, J=8.5 Hz), 7.10 (dd, 1H, J=2.5 & 8.7 Hz), 7.29–7.32 (m, 2H), 8.20 (s, 1H). Mass Spectrum ($NH_3$—CI): m/z 537 (M+1).

EXAMPLE 195

(5R,6S,7S)-6-(4-Fluorophenyl)-3-(2-isopropoxy-5-(2-(trifluoromethyl)tetrazol-1-yl)phenyl)-1-oxaspiro[4.4]non-3-ene-7-hydroxymethyl $^1$H-NMR (500 MHz, $CDCl_3$) δ 1.36–1.40 (m, 6H), 1.54–1.72 (m, 2H), 2.06–2.23 (m, 3H), 2.78–2.82 (m, 2H), 3.52–3.55 (m, 1H), 3.67–3.69 (m, 1H), 4.12 (dd, 1H, J=2.1 & 11.9 Hz), 4.63–4.68 (m, 1H), 4.74 (dd, 1H, J=2.1 & 11.9 Hz), 6.29 (t, 1H, J=2.1 Hz), 6.91–6.95 (m, 2H), 6.98 (d, 1H, J=8.9 Hz), 7.07 (d, 1H, J=2.7 Hz), 7.28–7.30 (m, 2H). Mass Spectrum ($NH_3$—CI): m/z 519 (M+1).

EXAMPLE 196

(5R,6S,7S)-6-(4-Fluorophenyl)-3-(2-isopropoxy-5-(2-(trifluoromethyl)tetrazol-1-yl)phenyl)-1-oxaspiro[4.4]nonane-7-ylmethyl)(1-fluoroethyl)amine $^1$H-NMR (500 MHz, $CDCl_3$) δ 1.33 (d, 3H, J=6.1 Hz), 1.36 (d, 3H, J=6.1 Hz), 1.47–1.53 (m, 1H), 1.63 (br s, 1H), 1.84–1.90 (m, 2H), 2.17–2.21 (m, 3H), 2.48–2.85 (m, 6H), 3.01 (t, 1H, J=8.7 Hz), 3.71–3.78 (m, 1H), 4.15 (t, 1H, J=7.8 Hz), 4.38 (t, 1H, J=4.6 Hz), 4.47 (t, 1H, J=4.6 Hz), 4.58–4.63 (m, 1H), 6.73 (d, 1H, J=2.5 Hz), 6.86–6.91 (m, 3H), 7.19 (dd, 1H, J=2.5 & 8.7 Hz), 7.28–7.30 (m, 2H). Mass Spectrum ($NH_3$—CI): m/z 566 (M+1).

EXAMPLE 197

(5R,6S,7S)-6-(4-Fluorophenyl)-3-(2-methoxy-5-(2,5-(dimethyl)triazol-1-yl)phenyl)-1-oxaspiro[4.4]non-3-ene-7-carboxylic acid methyl ester $^1$H-NMR (500 MHz, $CDCl_3$) δ 1.98–2.39 (m, 11H), 2.20 (s, 3H), 2.26 (s, 3H), 3.32 (d, 1H, J=11.7 Hz), 3.43–3.49 (m, 1H), 3.59 (s, 3H), 3.91 (s, 3H), 4.05 (dd, 1H, J=2.1 & 11.7 Hz), 4.71 (dd, 1H, J=2.1 & 11.9 Hz), 6.36 (t, 1H, J=1.8 Hz), 6.66 (d, 1H, J=2.3 Hz), 6.88–6.91 (m, 2H), 7.03–7.05 (m, 1H), 7.26–7.29 (m, 2H). Mass Spectrum ($NH_3$—CI): m/z 478 (M+1).

EXAMPLE 198

(5R,6S,7S)-6-(4-Fluorophenyl)-3-(2-phenoxy-5-(2-(trifluoromethyl)tetrazol-1-yl)phenyl)-1-oxaspiro[4.4]non-3-ene-7-carboxylic acid methyl ester $^1$H-NMR (500 MHz, $CDCl_3$) δ 1.95–2.41 (m, 4H), 3.30 (d, 1H, J=11.5 Hz), 3.43–3.50 (m, 1H), 3.58 (s, 3H), 4.12 (dd, 1H, J=2.1 & 11.9 Hz), 4.80 (dd, 1H, J=2.0 & 12.1 Hz), 6.47 (t, 1H, J=1.9 Hz), 6.85–6.88 (m, 2H), 6.95 (d, 1H, J=8.9 Hz), 7.01 (d, 1H, J=7.6 Hz), 7.12 (d, 1H, J=2.5 Hz), 7.20–7.29 (m, 4H), 7.45–7.48 (m, 2H). Mass Spectrum ($NH_3$—CI): m/z 581 (M+1).

EXAMPLE 199

(5R,6S,7S)-6-(4-Fluorophenyl)-3-(2-methoxy-5-(2,5-(dimethyl)triazol-1-yl)phenyl)-1-oxaspiro[4.4]nonane-7-carboxylic acid methyl ester $^1$H-NMR (500 MHz, $CDCl_3$) δ 1.90–2.39 (m, 10H), 2.16 (s, 3H), 2.23 (s, 3H), 2.83–3.37 (m, 5H), 3.58 (s, 3H), 3.60–3.75 (m, 1H), 3.79 (s, 3H), 4.12 (t, 1H, J=7.8 Hz), 6.54–7.36 (m, 7H). Mass Spectrum ($NH_3$—CI): m/z 480 (M+1).

EXAMPLE 200

(5R,6S,7S)-6-(4-Fluorophenyl)-3-(2-phenoxy-5-(2-(trifluoromethyl)tetrazol-1-yl)phenyl)-1-oxaspiro[4.4]nonane-7-carboxylic acid methyl ester $^1$H-NMR (500 MHz, $CDCl_3$) δ 1.90–2.34 (m, 6H), 3.22–3.37 (m, 3H), 3.56 (s, 3H), 3.85–3.89 (m, 1H), 4.15 (t, 1H, J=7.7 Hz), 6.81–6.97 (m, 6H), 7.16–7.43 (m, 6H). Mass Spectrum ($NH_3$—CI): m/z 583 (M+1).

EXAMPLE 201

(5R,6S,7S)-6-Phenyl-3-(2-(trifluoromethoxy)-5-(2-trifluoromethyl)tetrazole) phenyl-7-(hydroxymethyl)-1-oxaspiro[5.4]dec-3-ene

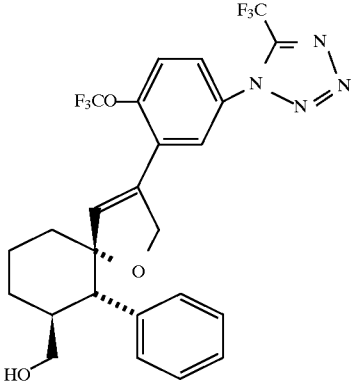

Step A: (5R,6S,7S)-6-Phenyl-3-(2-(trifluoro-methoxy)-5-(2-trifluoromethyl)tetrazole)phenyl-7-(t-butyldimethylsilyloxymethyl)-1-oxaspiro[5.4]dec-3-ene

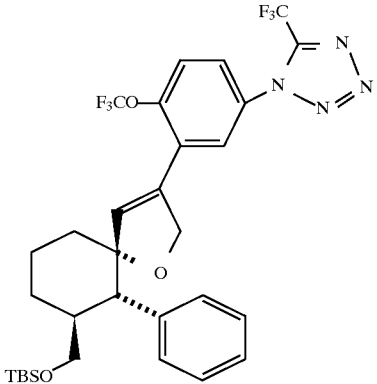

To a solution of the vinyl stannane from Example 81, step M (150.0 mg, 0.29 mmol) and 1-bromo-2-methoxy-5-(2-trifluoromethyl tetrazole)benzene (166.0 mg, 0.44 mmol) in dioxane (3.0 mL), degassed with Ar (3×) at room temperature was added $PdCl_2$ $(PPh_3)_2$ (6.0 mg, 0.009 mmol). The reaction mixture was heated to 100° C. for 5 h, whereupon it was quenched by addition of sat. aq. $NaHCO_3$ (5 mL), diluted with $H_2O$ (10 mL) and extracted with EtOAc (3×20 mL). The combined organic extracts were washed with brine, dried ($Na_2SO_4$), and concentrated in vacuo. The residue was purified by preparative chromatography (1000 μM silica gel plate, 5% EtOAc/hexanes) to afford the coupled adduct (100 mg, 52%) as a colorless glass. ¹H NMR (500 MHz, CDCl₃) δ 7.08–7.41 (m, 7H), 6.98 (d, 1H, J=2.6 Hz), 6.11 (t, 1H, J=2.1 Hz), 4.87 (dd, 1H, J=11.7, 2.1 Hz), 4.49 (dd, 1H, J=11.6, 2.0 Hz), 3.33 (dd, 1H, J=9.9, 2.5 Hz), 3.15 (dd, 1H, J=9.9, 5.7 Hz), 2.70 (d, 1H, J=11.7 Hz), 2.24–2.26 (m, 1H), 1.84–2.05 (m, 3H), 1.75–1.82 (m, 1H), 1.60–1.70 (m, 1H), 1.38–1.48 (m, 1H), 0.85 (s, 9H), −0.11 (s, 3H), −0.16 (s, 3H) ppm.

Step B: (5R,6S,7S)-6-Phenyl-3-(2-(trifluoromethoxy)-5-(2-trifluoromethyl)tetrazole)phenyl-7-(hydroxymethyl)-1-oxaspiro[5.4]dec-3-ene The silyl ether (100 mg, 0.15 mmol) from step A was treated-with 5 mL of a solution of THF/pyridine/95% HF-pyridine complex (5:1:0.5) at room temperature. After stirring for 12 h the reaction mixture was quenched by addition of H₂O (20 mL) and sat. NaHCO₃ (20 mL). The mixture was extracted with EtOAc (3×25 mL) and the combined organic extracts were washed with brine, dried (Na₂SO₄), and concentrated in vacuo. The residue was purified by column chromatography (10 g silica gel 60, 35 mm col. diam., 1–5% MeOH/CH₂Cl₂) to afford the 3-hydroxymethyl adduct (72 mg, 89%) as a colorless oil. ¹H NMR (CDCl₃, 500 MHz) δ 7.11–7.41 (m, 7H), 6.99 (d, 1H, J=2.2 Hz), 6.11 (s, 1H), 4.88 (dd, 1H, J=11.9, 1.6 Hz), 4.51 (dd, 1H, J=11.9, 1.6 Hz), 3.41 (dd, 1H, J=10.7, 2.7 Hz), 3.26 (dd, 1H, J=10.8, 5.7 Hz), 2.69 (d, 1H, J=11.7 Hz), 2.32–2.41 (m, 1H),1.89–2.03 (m, 3H), 1.80–1.83 (m, 1H), 1.63–1.70 (m, 1H), 1.39–1.43 (m, 1H), 1.1 (bs, 1H) ppm.

EXAMPLE 202

(3S,5R,6S,7S)-6-Phenyl-3-(2-(trifluoromethoxy)-5-(2-trifluoromethyl)tetrazole) phenyl-7-(hydroxymethyl)-1-oxaspiro[5.4]decane and (3R,5R,6S,7S)-6-Phenyl-3-(2-(trifluoromethoxy)-5-(2-trifluoromethyl)tetrazole) phenyl-7-(hydroxymethyl)-1-oxaspiro[5.4]decane

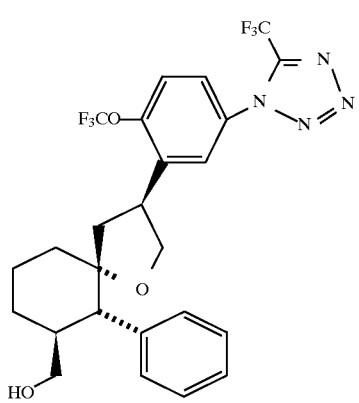

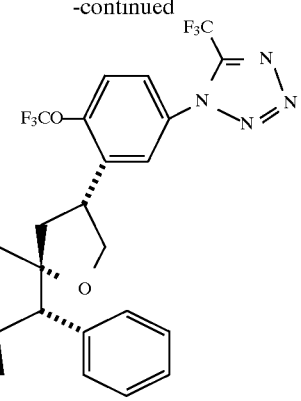

A mixture of 68 mg (0.13 mmol) of (5R,6S,7S)-6-Phenyl-3-(2-(trifluoromethoxy)-5-(2-trifluoromethyl)tetrazole)phenyl-7-(hydroxymethyl)-1-oxaspiro[5.4]dec-3-ene (from Example 201) and 50 mg of 20% Pd(OH)₂/C in 3 mL MeOH was hydrogenated at 50 psi for 4 h. The catalyst was filtered onto a pad of Celite, the reaction flask and filter cake were rinsed with 100 mL of MeOH and the filtrate was concentrated in vacuo. The residue was partitioned between 50 mL CH₂Cl₂ and 25 mL of sat'd NaHCO₃ and the layers were separated. The organic layer was washed with 25 mL of sat'd NaCl, dried(Na₂SO₄), and concentrated in vacuo to yield a 3:2 (S:R) mixture of diastereomers (48 mg, 71%) at C-3. The diastereomers were purified by Prep HPLC(YMC Sil-5, 4.6×250 mm column, 98:2 v/v hexanes/iPrOH, 10.0 mL/min, 220 nm. Retention times: 3-(S), 5-(R), 6-(S), 7-(S), diastereomer, 22.8 min; 3-(R), 5-(R), 6-(S), 7-(S), diastereomer, 24.5 min. For (3S,5R,6S,7S)-6-Phenyl-3-(2-(trifluoromethoxy)-5-(2-trifluoromethyl)tetrazole)phenyl-7-(hydroxymethyl)-1-oxaspiro[5.4]decane, ¹H NMR (CDCl₃, 500 MHz) δ 7.31 (dd, 1H, J=8.7, 1.3 Hz), 7.20 (dd, 1H, J=8.7, 2.5 Hz), 7.05–7.08 (m, 3H), 6.75–6.78 (m, 1H), 6.07 (d, 1H, J=2.5 Hz), 4.19 (t, 1H, J=8.5 Hz), 3.88 (p, 1H, J=8.0 Hz), 3.43 (app t, 1H, J=8.9 Hz), 3.34 (dd, 1H, J=11.0, 3.0 Hz), 3.18 (dd, 1H, J=10.7, 5.4 Hz), 2.55 (d, 1H, J=12.0 Hz), 2.33–2.34 (m, 1H), 2.03–2.11 (m, 3H), 1.97 (d, 1H, J=12.8 Hz), 1.80–1.83 (m, 1H), 1.71–1.86 (m, 3H), 1.38–1.45 (m, 3H), 1.1 (bs, 1H) ppm. For (3R,5R,6S,7S)-6-Phenyl-3-(2-(trifluoromethoxy)-5-(2-trifluoromethyl)tetrazole)phenyl-7-(hydroxymethyl)-1-oxaspiro[5.4]decane, ¹H NMR (CDCl₃, 500 MHz) δ 7.28–7.34 (m, 8H), 4.08 (t, 1H, J=7.6 Hz), 3.59 (dd, 1H, J=10.5, 8.2 Hz), 3.37 (dd, 1H, J=11.0, 3.2 Hz), 3.22 (dd, 1H, J=11.0, 5.8 Hz), 2.42–2.47 (m, 2H),2.27–2.32 (m, 2H), 1.89–1.97 (m, 3H), 1.74–1.78 (m, 1H), 1.36–1.64 (m, 5H) ppm.

EXAMPLE 203

(3S,5R,6S,7S)-6-Phenyl-3-(2-(trifluoromethoxy)-5-(2-trifluoromethyl)tetrazole)phenyl7-(morpholin-4-ylmethyl)-1-oxaspiro[5.4]decane

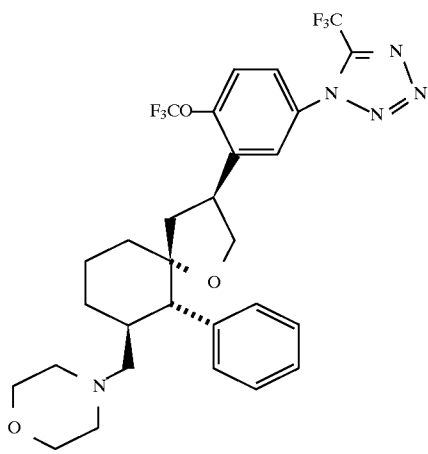

Step A: (3S,5R,6S,7S)-6-Phenyl-3-(2-(trifluoromethoxy)-5-(2-trifluoromethyl)tetrazole)phenyl-7-(methyl(methylsulfonate))-1-oxaspiro[5.4]decane

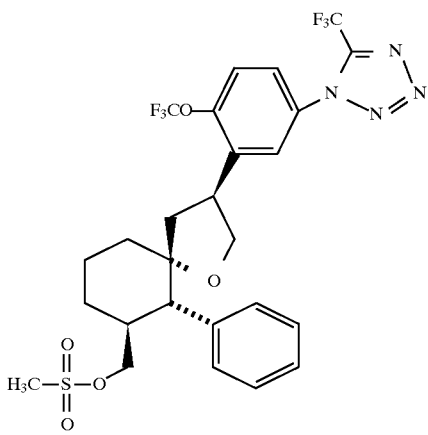

To a solution of the alcohol from Example 201, step B,(20 mg, 0.04 mmol) in CH$_2$Cl$_2$ (2 mL) at room temperature was added pyridine (6 µL, 0.07 mmol) followed by mesyl chloride (22 mg, 0.19 mmol). The reaction mixture was stirred for 0.5 hours, whereupon it was diluted with H$_2$O (10 mL) and extracted with CH$_2$Cl$_2$ (3×20 mL). The combined organic extracts were washed with brine, dried (Na$_2$SO$_4$), and concentrated in vacuo. The residue was purified by column chromatography (3 g silica gel 60, 35 mm col. diam., 25–50% EtOAc/Hex) to afford the mesylate (14 mg, 64%) as a colorless oil. $^1$H NMR (CDCl$_3$, 500 MHz) δ 7.31–7.34 (m, 2H) 7.21 (dd, 1H, J=9.0, 3.0 Hz), 7.06–7.14 (m, 4H), 6.79–6.82 (m, 1H), 6.07 (d, 1H, J=2.5 Hz), 4.19 (t, 1H, J=8.7 Hz), 3.86–3.96 (m, 2H), 3.71 (dd, 1H, J=9.7, 4.6 Hz), 3.43 (app t, 1H, J=8.7 Hz), 2.72 (m, 3H), 2.59–2.61 (m, 2H), 1.39–2.18 (m, 8H) ppm.

Step B: (3S,5R,6S,7S)-6-Phenyl-3-(2-(trifluoromethoxy)-5-(2-trifluoromethyl)tetrazole)phenyl-7-(methyl-morpholine)-1-oxaspiro[5.4]decane To a solution of the mesylate from Step A (7 mg, 0.01 mmol) in DMF (2 mL) was added morpholine (3.0 mg, 0.03 mmol) followed by DIPEA (2.8 mg, 0.02 mmol) and the reaction mixture was heated at 80° C. After 12 hours the reaction was concentrated in vacuo. The residue was purified by column chromatography (1 g silica gel 60, 35 mm col. diam., 2.5–8% MeOH/CH$_2$Cl$_2$) to afford the title compound (5 mg, 75%) as a colorless oil. Mass spectrum (EI): m/e=611 (M).

EXAMPLE 204

(3S,5R,6S,7S)-6-Phenyl-3-(2-(trifluoromethoxy)-5-(2-trifluoromethyl)tetrazole)phenyl-7-(pyrrolidin-1-ylmethyl)-1-oxaspiro[5.4]decane

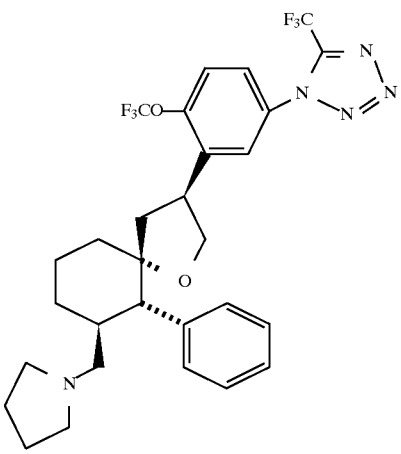

To a solution of the mesylate from Example 203, step A (7 mg, 0.01 mmol) in DMF (2 mL) was added pyrrolidine (2.5 mg, 0.03 mmol) followed by DIPEA (2.8 mg, 0.02 mmol) and the reaction mixture was heated at 80° C. After 12 hours the reaction was diluted with H$_2$O (20 mL) and extracted with CH$_2$Cl$_2$ (3×30 mL). The combined organic extracts were washed with brine, dried (Na$_2$SO$_4$) and concentrated in vacuo. The residue was purified by Prep HPLC (YMC Sil-5, 4.6×250 mm column, 98:2 v/v hexanes/iPrOH, 10.0 mL/min, 220 nm. Retention time: 24.2 min) to afford the title compound as an oil (2 mg, 31%). Mass spectrum (EI): m/e=595 (M).

EXAMPLE 205

(3S,5R,6S,7S)-6-Phenyl-3-(2-(trifluoromethoxy)-5-(2-trifluoromethyl)tetrazole)phenyl-7-(methyl-(2-fluoro ethylamino))-1-oxaspiro[5.4]decane

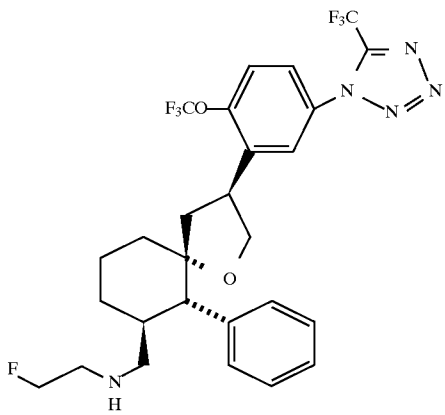

Step A: (3S,5R,6S,7S)-6-Phenyl-3-(2-(trifluoromethoxy)-5-(2-trifluoromethyl)tetrazole)phenyl-7-(carboxaldehyde)-1-oxaspiro[5.4]decane

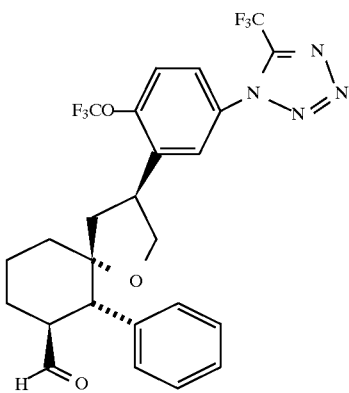

A solution of 10 mg (0.02 mmol) of (3S,5R,6S,7S)-6-Phenyl-3-(2-(trifluoromethoxy)-5-(2-trifluoromethyl)tetrazole)phenyl-7-(hydroxymethyl)-1-oxaspiro[5.4]decane (from Example 202) in 2 mL of $CH_2Cl_2$ was treated with 12 mg (0.03 mmol) of Dess-Martin reagent. After 30 min, the reaction was quenched with 10.0 mL of sat'd $NaHCO_3$ and diluted with 15 mL of $H_2O$. The resulting mixture was extracted with $CH_2Cl_2$ (3×30 mL). The combined organic extracts were washed with brine, 0.25M $Na_2S_2O_3$ (30 mL), dried ($Na_2SO_4$) and concentrated in vacuo. The residue was purified by column chromatography (2 g silica gel 60, 35 mm col. diam., 10–25% EtOAc/Hex) to afford the aldehyde (10 mg, 100%) as a colorless oil. $^1H$ NMR ($CDCl_3$, 500 MHz) δ 9.36 (d, 1H, J=2.5 Hz), 7.33 (d, 1H, J=8.7 Hz), 7.22 (dd, 1H, J=8.7, 2.5 Hz), 7.06–7.09 (m, 3H), 6.75–6.80 (m, 1H), 6.06 (d, 1H, J=2.5 Hz), 4.19 (t, 1H, J=8.7 Hz), 3.88 (p, 1H, J=8.0 Hz), 3.43 (app t, 1H, J=8.5 Hz), 3.28–3.24 (m, 1H), 2.82 (d, 1H, J=12.1 Hz), 1.27–2.16 (m, 8H), ppm.

Step B: (3S,5R,6S,7S)-6-Phenyl-3-(2-(trifluoromethoxy)-5-(2-trifluoromethyl)tetrazole)phenyl-7-(methyl-(2-fluoro ethylamino))-1-oxaspiro[5.4]decane To a solution of the aldehyde from step A (10 mg, 0.02 mmol) in MeOH was added 2-fluoroethylamine hydrochloride (9 mg, 0.09 mmol), 50 mg of 3 A molecular sieves, and DIPEA (5.0 mg, 0.02 mmol). After stirring for 8 hours, 4 mg (0.05 mmol) of $Na(CN)BH_3$ was added and the reaction was stirred for an additional 2 days. The reaction was filtered on a pad of Celite; the flask and filtered solids were rinsed well with EtOAc (250 mL). The filtrate was transferred to a separatory funnel, washed with 75 mL of sat'd $NaHCO_3$, 75 mL of sat'd NaCl, dried over $Na_2SO_4$, and concentrated in vacuo. The residue was purified by column chromatography (3 g silica gel 60, 35 mm col. diam., 1–5% MeOH/$CH_2Cl_2$) to afford the title compound (5 mg, 50%) as a colorless oil. Mass spectrum (EI): m/e=587 (M).

EXAMPLE 206

(3R,5R,6S,7S)-6-Phenyl-3-(2-(trifluoromethoxy)-5-(2-trifluoromethyl)tetrazole)phenyl-7-(methyl-(2-fluoro ethylamino))-1-oxaspiro[5.4]decane

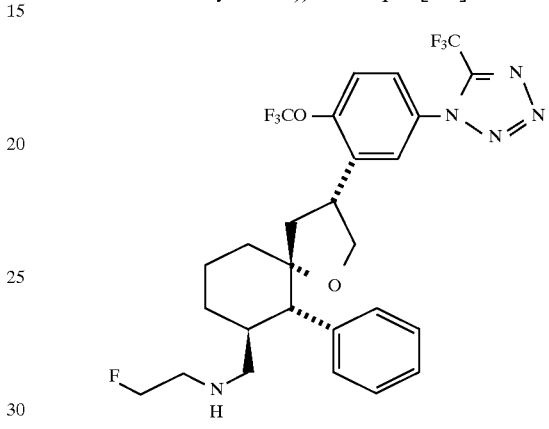

Step A: (3R,5R,6S,7S)-6-Phenyl-3-(2-(trifluoromethoxy)-5-(2-trifluoromethyl)tetrazole)phenyl-7-(carboxaldehyde)-1-oxaspiro[5.4]decane

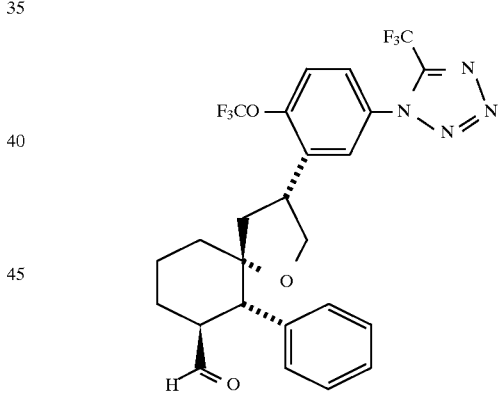

A solution of 8 mg (0.02 mmol) of (3R,5R,6S,7S)-6-Phenyl-3-(2-(trifluoromethoxy)-5-(2-trifluoromethyl)tetrazole) phenyl-7-(hydroxymethyl)-1-oxaspiro[5.4]decane (from Example 202) in 2 mL of $CH_2Cl_2$ was treated with 10 mg (0.02 mmol) of Dess-Martin reagent. After 30 min, the reaction was quenched with 10.0 mL of sat'd $NaHCO_3$ and diluted with 15 mL of $H_2O$. The resulting mixture was extracted with $CH_2Cl_2$ (3×30 mL). The combined organic extracts were washed with brine, 0.25M $Na_2S_2O_3$ (30 mL), dried ($Na_2SO_4$) and concentrated in vacuo. The residue was purified by column chromatography (2 g silica gel 60, 35 mm col. diam., 10–25% EtOAc/Hex) to afford the aldehyde (10 mg, 100%) as a colorless oil. $^1H$ NMR ($CDCl_3$, 500 MHz) δ 9.38 (d, 1H, J=2.7 Hz), 7.30–7.42 (m, 8H), 4.06–4.10 (m, 1H), 3.60 (app t, 1H, J=8.9 Hz), 3.19–3.26 (m, 1H), 2.73 (d, 1H, J=12.1 Hz), 2.36–2.46 (m, 2H), 1.25–1.29 (m, 7H) ppm.

155

Step B: (3R,5R,6S,7S)-6-Phenyl-3-(2-(trifluoromethoxy)-5-(2-trifluoromethyl)tetrazole)phenyl-7-(methyl-(2-fluoro ethylamino))-1-oxaspiro[5.4]decane To a solution of the aldehyde (8 mg, 0.02 mmol) from Example 9 in MeOH was added 2-fluoroethylamine hydrochloride (7.5 mg, 0.08 mmol), 50 mg of 3 A molecular sieves, and DIPEA (4.0 mg, 0.02 mmol). After stirring for 8 hours, 4 mg (0.05 mmol) of Na(CN)BH₃ was added and the reaction was stirred for an additional 12 hours. The reaction was filtered on a pad of Celite; the flask and filtered solids were rinsed well with EtOAc (250 mL). The filtrate was transferred to a separatory funnel, washed with 75 mL of sat'd NaHCO₃, 75 mL of sat'd NaCl, dried over Na₂SO₄, and concentrated in vacuo. The residue was purified by column chromatography (3 g silica gel 60, 35 mm col. diam., 1–8% MeOH/CH₂Cl₂) to afford the title compound (5 mg, 56%) as a colorless oil. $^1$H NMR (CDCl₃, 500 MHz) δ 7.27–7.34 (m, 8H), 4.44 (t, 1H, J=4.6 Hz), 4.35 (t, 1H, J=4.6 Hz), 4.07 (t, 1H, J=8.0 Hz) 3.56–3.59 (m, 2H), 2.68–2.80 (m, 2H), 0.84–2.41 (m, 13H) ppm.

EXAMPLE 207

(3R,5R,6S,7S)-6-Phenyl-3-(2-methoxy-5-(trifluoromethoxy))phenyl-7-(hydroxymethyl)-1-oxaspiro[5.4]decane and (3S,5R,6S,7S)-6-Phenyl-3-(2-methoxy-5-(trifluoromethoxy))phenyl-7-(hydroxymethyl)-1-oxaspiro[5.4]decane

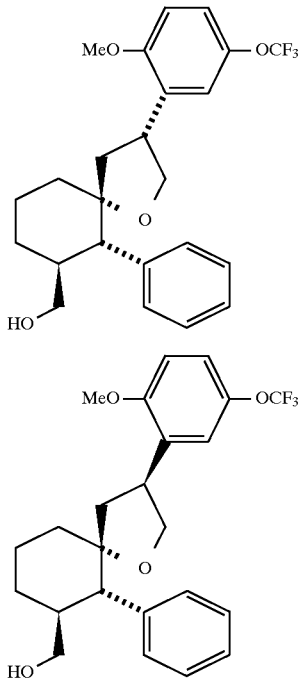

Step A: (5R,6S,7S)-6-Phenyl-3-(2-methoxy-5-(trifluoromethoxy)phenyl-7-(t-butyldimethyl silyloxymethyl)-1-oxaspiro[5.4]dec-3-ene

156

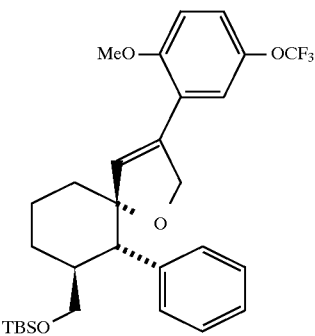

To a solution of the vinyl stannane from Example 81, step M (100.0 mg, 0.19 mmol) and 1-bromo-2-methoxy-5-(trifluoromethyl)phenyl (103.0 mg, 0.38 mmol) in N-methylpyrrolidone (3.0 mL), degassed with Ar (3×) at room temperature was added Pd₂(dba)₃HCl (10.0 mg, 0.01 mmol) and tri-2-furylphosphine (9.0 mg, 0.04 mmol). The reaction mixture was heated to 80° C. for 2 h, whereupon it was quenched by addition of sat. aq. NaHCO₃ (5 mL), diluted with H₂O (10 mL) and extracted with EtOAc (3×20 mL). The combined organic extracts were washed with brine, dried (Na₂SO₄), and concentrated in vacuo. The residue was purified by preparative chromatography (1000 μM silica gel plate, 5% EtOAc/hexanes) to afford the coupled adduct (54 mg, 51%) as a colorless glass. $^1$H NMR (500 MHz, CDCl₃) δ 7.07–7.16 (m, 4H), 6.98 (dd, 1H, J=8.9, 3.0 Hz), 6.74 (d, 1H, J=8.9 Hz), 6.61 (d, 1H, J=2.8 Hz), 6.03 (t, 1H, J=2.1 Hz), 4.88 (dd, 1H, J=11.7, 2.1 Hz), 4.44 (dd, 1H, J=11.7, 2.1 Hz), 3.74 (s, 3H), 3.33 (dd, 1H, J=9.9, 2.5 Hz), 3.15 (dd, 1H, J=9.9, 2.6 Hz), 2.66 (d, 1H, J=11.9 Hz), 2.28–2.31 (m, 1H), 1.98 (d, 1H, J=5.5 Hz), 1.59–1.92 (m, 3H), 1.27–1.43 (m, 2H), 0.86 (s, 9H), −0.10 (s, 3H), −0.15 (s, 3H) ppm.

Step B: (5R,6S,7S)-6-Phenyl-3-(2-methoxy-5-(trifluoromethoxy)phenyl-7-(hydroxymethyl)-1-oxaspiro[5.4]dec-3-ene The silyl ether from step A (54 mg, 0.10 mmol) was treated with 5 mL of a mixture of THF/pyridine/95% HF-pyridine complex (5:1:0.5) at room temperature. After stirring for 4 h the reaction mixture was quenched by addition of H₂O (20 mL) and sat. NaHCO₃ (20 mL). The mixture was extracted with EtOAc (3×25 mL) and the combined organic extracts were washed with brine, dried (Na₂SO₄), and concentrated in vacuo to yield a light brown oil (40 mg, 90%). The oil was used directly in the next step.

Step C: (3R,5R,6S,7S)-6-Phenyl-3-(2-methoxy-5-(trifluoromethoxy))phenyl-7-(hydroxymethyl)-1-oxaspiro[5.4]decane and (3S,5R,6S,7S)-6-Phenyl-3-(2-methoxy-5-(trifluoromethoxy))phenyl-7-(hydroxymethyl)-1-oxaspiro[5.4]decane A mixture of 40 mg (0.10 mmol) of (5R,6S,7S)-6-Phenyl-3-(2-methoxy-5-(trifluoromethoxy)phenyl-7-(hydroxymethyl)-1-oxaspiro[5.4]dec-3-ene (from step B) and 50 mg of 20% Pd(OH)₂/C in 3 mL MeOH was hydrogenated at 50 psi for 4 h. The catalyst was filtered onto a pad of Celite, the reaction flask and filter cake were rinsed with 100 mL MeOH of and the filtrate was concentrated in vacuo. The residue was partitioned between 50 mL CH₂Cl₂ and 25 mL of sat'd NaHCO₃ and the layers were separated. The organic layer was washed with 25 mL of sat'd NaCl, dried(Na₂SO₄), and concentrated in vacuo to yield a 3:1 (S:R) mixture of diastereomers (27 mg, 60%) at C-3. The diastereomers were purified by Prep HPLC(YMC Sil-5, 4.6×250 mm column, 99:2 v/v hexanes/iPrOH, 10.0 mL/min, 220 nm. Retention times: 3-(R),5-(R),6-(S),7-(S), diastereomer, 39.5 min. 3-(S),5-(R),6-(S),7-(S), diastereomer, 41.2 min;. For (3R,5R,6S,7S)-6-Phenyl-3-(2-methoxy-5-(trifluoromethoxy))phenyl-7-(hydroxymethyl)-1-oxaspiro[5.4]decane, $^1$H NMR (CDCl$_3$, 500 MHz) δ 7.27–7.33 (m, 5H), 6.96 (dd, 1H, J=8.7, 2.3 Hz), 6.84 (d, 1H, J=2.3 Hz), 6.68 (d, 1H, J=8.7 Hz), 3.99 (t, 1H, J=7.6 Hz), 3.61–3.65 (m, 4H), 3.36 (dd, 1H, J=11.0, 3.2 Hz), 3.22 (dd, 1H, J=10.8, 5.5 Hz), 2.44 (d, 1H, J=11.7 Hz), 2.24–2.36 (m, 1H), 2.15 (dd, 1H, J=12.5, 8.5 Hz), 1.88–1.98 (m, 2H), 1.72–1.77 (m, 1H), 1.53–1.67 (m, 3H), 1.27–1.37 (m, 3H) ppm. For (3S,5R,6S,7S)-6-Phenyl-3-(2-methoxy-5-(trifluoromethoxy))phenyl-7-(hydroxymethyl)-1-oxaspiro[5.4]decane, $^1$H NMR (CDCl$_3$, 500 MHz) δ 7.26–7.33 (m, 8H), 6.90 (dd, 1H, J=8.9, 2.7 Hz), 6.69 (d, 1H, J=8.9 Hz) 6.19 (d, 1H, J=2.5 Hz), 4.10 (t, 1H, J=8.0 Hz), 3.80–3.84 (m, 1H), 3.71 (s, 3H), 3.38 (dd, 1H, J=11.0, 3.2 Hz), 3.22–3.27 (m, 2H), 2.54 (d, 1H, J=11.7 Hz), 2.35–2.38 (m, 1H), 1.71–2.09 (m, 6H), 1.28–1.47 (m, 5H) ppm.

EXAMPLE 208

(3R,5R,6S,7S)-6-Phenyl-3-(2-methoxy-5-(trifluoromethoxy))phenyl-7-(methyl-(2-fluoroethylamino))-1-oxaspiro[5.4]decane

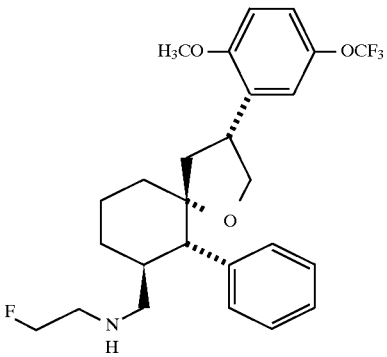

Step A: (3R,5R,6S,7S)-6-Phenyl-3-(2-methoxy-5-(trifluoromethoxy))phenyl -7-(carboxaldehyde)-1-oxaspiro[5.4]decane

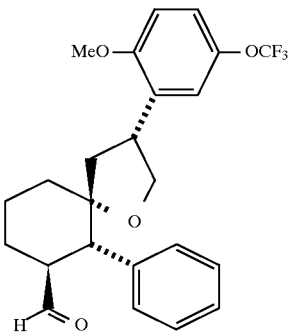

A solution of 4 mg (0.01 mmol) of (3R,5R,6S,7S)-6-Phenyl-3-(2-methoxy-5-(trifluoromethoxy))phenyl-7-(hydroxymethyl)-1-oxaspiro[5.4]decane (from Example 207) in 2 mL of CH$_2$Cl$_2$ was treated with 6 mg (0.01 mmol) of Dess-Martin reagent. After 30 min, the reaction was quenched with 10.0 mL of sat'd NaHCO$_3$ and diluted with 15 mL of H$_2$O. The resulting mixture was extracted with CH$_2$Cl$_2$ (3×30 mL). The combined organic extracts were washed with brine, 0.25M Na$_2$S$_2$O$_3$ (30 mL), dried (Na$_2$SO$_4$) and concentrated in vacuo. The residue was purified by column chromatography (2 g silica gel 60, 35 mm col. diam., 5–25% EtOAc/Hex) to afford the aldehyde (4 mg, 100%) as a colorless oil. $^1$H NMR (CDCl$_3$, 500 MHz) δ 9.37 (d, 1H, J=2.7 Hz), 7.27–7.73 (m, 5H), 6.97 (dd, 1H, J=8.4, 2.2 Hz), 6.83 (d, 1H, J=2.5 Hz), 6.69 (d, 1H, J=8.9 Hz), 3.98 (t, 1H, J=7.6 Hz), 3.62–3.68 (m, 1H), 3.21–3.27 (m, 1H), 2.71 (d, 1H, J=11.9 Hz), 2.31–2.35 (m, 2H), 2.23 (dd, 1H, J=12.4, 8.2 Hz), 0.84–1.98 (m, 8H) ppm.

Step B: (3R,5R,6S,7S)-6-Phenyl-3-(2-methoxy-5-(trifluoromethoxy))phenyl-7-(methyl-(2-fluoroethylamino))-1-oxaspiro[5.4]decane To a solution of the aldehyde (4 mg, 0.01 mmol) from step A in MeOH was added 2-fluoroethylamine hydrochloride (5.0 mg, 0.05 mmol), 50 mg of 3 A molecular sieves, and DIPEA (3.0 mg, 0.02 mmol). After stirring for 6 hours, 4 mg (0.05 mmol) of Na(CN)BH$_3$ was added and the reaction was stirred for an additional 12 hours. The reaction was filtered on a pad of Celite; the flask and filtered solids were rinsed well with EtOAc (250 mL). The filtrate was transferred to a separatory funnel, washed with 75 mL of sat'd NaHCO$_3$, 75 mL of sat'd NaCl, dried over Na$_2$SO$_4$, and concentrated in vacuo. The residue was purified by preparative chromatography (1000 μM silica gel plate, 5% MeOH/CH$_2$Cl$_2$) to afford the title compound (5 mg, 86%) as a colorless oil. Mass spectrum (EI): m/e=482 (M+H).

EXAMPLE 209

(5R,6S,7S)-6-Phenyl-3-(2,2 Difluoro-5-trifluoroacetamide)benzodioxole-7-(hydroxymethyl)-1-oxaspiro[5.41]dec-3-ene

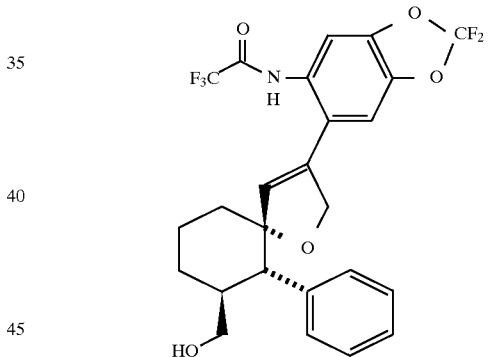

Step A: 2,2 Difluoro-5-(trifluoroacetamide) benzodioxole

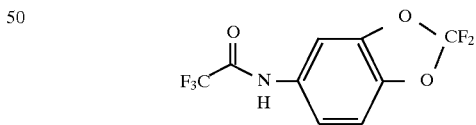

To a solution of 2,2-difluoro-5-aminobenzodioxole (300 mg, 1.73 mmol) in 2 mL of CH$_2$Cl$_2$ at 0° C. was added triethylamine (700 mg, 6.92 mmol) followed by trifluoroacetic anhydride (800 mg, 3.81 mmol). The reaction was allowed to warm to room temperature. After stirring for 3 hours the reaction was diluted with 50 mL of sat'd NaHCO$_3$ and 50 mL of H$_2$O. The resulting mixture was extracted with CH$_2$Cl$_2$ (3×30 mL). The combined organic extracts were washed with brine, dried (Na$_2$SO$_4$) and concentrated in vacuo to yield a yellow solid. The solid was purified by column chromatography (15 g silica gel 60, 35 mm col. diam., 5–25% EtOAc/Hex) to afford the acetamide (460 mg, 99%) as a light yellow solid. $^1$H NMR (CDCl$_3$, 500 MHz) δ 7.95 (bs, 1H), 7.60 (d, 1H, J=2.5 Hz), 7.13 (dd, 1H, J=8.5, 2.1 Hz) 7.08 (d, 1H, J=8.5 Hz) ppm.

Step B: 2,2 Difluoro-4-bromo-5-(trifluoroacetamide) benzodioxole

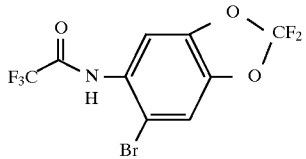

To a 25 mL round bottom flask wrapped in tin foil at room temperature was added a solution of 2,2 difluoro-5-(trifluoroacetamide)benzodioxole (100 mg, 0.37 mmol) in DMF (5 mL) followed by NBS (86 mg, 0.48 mmol). After stirring for 2 hours the reaction was diluted with 50.0 mL of H$_2$O. The resulting mixture was extracted with EtOAc (3×30 mL). The combined organic extracts were washed with brine, dried (Na$_2$SO$_4$) and concentrated in vacuo to yield a yellow oil. The oil was purified by column chromatography (15 g silica gel 60, 35 mm col. diam., 5–25% EtOAc/Hex) to afford the 4-bromo compound (82 mg, 64%) as a light yellow oil. $^1$H NMR (CDCl$_3$, 500 MHz) δ 8.40(bs, 1H), 8.19 (s, 1H) 7.36 (s, 1H) ppm.

Step C: (5R,6S,7S)-6-Phenyl-3-(2,2 Difluoro-5-trifluoroacetamide)benzodioxole-7-(t-butyldimethyl silyloxymethyl)-1-oxaspiro[5.4]dec-3-ene

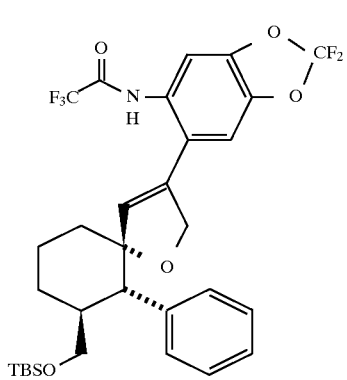

To a solution of the vinyl stannane from Example 81, step M (50.0 mg, 0.10 mmol) and 2,2 Difluoro-4-bromo-5-(trifluoroacetamide) benzodioxole (52.0 mg, 0.15 mmol) in dioxane (2.0 mL), degassed with Ar (3×) at room temperature was added PdCl$_2$ (PPh$_3$)$_2$ (2.0 mg, 0.003 mmol). The reaction mixture was heated to 100° C. for 5 h, whereupon it was quenched by addition of sat. aq. NaHCO$_3$ (5 mL), diluted with H$_2$O (10 mL) and extracted with EtOAc (3×20 mL). The combined organic extracts were washed with brine, dried (Na$_2$SO$_4$), and concentrated in vacuo. The residue was purified by preparative chromatography (1000 μM silica gel plate, 50% CH$_2$Cl$_2$/hexanes-(2×)) to afford the coupled adduct (16 mg, 25%) as a colorless glass. $^1$H NMR (500 MHz, CDCl$_3$) δ 7.92–7.95 (m, 2H), 7.17–7.32 (m, 6H) 6.19 (s, 1H), 5.70 (s, 1H), 4.67 (dd, 1H, J=12.6, 2.1 Hz), 3.74 (s, 3H), 4.36 (dd, 1H, J=12.6, 1.8 Hz), 3.35 (dd, 1H, J=9.9, 2.3 Hz), 3.18 (dd, 1H, J=9.8, 5.7 Hz), 2.68 (d, 1H, J=11.9 Hz), 2.28–2.33 (m, 1H), 1.27–1.99 (m, 5H), 0.85 (s, 9H), −0.09 (s, 3H), −0.15 (s, 3H) ppm.

Step D: (5R,6S,7S)-6-Phenyl-3-(2,2 Difluoro-5-trifluoroacetamide)benzodioxole-7-(hydroxymethyl)-1-oxaspiro[5.41]dec-3-ene The silyl ether from step C (16 mg, 0.03 mmol) was treated with 5 mL of a mixture of THF/pyridine/95% HF-pyridine complex (5:1:0.5) at room temperature. After stirring for 12 h the reaction mixture was quenched by addition of H$_2$O (20 mL) and sat. NaHCO$_3$ (20 mL). The mixture was extracted with EtOAc (3×25 mL) and the combined organic extracts were washed with brine, dried (Na$_2$SO$_4$), and concentrated in vacuo. The residue was purified by column chromatography (10 g silica gel 60, 35 mm col. diam., 1–5% MeOH/CH$_2$Cl$_2$) to afford the 7-hydroxymethyl adduct (10 mg, 77%) as a colorless oil. $^1$H NMR (CDCl$_3$, 500 MHz) δ 7.25–7.91 (m, 6H), 6.20 (s, 1H), 5.69 (s, 1H), 4.69 (dd, 1H, J=12.8, 1.4 Hz), 4.29–4.40 (m, 2H), 3.43 (dd, 1H, J=10.9, 2.7 Hz), 3.28 (dd, 1H, J=11.0, 5.7 Hz), 2.68 (d, 1H, J=11.7 Hz), 2.38–2.39 (m, 1H), 0.85–2.04 (m, 7H) ppm.

EXAMPLE 210

(3R,5R,6S,7S)-6-Phenyl-3-(2,2 Difluoro-5-trifluoroacetamide)benzodioxole-7-(hydroxymethyl) -1-oxaspiro[5.4]decane

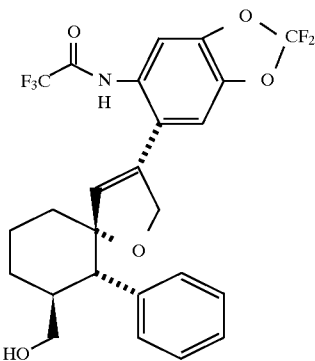

A mixture of 7 mg (0.01 mmol) of (5R,6S,7S)-6-Phenyl-3-(2,2 Difluoro-5-trifluoroacetamide) benzodioxole-7-(hydroxymethyl)-1-oxaspiro[5.4]dec-3-ene (from Example 209, step D) and 7 mg of 20% Pd(OH)$_2$/C in 3 mL MeOH was hydrogenated at 50 psi for 5 h. The catalyst was filtered onto a pad of Celite, the reaction flask and filter cake were rinsed with 100 mL MeOH of and the filtrate was concentrated in vacuo. The residue was partitioned between 50 mL CH$_2$Cl$_2$ and 25 mL of sat'd NaHCO$_3$ and the layers were separated. The organic layer was washed with 25 mL of sat'd NaCl, dried(Na$_2$SO$_4$), and concentrated in vacuo. The residue was purified by Prep HPLC(YMC Sil-5, 4.6×250 mm column, 98:2 v/v hexanes/iPrOH, 10.0 mL/min, 220 nm) to yield a single isomer (2 mg, 30%) at C-3. Retention time: 40.8 min. Mass spectrum (EI): m/e=513 (M).

EXAMPLE 211

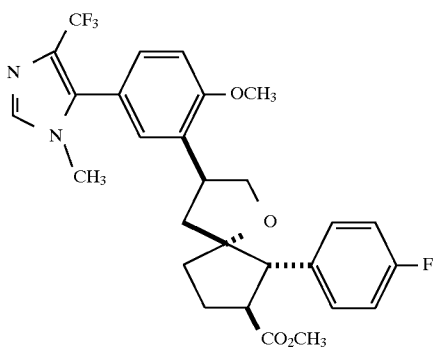

(3S,5R,6S,7S)-6-(4-Fluorophenyl)-3-(2-methoxy-5-
(4-(trifluoromethyl)-1-methylimidazol-5-yl)phenyl)-
1-oxaspiro[4.4]nonane-7-carboxylic acid methyl
ester The title compound was prepared according to the procedure of Example 6, Step G, replacing methyl[5-(RS),6-(SR),7-(SR)]-6-(4-fluorophenyl)-3-(2-methoxy-5-((5-trifluoromethyl)-tetrazol-1-yl)phenyl)-1-oxaspiro[4.4]non-3-ene-7-carboxylate with (5R,6S,7S)-6-(4-fluorophenyl)-3-(2-methoxy-5-(4-(trifluoromethyl)-1-methylimidazol-5-yl)phenyl)-1-oxaspiro[4.4]non-3-ene-7-carboxylic acid methyl ester (from Example 79). $^1$NMR (400 MHz, CD$_3$OD): δ7.77 (s, 1H), 7.35 (dd, 2H, J=9, 6 Hz), 7.13 (dd, 1H, J=8, 2 Hz), 6.97 (d, 1H, J=8 Hz), 6.90 (t,2H, J=9 Hz), 6.58 (d, 1H, J=2 Hz), 4.04 (t, 1H, J=8 Hz), 3.84–3.72 (m, 1H), 3.78 (s, 3H), 3.53 (s, 3H), 3.39–3.28 (m, 1H), 3.38 (s, 3H), 3.21 (d, 1H, J=11 Hz), 3.06 (t, 1H, J=8 Hz), 2.31–2.13 (m, 3H), 2.03–1.87 (m, 3H). Mass spectrum (NH$_3$/CI): m/z=533.1 (M+1).

EXAMPLE 212

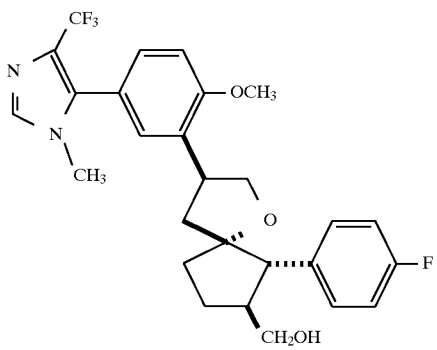

(3S,5R,6S,7S)-(6-(4-Fluorophenyl)-3-(2-methoxy-5-
(4-(trifluoromethyl)-1-methylimidazol-5-yl)phenyl)-
1-oxaspiro[4.4]non-7-yl)methanol The title compound was prepared according to the procedure of Example 10, Step A, replacing methyl[3-(S),5-(R),6-(S), 7-(S)]-6-(4-fluorophenyl)-3-(2-methoxy-5-((5-trifluoromethyl)tetrazol-1-yl)phenyl)-1-oxaspiro[4.4]nonane-7-carboxylate with (3S,5R,6S,7S)-6-(4-fluorophenyl)-3-(2-methoxy-5-(4-(trifluoromethyl)-1-methylimidazol-5-yl)phenyl)-1-oxaspiro[4.4]nonane-7-carboxylic acid methyl ester (from Example 211). $^1$NMR (400 MHz, CD$_3$OD): δ7.77 (s, 1H), 7.35 (dd, 2H, J=9, 6 Hz ), 7.13 (dd, 1H, J=8, 2 Hz ), 6.97 (d, 1H, J=8 Hz ),6.89 (t,2H, J=9 Hz ), 6.59 (d, 1H, J=2 Hz ), 4.02(t, 1H, J=8 Hz ), 3.82–3.72 (m, 1H), 3.79 (s, 3H), 3.49 (dd, 1H, J=11, 4 Hz), 3.38 (s, 3H), 3.31 (dd, 1H, J=11, 7 Hz ), 3.02 (t, 1H, J=8 Hz ), 2.71 (d, 1H, J=11 Hz ), 2.63–2.52 (m, 1H), 2.20 (dd, 1H, J12, 8 Hz), 2.18–2.06 (m, 2H), 1.95 (dd, 1H, J=12, 10 Hz ), 1.92–1.82 (m, 1H), 1.72–1.62 (m, 1H). Mass spectrum (NH3/CI): m/z=505.2 (M+1).

EXAMPLE 213

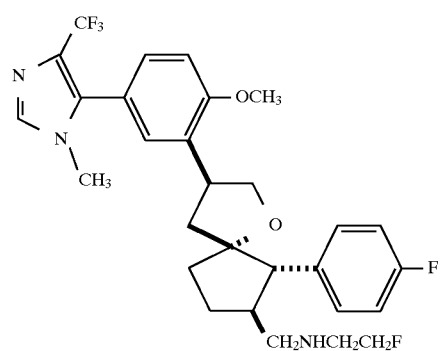

N-(2-Fluoroethyl)((3S,5R,6S,7S)-6-(4-fluorophenyl)
-3-(2-methoxy-5-(4-(trifluoromethyl)-1-
methylimidazol-5-yl)phenyl)-2-oxaspiro[4.4]non-7-
ylmethyl)amine The title compound was prepared according to the procedure of Example 10, Step B, replacing[3-(S), 5-(R), 6-(S), 7-(S)]-6-(4-fluorophenyl)-3-(2-methoxy-5-((5-trifluoromethyl)tetrazol-1-yl)phenyl)-1-oxaspiro[4.4]nonane-7-methanol with (3S, 5R, 6S, 7S)-(6-(4-fluorophenyl)-3-(2-methoxy-5-(4-(trifluoromethyl)-1-methylimidazol-5-yl)phenyl)-1-oxaspiro[4.4]non-7-yl)methanol (from Example 212), and replacing pyrrolidine with 2-fluoroethylamine hydrochloride and 1 eq. of triethylamine. $^1$NMR (400 MHz, CD$_3$OD): δ7.77 (s, 1H), 7.37 (dd, 2H, J=9, 6 Hz ), 7.13 (dd, 1H, J=8, 2 Hz ), 6.97 (d, 1H, J=8 Hz), 6.91 (t, 2H, J=9 Hz ), 6.59 (d, 1H, J=2 Hz ), 4.47 (t, 1H, J=5 Hz), 4.35 (t, 1H, J=5 Hz ), 4.02 (t, 1H, J=8 Hz ), 3.82–3.71 (m, 1H), 3.79 (s, 3H), 3.39 (s, 3H), 3.01 (t, 1H, J=8 Hz ), 2.85–2.48 (m, 4H), 2.24–2.11 (m, 3H), 2.01–1.89 (m, 2H), 1.54–1.43 (m, 1H). Mass spectrum (ESI): m/z= 550.3 (M+1).

EXAMPLE 214

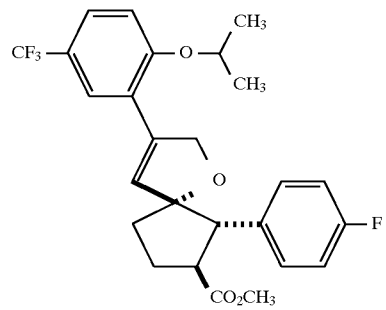

(5R,6S,7S)-6-(4-Fluorophenyl)-3-(2-isopropoxy-5-
(trifluoromethyl)phenyl)-1-oxaspiro[4.4]non-3-ene-
7-carboxylic acid methyl ester Step A: 2-Bromo-1-isopropoxy-4-(trifluoromethyl)benzene Powdered potassium carbonate (1.72 g, 12.5 mmol) and 2-iodopropane (1.16 mL, 1.98 g, 11.6 mmol) were added to a solution of 2-bromo-4-(trifluoromethyl)phenol (2.00 g, 8.30 mmol) in DMF. The mixture was stirred overnight at RT and then partitioned between hexane (100 mL) and water (100 mL). The organic layer was washed with saturated aqueous sodium chloride (50 mL) and the aqueous layers were extracted in succession with hexane (50 mL). The organic layers were dried over sodium sulfate, decanted, and evaporated. The crude product was purified by flash column chromatography, eluting with hexane, to give the title compound. Mass spectrum (EI): m/z=282 (M$^+$).

Step B: (5R,6S,7S)-6-(4-Fluorophenyl)-3-(2-isopropoxy-5-(trifluoromethyl)phenyl)-1-oxaspiro[4.4]non-3-ene-7-carboxylic acid methyl ester The title compound was prepared according to the procedure of Example 6, Step F(d), replacing 2-bromo-4-(5-(trifluoromethyl)tetrazol-1-yl)anisole with 2-bromo-4-(5-(trifluoromethyl)benzene. $^1$NMR (400 MHz, CDCl$_3$): δ7.42 (dd, 1H, J=9, 2 Hz ), 7.28 (dd, 2H, J=9, 6 Hz ), 7.19 (d, 1H, J=2 Hz ), 6.90 (t, 2H, J=9 Hz ), 6.88 (d, 1H, J=9 Hz ), 6.27 (t, 1H, J=2 Hz ), 4.75 (dd, 1H, J=12, 2 Hz ), 4.60 (septet, 1H, J=6 Hz ), 4.15 dd, 1H, J=12, 2 Hz), 3.59 (s, 3H), 3.47 (ddd, 1H, J=11, 9, 8 Hz ), 3.30 (d, 1H, J=11 Hz), 2.42–2.31 (m, 1H), 2.25 (ddd, 1H, J=14, 10, 7 Hz ), 2.09 (ddd, 1H, J=14, 9, 5 Hz ), 2.04–1.94 (m, 1H), 1.33 (d, 3H, J=6 Hz ), 1.31 (d, 3H, J=6 Hz ). Mass spectrum (NH3/CI): m/z=479.1 (M+1).

EXAMPLE 215

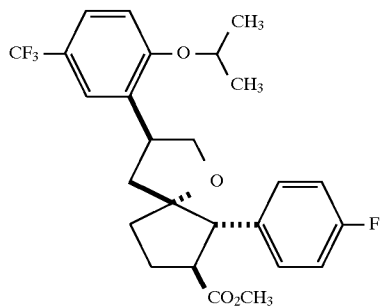

(3S,5R,6S,7S)-6-(4-Fluorophenyl)-3-(2-isopropoxy-5-(trifluoromethyl)phenyl-1-oxaspiro[4.4]nonane-7-carboxylic acid methyl ester The title compound was prepared according to the procedure of Example 6, Step G, replacing methyl[5-(RS),6-(SR),7-(SR)]-6-(4-fluorophenyl)-3-(2-methoxy-5-((5-trifluoromethyl)-tetrazol-1-yl)phenyl)-1-oxaspiro[4.4]non-3-ene-7-carboxylate with (5R,6S,7S)-6-(4-fluorophenyl)-3-(2-isopropoxy-5-(trifluoromethyl)phenyl)-1-oxaspiro[4.4]non-3-ene-7-carboxylic acid methyl ester (from Example 214). $^1$NMR (400 MHz, CDCl$_3$): δ 7.38–7.32 (m, 3H), 7.00 (t, 2H, J=9 Hz ), 6.91 (d, 1H, J=2 Hz ), 6.80 (d, 1H, J=9 Hz ), 4.55 (septet, 1 H, J=6 Hz ), 4.10 (t, 1H, J=8 Hz ), 3.76–3.64 (m, 1H), 3.57 (s, 3H), 3.40–3.30 (m, 1H), 3.22 (d, 1H, J=11 Hz ), 3.00 (dd, 1H, J=10, 8 Hz), 2.38–2.28 (m, 1H), 2.24–2.16 (m, 2H), 2.02–1.90 (m, 3H), 1.30 (d, 3H, J=6 Hz ), 1.27 (d, 3H, J=6 Hz ). Mass spectrum (NH3/CI): m/z= 481.1 (M+1).

EXAMPLE 216

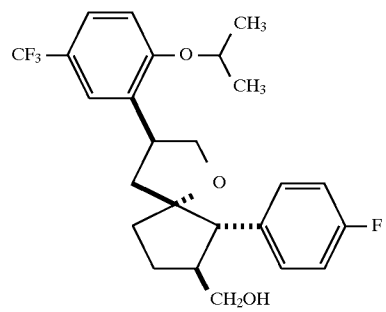

(3S,5R,6S,7S)-(6-(4-Fluorophenyl)-3-(2-isopropoxy-5-(trifluoromethyl)phenyl)-1-oxaspiro[4.4]non-7-yl)methanol The title compound was prepared according to the procedure of Example 10, Step A, replacing methyl[3-(S),5-(R),6-(S), 7-(S)]-6-(4-fluorophenyl)-3-(2-methoxy-5-((5-trifluoromethyl)tetrazol-1-yl)phenyl)-1-oxaspiro[4.4]nonane-7-carboxylate with (3S,5R,6S,7S)-6-(4-fluorophenyl)-3-(2-isopropoxy-5-(trifluoromethyl)phenyl)-1-oxaspiro[4.4]nonane-7-carboxylic acid methyl ester (from Example 215). $^1$NMR (400 MHz, CDCl$_3$): δ7.39–7.32 (m, 3H), 7.01 (t, 2H, J=9 Hz ), 6.93 (d, 1H, J=2 Hz ), 6.80 (d, 1H, J=9 Hz), 4.55 (septet, 1H, J=6 Hz ), 4.11 (t, 1H, J=8 Hz ), 3.75–3.60 (m, 2H), 3.50 (dd, 1H, J=10, 5 Hz ), 2.97 (dd, 1H, J=10, 8 Hz ), 2.72–2.62 (m, 2H), 2.23–2.09 (m, 2H), 1.68–1.55 (m, 1H), 1.30 (d, 3H, J=6 Hz ), 1.27 (d, 3H, J=6 Hz ). Mass spectrum (NH3/CI): m/z=453.1 (M+1).

EXAMPLE 217

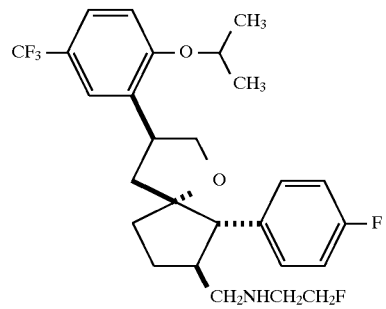

N-(2-Fluoroethyl)((3S,5R,6S,7S)-6-(4-fluorophenyl)-3-(2-isopropoxy-5-(trifluoromethyl)phenyl)-2-oxaspiro[4.4]non-7-ylmethyl)amine The title compound was prepared according to the procedure of Example 10, Step B, replacing[3-(S),5-(R),6-(S), 7-(S)]-6-(4-fluorophenyl)-3-(2-methoxy-5-((5-trifluoromethyl)tetrazol-1-yl)phenyl)-1-oxaspiro[4.4]nonane-7-methanol with (3S,5R,6S,7S)-(6-(4-fluorophenyl)-3-(2-isopropoxy-5-(trifluoromethyl)phenyl)-1-oxaspiro [4.4]non-7-yl)methanol (from Example 216), and replacing pyrrolidine with 2-fluoroethylamine hydrochloride and 1 eq. of triethylamine. $^1$NMR (400 MHz, CD$_3$OD): δ7.41 (dd, 2H, J=9, 6 Hz), 7.36 (dd, 1H, J=8, 2 Hz ), 7.03 (t, 2H, J=9 Hz ), 6.98 (d, 1H, J=9 Hz ), 6.89 (d, 1H, J=2 Hz ), 4.64 (septet, 1H, J=6 Hz ), 4.47 (t, 1H, J=5 Hz ), 4.35 (t, 1H, J=5 Hz ), 4.03 (t, 1H, J=8 Hz ), 3.78–3.67 (m, 1H), 2.95 (dd, 1H, J=9, 8 Hz ), 2.86–2.47 (m, 6 Hz), 2.24–2.10 (m, 3H), 2.01–1.90

(m, 2H), 1.54–1.43 (m, 1H), 1.28 (d, 3H, J=6 Hz), 1.26 (d, 3H, J=6 Hz ). Mass spectrum (ESI): m/z=498.4 (M+1).

EXAMPLE 218

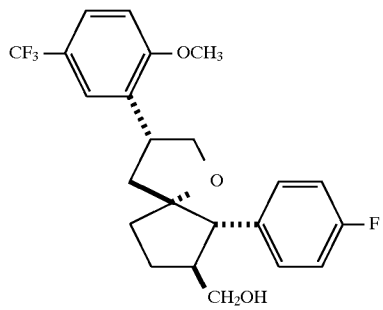

(3R,5R,6S,7S)-(6-(4-Fluorophenyl)-3-(2-methoxy-5-(trifluoromethyl)phenyl)-1-oxaspiro[4.4]non-7-yl) methanol Step A: (3S,5R,6S,7S)-7-(Benzyloxymethyl)-6-(4-fluorophenyl)-3-hydroxy-3-(2-methoxy-5-(trifluoromethyl) phenyl)-1-oxaspiro[4.4]nonane 2-Bromo-4-(trifluoromethyl)anisole (227 mg, 0.89 mmol), prepared according to the procedure of J. Alexander (*Org. Prep. Proced. Int.,* 1986, 18, 213–215), was dissolved in 3.7 mL of THF and cooled in a −78° C. bath. A solution of t-butyllithium (1.0 mL, 1.7M in hexane, 1.7 mmol) was added over a period of 2 min. After 30 min., a solution of 200 mg (0.56 mmol) of (5R,6S,7S)-7-(benzyloxymethyl)-6-(4-fluorophenyl)-1-oxaspiro[4.4]nonane-3-one (prepared from methyl (5R,6S,7S)-6-(4-fluorophenyl)-3-(methylene)-1-oxaspiro[4.4]nonane-7-carboxylate (from Example 9) by DIBALH reduction, benzylation with sodium hydride and benzyl bromide, and oxidation as described in Example 6, Step C) in 1.0 mL of THF was added, and the reaction was stirred for 45 min. at −78° C. followed by warming to −35° C. over 20 min. The reaction was quenched by the addition of 10 mL of saturated aqueous ammonium chloride and partioned between 30 mL of ethyl acetate and 10 mL of water. The organic layer was washed with 10 mL of saturated aqueous sodium bicarbonate and 10 mL of saturated aqueous sodium chloride, dried over sodium sulfate, decanted, and evaporated. The crude product was purified by flash column chromatography, eluting with 1.5–5% ethyl ether in toluene to give 154 mg of the title compound.

Step B: (3R,5R,6S,7S)-7-(Benzyloxymethyl)-6-(4-fluorophenyl)-3-(-2-methoxy-5-(trifluoromethyl)phenyl)-1-oxaspiro[4.4]nonane A solution was prepared by dissolving 10 mg (0.019 mmol) of (3S,5R,6S,7S)-7-(benzyloxymethyl)-6-(4-fluorophenyl)-3-hydroxy-3-(2-methoxy-5-(trifluoromethyl) phenyl)-1-oxaspiro[4.4]nonane in 0.20 mL of trifluoroacetic acid at RT, and triethylsilane (0.009 mL, 7 mg, 0.06 mmol) was added immediately. After 30 min., the reaction was diluted with 25 mL of ethyl acetate and washed with 5 m L of saturated aqueous sodium bicarbonate and 5 mL of saturated aqueous sodium chloride. The organic solution was dried over sodium sulfate, decanted, and evaporated. The crude product was purified by preparative TLC, eluting with 3% ethyl ether in toluene, to yield 2.4 mg of the title compound.

Step C: (3R,5R,6S,7S)-(6-(4-Fluorophenyl)-3-(-2-methoxy-5-(trifluoromethyl)phenyl)-1-oxaspiro[4.4]non-7-yl) methanol (3R,5R,6S,7S)-7-(Benzyloxymethyl)-6-(4-fluorophenyl)-3-(-2-methoxy-5-(trifluoromethyl)phenyl)-1-oxaspiro[4.4] nonane (2.4 mg, 0.0047 mmol) was stirred with 0.7 mg of 20% palladium(II) hydroxide m 0.5 mL of 95% ethanol under hydrogen at atmospheric pressure for 1.5 h. The mixture was filtered through a 0.45 micron filter and the catalyst was rinsed with additional 95% ethanol. The filtrate was evaporated to give 1.6 mg of the title compound. $^1$NMR (400 MHz, CDCl$_3$): δ 7.43–7.32 (m, 4H), 7.03 (t, 2H, J=9 Hz ), 6.80 (d, 1H, J=9 Hz ), 3.75 (s, 3H), 3.72 (t, 1H, J 8 Hz ), 3.65–3.58 (m, 2H), 3.48 (dd, 1H, J=10, 5 Hz ), 2.82 (quintet, 1H, J=8 Hz ), 2.73–2.58 (m, 2H), 2.23 (dd, 1H, J=12, 8 Hz ), 2.18–2.02 (m, 3H), 1.99–1.88 (m, 1H), 1.66–1.54 (m, 1H). Mass spectrum (EI): m/z=424.1 (M$^+$).

EXAMPLE 219

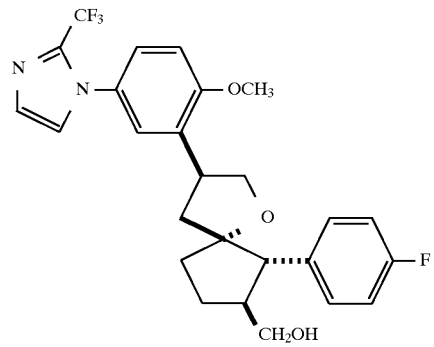

(3S,5R,6S,7S)-(6-(4-Fluorophenyl)-3-(2-methoxy-5-(2-trifluoromethylimidazol-1-yl)phenyl)-1-oxaspiro [4.4]non-7-yl)methanol The title compound was prepared according to the procedure of Example 10, Step A, replacing methyl[3-(S),5-(R) ,6-(S), 7-(S)]-6-(4-fluorophenyl)-3-(2-methoxy-5-((5-trifluoromethyl)tetrazol-1 -yl)phenyl)-1-oxaspiro[4.4] nonane-7-carboxylate with (3S,5R,6S,7S)-6-(4-fluorophenyl)-3-(2-methoxy-5-(2-trifluoromethylimidazol-1-yl)phenyl)-1-oxaspiro[4.4]nonane-7-carboxylic acid methyl ester (from Example 70). $^1$NMR (400 MHz, CDCl$_3$): δ7.32 (dd, 2H, J=9, 6 Hz ), 7.20 (d, 1H, J=1 Hz ), 7.09 (dd, 1H, J=9, 3 Hz ), 6.97 (d, 1H, J=1 Hz ), 6.91 (t, 2H, J=9 Hz ), 6.81 (d, 1H, J=9 Hz ), 6.63 (d, 1H, J=3 Hz ), 4.08 (t, 1H, J=8 Hz ), 3.78 (s, 3H), 3.78–3.68 (m, 1H), 3.62 (dd, 1H, J=10, 4 Hz ), 3.48 (dd, 1H, J=10, 6 Hz ), 3.02 (t, 1H, J=8 Hz ), 2.70–2.60 (m, 2H), 2.22–2.08 (m, 3H), 2.05 (s, 3H), 1.93–1.80 (m, 2H), 1.67–1.56 (m, 1H). Mass spectrum (ESI): m/z=491.2 (M+1).

EXAMPLE 220

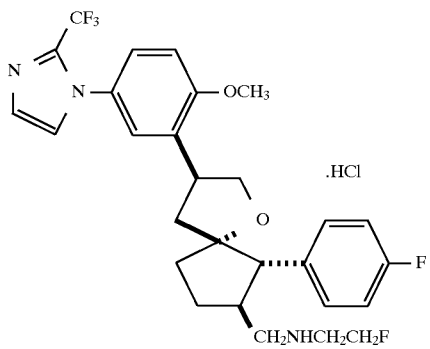

N-(2-Fluoroethyl)((3S,5R,6S,7S)-6-(4-fluorophenyl)
-3-(2-methoxy-5-(2-(trifluoromethyl)imidazol-1-yl)
phenyl)-1-oxaspiro[4.4]non-7-ylmethyl)amine
hydrochloride The free amine corresponding to title compound was prepared according to the procedure of Example 10, Step B, replacing [3-(S),5-(R),6-(S),7-(S)]-6-(4-fluorophenyl)-3-(2-methoxy-5-((5-trifluoromethyl)tetrazol-1-yl)phenyl)-1-oxaspiro[4.4]nonane-7-methanol with (3S,5R,6S,7S)-(6-(4-fluorophenyl)-3-(2-methoxy-5-(2-trifluoromethylimidazol-1-yl)phenyl)-1-oxaspiro[4.4]non-7-yl)methanol (from Example 219), and replacing pyrrolidine with 2-fluoroethylamine hydrochloride and 1 eq. of triethylamine.

A solution of the free amine dissolved in methanol was treated with 1.0M HCl in ethyl ether. Removal of the solvent under reduced pressure yielded the title compound. $^1$NMR (400 MHz, CD$_3$OD): δ7.40 (dd, 2H, J=9, 6 Hz ), 7.29 (d, 1H, J=1 Hz ), 7.21 (bs, 1H), 7.19 (dd, 1H, J=9, 2 Hz ), 7.00 (d, 1H, J=9 Hz ), 6.95 (t, 2H, J=9 Hz ), 6.61 (d, 1H, J=2 Hz ), 4.75–4.70 (m, 1H), 4.63–4.58 (m, 1H), 4.06 (t, 1H, J=8 Hz ), 3.86–3.74 (m, 1H), 3.80 (s, 3H), 3.37–3.22 (m, 2H), 3.04 (t, 1H, J=8 Hz ), 2.97 (d, 1H, J=12 Hz ), 2.89 (dd, 1H, J=12, 2 Hz ), 2.86–2.76 (m, 1H), 2.71 (d, 1H, J=12 Hz ), 2.32–2.18 (m, 3H), 2.08–1.98 (m, 1H), 1.93 (dd, 1H, J=12, 11 Hz ), 1.68–1.56 (m, 1H). Mass spectrum (NH3/CI): m/z=536.2 (M+1).

EXAMPLE 221

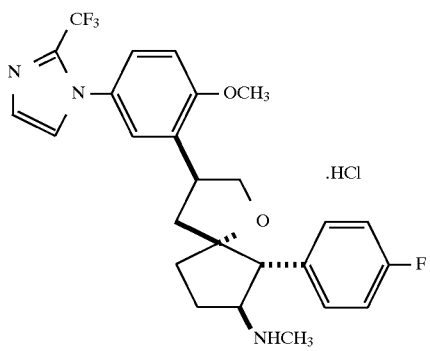

N-Methyl((3S,5R,6R,7S)-6-(4-fluorophenyl)-3-(2-
methoxy-5-(2-(trifluoromethyl)imidazol-1-yl)
phenyl)-1-oxaspiro[4.4]non-7-yl)amine
hydrochloride Step A: (3S,5R,6R,7S)-6-(4-Fluorophenyl)-3-(2-methoxy-5-(2-(trifluoromethyl)imidazol-1-yl)phenyl)-1-oxaspiro[4.4]nonane-7-carboxylic acid To an ice cold solution of 40 mg (0.077 mmol) (3S,5R,6S,7S)-6-(4-fluorophenyl)-3-(2-methoxy-5-(2-trifluoromethylimidazol-1-yl)phenyl)-1-oxaspiro[4.4]nonane-7-carboxylic acid methyl ester (from Example 70) in 1.0 mL of ethanol and 0.20 mL of water was added 0.050 mL of 2.5N aqueous NaOH. The mixture was stirred at 0° C., then warmed slowly to RT overnight. After neutralizing with 0.065 mL of 2N aqueous HCl, the mixture was partitioned between 25 mL of ethyl acetate and 25 mL of brine. The layers were separated and the organic layer was dried over sodium sulfate and evaporated to give 40 mg of title compound as a colorless syrup. Mass spectrum (NH3/CI): m/z= 505.0 (M+1).

Step B: (3S,5R,6R,7S)-7-(Benzyloxycarbonylamino)-6-(4-fluorophenyl)-3-(2-methoxy-5-(2-(trifluoromethyl) imidazol-1-yl)phenyl)-1-oxaspiro[4.4]nonane A mixture of (3S,5R,6R,7S)-6-(4-fluorophenyl)-3-(2-methoxy-5-(2-(trifluoromethyl)imidazol-1-yl)phenyl)-1-oxaspiro[4.4]nonane-7-carboxylic acid (40 mg, 0.079 mmol), diphenylphosphoryl azide (24 mg, 0.08 mmol), and diisopropylethylamine (0.017 mL, 0.095 mmol) in toluene was stirred at RT for 0.5 h, and then heated at 100° C. for 50 min. After addition of benzyl alcohol (0.5 mL), the mixture was heated at 100° C. overnight. Upon cooling to RT, the mixture was taken up in 25 mL of ethyl acetate and washed successively with 15 mL of saturated aqueous sodium bicarbonate and 15 mL of brine. Drying over sodium sulfate and evaporation afforded the crude product, which was purified by column chromatography, eluting with 3–5% ethyl acetate in dichloromethane, to give the title compound (30 mg, 62%) as a light brown syrup. Mass spectrum (NH3/CI): m/z=610.1 (M+1).

Step C: (3S,5R,6R,7S)-7-(N-(Benzyloxycarbonyl)methylamino)-6-(4-fluorophenyl)-3-(2-methoxy-5-(2-(trifluoromethyl)imidazol-1-yl)phenyl)-1-oxaspiro[4.4] nonane A THF solution of sodium bis(trimethylsily)amide (0.059 mL, 1.0M, 0.059 mmol) was added to an ice-cooled solution of (3S,5R,6R,7S)-7-(benzyloxycarbonylamino)-6-(4-fluorophenyl)-3-(2-methoxy-5-(2-(trifluoromethyl) imidazol-1-yl)phenyl)-1-oxaspiro[4.4]nonane (30 mg, 0.049 mmol) in 0.50 mL of dry THF. After stirring for 15 minutes at 0° C., iodomethane (0.0037 mL, 8.4 mg, 0.059 mmol) was added. The mixture was stirred at 0° C., then allowed to warm up to RT for 3 h. The reaction was diluted in 20 mL of ethyl acetate and washed with 10 mL of saturated aqueous sodium bicarbonate, followed by 10 mL of brine. Drying over sodium sulfate and concentration afforded the crude product. Purification by preparative TLC, eluting with 30% ethyl ether in 1:1 toluene/hexane, yielded 7.5 mg of pure title compound and 15 mg of a mixture containing the title compound and recovered starting material. Mass spectrum (NH3/CI): m/z=624.2 (M+1).

Step D: N-Methyl((3S,5R,6R,7S)-6-(4-fluorophenyl)-3-(2-methoxy-5-(2-(trifluoromethyl)imidazol-1-yl)phenyl)-1-oxaspiro[4.4]non-7-yl)amine hydrochloride (3S,5R,6R,7S)-7-(N-(Benzyloxycarbonyl)methylamino)-6-(4-fluorophenyl)-3-(2-methoxy-5-(2-(trifluoromethyl) imidazol-1-yl)phenyl)-1-oxaspiro[4.4]nonane (7.0 mg, 0.011 mmol) in 0.30 mL of ethanol and 0.24 mL of acetic acid was hydrogenated on the Parr shaker at 47 psi, using 2.3 mg of 20% palladium(II) hydroxide on carbon. After 3 h, the mixture was filtered through 0.45 micron filter and the filtrate was evaporated. The residue was taken in 2.0 mL of ethyl acetate and washed with 1.0 mL of saturated aqueous sodium bicarbonate followed by 1.0 mL of brine. Drying over sodium sulfate and evaporation gave N-methyl((3S,5R,6R,7S)-6-(4-fluorophenyl)-3-(2-methoxy-5-(2-

(trifluoromethyl)imidazol-1-yl)phenyl)-1-oxaspiro[4.4]non-7-yl)amine. 1NMR (400 MHz, CD₃OD): δ7.45 (dd, 2H, J=9, 6 Hz ), 7.29 (d, 1H, J=1 Hz ), 7.21 (d, 1H, J=1 Hz ), 7.19 (dd, 1H, J=9, 2 Hz ), 7.01 (t, 2H, J=9 Hz ), 7.00 (d, 1H, J=9 Hz ), 6.58 (d, 1H, J=2 Hz ), 4.12–4.00 (m, 2H), 3.84–3.75 (m, 1H), 3.79 (s, 3H), 3.13 (d, 1H, J=10 Hz ), 3.05 (t, 1H, J=8 Hz ), 2.54–2.42 (m, 1H), 2.52 (s, 3H), 2.28 (dd, 1H, J=13, 8 Hz ), 2.27–2.20 (m, 1H), 2.07 (ddd, 1H, J=13, 10, 9 Hz ), 1.91 (dd, 1H, J=13, 11 Hz ), 1.90–1.80 (m, 1H). Mass spectrum (NH3/CI): m/z=490.1 (M+1).

A solution of the free amine dissolved in methanol was treated with 1.0M HCl in ethyl ether. Removal of the solvent under under reduced pressure yielded the title compound. ¹NMR (400 MHz, CD₃OD): δ7.45 (dd, 2H, J=9, 6 Hz ), 7.29 (d, 1H, J=1 Hz ), 7.21 (d, 1H, J=1 Hz ), 7.19 (dd, 1H, J=9, 2 Hz ), 7.02 (t, 2H, J=9 Hz ), 7.00 (d, 1H, J=9 Hz ), 6.58 (d, 1H, J=2 Hz ), 4.10–4.02 (m, 2H), 3.85–3.75 (m, 1H), 3.79 (s, 3H), 3.13 (d, 1H, J=10 Hz ), 3.06 (t, 1H, J=9 Hz ), 2.54 (s, 3H), 2.54–2.43 (m, 1H), 2.29 (dd, 1H, J=13, 8 Hz), 2.28–2.20 (m, 1H), 2.07 (ddd, 1H, J=13, 10, 9 Hz ), 1.92 (dd, 1H, J=13, 10 Hz ), 1.90–1.80 (m, 1H).

EXAMPLE 222

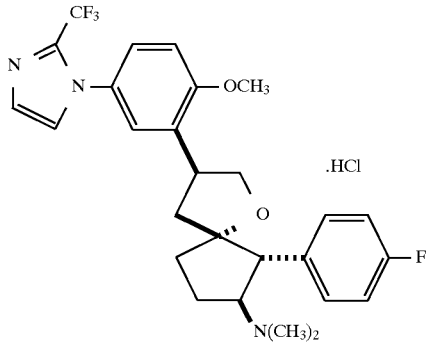

N,N-Dimethyl((3S,5R,6R,7S)-6-(4-Fluorophenyl)-3-(2-methoxy-5-(2-(trifluoromethyl)imidazol-1-yl)phenyl)-1-oxaspiro[4.4]non-7-yl)amine hydrochloride The mixture of (3S,5R,6R,7S)-7-(N-(benzyloxycarbonyl)methylamino)-6-(4-fluorophenyl)-3-(2-methoxy-5-(2-(trifluoromethyl)imidazol-1-yl)phenyl)-1-oxaspiro[4.4]nonane and (3S,5R,6R,7S)-7-(benzyloxycarbonylamino)-6-(4-fluorophenyl)-3-(2-methoxy-5-(2-(trifluoromethyl)imidazol-1-yl)phenyl)-1-oxaspiro[4.4]nonane (from Example 221, Step C) was hydrogenated using essentially the same conditions as described in Example 221, Step D (first paragraph), to give a mixture of N-methyl((3S,5R,6R,7S)-6-(4-fluorophenyl)-3-(2-methoxy-5-(2-(trifluoromethyl)imidazol-1-yl)phenyl)-1-oxaspiro[4.4]non-7-yl)amine and (3S,5R,6R,7S)-6-(4-fluorophenyl)-3-(2-methoxy-5-(2-(trifluoromethyl)imidazol-1-yl)phenyl)-1-oxaspiro[4.4]non-7-ylamine.

The resulting mixture of amines (11 mg) was dissolved in 0.40 mL of acetonitrile and 0.10 mL of water, and treated with 37% aqueous formaldehyde solution (0.0165 mL, 0.22 mmol). After 10 min. at RT, a solution of sodium cyanoborohydride (5.5 mg, 0.087 mmol) in acetonitrile was added in two portions. The mixture was stirred for 1 h with occasional addition of 1:4 acetic acid/acetonitrile to maintain the pH at 7. The reaction was diluted in 2.0 mL of ethyl acetate and washed with 1.5 mL of 2.5N sodium hydroxide, followed by 1.5 mL of brine. The organic layer was dried over sodium sulfate and evaporated. The residue was purified by flash column chromatography, eluting with 50 mL of 5% methanol in dichloromethane followed by 25 mL of 0.5% ammonium hydroxide and 5% methanol in dichloromethane gave 9.0 mg of the free base. Dissolving this material in 2.0 mL of methanol, adding 0.018 mL of 1.0M HCl in ethyl ether, and evaporation of the solvent yielded the title compound. ¹NMR (400 MHz, CD₃OD): δ7.48 (dd, 2H, J=9, 6 Hz ), 7.30(d, 1H, J=1 Hz ), 7.22(d, 1H, J=1 Hz ), 7.20(dd, 1H, J=9,3 Hz), 7.02 (t, 2H, J=9 Hz ), 7.00 (d, 1H, J=9 Hz ), 6.56 (d, 1H, J=3 Hz), 4.28 (td, 1H, J=10, 5 Hz ), 4.06 (t, 1H, J=8 Hz ), 3.84–3.74 (m, 1H), 3.79 (s, 3H), 3.35 (d, 1H, J=10 Hz ), 3.03 (t, 1H, J=8 Hz ), 2.78 (s, 3H), 2.70 (s, 3H), 2.53–2.40 (m, 1H), 2.32–2.21 (m, 2H), 2.09–1.98 (m, 2H), 1.91 (dd, 1H, J=13, 11 Hz ). Mass spectrum (NH3/CI): m/z=504.1 (M+1).

EXAMPLE 223

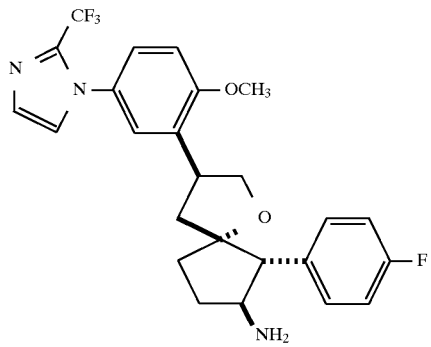

(3S,5R,6R,7S)-6-(4-Fluorophenyl)-3-(2-methoxy-5-(2-(trifluoromethyl)imidazol-1-yl)phenyl)-1-oxaspiro[4.4]non-7-ylamine The title compound was prepared according to the procedure of Example 221, Step D (first paragraph), replacing (3S,5R,6R,7S)-7-(N-(benzyloxycarbonyl)methylamino)-6-(4-fluorophenyl)-3-(2-methoxy-5-(2-(trifluoromethyl)imidazol-1-yl)phenyl)-1-oxaspiro[4.4]nonane with (3S,5R,6R,7S)-7-(benzyloxycarbonylamino)-6-(4-fluorophenyl)-3-(2-methoxy-5-(2-(trifluoromethyl)imidazol-1-yl)phenyl)-1-oxaspiro[4.4]nonane (from Example 221, Step B), the title compound was prepared. ¹NMR (400 MHz, CD₃OD): δ7.37 (dd, 2H, J=9, 6 Hz ), 7.28 (d, 1H, J=1 Hz ), 7.20 (d, 1H, J=1 Hz ), 7.18 (dd, 1H, J=9, 3 Hz ), 6.99 (d, 1H, J=9 Hz), 6.93 (t, 2H, J=9 Hz ), 6.63 (d, 1H, J=3 Hz ), 4.02 (t, 1H, J=8 Hz), 3.80 (s, 3H), 3.78–3.66 (m, 2H), 3.01 (t, 1H, J=8 Hz ), 2.66 (d, 1H, J=10 Hz ), 2.–30–2.20 (m, 2H), 2.17–2.01 (m, 2H), 1.92 (dd, 1H, J=12, 11 Hz ), 1.56–1.46 (m, 1H). Mass spectrum (NH3/CI): m/z=476.1 (M+1).

EXAMPLE 224

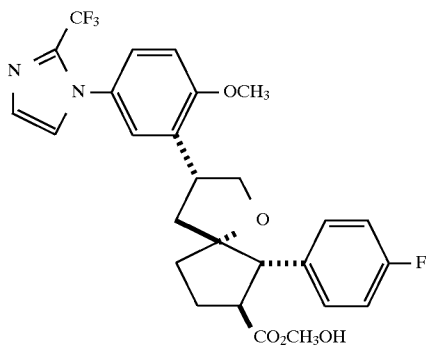

(3R,5R,6S,7S)-6-(4-Fluorophenyl)-3-(2-methoxy-5-(2-(trifluoromethyl)imidazol-1-yl)phenyl)-1-oxaspiro[4.4]nonane-7-carboxylic acid methyl ester Step A: (5R,6S,7S)-6-(4-Fluorophenyl)-3-(2-methoxy-5-(2-(trifluoromethyl)imidazol-1-yl)phenyl)-1-oxaspiro[4.4]non-2-ene-7-carboxylic acid methyl ester A mixture of 67 mg (0.13 mmol) of (5R,6S,7S)-6-(4-fluorophenyl)-3-(2-methoxy-5-(2-(trifluoromethyl)imidazol-1-yl)phenyl)-1-oxaspiro[4.4]non-3-ene-7-carboxylic acid methyl ester (from Example 69), 20% palladium(II) hydroxide on carbon (32 mg), acetic acid (1.2 mL), and methanol (6.0 mL) was stirred at RT under hydrogen at atmospheric pressure. After 20 min., the catalyst was removed using a 0.45 micron filter and washed with additional methanol. The filtrate was concentrated and the residue was purified by preparative TLC, eluting five times in 3% ethyl ether in dichloromethane. This yielded 15 mg of the title compound and 30 mg of (3S,5R,6S,7S)-6-(4-fluorophenyl)-3-(2-methoxy-5-(2-(trifluoromethyl)imidazol-1-yl)phenyl)-1-oxaspiro[4.4]nonane-7-carboxylic acid methyl ester.

Step B: (3R,5R,6S,7S)-6-(4-Fluorophenyl)-3-(2-methoxy-5-(2-(trifluoromethyl)imidazol-1-yl)phenyl)-1-oxaspiro[4.4]nonane-7-carboxylic acid methyl ester Triethylsilane (0.0062 mL, 4.5 mg, 0.039 mmol) was added to a solution of (5R,6S,7S)-6-(4-fluorophenyl)-3-(2-methoxy-5-(2-(trifluoromethyl)imidazol-1-yl)phenyl)-1-oxaspiro[4.4]non-2-ene-7-carboxylic acid methyl ester (6.8 mg, 0.013 mmol) in 0.204 mL of trifluoroacetic acid at RT. The mixture was stirred 1 h at RT, then overnight at 60° C. After removing the solvent under reduced pressure, the residue was dissolved in 3.0 mL of ethyl acetate, washed with 2.0 mL of saturated aqueous sodium bicarbonate, dried over sodium sulfate and evaporated. The crude product was purified by preparative TLC, eluting twice with 3% ethyl ether in dichloromethane, to give 1.0 mg of (3S,5R,6S,7S)-6-(4-fluorophenyl)-3-(2-methoxy-5-(2-(trifluoromethyl)imidazol-1-yl)phenyl)-1-oxaspiro[4.4]nonane-7-carboxylic acid methyl ester and 2.6 mg of the title compound. $^1$NMR (400 MHz, CDCl$_3$): δ 7.37 (dd, 2H, J=9, 6 Hz ), 7.19 (d, 1H, J=1 Hz), 7.15 (dd, 1H, J=9, 3 Hz ), 7.09 (d, 1H, J=2 Hz ), 7.08 (d, 1H, J=1 Hz ), 7.03 (t, 2H, J=9 Hz ), 6.82 (1H, J=9 Hz ), 3.78 (s, 3H), 3.70 (t, 1H, J=8 Hz ), 3.62 (t, 1H, J=8 Hz ), 3.56 (s, 3H), 3.14 (ddd, 1H, J=11, 10, 7 Hz ), 3.12 (d, 1H, J=11 Hz ), 2.87 (quintet, 1H, J=8 Hz ), 2.33–2.23 (m, 2H), 2.08–1.88 (m, 4H). Mass spectrum (ESI): m/z=519 (M+1).

EXAMPLE 225

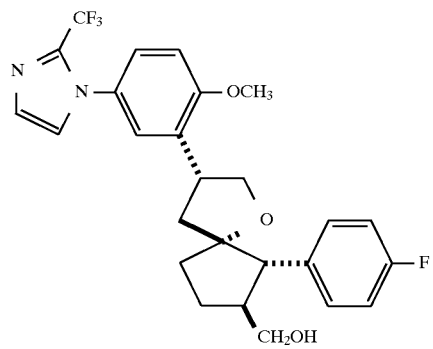

(3R,5R,6S,7S)-(6-(4-Fluorophenyl)-3-(2-methoxy-5-(2-trifuoromethylimidazol-1-yl)-phenyl)-1-oxaspiro [4.4]non-7-yl)methanol The title compound was prepared according to the procedure of Example 10, Step A, replacing methyl[3-(S),5-(R),6-(S),7-(S)]-6-(4-fluorophenyl)-3-(2-methoxy-5-((5-trifluoromethyl)tetrazol-1-yl)phenyl)-1-oxaspiro[4.4]nonane-7-carboxylate with (3R,5R,6S,7S)-6-(4-fluorophenyl)-3-(2-methoxy-5-(2-(trifluoromethyl)imidazol-1-yl)-phenyl)-1-oxaspiro[4.4]nonane-7-carboxylic acid methyl ester (from Example 224). $^1$NMR (400 MHz, CDCl$_3$): δ 7.37 (dd, 2H, J=9, 6 Hz ), 7.19 (d, 1H, J 1 Hz ), 7.14 (dd, 1H, J=9,2 Hz ), 7.10 (d, 1H, J=2 Hz ), 7.07 (d, 1H, J=Hz), 7.04 (t, 2H, J=9 Hz ), 6.82 (d, 1H, J=9 Hz ), 3.78 (s, 3H), 3.68 (t, 1H, J=8 Hz ), 3.61 (t, 1H, J=8 Hz ), 3.60 (dd, 1H, J=11, 4 Hz ), 3.48 (dd, 1H, J=11, 6 Hz ), 2.88 (quintet, 1H, J=8 Hz ), 2.71–2.61 (m, 1 H ), 2.60 (d, 1H, J=11 Hz ), 2.24 (dd, 1H, J=13, 7 Hz ), 2.16–1.98 (m, 3H), 1.89 (ddd, 1H, J=13, 10, 7 Hz ), 1.64–1.54 (m, 1H). Mass spectrum (NH3/CI): m/z=491 (M+1).

EXAMPLE 226

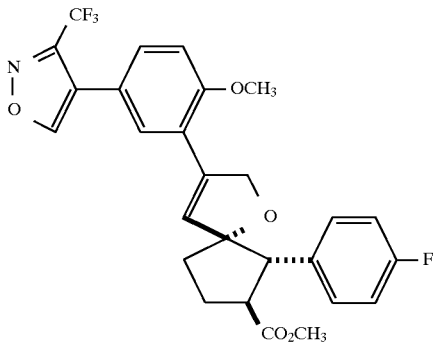

(5R,6S,7S)-6-(4-Fluorophenyl)-3-(2-methoxy-5-(3-(trifluoromethyl)isoxazol-4-yl)phenyl)-1-oxaspiro [4.4]non-3-ene-7-carboxylic acid methyl ester Step A: 4-(3-Bromo-4-methoxyphenyl)-3-trifluoromethyl) isoxazole Following the general procedure of K. Tanaka, H. Masuda and K. Mitsuhashi (Bull Chem. Soc. Jpn., 1984 57, 2184–2187) for the generation of trifluoroacetonitrile oxide, a solution of 0.440 mL (319 mg, 3.16 mmol) of triethylamine in 0.50 mL of toluene was added by syringe pump over 1.5 h to a solution of 304 mg (1.58 mmol) of trifluoroacetohydroximoyl bromide and 500 mg (2.06 mmol) of 2-bromo-1-methoxy-4-(2-methoxyvinyl)benzene (from Example 74, Step A) and in 5.5 mL of toluene. The mixture was then stirred at RT for additional 15 h. Hexane (25 mL) was added to the reaction mixture, and the resulting precipitate was collected on a filter. The filtrate was washed with 25 mL of water followed by 25 mL of brine, dried over sodium sulfate, and evaporated to provide the crude product. Purification by flash column chromatography, eluting with 2–5% $Et_2O$ in hexane gave 211 mg of a 1:1 mixture of 4-(3-bromo-4-methoxyphenyl)-5-methoxy-3-(trifluoromethyl)-4,5-dihydroisoxazole and 4-(3-bromo-4-methoxyphenyl)-3-(trifluoromethyl)isoxazole.

The mixture was dissolved in 15 mL of a 1:5 mixture of concentrated aqueous HCl and ethanol, and the solution was refluxed overnight. Additional concentrated aqueous HCl (3 mL) and ethanol (8 mL) were added and the mixture was refluxed for 6 h longer. After concentrating the reaction under reduced pressure, the residue was partitioned between 50 mL of ethyl acetate and 30 mL of saturated aqueous sodium bicarbonate. The aqueous layer was extracted with additional ethyl acetate (2×30 mL). The combined organic layers was washed with brine (50 mL), dried over sodium sulfate, and evaporated to provide 200 mg of yellow syrup. Purification by flash chromatography, eluting with 20% dichloromethane in hexane, gave 100 mg of the title compound.

Step B: (5R,6S,7S)-6-(4-Fluorophenyl)-3-(2-methoxy-5-(3-(trifluoromethyl)isoxazol-4-yl)phenyl)-1-oxaspiro[4.4]non-3-ene-7-carboxylic acid methyl ester The title compound was prepared according to the procedure of Example 6, Step F(d), replacing 2-bromo-4-(5-(trifluoromethyl)tetrazol-1-yl)anisole with 4-(3-bromo-4-methoxyphenyl)-3-(trifluoromethyl)isoxazole. $^1$NMR (400 MHz, $CDCl_3$): δ 8.52(s, 1H), 7.30–7.22 (m, 3H), 6.94–6.86 (m, 4H), 6.32 (s, 1H), 4.74 (dd, 1H, J=12, 2 Hz ), 4.06 (dd, 1H, J=12, 2 Hz ), 3.87 (s, 3H), 3.58 (s, 3H), 3.46 (dt, 1H, J=11, 9 Hz ), 3.31 (d, 1H, J=11 Hz), 2.42–2.22 (m, 2H), 2.14–1.94 (m, 2H). Mass spectrum (NH3/CI): m/z=518.1 (M+1).

EXAMPLE 227

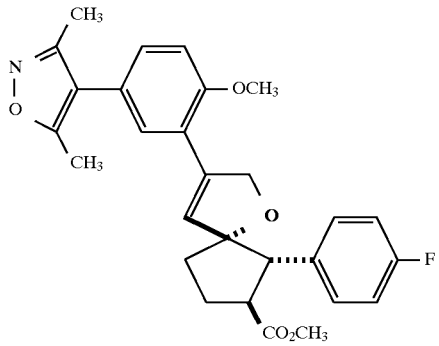

(5R,6S,7S)-6-(4-Fluorophenyl)-3-(2-methoxy-5-(3,5-dimethylisoxazol-4-yl)phenyl)-1-oxaspiro[4.4]non-3-ene-7-carboxylic acid methyl ester Step A: 1-(3-Bromo-4-methoxyphenyl)acetone A solution of 790 mg (2.90 mmol) of 1-(3-bromo-4-methoxyphenyl)-2-nitropropene (from Example 80, Step A) in 5.0 mL of toluene was combined with water (2.0 mL), iron powder (730 mg, 13.45 mmol), and ferric chloride (14.2 mg, 0.088 mmol) in a 25-mL three-neck round bottom flask fitted with a mechanical stirrer and reflux condenser. With vigorous agitation, the suspension was heated at 80° C., and 1.3 mL of conc. HCl was added over a period of 2 h via syringe. After the addition was completed, the heating and stirring were continued for an additional 30 min. After the reaction had cooled to RT, ethyl acetate (50 mL) was added to the solid was removed by filtration. The filtrate was washed with 20 mL of saturated aqueous sodium bicarbonate and the layers were separated. The aqueous layer was filtered again and the filtrate was extracted with 2×40 mL of ethyl acetate. The combined ethyl acetate extracts were washed with 50 mL of brine. Drying over sodium sulfate and concentration afforded a red oil which was purified by flash column chromatography, eluting with 30% dichloromethane in hexane followed by dichloromethane, to give 411 mg of the title compound as a yellow syrup.

Step B: 3-(3-Bromo-4-methoxyphenyl)pentane-2,4-dione

A mixture of 1-(3-bromo-4-methoxyphenyl)acetone (410 mg, 1.69 mmol), acetic anhydride (0.318 mL, 344 mg, 3.37 mmol), and p-toluenesulfonic acid (12.7 mg, 0.067 mmol) was stirred for 30 min. at RT. Boron trifluoride-acetic acid complex (0.275 mL, 372 mg, 2.92 mmol) was added and stirring was continued for 20 h. Sodium acetate trihydrate (919 mg, 6.76 mmol) in 1.7 mL of water was added and the mixture was refluxed for 3 h. Upon cooling, the reaction was partitioned between 50 mL of ethyl acetate and 30 mL of saturated aqueous sodium bicarbonate. The layers were separated and the organic layer was washed with 30 mL of brine. Drying over sodium sulfate and evaporation provided 450 mg of crude product. Purification by flash column chromatography, eluting with 10% ethyl ether in hexane, gave the 234 mg of the title compound as pale crystals. Mass spectrum (NH3/CI): m/z=285.0 (M+1).

Step C: 4-(3-Bromo-4-methoxyphenyl)-3,5-dimethylisoxazole

A mixture of 3-(3-bromo-4-methoxyphenyl)pentane-2,4-dione (40 mg, 0.14 mmol) and hydroxylamine hydrochloride (30 mg, 0.43 mmol) in 95% ethanol (0.50 mL) was refluxed for 4 h. After cooling to RT, the mixture was taken up in 30 mL of ether and washed with 10 mL of saturated sodium bicarbonate solution followed by 10 mL of brine. Drying over sodium sulfate and concentration afforded 40 mg of crude product which was purified by flash column chromatography, eluting with 50% dichloromethane in hexane, to yield 28 mg of the title compound as a white solid. Mass spectrum (NH3/CI): m/z=282 (M+1).

Step D: (5R,6S,7S)-6-(4-Fluorophenyl)-3-(2-methoxy-5-(3,5-dimethylisoxazol-4-yl)phenyl)-1-oxaspiro[4.4]non-3-ene-7-carboxylic acid methyl ester The title compound was prepared according to the procedure of Example 6, Step F(d), replacing 2-bromo-4-(5-(trifluoromethyl)tetrazol-1-yl)anisole with 4-(3-bromo-4-methoxyphenyl)-3,5-dimethylisoxazole. $^1$NMR (400 MHz, $CDCl_3$): δ 7.28 (dd, 2H, J=9, 6 Hz ), 7.08 (dd, 1H, J=9, 2 Hz ), 6.93 (d, 1H, J=9 Hz ), 6.89 (t, 2H, J=9 Hz ), 6.71 (d, 1H, J=2 Hz ), 6.31 (t, 1H, J=2 Hz), 4.74 (dd, 1H, J=12, 2 Hz ), 4.06 (dd, 1H, J=12, 2 Hz ), 3.87 (s, 3H), 3.59 (s, 3H), 3.47 (dt, 1H, J=12, 8 Hz ), 3.31 (d, 1H, J=12 Hz ), 2.41–2.22 (m, 2H), 2.33 (s, 3H), 2.19 (s, 3H), 2.15–1.92 (m, 2H). Mass spectrum (NH3/CI): m/z=478.1 (M+1).

EXAMPLE 228

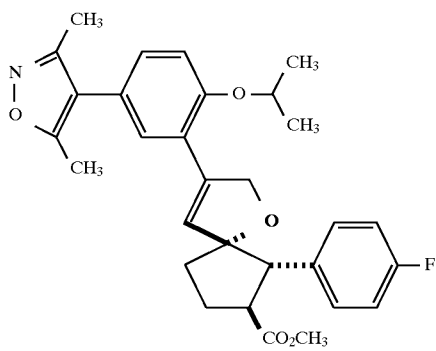

(5R,6S,7S)-6-(4-Fluorophenyl)-3-(2-isopropoxy-5-(3,5-dimethylisoaxol-4-yl)phenyl)-1-oxaspiro[4.4]non-3-ene-7-carboxylic acid methyl ester Step A: 3-Bromo-4-isopropoxybenzaldehyde 4-Isopropoxybenzaldehyde was brominated using conditions similar to those described for the bromination of p-anisaldehyde (see M. S. Gibson, G. W. Prenton, and J. M. Walthes, *J. Chem. Soc.* (C), 1970, 2234–2238).

Step B: 1-(3-Bromo-4-methoxyphenyl)-2-nitropropene

The title compound was prepared according to the procedure of Example 80, Step A, replacing 3-bromo-4-methoxybenzaldehyde with 3-bromo-4-isopropoxybenzaldehyde.

Step C: 1-(3-Bromo-4-isopropoxyphenyl)acetone

The title compound was prepared according to the procedure of Example 227, Step A, replacing 1-(3-bromo-4-methoxyphenyl)-2-nitropropene with 1-(4-isopropoxy-3-bromophenyl)-2-nitro-1-propene.

Step D: 3-(3-Bromo-4-isopropoxyphenyl)-1 3-pentane-2.4-dione

The title compound was prepared according to the procedure of Example 227, Step B, replacing 1-(3-bromo-4-methoxyphenyl)acetone with 1-(3-bromo-4-isopropoxyphenyl)acetone.

Step E: 4-(3-Bromo-4-isopropoxyphenyl)-3 5-dimethylisoxazole

The title compound was prepared according to the procedure of Example 227, Step C, replacing 3-(3-bromo-4-methoxyphenyl)pentane-2,4-dione with 3-(3-bromo-4-isopropoxyphenyl)-1,3-pentane-2,4-dione.

Step F: (5R,6S,7S)-6-(4-Fluorophenyl)-3-(2-isopropoxy-5-(3,5-dimethylisoxazol-4-yl)phenyl)-1-oxaspiro[4.4]non-3-ene-7-carboxylic acid methyl ester The title compound was prepared according to the procedure of Example 6, Step F(d), replacing 2-bromo-4-(5-(trifluoromethyltetrazo-1-yl)anisole with 4-(3-bromo-4-isopropoxyphenyl)-3,5-dimethylisoxazole. $^1$NMR (400 MHz, CDCl$_3$): δ 7.28 (dd, 2H, J=9, 6 Hz ), 7.04 (dd, 1H, J=9, 2 Hz ), 6.93–6.86 (m, 3H), 6.79 (d, 1H, J=2 Hz ), 6.24 (t, 1H, J=2 Hz ), 4.77 (dd, 1H, J=12, 2 Hz ), 4.58 (septet, 1H, J=6 Hz ), 4.12 (dd, 1H, J=12, 2 Hz ), 3.59 (s, 3H), 3.47 (ddd, 1H, J=12, 9, 8 Hz ), 3.30 (d, 1H, J=12 Hz ), 2.42–2.20 (m, 2H), 2.34 (s, 3H), 2.21 (s, 3H), 2.14–1.94 (m, 2H), 1.35 (d, 3H, J=6 Hz ), 1.33 (d, 3H, J=6 Hz ). Mass spectrum (NH3/Cl): m/z=506.2 (M+1).

EXAMPLE 229

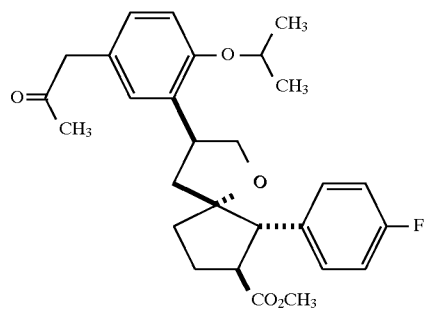

(3S,5R,6S,7S)-6-(4-Fluorophenyl)-3-(2-isopropoxy-5-(2-oxopropyl)phenyl)-1-oxaspiro[4.4]nonane-7-carboxylic acid methyl ester Step A: (5R,6S,7S)-6-(4-Fluorophenyl)-3-(2-isopropoxy-5-(2-oxopropyl)phenyl)-1-oxaspiro[4.4]non-3-ene-7-carboxylic acid methyl ester The title compound was prepared according to the procedure of Example 6, Step F(d), replacing 2-bromo-4-(5-(trifluoromethyl)tetrazol-1-yl)anisole with 1-(3-bromo-4-isopropoxyphenyl)acetone (from Example 228, Step C). Mass spectrum (NH3/CI): m/z=465 (M+1).

Step B: (3 S,5R,6S,7S)-6-(4-Fluorophenyl)-3-(2-isopropoxy-5-(2-oxopropyl)phenyl)-1-oxaspiro[4.4]nonane-7-carboxylic acid methyl ester The title compound was prepared according to the procedure of Example 6, Step G, replacing methyl[5-(RS),6-(SR),7-(SR)]-6-(4-fluorophenyl)-3-(2-methoxy-5-((5-trifluoromethyl)-tetrazol-1-yl)phenyl)-1-oxaspiro[4.4]non-3-ene-7-carboxylate with (5R,6S,7S)-6-(4-fluorophenyl)-3-(2-isopropoxy-5-(2-oxopropyl)phenyl)-1-oxaspiro[4.4]non-3-ene-7-carboxylic acid methyl. $^1$NMR (400 MHz, CDCl$_3$): δ 7.37 (dd, 2H, J=9, 6 Hz ), 7.00 (t, 2H, J=9 Hz ), 6.90 (dd, 1H, J=9, 2 Hz ), 6.72 (d, 1H, J=9 Hz ), 6.40 (d, 1H, J=2 Hz ), 4.45 (septet, 1H, J=6 Hz ), 4.10 (t, 1H, J=8 Hz ), 3.76–3.65 (m, 1H), 3.57 (s, 3H), 3.47 (s, 3H), 3.39–3.31 (m, 1H), 3.22 (d, 1H, J=11 Hz ), 3.04 (dd, 1H, J=9, 8 Hz ), 2.38–2.15 (m, 3H), 2.09 (s, 3H) 2.01–1.86 (m, 3H), 1.28 (d, 3H, J=6 Hz ), 1.25 (d, 3H, J=6 Hz ). Mass spectrum (EI): m/z=468 (M+).

EXAMPLE 230

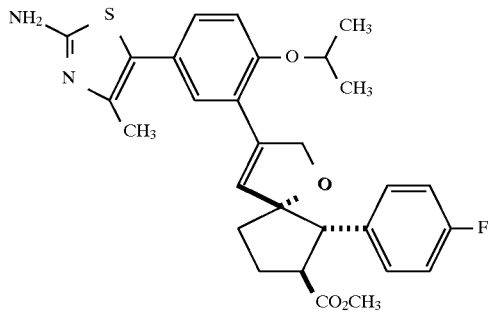

(5R,6S,7S)-6-(4-Fluorophenyl)-3-(2-isopropoxy-5-(2-amino-4-methylisoxazol-5-yl)phenyl)-1-oxaspiro[4.4]non-3-ene-7-carboxylic acid methyl ester Step A: 1-(3-Bromo-4-isopropoxyphenyl)-1-bromoacetone To a solution of 100 mg (0.369 mmol) of 1-(3-bromo-4-isopropoxyphenyl)acetone (from Example 228, Step C) in toluene (0.26 mL) was added bromine (0.019 mL, 0.369 mmol) dropwise via syringe. After stirring 30 min. At RT, a solution of sodium sulfite (676 mg) in water (1.5 mL)) was added and the mixture was extracted with 3×15 mL of ethyl ether. The combined organic layers were washed 20 mL of saturated sodium bicarbonate followed by 20 mL of brine. Drying over sodium sulfate and evaporation gave 119 mg of product as a red oil. Mass spectrum (NH3/CI): m/z=349 (M+1)

Step B: 2-Amino-5-(3-bromo-4-isopropoxyphenyl)-4-methylthiazole

Thiourea (65 mg, 0.857 in mol) was added to 1-(3-bromo-4-isopropoxyphenyl)-1-bromo acetone (200 mg, 0.571 mmol) in 0.5 mL of methanol and the mixture was heated to 40° C. The mixture was then heated to 80° C. And 1.0 mL of methanol was added to facilitate stirring. After refluxing 3 h, the reaction was transferred to a separatory funnel with 50 mL of ethyl acetate and 30 mL of saturate aqueous sodium bicarbonate, the layers were separated, and the organic layer was washed with 30 mL of brine. Drying over sodium sulfate and evaporation gave the crude product. Purification by flash chromatography, eluting with 30–50% ethyl acetate in hexane, gave 124 mg of the title compound as a white solid. Mass spectrum (NH3/CI): m/z=327 (M+1).

Step C: (5R,6S,7S)-6-(4-Fluorophenyl)-3-(2-isopropoxy-5-(2-amino-4-methylisoxazol-5-yl)phenyl)-1-oxaspiro[4.4]non-3-ene-7-carboxylic acid methyl ester The title compound was prepared according to the procedure of Example 6, Step F(d), replacing 2-bromo-4-(5-(trifluoromethyl)tetrazol-1-yl)anisole with 2-amino-5-(3-bromo-4-isopropoxyphenyl)-4-methylthiazole. ¹NMR (400 MHz, CDCl₃): δ 7.28 (dd, 2H, J=9, 6 Hz ), 7.15 (dd, 1H, J=9, 2 Hz ), 6.92 (d, 1H, J=2 Hz), 6.90 (t, 2H, J=9 Hz ), 6.84 (d, 1H, J=9 Hz ), 6.23 (t, 1H, J=2 Hz), 4.76 (dd, 1H, J=12, 2 Hz ), 4.56 (septet, 1H, J=6 Hz ), 4.12 (dd, H, J=12, 2 Hz ), 3.59 (s, 3H), 3.47 (ddd, 1H, J=12, 9, 8 Hz ), 3.30 (d, 1H, J=12 Hz ), 2.41–2.31 (m, 1H), 2.29–2.20 (m, 1H), 2.23 (s, 3H), 2.15–1.94 (m, 2H), 1.32 (d, 3H, J=6 Hz ), 1.30 (d, 3H, J=6 Hz ). Mass spectrum (NH3/CI): m/z=523.3 (M+1).

EXAMPLE 231

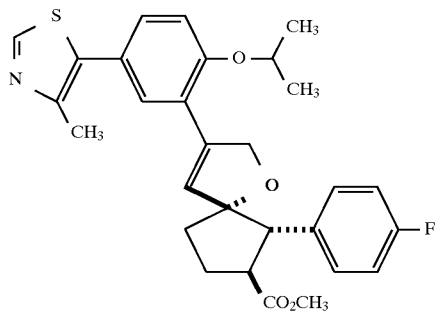

(5R,6S,7S)-6-(4-Fluorophenyl)-3-(2-isopropoxy-5-(4-methylthiazol-5-yl)phenyl)-1-oxaspiro[4.4]non-3-ene-7-carboxylic acid methyl ester Step A: 5-(3-Bromo-4-isopropoxyphenyl)-4-methylthiazole A solution of 118 mg (0.361 mmol) of 2-amino-5-(3-bromo-4-isopropoxyphenyl)-4-methylthiazole (from Example 230, Step B) in 3.6 mL of THF was added to a solution of 0.107 mL (93 mg, 0.80 mmol) of isoamyl nitrite in 2.4 mL of THF. The resulting solution was refluxed for 1 h. The cooled mixture was partitioned between 25 mL of dichloromethane and 10 mL of water, and the aqueous layer was extracted with 2×25 mL of dichloromethane. The combined organic layers were dried over sodium sulfate, decanted, and evaporated. The crude product was purified by flach column chromatography, eluting with 5% ethyl acetate in hexane, to give 51 mg of the title compound as a yellow solid. Mass spectrum (NH3/CI): m/z=312 (M+1).

Step B: (5R,6S,7S)-6-(4-Fluorophenyl)-3-(2-isopropoxy-5-(4-methylthiazol-5-yl)phenyl)-1-oxaspiro[4.4]non-3-ene-7-carboxylic acid methyl ester The title compound was prepared according to the procedure of Example 6, Step F(d), replacing 2-bromo-4-(5-(trifluoromethyl)tetrazol-1-yl)anisole with 5-(3-bromo-4-isopropoxyphenyl)-4-methylthiazole. ¹NMR (400 MHz, CDCl₃): δ 8.67 (s,1H),7.28(d,2H, J=9, 6 Hz ),7.23 (dd,1H, J=9,2 Hz ),7.00 (d, 1H, J=2 Hz ), 6.90 (t, 2H, J=9 Hz ), 6.89 (d, 1H, J=9 Hz ), 6.25 (t, H, J=2 Hz ), 4.77 (dd, 1H, J=12, 2 Hz ), 4.58 (septet, 1H, J=6 Hz ), 4.14 (dd, 1H, J=12, 2 Hz ), 3.59 (s, 3H), 3.47 (ddd, 1H, J=12, 9, 8 Hz), 3.30 (d, 1H, J=12 Hz ), 2.47 (s, 3H), 2.42–2.31 (M, 1H), 2.25 (ddd, 1H, J=14, 10, 7 Hz ), 2.10 (ddd, 1H, J=14, 9, 5 Hz ), 2.04–1.94 (m, 1H), 1.34 (d, [3H, J=6 Hz ), 1.32 (d, 3H, J=6 Hz ). Mass spectrum (ESI): m/z=508.3 (M+1).

EXAMPLE 232

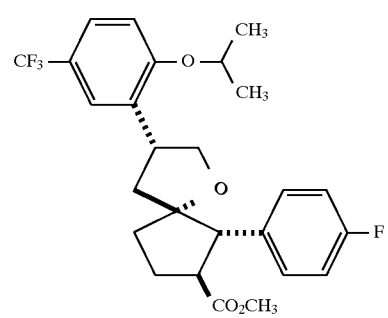

(3R,5R,6S,7S)-6-(4-Fluorophenyl)-3-(2-isopropoxy-5-(trifluoromethyl)phenyl)-1-oxaspiro[4.4]nonane-7-carboxylic acid methyl ester The title compound was prepared according to the procedure of Example 224, replacing (5R,6S,7S)-6-(4-fluorophenyl)-3-(2-methoxy-5-(2-(trifluoromethyl)imidazol-1-yl)phenyl)-1-oxaspiro[4.4]non-3-ene-7-carboxylic acid methyl ester with (5R,6S,7S)-6-(4-fluorophenyl)-3-(2-isopropoxy-5-(trifluoromethyl)phenyl)-1-oxaspiro[4.4]non-3-ene-7-carboxylic acid methyl ester (from Example 214). ¹NMR (400 MHz, CDCl₃): δ 7.40–7.35 (m, 3H), 7.29 (d, 1H, J=2 Hz ), 7.02 (t, 2H, J=9 Hz ), 6.78 (d, 1H, J=9 Hz ), 4.50 (septet, 1H, J=6 Hz ), 3.83 (t, 1H, J=8 Hz ), 3.59–3.53 (m, 1H), 3.56 (s, 3H), 3.35 (ddd, 1H, J=12, 10, 7 Hz ), 3.13 (d, 1H, J=12 Hz ), 2.78–2.68 (m, 1H), 2.37–2.26 (m, 1H), 2.23 (dd, 1H, J=12, 7 Hz ), 2.14 (dd, 1H, J=12,11 Hz ), 2.08 (t,2H, J=8 Hz ), 1.95 (ddd, 1H, J=14, 12, 7 Hz), 1.23 (d, 3H, J=6 Hz ), 1.22 (d, 3H, J=4 Hz ). Mass spectrum (NH3/CI): m/z=481.0 (M+1).

EXAMPLE 233

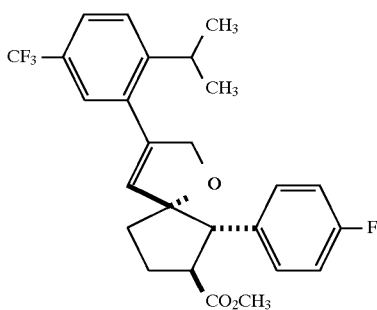

(5R,6S,7S)-6-(4-Fluorophenyl)-3-(2-isopropyl-5-(trifluoromethyl)phenyl)-1-oxaspiro[4.4]non-3-ene-7-carboxylic acid methyl ester Step A: 2-(4-(Trifluoromethyl)phenyl)-2-propanol Methylmagnesium bromide (10.5 mL, 1.4M in toluene/THF, 14.7 mmol) was added dropwise to a stirred solution of methyl 4-(trifluoromethyl)benzoate (1.5 g, 7.4 mmol) in THF (10.0 mL) at −45° C. The mixture was maintained at −45° C. for 30 min., then warmed up slowly to 0° C. in 1 h. The reaction was quenched with buffer solution (pH 7.0) and partitioned between 20 mL of water and 100 mL of ethyl acetate. The organic layer was then washed with 20 mL of brine, dried over sodium sulfate and concentrated to give 998 mg of the title compound. Mass spectrum (EI): m/z= 186.0 (M-18).

Step B: 4-Isopropyl-1-(trifluoromethyl)benzene 2-(4-(Trifluoromethyl)phenyl)-2-propanol (233 mg, 1.14 mmol), acetic acid (0.50 mL) and 20% palladium(II) hydroxide (120 mg) were combined in 2.0 mL of methanol and subjected to hydrogenation at 48 psi on a Parr shaker overnight. The mixture was centrifuged and the supernatant was filtered through 0.45 micron filter. The catalyst was washed with 3.0 mL of methanol followed by 2×3.0 mL of pentane. The combined filtrates were diluted with 20 mL of pentane and washed with 35 mL of saturated sodium bicarbonate. After extracting the aqueous layer with 2×20 mL of pentane, the combined organic layers were dried over sodium sulfate. The solvents were removed by distillation at atmospheric pressure to give the title compound.

Step C: 2-Bromo-1-isopropyl-4-(trifluoromethyl)benzene

Using the general conditions described by H. Eguchi, H. Kawaguchi, S. Yoshinaga, A. Nishida, T. Nishiguchi, and S. Fujisaki (*Bull. Chem. Soc. Jpn.*, 1994, 67, 1918–1921), 1,3-dibromo-5,5-dimethylhydantoin (454 mg, 3.18 mmol) was added in one portion to a solution of 4-isopropyl-1-(trifluoromethyl)benzene (500 mg, 2.65 mmol) and trifluoromethanesulfonic acid (0.281 mL, 3.18 mmol) in dichloromethane (5.0 mL). The mixture was stirred in the dark at RT for 3 h. Saturated aqueous sodium bisulfite was added to the reaction mixture until the brown organic layer was decolorized. The mixture was neutralized by the addition saturated aqueous sodium bicarbonate solution (100 mL). The organic layer was separated, dried over sodium sulfate, and evaporated. The crude material was filtered through a column packed with silica gel and eluted with hexane to isolate a mixture containing the title compound.

Step D: (5R,6S,7S)-6-(4-Fluorophenyl)-3-(2-isopropyl-5-(trifluoromethyl)phenyl)-1-oxaspiro[4.4]non-3-ene-7-carboxylic acid methyl ester The title compound was prepared according to the procedure of Example 6, Step F(d), replacing 2-bromo-4-(5-(trifluoromethyl)tetrazol-1-yl)anisole with 2-bromo-1-isopropyl-4-(trifluoromethyl)benzene. $^1$NMR (400 MHz, CDCl$_3$): δ 7.46 (dd, 1H, J=9, 2 Hz ), 7.35 (dd, 2H, J=9, 6 Hz ), 7.30 (d. 1H, J=9 Hz ), 7.13 (d, 1H, J=2 Hz ), 6.99 (t, 2H, J=9 Hz ), 5.58 (t, 1H, J=2 Hz ), 4.56 (dd, 1H, J=12, 2 Hz ), 4.07 (dd, 1H, J=12, 2 Hz ), 3.58 (s, 3H), 3.46 (ddd, 1H, J=12, 10, 8 Hz ), 3.28 (d, 1H, J=12 Hz ), 2.46–2.34 (m, 1H), 2.30 (septet, 1H, J=7 Hz ), 2.24 (ddd, 1H, J=14, 10, 7 Hz ), 2.15 (ddd, 1H, J=14, 9, 5 Hz ), 2.07–1.96 (m 1H), 1.03 (d, 3H, J=7 Hz ), 0.96 (d, 3H, J=7 Hz ). Mass spectrum (NH3/CI): m/z=463.1 (M+1).

EXAMPLE 234

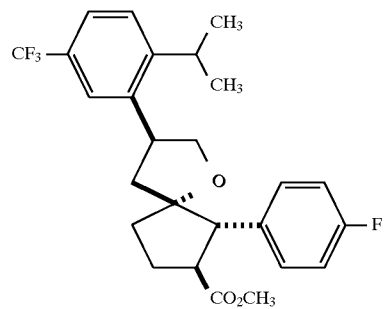

(3S,5R,6S,7S)-6-(4-Fluorophenyl)-3-(2-isopropyl-5-(trifluoromethyl)phenyl)-1-oxaspiro[4.4]nonane-7-carboxylic acid methyl ester The title compound was prepared according to the procedure of Example 6, Step G, replacing methyl[5-(RS), 6-(SR), 7-(SR)]-6-(4-fluorophenyl)-3-(2-methoxy-5-((5-trifluoromethyl)-tetrazol-1-yl)phenyl)-1-oxaspiro[4.4]non-3-ene-7-carboxylate with (5R,6S,7S)-6-(4-fluorophenyl)-3-(2-isopropyl-5-(trifluoromethyl)phenyl)-1-oxaspiro[4.4]non-3-ene-7-carboxylic acid methyl ester (from Example 233). $^1$NMR (400 MHz, CDCl$_3$): δ 7.38 (dd, 2H, J=9,6 Hz ), 7.34 (dd, 1H, J=8,2 Hz ),7.28(d, 1H, J=8 Hz ),7.05(t,2H, J=9 Hz ), 6.74 (s, 1H), 3.96 (t, 1H, J=8 Hz ), 3.74–3.64 (m 1H), 3.58 (s, 3H), 3.43–3.35 (m, 1H), 3.23 (d, 1H, J=11 Hz ), 3.19 (septet, 1H, J=7 Hz), 3.03 (t, 1H, J=9 Hz ), 2.59–2.18 (m, 3H), 2.04–1.93 (m, 3H), 1.21 (d, 3H, J=7 Hz ), 1.16 (d, 3H, J=7 Hz ). Mass spectrum (NH3/CI): m/z=465.1 (M+1).

EXAMPLE 235

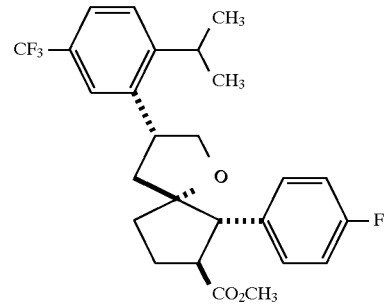

(3R,5R,6S,7S)-6-(4-Fluorophenyl)-3-(2-isopropyl-5-(trifluoromethyl)phenyl)-1-oxaspiro[4.4]nonane-7-carboxylic acid methyl ester The title compound was prepared according to the procedure of Example 224, replacing (5R,6S,7S)-6-(4-fluorophenyl)-3-(2-methoxy-5-(2-(trifluoromethyl)imidazol-1-yl)

phenyl)-1-oxaspiro[4.4]non-3-ene-7-carboxylic acid methyl ester with (5R,6S,7S)-6-(4-fluorophenyl)-3-(2-isopropyl-5-(trifluoromethyl)phenyl)-1-oxaspiro[4.4]non-3-ene-7-carboxylic acid methyl ester (from Example 233). $^1$NMR (400 MHz, CDCl$_3$): δ 7.42–7.36 (m, 4H), 7.26 (d, 1H, J=8 Hz ), 7.06 (t, 2H, J=9 Hz ), 3.74 (t, 1H, J=8 Hz ), 3.62 (dd, 1H, J=10, 8 Hz ), 3.57 (s, 3H), 3.38 (ddd, 1H, J=12, 10, 7 Hz ), 3.13 (d, 1 H, J=12 Hz ), 2.72–2.62 (m, 1H), 2.56 (septet, 1H, J=7 Hz ), 2.40–2.29 (m, 1H), 2.21 (dd, 1H, J=13, 7 Hz ), 2.17–2.06 (m, 3H), 2.03–1.93 (m, 1H), 1.05 (d, 3H, J=7 Hz ), 0.98 (d, 3H, J=7 Hz ). Mass spectrum (NH3/CI): m/z=465.0 (M+1).

EXAMPLE 236

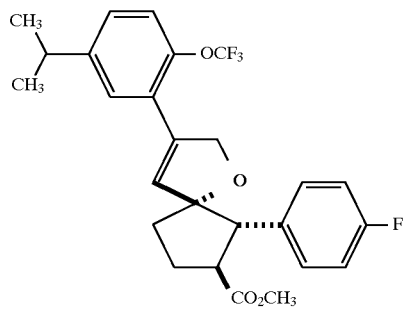

(5R,6S,7S)-6-(4-Fluorophenyl)-3-(2-(trifluoromethoxy)-5-isopropylphenyl)-1-oxaspiro[4.4]non-3-ene-7-carboxylic acid methyl ester Step A: S-Phenyl-O-(2-bromo-4-isopropylphenyl)-dithiocarbonate N-Methylmorpholine (0.433 mL, 399 mg, 3.94 mmol) and 500 mg (2.32 mmol) of 2-bromo-4-isopropylphenol (prepared by treatment of 4-isopropylphenol with bromine in acetic acid) were dissolved in 5.0 mL THF. Phenyl chlorodithioformate (0.321 mL, 427 mg, 2.26 mmol) was added dropwise. After 1 h the reaction was diluted with 100 mL of ethyl acetate and washed with 50 mL of saturated aqueous sodium bicarbonate, followed by 50 mL of brine. The organic layer was dried over sodium sulfate and concentrated to give the title compound. Mass spectrum (NH3/CI): m/z=367 (M+1).

Step B: 2-Bromo-4-isopropyl-1-(trifluoromethoxy)benzene

A suspension of 1,3-dibromo-5,5-dimethylhydantoin (2.63 g, 9.2 mmol) in dichloromethane (15 mL) was stirred and cooled in dry ice bath. Pyridinium poly(hydrogen fluoride) (4.9 mL, 70% HF) was added, followed by S-phenyl-O-(2-bromo-4-isopropylphenyl)dithiocarbonate (846 mg, 2.30 mmol) as a solution in dichloromethane (2.0 mL). The heterogeneous mixture was stirred 5 min. At –78° C., then warmed to 0° C. in an ice bath. The reaction rapidly became a red homogeneous solution. After 45 min., the mixture was diluted with 100 mL of dichloromethane and washed with 80 mL of water containing 10 g of sodium bisulfite. The aqueous layer was then extracted with 2×50 mL of dichloromethane and the combined organic layers was washed with 100 mL of saturated aqueous sodium bicarbonate followed by 100 mL of brine, dried over sodium sulfate, and concentrated. The residue was purified by flash column chromatography, eluting with of 2.5% ethyl ether in hexane to give 526 mg of the title compound as an amber oil. Mass spectrum (EI): m/z=282 (M$^+$).

Step C: (5R,6S,7S)-6-(4-Fluorophenyl)-3-(2-trifluoromethoxy-5-isopropyl)phenyl)-1-oxaspiro[4.4]non-3-ene-7-carboxylic acid methyl ester The title compound was prepared according to the procedure of Example 6, Step F(d), replacing 2-bromo-4-(5-(trifluoromethyl)tetrazol-1-yl)anisole with 2-bromo-4-isopropyl-1-(trifluoromethoxy)benzene. $^1$NMR (400 MHz, CDCl$_3$): δ 7.28 (dd, 2 H, J=9, 6 Hz ), 7.13 (bd, 1H, J=8 Hz ), 7.10 (dd, 1H, J=8, 2 Hz ), 6.70 (t, 2H, J=9 Hz ), 6.84 (d, 1H, J=2 Hz ), 6.15 (t, 1H, J=2 Hz ), 4.74 (dd, 1H, J=12, 2 Hz ), 4.11 (dd, 1H, J=12, 2 Hz ), 3.59 (s, 3H), 3.47 (ddd, 1H, J=12, 9, 8 Hz ), 3.32 (d, 1H, J=11 Hz ), 2.84 (septet, 1H, J=6 Hz ), 2.41–2.31 (m, 1H), 2.25 (ddd, 1H, J=14, 10, 7 Hz ), 2.09 (ddd, 1H, J=14, 9, 5 Hz ), 2.04–1.94 (m, 1H), 1.20 (d, 6H, J=6 Hz ). Mass spectrum (NH3/CI): m/z=479.1 (M+1).

EXAMPLE 237

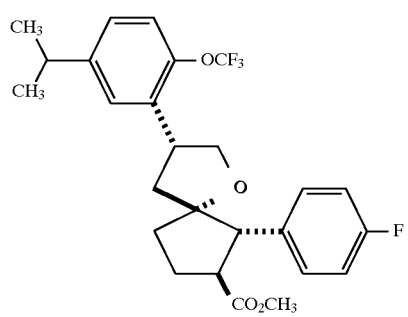

(3R,5R,6S,7S)-6-(4-Fluorophenyl)-3-(2-trifluoromethoxy-5-isopropyl)phenyl)-1-oxaspiro[4.4]nonane-7-carboxylic acid methyl ester The title compound was prepared according to the procedure of Example 224, replacing (5R,6S,7S)-6-(4-fluorophenyl)-3-(2-methoxy-5-(2-(trifluoromethyl)imidazol-1-yl)phenyl)-1-oxaspiro[4.4]non-3-ene-7-carboxylic acid methyl ester with (5R,6S,7S)-6-(4-fluorophenyl)-3-(2-trifluoromethoxy-5-isopropyl)phenyl)-1-oxaspiro[4.4]non-3-ene-7-carboxylic acid methyl ester (from Example 236). $^1$NMR (400 MHz, CDCl$_3$): δ 7.36 (dd, 2H, J=9, 6 Hz ), 7.07–6.98 (m, 5H), 3.76 (t, 1H, J=8 Hz ), 3.62 (t, 1H, J=8 Hz ), 3.56 (s, 3 H), 3.36 (ddd, 1H, J=12, 10, 8 Hz ), 3.10 (d, 1H, J=12 Hz ), 2.86 (septet, 1H, J=7 Hz ), 2.81–2.71 (m, 1H), 2.37–2.25 (m, 2H), 2.16– 1.91 (m, 4H), 1.21 (d, 6H, J=7 Hz ). Mass spectrum (NH3/CI): m/z=481.2 (M+1).

EXAMPLE 238

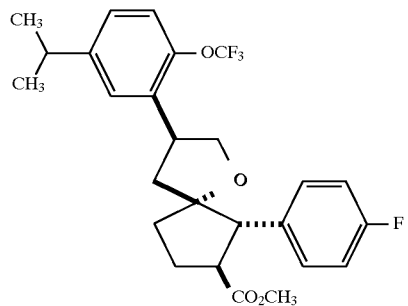

(3S,5R,6S,7S)-6-(4-Fluorophenyl)-3-(2-trifluoromethoxy-5-isopropyl)phenyl)-1-oxaspiro[4.4]nonane-7-carboxylic acid methyl ester The title compound was prepared according to the procedure of Example 6, Step G, replacing methyl[5-(RS),6-

(SR),7-(SR)]-6-(4-fluorophenyl)-3-(2-methoxy-5-((5-trifluoromethyl)-tetrazol-1-yl)phenyl)-1-oxaspiro[4.4]non-3-ene-7-carboxylate with (5R,6S,7S)-6-(4-fluorophenyl)-3-(2-trifluoromethoxy-5-isopropyl)phenyl)-1-oxaspiro[4.4]non-3-ene-7-carboxylic acid methyl ester (from Example 236). $^1$NMR (400 MHz, CDCl$_3$): δ 7.40 (dd, 2H, J=9, 6 Hz ), 7.05 (t, 2H, J=9 Hz ), 7.04 (d, 1H, J=9 Hz ), 6.98 (dd, 1H, J=9, 2 Hz ), 6.37 (d, 1H, J=2 Hz ), 4.01 (t, 1H, J=9 Hz ), 3.77–3.66 (m, 1H), 3.58 (s, 3H), 3.42–3.33 (m, 1H), 3.23 (d, 1H, J=11 Hz ), 3.08 (t, 1H, J=9 Hz ), 2.67 (septet, 1H, J=7 Hz ), 2.39–2.17 (m, 3H), 2.02–1.90 (m, 2H), 1.87 (dd, 1H, J=13, 11 Hz ), 1.09 (d, 3H, J=7 Hz ), 1.08 (d, 3H, J=7 Hz ). Mass spectrum (EI): m/z=480.7 (M+).

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula:

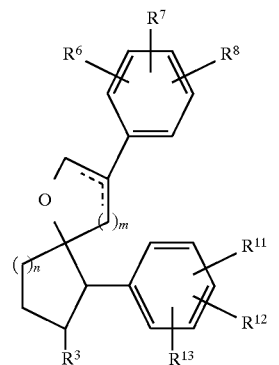

or a pharmaceutically acceptable salt thereof, wherein:
$R^3$ is selected from the group consisting of:
  (1) hydrogen,
  (2) $C_{1-8}$ alkyl,
  (3) —$R_4$, and
  (4) $C_{1-6}$ alkyl substituted with —$R^4$;
$R^4$ is selected from the group consisting of:
  (1) hydroxy,
  (2) $C_{1-6}$ alkoxy,
  (3) phenyl-$C_{1-3}$ alkoxy,
  (4) phenyl,
  (5) —CN,
  (6) halo, wherein halo is fluoro, chloro, bromo or iodo,
  (7) —NR$^9$R$^{10}$, wherein R$^9$ and R$^{10}$ are independently selected from:
    (a) hydrogen,
    (b) $C_{1-6}$ alkyl,
    (c) $C_{2-6}$ alkenyl,
    (d) $C_{2-6}$ alkoxy,
    (e) phenyl,
    (f) ($C_{1-6}$ alkyl)-phenyl,
    (g) ($C_{1-6}$ alkyl)-hydroxy,
    (h) ($C_{1-6}$ alkyl)-halo,
    (i) ($C_{1-6}$ alkyl)-poly-halo,
    (j) ($C_{1-6}$ alkyl)-CONR$^{11}$R$^{12}$, wherein R$^{11}$ and R$^{12}$ are independently selected from hydrogen and $C_{1-4}$ alkyl; and
    (k) ($C_{1-6}$ alkyl)-($C_{1-4}$ alkoxy),
    or R$^9$ and R$^{10}$ may be joined together to form a 3–8 membered heterocyclic ring which may contain another heterogroup selected from: —O—, —NH—, —N($C_{1-6}$ alkyl)-, and —S—,
  (8) —NR$^9$—COR$^{10}$,
  (9) —NR$^9$—CO$_2$R$^{10}$,
  (10) —CO—NR$^9$R$^{10}$,
  (11) —COR$^9$,
  (12) —CO$_2$R$^9$,
  (13) heterocycle, wherein the heterocycle is selected from the group consisting of:
    (A) tetrazolyl,
    (B) thiadiazolyl,
    (C) triazolyl,
    (D) azetidinyl,
    (E) dihydrotetrazolyl,
    (F) dihydrothiadiazolyl,
    (G) dihydrotriazolyl,
    (H) dihydroazetidinyl,
    (I) pyrrolidinyl, with the proviso that heterocycle is pyrrolidinyl only if one of R$^6$, R$^7$ or R$^8$ contains a heterocycle,
  and wherein the heterocycle is unsubstituted or substituted with one or more substituent(s) selected from:
    (i) $C_{1-6}$ alkyl, unsubstituted or substituted with halo, —CF$_3$, —OCH$_3$, or phenyl,
    (ii) $C_{1-6}$ alkoxy,
    (iii) oxo,
    (iv) hydroxy,
    (v) thioxo,
    (vi) —SR$^9$,
    (vii) halo,
    (viii) cyano,
    (ix) phenyl,
    (x) trifluoromethyl,
    (xi) —(CH$_2$)$_p$—NR$^9$R$^{10}$, wherein p is 0, 1, 2, 3 or 4,
    (xii) —NR$^9$COR$^{10}$,
    (xiii) —CONR$^9$R$^{10}$,
    (xiv) —CO$_2$R$^9$, and
    (xv) —(CH$_2$)$_p$—OR$^9$,
  (14) —CO-heterocycle, wherein heterocycle is as defined above,
  (15) —NR$^9$-heterocycle, wherein heterocycle is as defined above,
  (16) —NR$^9$—C$_{1-4}$ alkyl-heterocycle, wherein heterocycle is as defined above;
$R^6$, $R^7$ and $R^8$ are independently selected from the group consisting of:
  (1) hydrogen,
  (2) $C_{1-6}$alkoxy,
  (3) halo,
  (4) $C_{1-6}$ alkyl, unsubstituted or substituted with one or more of the substituents selected from:
    (a) hydroxy,
    (b) oxo, (c) $C_{1-6}$ alkoxy,
(d) phenyl-$C_{1-3}$ alkoxy,
(e) phenyl,
(f) —CN,
(g) halo,
(h) —$NR^9R^{10}$,
(i) —$NR^9$—$COR^{10}$,
(j) —$NR^9$—$CO_2R^{10}$,
(k) —CO—$NR^9R^{10}$,
(l) —$COR^9$,
(m) —$CO_2R^9$,
(n) heterocycle, wherein heterocycle is as defined above with the proviso that heterocycle is other than pyrrolidinyl,
(5) hydroxy,
(6) —CN,
(7) —$CF_3$,
(8) —$OCF_3$,
(9) —$OCF_2H$,
(10) —$OCFH_2$,
(11) —$NO_2$,
(12) —$SR^{14}$, wherein $R^{14}$ is hydrogen or $C_{1-6}$alkyl,
(13) —$SOR_{14}$,
(14) —$SO_2R^{14}$,
(15) —$NR^9$—$COR^{10}$,
(16) —CO—$NR^9$—$COR^{10}$,
(17) —$NR^9R^{10}$,
(18) —$NR^9$—$CO_2R^{10}$,
(19) —$COR^9$,
(20) —$CO_2R^9$,
(21) heterocycle, wherein heterocycle is as defined above with the proviso that heterocycle is other than pyrrolidinyl,
(22) —($C_{1-6}$alkyl)-heterocycle, wherein heterocycle is as defined above with the proviso that heterocycle is other than pyrrolidinyl,
(23) —N(heterocycle)-$SO_2R^{14}$, wherein heterocycle is as defined above with the proviso that heterocycle is other than pyrrolidinyl;
$R^{11}$, $R^{12}$ and $R^{13}$ are independently selected from:
(1) hydrogen,
(2) $C_{1-6}$ alkyl, unsubstituted or substituted with one or more of the substituents selected from:
(a) hydroxy,
(b) oxo,
(c) $C_{1-6}$ alkoxy,
(d) phenyl-$C_{1-3}$ alkoxy,
(e) phenyl,
(f) —CN,
(g) halo,
(h) —$NR^9R^{10}$,
(i) —$NR^9$—$COR^{10}$,
(j) —$NR^9$—$CO_2R^{10}$,
(k) —CO—$NR^9R^{10}$,
(l) —$COR^9$, and
(m) —$CO_2R^9$,
(3) halo,
(4) —CN,
(5) —$CF_3$,
(6) —$NO_2$,
(7) hydroxy,
(8) $C_{1-6}$alkoxy,
(9) —$COR^9$, and
(10) —$CO_2R^9$;
m is an integer selected from 1 or 2;
n is an integer selected from 0, 1 or 2;
each of the two dashed lines denotes the presence of a either a single or a double bond between the indicated carbon atoms, with the proviso that at least one of the dashed lines indicates the presence of a single bond.

2. The compound of claim 1, or a pharmaceutically acceptable salt thereof, wherein:
$R^3$ is selected from the group consisting of:
(1) —$R^4$, and
(2) $C_{1-6}$ alkyl substituted with —$R^4$;
$R^4$ is selected from the group consisting of:
(1) —$NR^9R^{10}$, wherein $R^9$ and $R^{10}$ are independently selected from:
(a) hydrogen,
(b) $C_{1-6}$ alkyl,
(c) ($C_{1-6}$ alkyl)-hydroxy, and
(d) ($C_{1-6}$ alkyl)-($C_{1-4}$ alkoxy),
(2) —CO—$NR^9R^{10}$,
(3) —$NR^9$—$COR^{10}$,
(4) heterocycle, wherein the heterocycle is selected from the group consisting of:
(A) tetrazolyl,
(B) thiadiazolyl,
(C) triazolyl,
(D) azetidinyl,
(E) dihydrotetrazolyl,
(F) dihydrothiadiazolyl,
(G) dihydrotriazolyl,
(H) dihydroazetidinyl,
(I) pyrrolidinyl
and wherein the heterocycle is unsubstituted or substituted with one or more substituent(s) selected from:
(i) $C_{1-6}$ alkyl, unsubstituted or substituted with halo, —$CF_3$, —$OCH_3$, or phenyl,
(ii) $C_{1-6}$ alkoxy,
(iii) oxo, and
(iv) hydroxy,
(5) —CO-heterocycle, wherein heterocycle is as defined above;
$R^6$, $R^7$ and $R^8$ are independently selected from the group consisting of:
(1) hydrogen,
(2) —$CF_3$,
(3) —$OCF_3$,
(4) —F,
(5) $C_{1-6}$alkyl,
(6) $C_{1-6}$alkoxy, and
(7) heterocycle, wherein heterocycle is as defined above with the proviso that heterocycle is other than pyrrolidinyl;
$R^{11}$, $R^{12}$ and $R^{13}$ are independently selected from:
(1) hydrogen, and
(2) fluoro;
m is an integer selected from 1 or 2;
n is an integer selected from 1 or 2;
the dashed line denotes the presence of a single or a double bond.

3. The compound of claim 1, or a pharmaceutically acceptable salt thereof, wherein $R^3$ is selected from the group consisting of:
(1) —$CH_2$—N($C_{1-6}$ alkyl)($C_{1-6}$ alkyl),
(2) —$CH_2$—NH($C_{1-6}$ alkyl),
(3) —$CH_2$—N($C_{1-6}$ alkyl)($CH_2CH_2$—F),
(4) —N($C_{1-6}$ alkyl)($C_{1-6}$ alkyl), and
(5) —NH($C_{1-6}$ alkyl).

4. The compound of claim 1, or a pharmaceutically acceptable salt thereof, wherein $R^3$ is selected from the group consisting of:

(1) —$R^4$, and (2) $C_{1-6}$ alkyl substituted with —$R^4$.

5. The compound of claim 1, or a pharmaceutically acceptable salt thereof,
wherein $R^3$ is —$R^4$ or $C_{1-6}$ alkyl substituted with —$R^4$, and $R^4$ is selected from the group consisting of:
  (1) —$NR^9R^{10}$, wherein $R^9$ and $R^{10}$ are independently selected from:
    (a) hydrogen,
    (b) $C_{1-6}$ alkyl,
    (c) ($C_{1-6}$ alkyl)-hydroxy, and
    (d) ($C_{1-6}$ alkyl)-halo,
  (2) —CO—$NR^9R^{10}$,
  (3) —$NR^9$—$COR^{10}$,
  (4) heterocycle, wherein the heterocycle is selected from the group consisting of:
    (A) tetrazolyl,
    (B) thiadiazolyl,
    (C) triazolyl,
    (D) azetidinyl,
    (E) dihydrotetrazolyl,
    (F) dihydrothiadiazolyl,
    (G) dihydrotriazolyl,
    (H) dihydroazetidinyl,
  and wherein the heterocycle is unsubstituted or substituted with one or more substituent(s) selected from:
    (i) $C_{1-6}$ alkyl, unsubstituted or substituted with halo, —$CF_3$, —$OCH_3$, or phenyl,
    (ii) $C_{1-6}$ alkoxy,
    (iii) oxo, and
    (iv) hydroxy,
  (5) —CO-heterocycle, wherein heterocycle is as defined above.

6. The compound of claim 1, or a pharmaceutically acceptable salt thereof, wherein $R^6$, $R^7$ and $R^8$ are independently selected from the group consisting of:
  (1) hydrogen,
  (2) —$CF_3$,
  (3) —$OCF_3$,
  (4) $C_{1-4}$alkoxy, and
  (5) heterocycle, wherein the heterocycle is tetrazolyl selected from the group consisting of:
    (A) tetrazolyl, and
    (B) triazolyl,
  and wherein the heterocycle is unsubstituted or substituted with one or more substituent(s) selected from:
    (i) $C_{1-4}$ alkyl,
    (ii) -cyclopropyl, and
    (iii) —$CF_3$.

7. The compound of claim 1, or a pharmaceutically acceptable salt thereof, wherein $R^6$, $R^7$ and $R^8$ are independently selected from the group consisting of:
  (1) 2-methoxy,
  (2) 2-trifluoromethoxy,
  (3) 5-trifluoromethoxy,
  (4) 2-isopropyl,
  (5) 2-chloro,
  (6) 2-isopropoxy,
  (7) 2-methylthio,
  (8) 5-(5-trifluoromethyl-tetrazol-1-yl), and
  (9) 5-(N-trifluoroacetyl)(N-methyl)amino.

8. The compound of claim 1, or a pharmaceutically acceptable salt thereof, wherein the phenyl ring bearing $R^6$, $R^7$ and $R^8$ is selected from:

3,5-bis(trifluoromethyl)phenyl,
2-methoxy-5-tetrazol-1-yl-phenyl,
2-methoxy-5-(5-methyl-tetrazol-1-yl)-phenyl,
2-methoxy-5-(5-ethyl-tetrazol-1-yl)-phenyl,
2-methoxy-5-(5-propyl-tetrazol-1-yl)-phenyl,
2-methoxy-5-(5-trifluoromethyl-tetrazol-1-yl)-phenyl,
2-methoxy-5-(5-cyclopropyl-tetrazol-1-yl)-phenyl,
2-methoxy-5-(5-methylsulfanyl-tetrazol-1-yl)-phenyl,
2-trifluoromethoxy-phenyl,
2-isopropyl-5-(5-trifluoromethyl-tetrazol-1-yl)-phenyl,
2-methoxy-5-trifluoromethoxy-phenyl, and
2-isopropyl-5-trifluoromethoxy-phenyl.

9. The compound of claim 1, or a pharmaceutically acceptable salt thereof, wherein $R^{11}$, $R^{12}$ and $R^{13}$ are independently selected from: hydrogen, and fluoro.

10. The compound of claim 1, or a pharmaceutically acceptable salt thereof, wherein m is 1 or 2 and n is 1.

11. The compound of claim 1, or a pharmaceutically acceptable salt thereof, wherein the phenyl ring bearing $R^{11}$, $R^{12}$ and $R^{13}$ is unsubstituted phenyl or is para-fluorophenyl.

12. A compound which is selected from the group consisting of:
methyl[3-(S),5-(R),6-(S),7-(S)]-6-(4-fluorophenyl)-3-(2-methoxy-5-((5-trifluoromethyl)tetrazol-1-yl)phenyl)-1-oxaspiro[4.4)nonane-7-carboxylate;
[3-(S),5-(R),6-(S),7-(S)]-7-(1-(pyrrolidinyl)methyl)-6-(4-fluorophenyl)-3-(2-methoxy-5-((5-trifluoromethyl)tetrazol-1-yl)phenyl)-1-oxaspiro[4.4]nonane;
(3S,5R,6S,7S)-6-(4-fluorophenyl)-7-(pyrrolidin-1-yl)methyl-3-(2-methyl-3-fluoro-5-(5-trifluoromethyltetrazo-1-yl)phenyl)-1-oxaspiro[4.4]nonane;
(5R,6S,7S)-6-(4fluorophenyl)-3-[2-methoxy-5-(N-methyl-N-acetylamino)phenyl]-1-oxaspiro[4.4]non-3-ene-7-carboxylic acid methyl ester;
(5R,6S,7S)-6-(4-fluorophenyl)-3-(2-methoxy-5-(N-methyl-N-trifluoroacetylamino)phenyl]-1-oxaspiro[4.4]non-3-ene-7-carboxylic acid methyl ester;
(5R,6S,7S)-6-(4-fluorophenyl)-3-[2-methoxy-5-(N-ethyl-N-acetylamino)phenyl]-1-oxaspiro[4.4]non-3-ene-7-carboxylic acid methyl ester;
(3S,5R,6S,7S)-6-(4-fluorophenyl)-3-[2-methoxy-5-(N-methyl-N-acetylamino)phenyl]-1-oxaspiro[4.4]nonane-7-carboxylic acid methyl ester;
(3S,5R,6S,7S)-6-(4-fluorophenyl)-3-[2-methoxy-5-(N-methyl-N-trifluoroacetylamino)phenyl]-1-oxaspiro[4.4]nonane-7-carboxylic acid methyl ester;
(3S,5R,6S,7S)-6-(4-fluorophenyl)-3-[2-methoxy-5-(N,N-dimethylamino)phenyl]-1-oxaspiro[4.4]nonane-7-carboxylic acid methyl ester;
(3S,5R,6S,7S)-6-(4-fluorophenyl)-3-(5-cyano-2-isopropoxy-phenyl)-1-oxaspiro[4.4]nonane-7-carboxylic acid methyl ester;
(5R,6S,7S)-6-phenyl-3-(2-methoxy-5-(trifluoromethoxy)phenyl)-7-(hydroxymethyl)-1-oxaspiro[5.4]dec-3-ene;
(5R,6S,7S)-6-(4-fluorophenyl)-3-(2-methoxy-5-fluoro)phenyl-1-oxaspiro[5.4]non-3-ene-7-carboxylic acid methyl ester;
(5R,6S,7S)-6-(4-fluorophenyl)-3-(2-isopropoxy-5-fluoro)phenyl-1-oxaspiro[5.4]non-3-ene-7-carboxylic acid methyl ester;
(5R,6S,7S)-6-(4-fluorophenyl)-3-(2-isopropyl-5-(N-trifluoroacetyl-N-methyl)amino)phenyl-1-oxaspiro[5.4]non-3-ene-7-carboxylic acid methyl ester;
(5R,6S,7S)-6-(4-fluorophenyl)-3-(2-isopropyl-5-(5-(trifluoromethyl)tetrazol-1-yl)phenyl-1-oxaspiro[5.4]non-3-ene-7-carboxylic acid methyl ester;

(3S,5R,6S,7S)-6-(4-fluorophenyl)-3-(2-methoxy-5-(N-(dimethylaminosulfonyl)-N-methyl)amino)phenyl-1-oxaspiro[5.4]nonane-7-carboxylic acid methyl ester;

(5R,6S,7S)-6-(4-fluorophenyl)-3-(2-methoxy-5-(dimethylaminocarbonyl))-phenyl-1-oxaspiro[5.4]non-3-ene-7-carboxylic acid methyl ester;

(5R,6S,7S)-6-(4-fluorophenyl)-3-(2-trifluoromethoxy-5-(N-(methanesulfonyl)-N-methyl)amino)phenyl-1-oxaspiro[5.4]non-3-ene-7-carboxylic acid methyl ester;

(3S,5R,6S,7S)-6-(4-fluorophenyl)-3-(2-methoxy-5-fluoro)phenyl-1-oxaspiro[5.4]nonane-7-carboxylic acid methyl ester;

(3S,5R,6S,7S)-6-(4-fluorophenyl)-3-(2-isopropoxy-5-fluoro)phenyl-1-oxaspiro[5.4]nonane-7-carboxylic acid methyl ester;

(3S,5R,6S,7S)-6-(4-fluorophenyl)-3-(2-methoxy-5-(N-(methanesulfonyl)-N-methyl)amino)phenyl-1-oxaspiro[5.4]nonane-7-carboxylic acid methyl ester;

(3S,5R,6S,7S)-6-(4-fluorophenyl)-3-(2-isopropyl-5-(N-trifluoroacetyl-N-methyl)amino)phenyl-1-oxaspiro[5.4]nonane-7-carboxylic acid methyl ester;

(3S,5R,6S,7S)-6-(4-fluorophenyl)-3-(2-isopropyl-5-(5-(trifluoromethyl)tetrazol-1-yl)phenyl-1-oxaspiro[5.4]nonane-7-carboxylic acid methyl ester;

(3S,5R,6S,7S)-6-(4-fluorophenyl)-3-(2-methoxy-5-(dimethylaminocarbonyl))phenyl-1-oxaspiro[5.4]nonane-7-carboxylic acid methyl ester;

(3S,5R,6S,7S)-6-(4-fluorophenyl)-3-(2-trifluoromethoxy-5-(N-(methanesulfonyl)-N-methyl)amino)phenyl-1-oxaspiro[5.4]nonane-7-carboxylic acid methyl ester;

(5R,6S,7S)-6-(4-fluorophenyl)-3-(2-isopropoxy-5-fluoro)phenyl-7-(hydroxymethyl)-1-oxaspiro[5.4]non-3-ene;

(5R,6S,7S)-6-(4-fluorophenyl)-3-(2-isopropyl-5-(5-(trifluoromethyl)tetrazol-1-yl)phenyl-7-(hydroxymethyl)-1-oxaspiro[5.4]non-3-ene;

(5R,6S,7S)-6-(4-fluorophenyl)-3-(2-isopropoxy-5-chloro)phenyl-7-(hydroxymethyl)-1-oxaspiro[5.4]non-3-ene;

(5R,6S,7S)-6-(4-fluorophenyl)-3-(2,5-dichloro)phenyl-7-(hydroxymethyl)-1-oxaspiro[5.4]non-3-ene;

(5R,6S,7S)-6-(4-fluorophenyl)-3-(2-fluoro-5-trifluoromethyl)phenyl-7-(hydroxymethyl)-1-oxaspiro[5.4]non-3-ene;

(5R,6S,7S)-6-(4-fluorophenyl)-3-(2-isopropoxy-5-isopropyl)phenyl-7-(hydroxymethyl)-1-oxaspiro[5.4]non-3-ene;

(5R,6S,7S)-6-(4-fluorophenyl)-3-(2-methyl-5-chloro)phenyl-7-(hydroxymethyl)-1-oxaspiro[5.4]non-3-ene;

(5R,6S,7S)-6-(4-fluorophenyl)-3-(2-isopropoxy-5-methyl)phenyl-7-(hydroxymethyl)-1-oxaspiro[5.4]non-3-ene;

(5R,6S,7S)-6-(4-fluorophenyl)-3-(2-chloro-5-methyl)phenyl-7-(hydroxymethyl)-1-oxaspiro[5.4]non-3-ene;

(5R,6S,7S)-6-(4-fluorophenyl)-3-(2-methoxy-5-methyl)phenyl-7-(hydroxymethyl)-1-oxaspiro[5.4]non-3-ene;

(5R,6S,7S)-6-(4-fluorophenyl)-3-(2-cyclopropylmethyl-5-fluoro)phenyl-7-(hydroxymethyl)-1-oxaspiro[5.4]non-3-ene;

(5R,6S,7S)-6-(4-fluorophenyl)-3-(2-isopropyl-5-methyl)phenyl-7-(hydroxymethyl)-1-oxaspiro[5.4]non-3-ene;

(5R,6S,7S )-6-(4-fluorophenyl)-3-(2-methoxy-5-isopropyl)phenyl-7-(hydroxymethyl)-1-oxaspiro[5.4]non-3-ene;

(5R,6S,7S)-6-(4-fluorophenyl)-3-(2-fluoro-5-methyl)phenyl-7-(hydroxymethyl)-1-oxaspiro[5.4]non-3-ene;

(5R,6S,7S)-6-(4-fluorophenyl)-3-(2-cyclobutyloxy-5-fluoro)phenyl-7-(hydroxymethyl)-1-oxaspiro[5.4]non-3-ene;

(5R,6S,7S)-6-(4-fluorophenyl)-3-(2-methoxy-5-((N,N-dimethylamino)carbonylmethyl)phenyl-7-(hydroxymethyl)-1-oxaspiro[5.4]non-3-ene;

(5R,6S,7S)-6-(4-fluorophenyl)-3-(2-trifluoromethoxy-5-(N-(methanesulfonyl)-N-methylamino)phenyl-7-(hydroxymethyl)-1-oxaspiro[5.4]non-3-ene;

(5R,6S,7S)-6-(4-fluorophenyl)-3-(2-isopropyl-5-(5-(trifluoromethyl)tetrazol-1-yl)phenyl-7-(N,N-dimethylaminomethyl)-1-oxaspiro[5.4]non-3-ene;

(5R,6S,7S)-6-(4-fluorophenyl)-3-(2-isopropyl-5-(5-(trifluoromethyl)tetrazol-1-yl)phenyl-7-(pyrrolidin-1-ylmethyl)-1-oxaspiro[5.4]non-3-ene;

(5R,6S,7S)-6-(4-fluorophenyl)-3-(2-isopropyl-5-(5-(trifluoromethyl)tetrazol-1-yl)phenyl-7-(N-(2-fluoroethyl)aminomethyl)-1-oxaspiro[5.4]non-3-ene;

(5R,6S,7S)-6-(4-fluorophenyl)-3-(2-isopropyl-5-(5-(trifluoromethyl)tetrazol-1-yl)phenyl-7-(N-cyclopropylaminomethyl)-1-oxaspiro[5.4]non-3-ene;

(3S,5R,6S,7S)-6-(4-fluorophenyl)-3-(2-isopropyl-5-(5-(trifluoromethyl)tetrazol-1-yl)phenyl-7-(hydroxymethyl)-1-oxaspiro[5.4]nonane;

(3S,5R,6S,7S)-6-(4-fluorophenyl)-3-(2-isopropoxy-5-fluoro)phenyl-7-(hydroxymethyl)-1-oxaspiro[5.4]nonane;

(3S,5R,6S,7S)-6-(4-fluorophenyl)-3-(2-isopropoxy)phenyl-7-(hydroxymethyl)-1-oxaspiro[5.4]nonane;

(3S,5R,6S,7S)-6-(4-fluorophenyl)-3-phenyl-7-(hydroxymethyl)-1-oxaspiro[5.4]nonane;

(3S,5R,6S,7S)-6-(4-fluorophenyl)-3-(2-fluoro-5-trifluoromethyl)-phenyl-7-(hydroxymethyl)-1-oxaspiro[5.4]nonane;

(3S,5R,6S,7S)-6-(4-fluorophenyl1)-3-(2-isoproxy-5-isopropyl)phenyl-7-(hydroxymethyl)-1-oxaspiro[5.4]nonane;

(3S,5R,6S,7S)-6-(4-fluorophenyl)-3-(2-methoxy-5-(N-(2,2,2-trifluoroethyl)-N-isopropyl)amino)phenyl-7-(hydroxymethyl)-1-oxaspiro[5.4]nonane;

(3S,5R,6S,7S)-6-(4-fluorophenyl)-3-(2-trifluoromethoxy-5-(N-(methanesulfonyl)-N-methyl)amino)phenyl-7-(hydroxymethyl)-1-oxaspiro[5.4]nonane;

(3S,5R,6S,7S)-6-(4-fluorophenyl)-3-(2-isopropoxy-5-methyl)phenyl-7-(hydroxymethyl)-1-oxaspiro[5.4]nonane;

(3S,5R,6S,7S)-6-(4-fluorophenyl)-3-(3-methyl)phenyl-7-(hydroxymethyl)-1-oxaspiro[5.4]nonane;

(3S,5R,6S,7S)-6-(4-fluorophenyl)-3-(2-methyl)phenyl-7-(hydroxymethyl)-1-oxaspiro[5.4]nonane;

(3S,5R,6S,7S)-6-(4-fluorophenyl)-3-(2-methoxy-5-methyl)phenyl-7-(hydroxymethyl)-1-oxaspiro[5.4]nonane;

(3S,5R,6S,7S)-6-(4-fluorophenyl)-3-(2-cyclopropylmethyl-5-fluoro)phenyl-7-(hydroxymethyl)-1-oxaspiro[5.4]nonane;

(3S,5R,6S,7S)-6-(4-fluorophenyl)-3-(2-isopropyl-5-methyl)phenyl-7-(hydroxymethyl)-1-oxaspiro[5.4]nonane;

(3S,5R,6S,7S)-6-(4-fluorophenyl)-3-(2-fluoro5-methyl)phenyl-7-(hydroxymethyl)-1-oxaspiro[5.4]nonane;

(3S,5R,6S,7S)-6-(4-fluorophenyl)-3-(2-methoxy-5-isopropyl)phenyl-7-(hydroxymethyl)-1-oxaspiro[5.4]nonane;

(3S,5R,6S,7S)-6-(4-fluorophenyl)-3-(2-cyclobutyloxy-5-fluoro)phenyl-7-(hydroxymethyl)-1-oxaspiro[5.4]nonane;

(3S,5R,6S,7S)-6-(4-fluorophenyl)-3-(2-methoxy-5-((N,N-dimethylamino)carbonylmethyl)phenyl-7-(hydroxymethyl)-1-oxaspiro[5.4]nonane;

(3S,5R,6S,7S)-6-(4-fluorophenyl)-3-(2-isopropyl-5-(5-(trifluoromethyl)tetrazol-1-yl)phenyl-7-(aminomethyl)-1-oxaspiro[5.4]nonane;

(3S,5R,6S,7S)-6-(4-fluorophenyl)-3-(2-isopropoxy-5-fluoro)phenyl-7-(N,N-dimethylaminomethyl)-1-oxaspiro[5.4]nonane;

(3S,5R,6S,7S)-6-(4-fluorophenyl)-3-(2-isopropoxy-5-fluoro)phenyl-7-(pyrrolidin-1-ylmethyl)-1-oxaspiro[5.4]nonane;

(3S,5R,6S,7S)-6-(4-fluorophenyl)-3-(2-isopropoxy-5-fluoro)phenyl-7-(N-(2,2,2-trifluoroethyl)aminomethyl)-1-oxaspiro[5.4]nonane;

(3S,5R,6S,7S)-6-(4-fluorophenyl)-3-(2-isopropoxy-5-fluoro)phenyl-7-(N-(2,2,2-trifluoroethyl)-N-methylaminomethyl)-1-oxaspiro[5.4]nonane;

(3S,5R,6S,7S)-6-(4-fluorophenyl)-3-(2-isopropoxy-5-fluoro)phenyl-7-(N-(cyclopropyl)aminomethyl)-1-oxaspiro[5.4]nonane;

(3S,5R,6S,7S)-6-(4-fluorophenyl)-3-(2-isopropoxy-5-fluoro)phenyl-7-(N-(cyclopropyl)-N-methylaminomethyl)-1-oxaspiro[5.4]nonane;

(3S,5R,6S,7S)-6-(4-fluorophenyl)-3-(2-isopropoxy-5-fluoro)phenyl-7-(2-(fluoroethyl)aminomethyl)-1-oxaspiro[5.4]nonane;

(5R,6S,7S)-6-(4-fluorophenyl)-3-(5-cyano-2-isopropoxy-phenyl)-1-oxaspiro[4.4]non-3-ene-7-methanol;

(5R,6S,7S)-7-(dimethylamino)-6-(4-fluorophenyl)-3-(5-cyano-2-isopropoxy-phenyl)-1-oxaspiro[4.4]non-3-ene;

(3S,5R,6S,7S)-6-(4-fluorophenyl)-3-(2-methylthio-5-(5-(trifluoromethyl)tetrazol-1-yl)phenyl)-1-oxaspiro[4.4]non-3-ene-7-methanol;

(3S,5R,6S,7S)-6-(4-fluorophenyl)-3-(2-methylthio-5-(5-(trifluoromethyl)tetrazol-1-yl)phenyl)-1-oxaspiro[4.4]nonane-7-methanol;

(3R,5R,6S,7S)-6-(4-fluorophenyl)-3-(2-methylthio-5-(5-(trifluoromethyl)tetrazol-1-yl)phenyl)-1-oxaspiro[4.4]nonane-7-carboxylic acid methyl ester;

(3S,5R,6S,7S)-6-(4-fluorophenyl)-3-(2-methylthio-5-(5-(trifluoromethyl)tetrazol-1-yl)phenyl)-1-oxaspiro[4.4]nonane-7-carboxylic acid methyl ester;

(3S,5R,6S,7S)-6-(4-fluorophenyl)-3-(2-methylthio-5-(5-(trifluoromethyl)tetrazol-1-yl)phenyl)-1-oxaspiro[4.4]non-3-ene-7-carboxylic acid methyl ester;

(3S,5R,6S,7S)-6-(4-fluorophenyl)-3-(2-methylthio-5-(5-(trifluoromethyl)tetrazol-1-yl)phenyl)-1-oxaspiro[4.4]non-3-ene-7-carboxylic acid methyl ester;

(3S,5R,6S,7S)-6-(4-fluorophenyl)-3-(2-methylthio-5-(5-(trifluoromethyl)tetrazol-1-yl)phenyl)-1-oxaspiro[4.4]non-4-ene-7-carboxylic acid methyl ester;

(3S,5R,6S,7S )-6-(4-fluorophenyl)-3-(2-isopropylthio-5-(5-(trifluoromethyl)tetrazol-1-yl)phenyl)-1-oxaspiro[4.4]nonane-7-carboxylic acid methyl ester;

methyl[3-(S),5-(R),6-(S),7-(S)]-6-(4-fluorophenyl)-3-(2-methoxy-5-((5-trifluoromethyl)tetrazol-1-yl)phenyl)-1-oxaspiro4.4]nonane-7-ylmethyl)methylamine;

(5R,6S,7S)-6-(4-fluorophenyl)-3-(2-methoxy-5-(2-(trifluoromethyl)triazol-1-yl)phenyl)-1-oxaspiro[4.4]non-3-ene-7-carboxylic acid methyl ester;

(5R,6S,7S)-6-(4-fluorophenyl)-3-(2-methoxy-5-(2-(trifluoromethyl)triazol-1-yl)phenyl)-1-oxaspiro[4.4]nonane-hydroxymethyl;

(5R,6S,7S)-6-(4-fluorophenyl)-3-(2-methoxy-5-(triazol-1-yl)phenyl)-1-oxaspiro[4.4]nonane-7-hydroxymethyl;

(5R,6S,7S)-6-(4-fluorophenyl)-3-(2-(N,N-dimethylamino)-5-(2-(trifluoromethyl)tetrazol-1-yl)phenyl)-1-oxaspiro[4.4]non-3-ene-7-carboxylic acid methyl ester;

(5R,6S,7S)-6-(4-fluorophenyl)-3-(2-isopropoxy-5-(2-(trifluoromethyl)tetrazol-1-yl)phenyl)-1-oxaspiro[4.4]non-3-ene-7-carboxylic acid methyl ester;

(5R,6S,7S)-6-(4-fluorophenyl)-3-(2-methoxy-5-(2-(methyl)triazol-1-yl)phenyl)-1-oxaspiro[4.4]non-3-ene-7-carboxylic acid methyl ester;

(5R,6S,7S)-6-(4-fluorophenyl)-3-(2-(N,N-dimethylamino)-5-(2-(trifluoromethyl)tetrazol-1-yl)phenyl)-1-oxaspiro[4.4]nonane-7-carboxylic acid methyl ester;

(5R,6S,7S)-6-(4-fluorophenyl)-3-(2-isopropoxy-5-(2-(trifluoromethyl)tetrazol-1-yl)phenyl)-1-oxaspiro[4.4]nonane-7-carboxylic acid methyl ester;

(5R,6S,7S)-6-(4-fluorophenyl)-3-(2-methoxy-5-(2-(methyl)triazol-1-yl)phenyl)-1-oxaspiro[4.4]nonane-7-carboxylic acid methyl ester;

(5R,6S,7S)-6-(4-fluorophenyl)-3-(2-methoxycarbonyl-5-(triazol-1-yl)phenyl)-1-oxaspiro[4.4]non-3-ene-7-carboxylic acid methyl ester;

(5R,6S,7S)-6-(4-fluorophenyl)-3-(2-methoxycarbonyl-5-(2-(trifluoromethyl)tetrazol-1-yl)phenyl)-1-oxaspiro[4.4]non-3-ene-7-carboxylic acid methyl ester;

(5R,6S,7S)-6-(4-fluorophenyl)-3-(2-cyclopentoxy-5-(2-(trifluoromethyl)tetrazol-1-yl)phenyl)-1-oxaspiro[4.4]non-3-ene-7-carboxylic acid methyl ester;

(5R,6S,7S)-6-(4-fluorophenyl)-3-(2-methoxycarbonyl-5-(triazol-1-yl)phenyl)-1-oxaspiro[4.4]nonane-7-carboxylic acid methyl ester;

(5R,6S,7S)-6-(4-fluorophenyl)-3-(2-methoxycarbonyl-5-(2-(trifluoromethyl)tetrazol-1-yl)phenyl)-1-oxaspiro[4.4]nonane-7-carboxylic acid methyl ester;

(5R,6S,7S)-6-(4-fluorophenyl)-3-(2-cyclopentoxy-5-(2-(trifuoromethyl)tetrazol-1-yl)phenyl)-1-oxaspiro[4.4]nonane-7-carboxylic acid methyl ester;

(5R,6S,7S)-6-(4-fluorophenyl)-3-(2-methoxy-5-(2-(trifluoromethyl)triazol-1-yl)phenyl)-1-oxaspiro[4.4]non-3-ene-7-hydroxymethyl;

(5R,6S,7S)-6-(4-fluorophenyl)-3-(2-methoxy-5-(2-(trifluoromethyl)triazol-1-yl)phenyl)-1-oxaspiro[4.4]nonane-7-ylmethyl)(1-fluoroethyl)amine;

(5R,6S,7S)-6-(4-fluorophenyl)-3-(2-isopropoxy-5-(2-(trifluoro-methyl)tetrazol-1-yl)phenyl)-1-oxaspiro[4.4]non-3-ene-7-hydroxymethyl;

(5R,6S,7S)-6-(4-fluorophenyl)-3-(2-isopropoxy-5-(2-(trifluoromethyl)tetrazol-1-yl)phenyl)-1-oxaspiro[4.4]nonane-7-ylmethyl)(1-fluoroethyl)amine;

5R,6S,7S)-6-(4-fluorophenyl)-3-(2-methoxy-5-(2,5-(dimethyl)triazol-1-yl)phenyl)-1-oxaspiro[4.4]non-3-ene-7-carboxylic acid methyl ester;

(5R,6S,7S)-6-(4-fluorophenyl)-3-(2-phenoxy-5-(2-(trifluoromethyl)tetrazol-1-yl)phenyl)-1-oxaspiro[4.4]non-3-ene-7-carboxylic acid methyl ester;

(5R,6S,7S)-6-(4-fluorophenyl)-3-(2-methoxy-5-(2,5-(dimethyl)trazol-1-yl)phenyl)-1-oxaspiro[4.4]nonane-7-carboxylic acid methyl ester;

(5R,6S,7S)-6-(4-fluorophenyl)-3-(2-phenoxy-5-(2-(trifluoromethyl)tetrazol-1-yl)phenyl)-1-oxaspiro[4.4]nonane-7-carboxylic acid methyl ester;

(5R,6S,7S)-6-phenyl-3-(2-(trifluoromethoxy)-5-(2-trifluoromethyl)tetrazole)phenyl-7-(hydroxymethyl)-1-oxaspiro[5.4]dec-3-ene;

(3S,5R,6S,7S)-6-phenyl-3-(2-(trifluoromethoxy)-5-(2-trifluoromethyl)tetrazole)phenyl-7-(hydroxymethyl)-1-oxaspiro[5.4]decane;

(3R,5R,6S,7S)-6-phenyl-3-(2-(trifluoromethoxy)-5-(2-trifluoromethyl)tetrazole)phenyl-7-(hydroxymethyl)-1-oxaspiro[5.4]decane;

(3S,5R,6S,7S)-6-phenyl-3-(2-(trifluoromethoxy)-5-(2-trifluoromethyl)tetrazole)phenyl-7-(pyrrolidin-1-ylmethyl)-1-oxaspiro[5.4]decane;

(3S,5R,6S,7S)-6-phenyl-3-(2-(trifluoromethoxy)-5-(2-trifluoromethyl)tetrazole)phenyl-7-(methyl-(2-fluoroethylamino))-1-oxaspiro[5.4]decane;

(3R,5R,6S,7S)-6-phenyl-3-(2-(trifluoromethoxy)-5-(2-trifluoromethyl)tetrazole)phenyl-7-(methyl-(2-fluoroethylamino))-1-oxaspiro[5.4]decane;

(3R,5R,6S,7S)-6-phenyl-3-(2-methoxy-5-(trifluoromethoxy))phenyl-7-(hydroxymethyl)-1-oxaspiro[5.4]decane;

(3S,5R,6S,7S)-6-phenyl-3-(2-methoxy-5-(trifluoromethoxy))phenyl-7-(hydroxymethyl)-1-oxaspiro[5.4]decane;

(3R,5R,6S,7S)-6-phenyl-3-(2-methoxy-5-(trifluoromethoxy))phenyl-7-(methyl-(2-fluoroethylamino))-1-oxaspiro[5.4]decane;

(5R,6S,7S)-6-(4-fluorophenyl)-3-(2-isopropoxy-5-(trifluoromethyl)phenyl)-1-oxaspiro[4.4]non-3-ene-7-carboxylic acid methyl ester;

(3S,5R,6S,7S)-6-(4-fluorophenyl)-3-(2-isopropoxy-5-(trifluoromethyl)phenyl)-1-oxaspiro[4.4]nonane-7-carboxylic acid methyl ester;

(3S,5R,6S,7S)-(6-(4-fluorophenyl)-3-(2-isopropoxy-5-(trifluoromethyl)phenyl)-1-oxaspiro[4.4]non-7-yl)methanol;

N-(2-fluoroethyl)((3S,5R,6S,7S)-6-(4-fluorophenyl)-3-(2-isopropoxy-5-(trifluoromethyl)phenyl)-2-oxaspiro[4.4]non-7-ylmethyl)amine;

(3R,5R,6S,7S)-(6-(4-fluorophenyl)-3-(2-methoxy-5-(trifluoromethyl)phenyl)-1-oxaspiro[4.4]non-7-yl)methanol;

(3S,5R,6S,7S)-6-(4-fluorophenyl)-3-(2-isopropoxy-5-(2-oxopropyl)phenyl)-1-oxaspiro[4.4]nonane-7-carboxylic acid methyl ester;

(3R,5R,6S,7S)-6-(4-fluorophenyl)-3-(2-isopropoxy-5-(trifluoromethyl)phenyl)1-oxaspiro[4.4]nonane-7-carboxylic acid methyl ester;

(5R,6S,7S)-6-(4-fluorophenyl)-3-(2-isopropyl-5-(trifluoromethyl)phenyl)-1-oxaspiro[4.4]non-3-ene-7-carboxylic acid methyl ester;

(3S,5R,6S,7S)-6-(4-fluorophenyl)-3-(2-isopropyl-5-(trifluoromethyl)phenyl)-1-oxaspiro[4.4]nonane-7-carboxylic acid methyl ester;

(3R,5R,6S,7S)-6-(4-fluorophenyl)-3-(2-isopropyl-5-(trifluoromethyl)phenyl)-1-oxaspiro[4.4]nonane-7-carboxylic acid methyl ester;

(5R,6S,7S)-6-(4-fluorophenyl)-3-(2-(trifluoromethoxy)-5-isopropylphenyl)-1-oxaspiro[4.4]non-3-ene-7-carboxylic acid methyl ester;

(3R,5R,6S,7S)-6(4-fluorophenyl)-3-(2-trifluoromethoxy-5-isopropyl)phenyl)-1-oxaspiro[4.4]nonane-7-carboxylic acid methyl ester;

(3S,5R,6S,7S)-6-(4-fluorophenyl)-3-(2-trifluoromethoxy-5-isopropyl)phenyl)-1-oxaspiro[4.4]nonane-7-carboxylic acid methyl ester;

[3-(S),5-(R),6-(S),7-(S)]-7-(1-(pyrrolidinyl)methyl)-6-(4-fluorophenyl)-3-(2-methoxy-5-((5-trifluoromethyl)tetrazol-1-yl)phenyl)-1-oxaspiro[4.4]nonane;

(5R,6S,7S)-6-(4-fluorophenyl)-3-(2-isopropyl-5-(5-(trifluoromethyl)tetrazol-1-yl)phenyl-7-(pyrrolidin-1-ylmethyl)-1-oxaspiro[5.4]non-3-ene;

(3S,5R,6S,7S)-7-(1-(pyrrolidinyl)methyl)-6-(4-fluorophenyl)-3-(2-methylthio-5-(5-(trifluoromethyl)tetrazol-1-yl)phenyl)-1-oxaspiro[4.4]nonane;

and pharmaceutically acceptable salts and individual diasteromers thereof.

13. A pharmaceutical composition comprising a pharmaceutically acceptable carrier and an effective amount of the compound of claim 1.

14. A pharmaceutical composition comprising a pharmaceutically acceptable carrier and an effective amount of the compound of claim 12.

15. A method for antagonizing the effect of substance P at its receptor site or for the blockade of neurokinin-1 receptors in a mammal which comprises the administration to the mammal of the compound of claim 1 in an amount that is effective for antagonizing the effect of substance P at its receptor site or for the blockade of neurokinin-1 receptors in the mammal.

16. A method for antagonizing the effect of substance P at its receptor site or for the blockade of neurokinin-1 receptors in a mammal which comprises the administration to the mammal of the compound of claim 12, wherein an amount that is effective for antagonizing the effect of substance P at its receptor site or for the blockade of neurokinin-1 receptors in the mammal.

* * * * *